(12) United States Patent
Wang et al.

(10) Patent No.: US 12,312,397 B2
(45) Date of Patent: May 27, 2025

(54) ANTI-O2 ANTIBODIES AND USES THEREOF

(71) Applicants: MedImmune, LLC, Gaithersburg, MD (US); Humabs BioMed SA, Bellinzona (CH)

(72) Inventors: Qun Wang, Gaithersburg, MD (US); Meghan Pennini, Gaithersburg, MD (US); Xiaodong Xiao, Gaithersburg, MD (US); Davide Corti, Bellinzona (CH); Elisabetta Cameroni, Bellinzona (CH); Martina Beltramello, Bellinzona (CH); Gilad Kaplan, Gaithersburg, MD (US); Anna DeMarco, Bellinzona (CH); Charles K. Stover, Gaithersburg, MD (US)

(73) Assignees: MedImmune, LLC, Gaithersburg, MD (US); Humabs BioMed SA, Bellinzona (CH)

( * ) Notice: Subject to any disclaimer, the term of this patent is extended or adjusted under 35 U.S.C. 154(b) by 191 days.

(21) Appl. No.: 17/819,199

(22) Filed: Aug. 11, 2022

(65) Prior Publication Data

US 2023/0079661 A1 Mar. 16, 2023

Related U.S. Application Data

(62) Division of application No. 16/323,185, filed as application No. PCT/US2017/045480 on Aug. 4, 2017, now Pat. No. 11,447,542.

(60) Provisional application No. 62/371,402, filed on Aug. 5, 2016.

(51) Int. Cl.
| | |
|---|---|
| *C07K 16/12* | (2006.01) |
| *A61K 31/407* | (2006.01) |
| *A61K 39/00* | (2006.01) |
| *A61K 39/40* | (2006.01) |
| *A61P 31/04* | (2006.01) |

(52) U.S. Cl.
CPC ........ *C07K 16/1228* (2013.01); *A61K 31/407* (2013.01); *A61K 39/40* (2013.01); *A61P 31/04* (2018.01); *A61K 2039/505* (2013.01); *A61K 2039/545* (2013.01); *C07K 2317/565* (2013.01); *C07K 2317/73* (2013.01); *C07K 2317/76* (2013.01); *C07K 2317/92* (2013.01)

(58) Field of Classification Search
CPC .............. A61K 39/0266; A61K 40/456; A61K 2039/505; A61K 2039/507; A61P 31/04
See application file for complete search history.

(56) References Cited

U.S. PATENT DOCUMENTS

| | | |
|---|---|---|
| 4,474,893 A | 10/1984 | Readinq |
| 4,714,681 A | 12/1987 | Readinq |
| 4,816,567 A | 3/1989 | Cabilly et al. |
| 4,925,648 A | 5/1990 | Hansen et al. |
| 4,946,778 A | 8/1990 | Ladner et al. |
| 5,179,018 A | 1/1993 | Bogard et al. |
| 5,545,806 A | 8/1996 | Lonberg et al. |
| 5,545,807 A | 8/1996 | Surani et al. |
| 5,569,825 A | 10/1996 | Lonberg et al. |
| 5,573,920 A | 11/1996 | Randle |
| 5,601,819 A | 2/1997 | Wonq et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,677,425 A | 10/1997 | Bodmer et al. |
| 5,731,168 A | 3/1998 | Carter et al. |
| 5,750,373 A | 5/1998 | Garrard et al. |
| 5,807,706 A | 9/1998 | Carter et al. |
| 5,821,333 A | 10/1998 | Carter et al. |
| 5,869,046 A | 2/1999 | Presta et al. |
| 5,885,573 A | 3/1999 | Bluestone et al. |
| 5,885,793 A | 3/1999 | Griffiths et al. |
| 5,969,108 A | 10/1999 | McCafferty et al. |
| 6,121,022 A | 9/2000 | Presta et al. |
| 6,165,745 A | 12/2000 | Ward et al. |
| 6,172,197 B1 | 1/2001 | McCafferty et al. |

(Continued)

FOREIGN PATENT DOCUMENTS

| | | |
|---|---|---|
| CN | 102015754 A | 4/2011 |
| EP | 0184187 A2 | 6/1986 |

(Continued)

OTHER PUBLICATIONS

CDC, https://www.cdc.gov/klebsiella/about/index.html#:~: text=Klebsiella%20is%20a%20type%20of,becoming%20increasingly%20resistant%20to%20antibiotics.; accessed on Jul. 11, 2024 (Year: 2024).*

(Continued)

*Primary Examiner* — Brian Gangle
*Assistant Examiner* — Lakia J Jackson-Tongue
(74) *Attorney, Agent, or Firm* — Sterne, Kessler, Goldstein & Fox P.L.L.C.

(57) ABSTRACT

The present disclosure provides binding proteins (e.g., antibodies or antigen binding fragments thereof) that specifically bind to *Klebsiella pneumoniae* O2 and induce opsonophagocytic killing of Klebsiella (e.g., Klebsiellapneumoniae) and/or protects mice from a lethal *Klebsiella* challenge. The present disclosure also provides methods of reducing *Klebsiella* (e.g., *Klebsiella pneumoniae*) or treating or preventing *Klebsiella* (e.g., *Klebsiella pneumoniae*) infection in a subject comprising administering the *Klebsiella* pneumoniae O2 binding proteins, (e.g., antibodies or antigen-binding fragments thereof) to the subject.

15 Claims, 15 Drawing Sheets

Specification includes a Sequence Listing.

(56) References Cited

U.S. PATENT DOCUMENTS

| | | |
|---|---|---|
| 6,180,377 B1 | 1/2001 | Morgan et al. |
| 6,194,551 B1 | 2/2001 | Idusogie et al. |
| 6,277,375 B1 | 8/2001 | Ward et al. |
| 6,300,064 B1 | 10/2001 | Knappik et al. |
| 6,521,404 B1 | 2/2003 | Griffiths et al. |
| 6,528,624 B1 | 3/2003 | Idusogie et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,653,068 B2 | 11/2003 | Frisch et al. |
| 6,706,484 B1 | 3/2004 | Knappik et al. |
| 6,737,056 B1 | 5/2004 | Presta |
| 6,821,505 B2 | 11/2004 | Ward |
| 7,083,784 B2 | 8/2006 | Dall'Acqua et al. |
| 7,122,637 B2 | 10/2006 | Presta |
| 7,183,387 B1 | 2/2007 | Presta |
| 7,264,963 B1 | 9/2007 | Knappik et al. |
| 7,317,091 B2 | 1/2008 | Lazar et al. |
| 7,332,581 B2 | 2/2008 | Presta |
| 7,335,742 B2 | 2/2008 | Presta |
| 7,355,008 B2 | 4/2008 | Stavenhagen et al. |
| 7,371,826 B2 | 5/2008 | Presta |
| 7,658,921 B2 | 2/2010 | Dall'Acqua et al. |
| 11,117,956 B2 | 9/2021 | Wang et al. |
| 11,447,542 B2 | 9/2022 | Wang et al. |
| 2002/0155537 A1 | 10/2002 | Carter et al. |
| 2003/0020734 A1 | 1/2003 | Yin et al. |
| 2004/0002587 A1 | 1/2004 | Watkins et al. |
| 2004/0132101 A1 | 7/2004 | Lazar et al. |
| 2005/0074821 A1 | 4/2005 | Wild, Jr. et al. |
| 2007/0065444 A1 | 3/2007 | North et al. |
| 2010/0330078 A1 | 12/2010 | Bender et al. |
| 2011/0236410 A1 | 9/2011 | Bakshi et al. |
| 2013/0243792 A1 | 9/2013 | Vogels et al. |
| 2015/0252025 A1 | 9/2015 | Poyurovsky et al. |
| 2016/0136285 A1 | 5/2016 | Gozdziewicz et al. |
| 2017/0073397 A1 | 3/2017 | Wang et al. |

FOREIGN PATENT DOCUMENTS

| | | |
|---|---|---|
| EP | 0239400 A2 | 9/1987 |
| GB | 2188638 A | 10/1987 |
| WO | WO-9100360 A1 | 1/1991 |
| WO | WO-9201047 A | 1/1992 |
| WO | WO-9205793 A1 | 4/1992 |
| WO | WO-9208802 A1 | 5/1992 |
| WO | WO-9311161 A1 | 6/1993 |
| WO | WO-9317715 A1 | 9/1993 |
| WO | WO-9413804 A1 | 6/1994 |
| WO | WO-9958572 A | 11/1999 |
| WO | WO-0044788 A1 | 8/2000 |
| WO | WO-0296948 A2 | 12/2002 |
| WO | WO-2011069164 A2 | 6/2011 |
| WO | WO-2012006635 A1 | 1/2012 |
| WO | WO-2015175874 A2 | 11/2015 |
| WO | WO-2016131503 A1 | 8/2016 |
| WO | WO-2017064258 A1 | 4/2017 |
| WO | WO-2018027124 A1 | 2/2018 |
| WO | WO-2018075375 A1 | 4/2018 |

OTHER PUBLICATIONS

Healthline, https://www.healthline.com/health/klebsiella-pneumonia#infection-symptoms; accessed on Jul. 11, 2024 (Year: 2024).*

Ahmad, T. A., et al., "Development of immunization trials against Klebsiella pneumoniae," Vaccine 30(14):2411-2420, Elsevier, Netherlands (Mar. 2012).

Calfee. D. P., "Recent advances in the understanding and management of Klebsiella pneumonia," F1000Res. 6:1760, United Kingdom (Sep. 2017), 9 pages.

Andersen, D. C., and Krummen, L., "Recombinant protein expression for therapeutic applications," Curr Opin Biotechnol 13(2):117-123, Elsevier, Netherlands (Apr. 2002).

Barbas, 3rd, C. F., et al., "In vitro evolution of a neutralizing human antibody to human immunodeficiency virus type 1 to enhance affinity and broaden strain cross-reactivity," Proc Natl Acad Sci USA 91(9):3809-3813, National Academy of Sciences, United States (Apr. 1994).

Beltramello, M., et al., "The human immune response to Dengue virus is dominated by highly cross-reactive antibodies endowed with neutralizing and enhancing activity," Cell Host Microbe 8(3):271-283, Cell Press, United States (Sep. 2010).

Bird, R. E., et al., "Single-chain antigen-binding proteins," Science 242(4877):423-426, American Association for the Advancement of Science, United States (Oct. 1988).

Boerner, P., et al., "Production of antigen-specific human monoclonal antibodies from in vitro-primed human splenocytes," J Immunol 147(1):86-95, American Association of Immunologists, United States (Jul. 1991).

Brade, L., et al., "A monoclonal antibody with specificity for the genus Klebsiella binds to a common epitope located in the core region of Klebsiella lipopolysaccharide," J Endotoxin Res 7(2):119-124, Sage Publications, United States (2001).

Chadd, H. E., and Chamow, S. M., "Therapeutic antibody expression technology," Curr Opin Biotechnol 12(2):188-194, Elsevier, Netherlands (Apr. 2001).

Cheung, R. C., et al., "Epitope-specific antibody response to the surface antigen of duck hepatitis B virus in infected ducks," Virology 176(2):546-552, Academic Press Inc., United States (Jun. 1990).

Chothia, C., and Lesk, A. M., "Canonical structures for the hypervariable regions of immunoglobulins," J Mol Biol 196(4):901-917, Elsevier, Netherlands (Aug. 1987).

Clackson, T., et al., "Making antibody fragments using phage display libraries," Nature 352(6336):624-628, Nature Publishing Group, United Kingdom (Aug. 1991).

Clarke, B. R., and Whitfield, C., "Molecular cloning of the rfb region of Klebsiella pneumoniae serotype O1:K20: the rfb gene cluster is responsible for synthesis of the D-galactan I O polysaccharide," J Bacteriol 174(14):4614-4621, American Society for Microbiology, United States (Jul. 1992).

Dall'acqua, W. F., et al., "Properties of human IgG1s engineered for enhanced binding to the neonatal Fc receptor (FcRn)," J Biol Chem 281(33):23514-23524, Elsevier, Netherlands (Aug. 2006).

Gram, H., et al., "In vitro selection and affinity maturation of antibodies from a naive combinatorial immunoglobulin library," Proc Natl Acad Sci USA 89(8):3576-3580, National Academy of Sciences, United States (Apr. 1992).

Hoogenboom, H. R., and Winter, G., "By-passing immunisation. Human antibodies from synthetic repertoires of germline VH gene segments rearranged in vitro," J Mol Biol 227(2):381-388, Elsevier, Netherlands (Sep. 1992).

Hu, S., et al., "Minibody: A novel engineered anti-carcinoembryonic antigen antibody fragment (single-chain Fv-CH3) which exhibits rapid, high-level targeting of xenografts," Cancer Res 56(13):3055-3061, American Association for Cancer Research Inc., United States (Jul. 1996).

Huse, W. D., et al., "Generation of a large combinatorial library of the immunoglobulin repertoire in phage lambda," Science 246(4935):1275-1281, American Association for the Advancement of Science, United States (Dec. 1989).

Huston, J. S., et al., "Protein engineering of antibody binding sites: recovery of specific activity in an anti-digoxin single-chain Fv analogue produced in Escherichia coli," Proc Natl Acad Sci USA 85(16):5879-5883, National Academy of Sciences, United States (Aug. 1988).

International Application No. PCT/US2017/045480, International Preliminary Report on Patentability, dated Feb. 5, 2019.

International Application No. PCT/US2017/045480, International Search Report and Written Opinion, dated Dec. 14, 2017.

Iredell, J., et al., "Antibiotic resistance in Enterobacteriaceae: mechanisms and clinical implications," BMJ 352:h6420, BioMed Central Ltd., United Kingdom (Feb. 2016).

(56) References Cited

OTHER PUBLICATIONS

Kirkland, T. N., et al., "Analysis of the fine specificity and cross-reactivity of monoclonal anti-lipid A antibodies," J Immunol 137(11):3614-3619, American Association of Immunologists, United States (Dec. 1986).
Knappik, A., et al., "Fully synthetic human combinatorial antibody libraries (HuCAL) based on modular consensus frameworks and CDRs randomized with trinucleotides," J Mol Biol 296(1):57-86, Elsevier, Netherlands (Feb. 2000).
Kohler, G., and Milstein, C., "Continuous cultures of fused cells secreting antibody of predefined specificity," Nature 256(5517):495-497, Nature Publishing Group, United Kingdom (Aug. 1975).
Larrick, J. W., and Thomas, D. W., "Producing proteins in transgenic plants and animals," Curr Opin Biotechnol 12(4):411-418, Elsevier, Netherlands (Aug. 2001).
Ledermann, J. A., et al., "A phase-I study of repeated therapy with radiolabelled antibody to carcinoembryonic antigen using intermittent or continuous administration of cyclosporin A to suppress the immune response," Int J Cancer 47(5):659-664, John Wiley & Sons on behalf of the Union for International Cancer Control, United States (Mar. 1991).
Lefranc, M.-P., et al., "IMGT unique numbering for immunoglobulin and T cell receptor variable domains and Ig superfamily V-like domains," Dev Comp Immunol 27(1):55-77, Elsevier, Netherlands (Jan. 2003).
Marks, J. D., et al., "By-passing immunization. Human antibodies from V-gene libraries displayed on phage," J Mol Biol 222(3):581-597, Elsevier, Netherlands (Dec. 1991).
Marks, J. D., et al., "By-passing immunization: building high affinity human antibodies by chain shuffling," Biotechnology (NY) 10(7):779-783, Wiley, United States (Jul. 1992).
McCafferty, J., et al., "Phage antibodies: filamentous phage displaying antibody variable domains," Nature 348(6301):552-554, Nature Publishing Group, United Kingdom (Dec. 1990).
Moldenhauer, G., et al., "Identity of HML-1 antigen on intestinal intraepithelial T cells and of B-ly7 antigen on hairy cell leukaemia," Scand J Immunol 32(2):77-82, Wiley-Blackwell Publishing Ltd., United Kingdom (Aug. 1990).
Morel, G. A., et al., "Monoclonal antibodies to bovine serum albumin: affinity and specificity determinations," Mol Immunol 25(1):7-15, Pergamon Press, United Kingdom (Jan. 1988).
Pinna, D., et al., "Clonal dissection of the human memory B-cell repertoire following infection and vaccination," Eur J Immunol 39(5):1260-1270, Wiley-VCH, Germany (May 2009).
Reiter, Y., et al., "Engineering antibody Fv fragments for cancer detection and therapy: disulfide-stabilized Fv fragments," Nat Biotechnol 14(10):1239-1245, Nature Publishing Group, United Kingdom (Oct. 1996).
Rothe, C., et al., "The human combinatorial antibody library HuCAL GOLD combines diversification of all six CDRs according to the natural immune system with a novel display method for efficient selection of high-affinity antibodies," J Mol Biol 376(4):1182-1200, Elsevier, Netherlands (Feb. 2008).
Sahly, H., et al., "Serum antibodies to Klebsiella capsular polysaccharides in ankylosing spondylitis," Arthritis Rheum 37(5):754-759, John Wiley and Sons Ltd., United Kingdom (May 1994).
Sahly, H., et al., "Surfactant protein D binds selectively to Klebsiella pneumoniae lipopolysaccharides containing mannose-rich O-antigens," J Immunol 169(6):3267-3274, American Association of Immunologists, United States (Sep. 2002).
Schier, R., et al., "Isolation of picomolar affinity anti-c-erbB-2 single-chain Fv by molecular evolution of the complementarity determining regions in the center of the antibody binding site," J Mol Biol 263(4):551-567, Elsevier, Netherlands (Nov. 1996).
Sheets, M. D., et al., "Efficient construction of a large nonimmune phage antibody library: the production of high-affinity human single-chain antibodies to protein antigens," Proc Natl Acad Sci USA 95(11):6157-6162, National Academy of Sciences, United States (May 1998).
Stahli, C., et al., "Distinction of epitopes by monoclonal antibodies," Methods Enzymol 92:242-253, Academic Press Inc., United States (1983).
Stemmer, W. P., "Rapid evolution of a protein in vitro by DNA shuffling," Nature 370(6488):389-391, Nature Publishing Group, United Kingdom (Aug. 1994).
Szijarto, V., et al., "Both clades of the epidemic KPC-producing Klebsiella pneumoniae clone ST258 share a modified galactan O-antigen type," Int J Med Microbiol 306(2):89-98, Elsevier, Netherlands (Feb. 2016).
Traggiai, E., et al., "An efficient method to make human monoclonal antibodies from memory B cells: potent neutralization of SARS coronavirus," Nat Med 10(8):871-875, Nature Publishing Group, United Kingdom (Aug. 2004).
Trautmann, M., et al., "O antigen seroepidemiology of Klebsiella clinical isolates and implications for immunoprophylaxis of Klebsiella infections," Vaccine 22(7):818-821, Elsevier, Netherlands (Feb. 2004).
Vaughan, T. J., et al., "Human antibodies with sub-nanomolar affinities isolated from a large non-immunized phage display library," Nat Biotechnol 14(3):309-314, Nature Publishing Group, United Kingdom (Mar. 1996).
Wang, Q., et al., "Target-Agnostic Identification of Functional Monoclonal Antibodies Against Klebsiella pneumoniae Multimeric MrkA Fimbrial Subunit," J Infect Dis 213(11):1800-1808, Oxford University Press, United Kingdom (Jun. 2016).
Ward, E. S., et al., "Binding activities of a repertoire of single immunoglobulin variable domains secreted from *Escherichia coli*," Nature 341(6242):544-546, Nature Publishing Group, United Kingdom (Oct. 1989).
Whitfield, C., et al., "Expression of two structurally distinct D-galactan O antigens in the lipopolysaccharide of Klebsiella pneumoniae serotype O1," J Bacteriol 173(4):1420-1431, American Society for Microbiology, United States (Feb. 1991).
Whitfield, C., et al., "Structural analysis of the O-antigen side chain polysaccharides in the lipopolysaccharides of Klebsiella serotypes O2(2a), O2(2a,2b), and O2(2a,2c)," J Bacteriol 174(15):4913-4919, American Society for Microbiology, United States (Aug. 1992).
Held, T.K., et al., "Binding to and Opsonophagocytic Activity of O-Antigen-Specific Monoclonal Antibodies against Encapsulated and Nonencapsulated *Klebsiella pneumoniae* Serotype O1 Strains," 68(5):2402-2409, American Society for Microbiology, United States (2000).
Rukavina, T., et al., "Protective effect of antilipopolysaccharide monoclonal antibody in experimental *Klebsiella* infection," Infect Immunology 65(5):1754-1760, American Society for Microbiology, United States (1997).
Van, N.M., et al., "Binding Studies of a Monoclonal Antibody Specific for 3-Deoxy-D-manno-Octulosonic Acid with a Panel of *Klebsiella pneumoniae* Lipopolysaccharides Representing All of the O Serotypes," Infection and Immunity 62(3):1052-1057, American Society for Microbiology, United States (1994).
International Search Report and Written Opinion mailed Apr. 3, 2018 for International Application No. PCT/US2017/056725, Isa, United States, 14 pages.
International Search Report and Written Opinion mailed Dec. 14, 2017 for International Application No. PCT/US2017/045480, Isa, United States, 18 pages.
Sahly, H., et al., "Serum antibodies to klebsiella capsular polysaccharides in ankylosing spondylitis," Arthritis & Rheumatology 37(5): 754-759, American College of Rheumatology, United States (1994).
Sahly, H., et al., "Surfactant Protein D Binds selectively to Klebsiella pneumonia Lipopolysaccharides Containing Mannose-Rich O-Antigens," Journal of Immunology 169(6):3267-3274, American Association of Immunologists, United States (2002).
Whitefield, C., et al., "Structural analysis of the O-antigen side chain polysaccharides in the lipopolysaccharides of Klebsiella serotypes O2(2a), O2(2a,2b), and O2(2a,2c)," Journal of Bacteriology, 174(15):4913-4919, American Society for Microbiology, United States (1992).

(56) References Cited

OTHER PUBLICATIONS

Hsieh, P-F., et al., "Lipopolysaccharide O1 Antigen Contributes to the Virulence in *Klebsiella pneumoniae* Causing Pyogenic Live Abscess," PLoS One, 7(3):e33155, 13 pages, Public Library of Science, United States (2012).
Hsieh, P-F., et al., "D-galactan II is an immunodominant antigen in O1 lipopolysaccharide and affects virulence in Klebsiella pneumonia: implication in vaccine design," Frontiers in Microbiology, 5(608), 14 pages, Frontiers Media, Switzerland (2014).
Ahmadi, K., et al., "Antibodies to Klebsiella pneumoniae lipopolysaccharide in patients with ankylosing spondylitis." British journal of rheumatology 37(12): 1330-1333, British Society for Rheumatology, United Kingdom (1998).
Goel, M., et al., "Plasticity within the antigen-combining site may manifest as molecular mimicry in the humoral immune response." The Journal of Immunology 173(12): 7358-7367, American Association of Immunologists, United States (2004).
Lloyd, C., et al., "Modelling the human immune response: performance of a 1011 human antibody repertoire against a broad panel of therapeutically relevant antigens." Protein Engineering, Design & Selection 22(3): 159-168, Oxford University Press, United Kingdom (2009).
Sela-Culang, I., et al., "The structural basis of antibody-antigen recognition." Frontiers in Immunology 4:302, 13 pages, Frontiers Publishing, Switzerland (2013).
Bagshawe, K.D., et al., "Antibodyenzyme conjugates can generate cytotoxic drugs from inactive precursors at tumor sites.Antibody," Immunoconjugates and Radiopharmaceuticals 4: 915-22, Mary Ann Liebert Publishers, United Sates (1991).
Holliger, P., et al., "Diabodies": small bivalent and bispecific antibody fragments, Proc. Natl. Acad. Sci. USA, 90(14):6444-8, National Academy of Sciences, United States (Jul. 1993).
Holliger, P., et al., "Engineering bispecific antibodies," Curr Opin Biotechnol 4(4):446-9, Current Biology Ltd., United States (Aug. 1993).
Lowe, D., et al., "Combinatorial protein biochemistry for therapeutics and proteomics," Curr Pharm D Biotechnol 5(1):17-27, Bentham Science Publishers Ltd., United Kingdom (2004).
Oganesyan, V., et al., "Structural characterization of a human Fc fragment engineered for lack of D effector functions," Acta Crystalloqr D Biol Crystalloqr 64(Pt. 6):700-4, Elsevier, Netherlands (Jun. 2008).
Pluckthun, A., "Antibody engineering: advances from the use of *Escherichia coli* expression systems," Biotechnology (NY):9(6):545-51 (Jun. 1991).
Podschun, R., et al., "*Klebsiella* spp. as nosocomial pathogens: epidemiology, taxonomy, typing methods, and pathogenicity factors," Clin Microbiol Rev 11(4):589-603, American Society for Microbiology, United States (Oct. 1998).
Ridgway, J.B.B., et al., "'Knobs-into-holes' engineering of antibody CH3 domains for heavy chain heterodimerization," Protein Eng 9(7):617-21, Oxford University Press, United Kingdom (Jul. 1996).
Tutt, A., et al., "Trispecific F(ab')3 derivatives that use cooperative signaling via the TCR/CD3 complex and CO2 to activate and redirect resting cytotoxic T cells," J Immunol 147(1):60-9, American Association of Immunologists, United States (Jul. 1991).
Kostelny, S.A., et al., "Formation of a bispecific antibody by the use of leucine zippers," J Immunol 148(5):1547-53, American Association of Immunologists, United States (Mar. 1992).
Krebs, B., et al., "High-throughput generation and engineering of recombinant human antibodies," J Immunol Methods 254(1-2):67-84, Elsevier, Netherlands (Aug. 2001).
Trautmann, M., et al., "Evaluation of a competitive ELISA method for the determination of Klebsiella O antigens," J Med Microbiol 44(1):44-51, The Pathological Society of Great Britain and Ireland, United Kingdom (Jan. 1996).
Trautmann, M., et al., "O-antigen seroepidemiology of Klebsiella clinical isolates and implications for immunoprophylaxis of Klebsiella infections," Clinical and Diagnostic Laboratory Immunology 4(5):550-555, American Society for Microbiology, United States (Sep. 1997).
Paul, W. E., ed., "Chapter 9: Structure and Function of Immunoglobulins," in *Fundamental Immunology*, $3^{rd}$ Edition, pp. 292-295, Raven Press, Ltd., United States (1993).
Rudikoff, S., et al., "Single amino acid substitution altering antigen-binding specificity," Proc Natl Acad Sci USA 79(6):1979-1983, National Academy of Sciences, United Kingdom (Mar. 1982).
Tamura, M., et al., "Structural correlates of an anticarcinoma antibody: identification of specificity-determining residues (SDRs) and development of a minimally immunogenic antibody variant by retention of SDRs only," J Immunol 164(3): 1432-1441, American Association of Immunologists, United States (Feb. 2000).
Li, T., et al., "Identification of Specific Diagnostic Antigen for Klebsiella pneumonia," Chinese Journal of Comparative Medicine 20(7):21-26, China Association for Science and Technology, China (2010).

\* cited by examiner

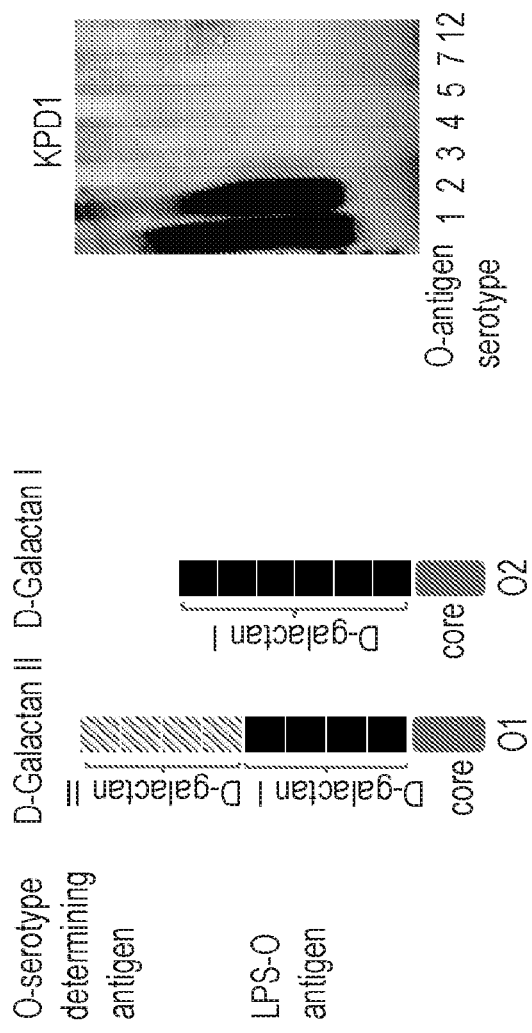

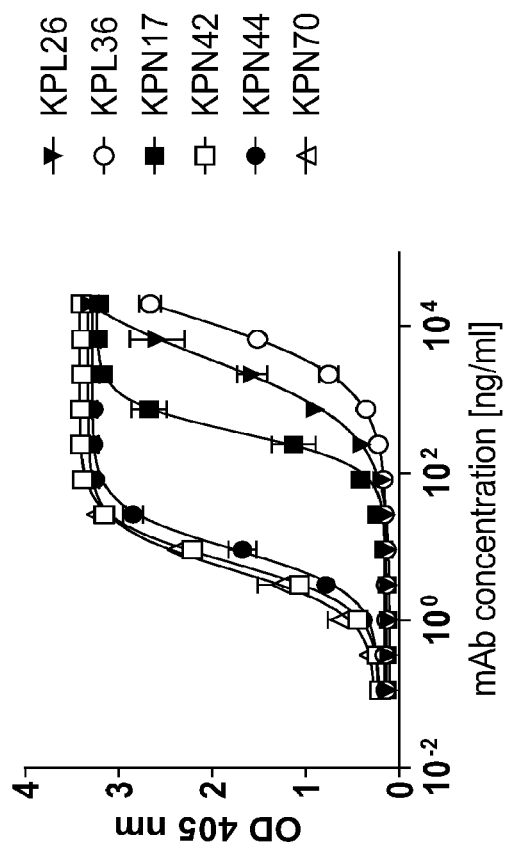
FIG. 2A
FIG. 2B
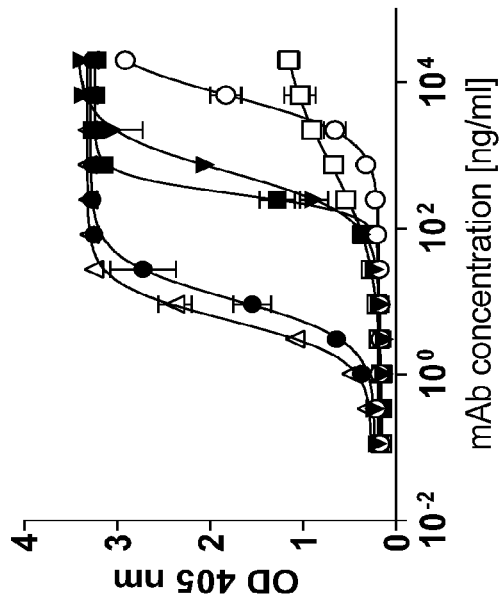
FIG. 2C

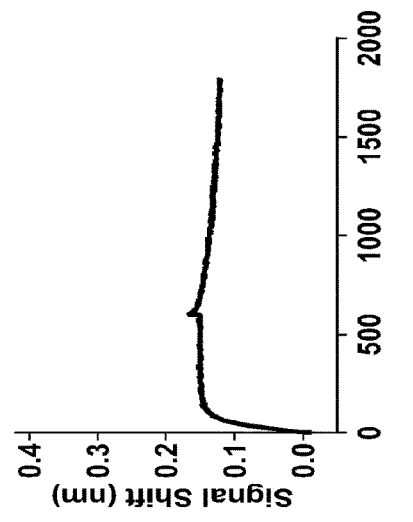
FIG. 3A KPN17-rIgG1
FIG. 3B KPN42-rIgG1
FIG. 3C KPN44-rIgG1
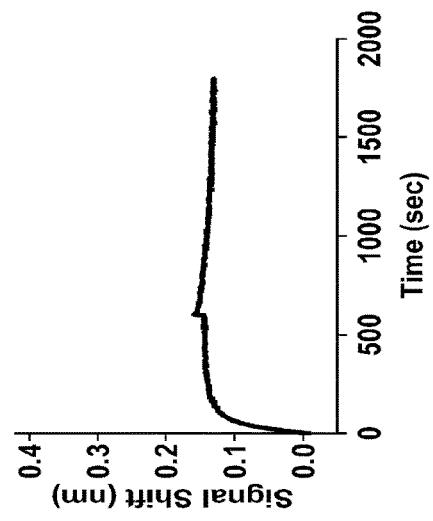
FIG. 3D KPN70-rIgG1
FIG. 3E KPL26 (IgG2)
FIG. 3F KPL36 (IgG2)

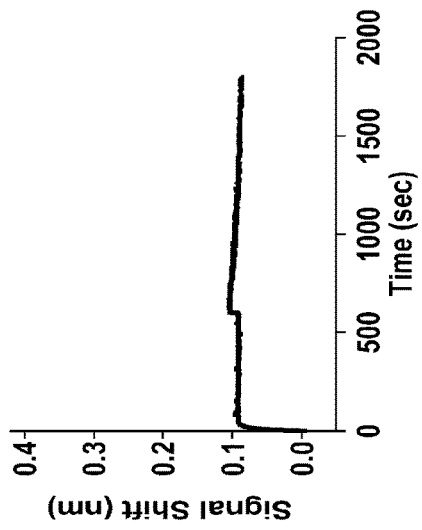
FIG. 3G KPN17-rIgG1
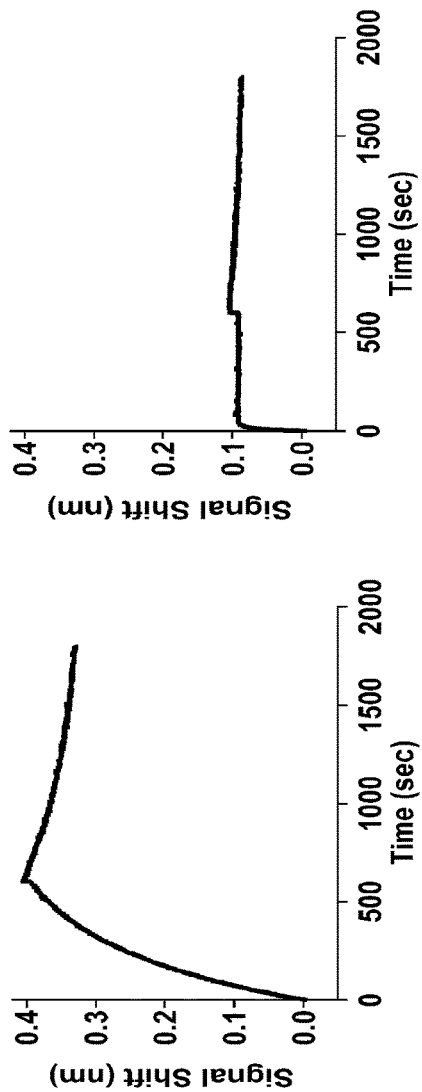
FIG. 3H KPN42-rIgG1
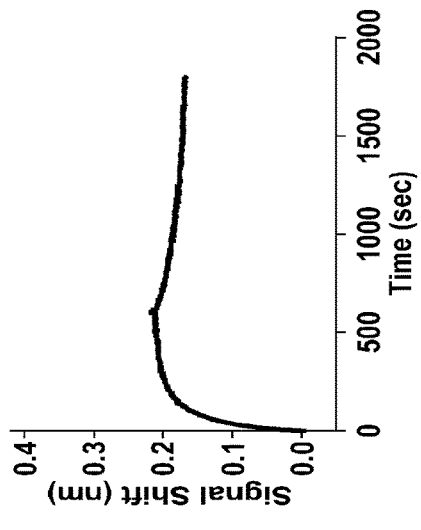
FIG. 3I KPN44-rIgG1
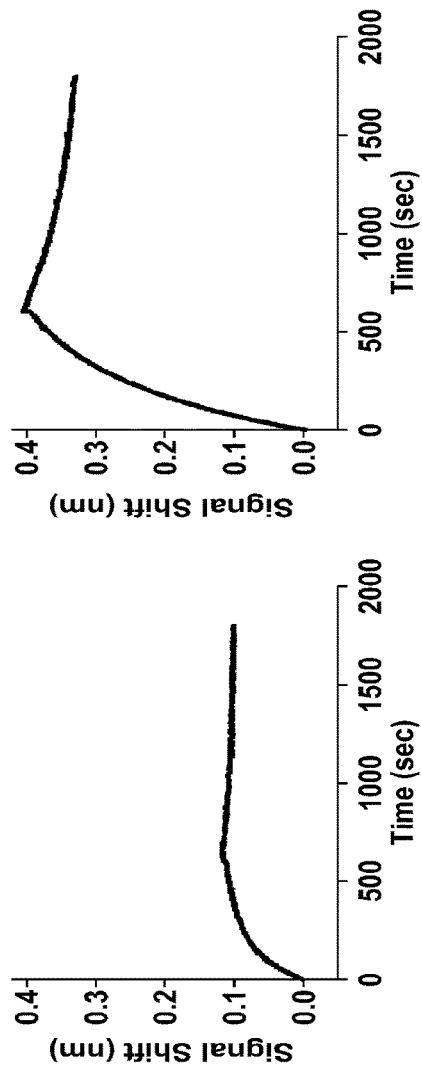
FIG. 3J KPN70-rIgG1
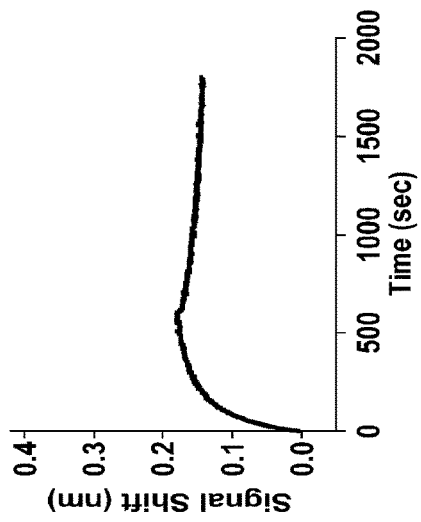
FIG. 3K KPL26 (IgG2)
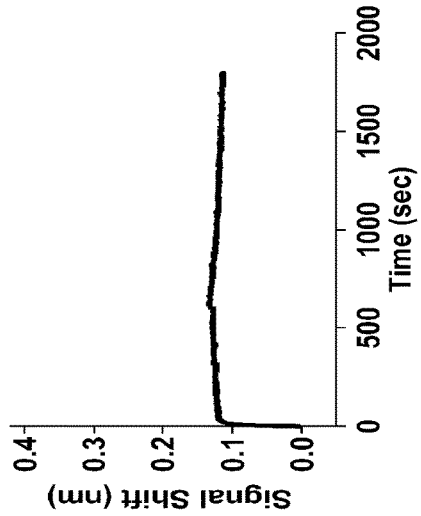
FIG. 3L KPL36 (IgG2)

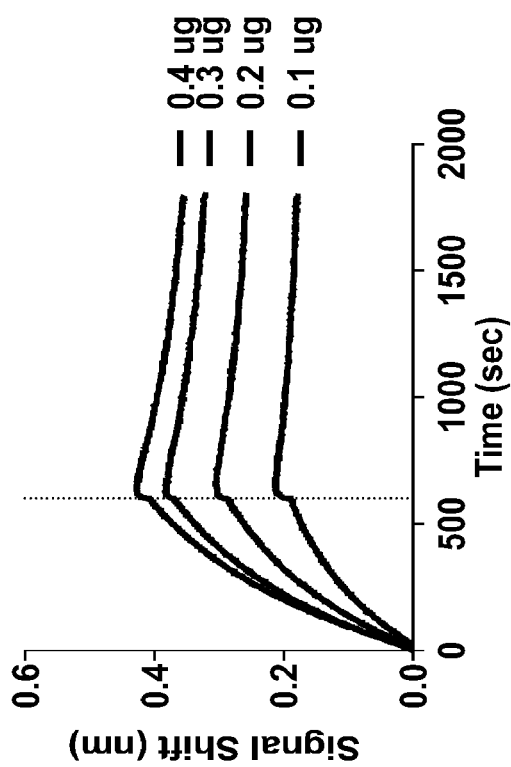
FIG. 3N
FIG. 3M
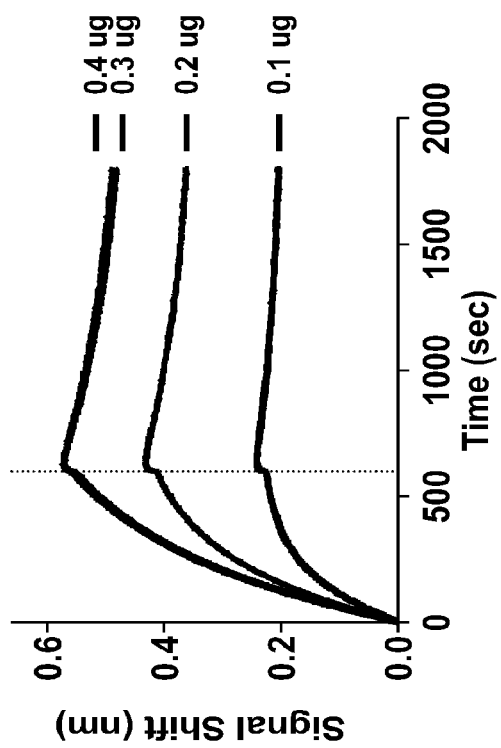
FIG. 3O
| | 0.1 ug | 0.2 ug | 0.3 ug | 0.4 ug |
|---|---|---|---|---|
| KPN42-rIgG1 | 3.23e-009 | 4.68e-009 | 5.17e-009 | 6.03e-009 |
| KPN179-rIgG1 | 8.93e-009 | 7.79e-009 | 6.95e-009 | 8.25e-009 |

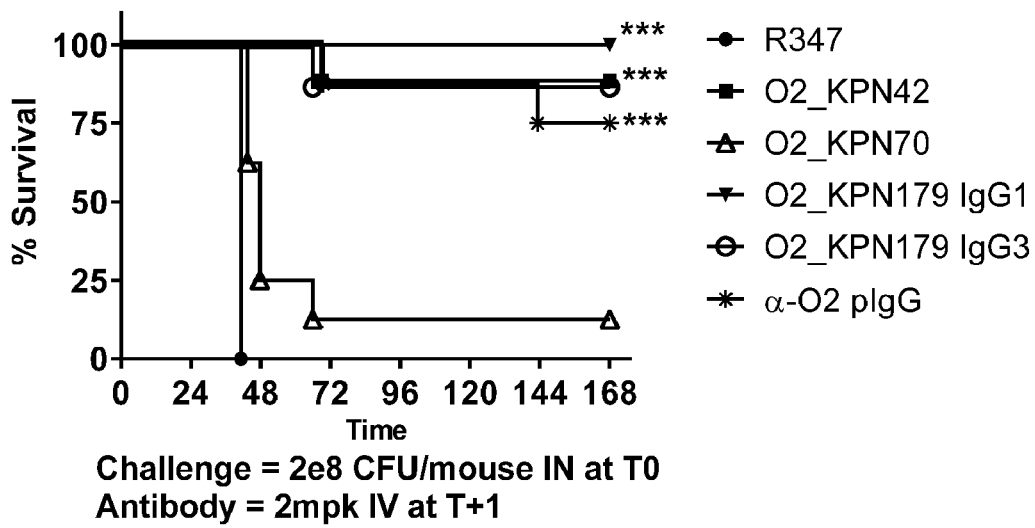
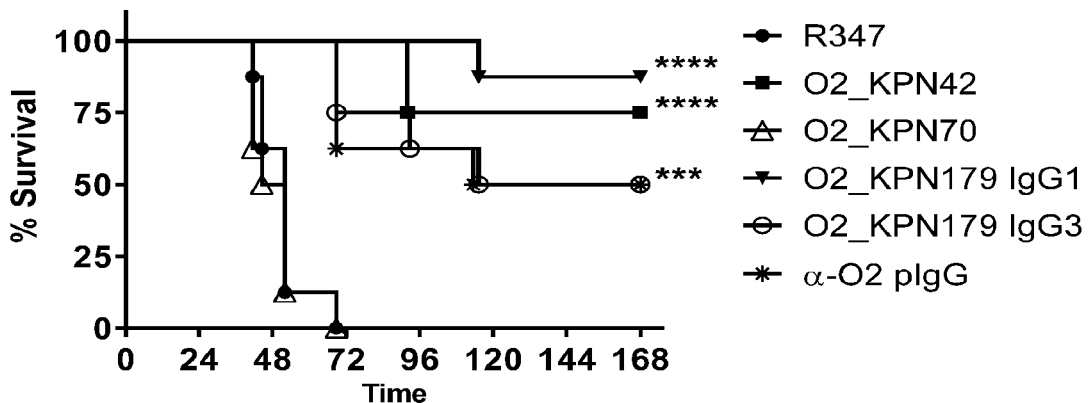

FIG. 9A

KPN42
VH
EVQLVESGGGLVKPGGSLRLSCAASGFTFNDAWMNWVRQAPGKGLEWVARIKKK
HEGVTTDYPASVRGRFTISRDDSKNTVYLQMGRLRIEDTAIYYCTTRIVTTNDYWG
QGTLVTVSS (SEQ ID NO:8)
VL
QSALTQPPSVSGSPGQSVTISCTGTSSDVGAYDYVSWYQQYAGKVPKHIIYDVNER
PSGVPDRFSGSKSGNTAALTISGLQAEDEADYYC<u>C</u>SYAGGDIFVFGTGTQVTVL
(SEQ ID NO:9)

FIG. 9B

KPN179
VH
EVQVVESGGGLVKPGGSLRLSCAASGFTF<u>N</u>NAWMNWVRQAPGKGLEWVGRIKRK
ADGETTDYPASVKGRFTVSRDDSKNTIYLQMNSLKTEDTAIYYCTTRIVTTNDYWG
QGTLVTVSS (SEQ ID NO:53)
VL
QSALTQPPSVSGSPGQSVTISCTGTSSDVGYYDYVSWYQQHHPGKAPKHMIYDVN
KRPSGVPDRFSGSKSGNTASLTISGLQAEDEADYYC<u>C</u>SYAGGDTFVFGTGTKVTVL
(SEQ ID NO:54)

FIG. 9C

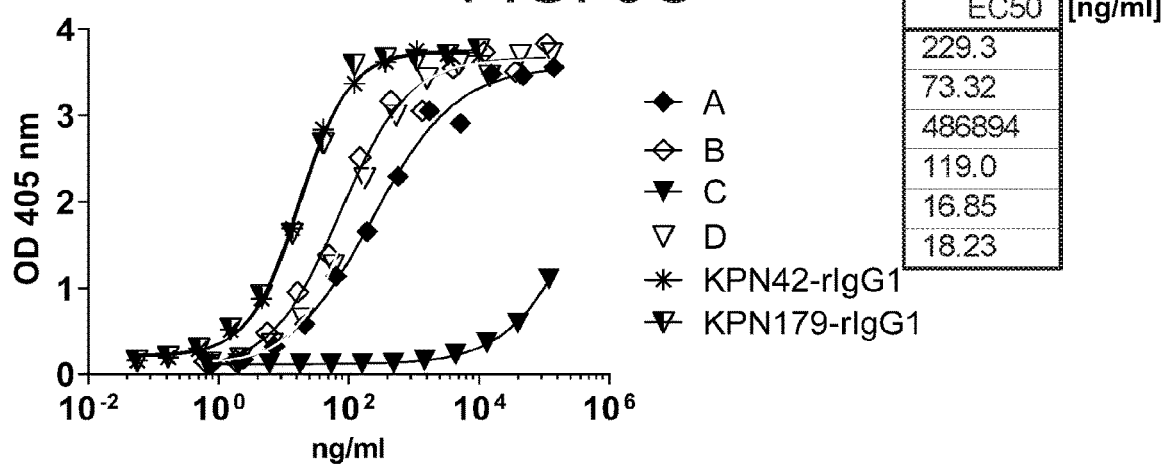

| EC50 | [ng/ml] |
|---|---|
| 229.3 | |
| 73.32 | |
| 486894 | |
| 119.0 | |
| 16.85 | |
| 18.23 | |

A: KPN42-FR-GL-VH/KPN42-FR-GL-C105A-VL
B: KPN42-FR-1-2-4-GL-VH/KPN42-FR-GL-C105A-VL
C: KPN179-FR-GL-N35S-VH/KPN179-FR-GL-C105A-VL
D: KPN179-FR1-2-4-GL-N35S-VH/KPN179-FR-GL-C105A-VL

| Clone name | KD (nM) |
|---|---|
| KPS44 | 2.86 |
| KPS44-v2017 | 3.82 |
| KPS44-G1 | 5.91 |
| KPS44-G2 | 6.51 |
| KPS44-G3 | 2.93; 7.49 |
| KPS44-G4 | 11.20 |
| KPS44-G6 | 5.02 |
| KPS44-G8 | 4.06 |
| KPS44-G10 | 8.06 |
| KPS44-G11 | 1.60 |
| KPS44-G14 | 7.84 |

OPK
8570dcpsB lux (O2)

ANTI-O2 ANTIBODIES AND USES THEREOF

CROSS-REFERENCE TO RELATED APPLICATIONS

This application is a Divisional of application Ser. No. 16/323,185 (now. U.S. Pat. No. 11,447,542); 371(c) Date: Feb. 4, 2019, which is the U.S. National Stage application of International Application No. PCT/US2017/045480, filed on Aug. 4, 2017, said International Application No. PCT/US2017/045480 claims benefit under 35 U.S.C. § 119(e) of the U.S. Provisional Application No. 62/371,402, filed Aug. 5, 2016. Each of the above listed applications is incorporated by reference herein in its entirety for all purposes.

REFERENCE TO SEQUENCE LISTING SUBMITTED ELECTRONICALLY

The content of the electronically submitted sequence listing (Name: 2943_1410002_Seglisting_ST26; Size: 355,457 bytes; and Date of Creation: Aug. 4, 2022) is incorporated herein by reference in its entirety.

BACKGROUND OF THE INVENTION

Field of the Invention

The field of the invention generally relates to antigen binding proteins (e.g., antibodies and antigen-binding fragments thereof) that specifically bind to *Klebsiella pneumoniae* O2 antigen and the use of those binding proteins for prevention or treatment of *Klebsiella* infections.

Background of the Invention

*Klebsiella* is a Gram negative bacterium that is rapidly gaining clinical importance as a causative agent for opportunistic and nosocomial infection, including pneumonia, urinary tract infection, neonatal septicemia, and surgery wound infection. In addition, there are emerging syndromes associated with *Klebsiella* infections such as pyogenic liver abscesses (PLA), endophthalmitis, meningitis, and necrotizing meningitis. (See Iredell et al. *BMJ* 351: h6420 (2015).)

Antibiotic resistance has emerged as one of the major challenges in the fight against bacterial infections. While some progress has been made against drug resistant *Staphylococcus aureus*, Gram negative opportunistic infections are most problematic. Among these, *Klebsiella pneumoniae* has become particularly challenging with multi-drug resistant strains widely circulating. Antibiotic resistances such as Extended-Spectrum Beta Lactamase (ESBL), *K. pneumoniae* carbapenemase (KPC), and New Delhi metallo-beta-lactamase 1 (NDM-1) have spread worldwide and rendered current antibiotic classes largely inadequate. This reality coupled with the dwindling antibiotics pipeline leaves few therapeutic alternatives. Several recent high profile outbreaks underscore the urgency associated with *K. pneumoniae* antibiotic resistance. It is therefore critical to develop strategies to complement antibiotics therapies.

Multiple virulence factors have been implicated in *K. pneumoniae* pathogenesis, including capsular polysaccharides (CPS) and lipopolysaccharides (LPS). Polyclonal antibodies directed against LPS and CPS are protective in preclinical models of lethal *K. pneumoniae* infections. However targeting these two antigens with antibodies poses a significant challenge with respect to strain coverage. There are more than seventy-seven known capsule serotypes and eight 0-antigen serotypes, and it is not clear which are the most prevalent or associated with pathogenesis. In addition, the limited number of monoclonal antibodies targeting conserved epitopes within LPS have no reported protective effect (Brade et al. 2001, J Endotoxin Res, 7(2):119-24).

Thus, there is a great need to identify and develop antibodies that have protective effect against *Klebsiella*, (e.g., *K. pneumoniae*), especially antibiotic resistant *Klebsiella*, infections.

BRIEF SUMMARY OF THE INVENTION

The present disclosure provides *K. pneumoniae* O2 binding proteins, e.g., antibodies or antigen binding fragments thereof, and methods of treating *Klebsiella* infections using *K. pneumoniae* O2 binding proteins.

In one instance provided herein is an isolated antigen binding protein that specifically binds to *Klebsiella pneumoniae* O2 antigen, wherein the antigen binding protein induces opsonophagocytic killing (OPK) of *Klebsiella*. In one instance, the antigen binding protein induces OPK of O1 serotype *Klebsiella* and O2 serotype *Klebsiella*. In one instance, the antigen binding protein induces OPK of O2 serotype *Klebsiella*, but does not induce OPK of O1 serotype *Klebsiella*.

In one instance, the antigen binding protein that specifically binds to *Klebsiella pneumoniae* O2 antigen protects mice from a lethal *Klebsiella* challenge.

In one instance, the antigen binding protein that specifically binds to *Klebsiella pneumoniae* O2 antigen neutralizes lipopolysaccharide (LPS). In one instance, the antigen binding protein that specifically binds to *Klebsiella pneumoniae* O2 antigen inhibits, reduces, or prevents NF-kB activation induced by LPS. In one instance, the antigen binding protein inhibits, reduces, or prevents NF-kB activation induced by both *Klebsiella pneumoniae* O1 LPS and *Klebsiella pneumoniae* O2 LPS. In one instance, the antigen binding protein inhibits, reduces, or prevents NF-kB activation induced by *Klebsiella pneumoniae* O2 LPS, but does not inhibit, reduce, or prevent NF-kB activation induced by *Klebsiella pneumoniae* O1 LPS.

In one instance, the antigen binding protein that specifically binds to *Klebsiella pneumoniae* O2 antigen: (i) neutralizes O1 and/or O2 LPS and induces OPK of O2 serotype *Klebsiella* but does not induce OPK of O1 serotype *Klebsiella*; (ii) neutralizes O1 and/or O2 LPS and induces OPK of O1 serotype *Klebsiella* and O2 serotype *Klebsiella*; or (iii) does not neutralize O1 LPS and induces OPK of O2 serotype *Klebsiella* but does not induce OPK of O1 serotype *Klebsiella*.

In one instance, the antigen binding protein that specifically binds to *Klebsiella pneumoniae* O2 antigen induces OPK of *K. pneumoniae, K. oxytoca, K. granulomatis*, K. ozaenae, K. rhinosclermoatis and/or *K. planticola*. In one instance, the antigen binding protein induces OPK of *K. pneumoniae*.

In one instance, the antigen binding protein that specifically binds to *Klebsiella pneumoniae* O2 antigen also binds to *Klebsiella pneumoniae* O1 antigen.

In one instance, the antigen binding protein that specifically binds to *Klebsiella pneumoniae* O2 antigen a) induces OPK in a multi-drug resistant *Klebsiella*, b) protects mice from a lethal multi-drug resistant *Klebsiella* challenge, or c) induces OPK of a multi-drug resistant *Klebsiella* and protects mice from a lethal multi-drug resistant *Klebsiella* challenge. In one instance, the multi-drug resistant *Klebsiella* is strain Kp961842 or Kp977778 (both of which are ST258 strains). In one instance, the multi-drug resistant *Klebsiella* is a strain listed in one of rows 1-226 of Table 8.

In one instance, the antigen binding protein that specifically binds to *Klebsiella pneumoniae O*2 antigen renders a multi-drug resistant *K. pneumoniae* strain sensitive to at least one antibiotic.

In one instance, the antigen binding protein that specifically binds to *Klebsiella pneumoniae O*2 antigen a) induces OPK in a *Klebsiella* that is susceptible to antibiotics, b) protects mice from a lethal *Klebsiella* challenge, wherein the *Klebsiella* is susceptible to antibiotics, or c) induces OPK in a *Klebsiella* that is susceptible to antibiotics and protects mice from a lethal *Klebsiella* challenge, wherein the *Klebsiella* is susceptible to antibiotics. In one instance, the *Klebsiella* is a strain listed in one of rows 227-254 of Table 8.

In one instance, the antigen binding protein that specifically binds to *Klebsiella pneumoniae O*2 antigen binds to gml-*Klebsiella*. In one instance, the antigen binding protein that specifically binds to *Klebsiella pneumoniae O*2 antigen binds to gml+ *Klebsiella.*

In one instance, the antigen binding protein that specifically binds to *Klebsiella pneumoniae O*2 antigen binds to the D-Galactan I domain of *K. pneumoniae O*2 antigen.

In one instance, provided herein is an isolated antigen binding protein that specifically binds to *Klebsiella pneumoniae* O2 antigen comprising a set of Complementarity-Determining Regions (CDRs): HCDR1, HCDR2, HCDR3, LCDR1, LCDR2, and LCDR3 wherein: HCDR1 has the amino acid sequence of SEQ. ID. NO:1; HCDR2 has the amino acid sequence of SEQ. ID. NO: 2; HCDR3 has the amino acid sequence of SEQ. ID. NO: 3; LCDR1 has the amino acid sequence of SEQ. ID. NO: 4; LCDR2 has the amino acid sequence of DVN or SEQ. ID. NO: 6; and LCDR3 has the amino acid sequence of SEQ. ID. NO: 7.

In one instance, provided herein is an isolated antigen binding protein that specifically binds to *Klebsiella pneumoniae* O2 antigen comprising a set of Complementarity-Determining Regions (CDRs): HCDR1, HCDR2, HCDR3, LCDR1, LCDR2, and LCDR3 wherein: HCDR1 has the amino acid sequence of SEQ. ID. NO:109; HCDR2 has the amino acid sequence of SEQ. ID. NO: 110; HCDR3 has the amino acid sequence of SEQ. ID. NO: 199; LCDR1 has the amino acid sequence of SEQ. ID. NO: 200; LCDR2 has the amino acid sequence of ENN or SEQ. ID. NO: 114, and LCDR3 has the amino acid sequence of SEQ. ID. NO: 201

In one instance, provided herein is an isolated antigen binding protein that specifically binds *Klebsiella pneumoniae O*2 antigen, wherein the antigen binding protein comprises a heavy chain variable region (VH) at least 95%, 96%, 97%, 98% or 99% identical to SEQ ID NO:8 and/or a light chain variable region (VL) at least 95%, 96%, 97%, 98% or 99% identical to SEQ ID NO:9. In one instance, the antigen binding protein thereof comprises a VH comprising SEQ ID NO:8 and a VL comprising SEQ ID NO:9.

In one instance, provided herein is an isolated antigen binding protein that specifically binds *Klebsiella pneumoniae O*2 antigen, wherein the antigen binding protein comprises a heavy chain variable region (VH) at least 95%, 96%, 97%, 98% or 99% identical to SEQ ID NO:202 and/or a light chain variable region (VL) at least 95%, 96%, 97%, 98% or 99% identical to SEQ ID NO:203. In one instance, the antigen binding protein thereof comprises a VH comprising SEQ ID NO:202 and a VL comprising SEQ ID NO:203.

In one instance, provided herein is an isolated antigen binding protein that specifically binds to *Klebsiella pneumoniae O*2 antigen comprising a VH comprising SEQ ID NO:8.

In one instance, provided herein is an isolated antigen binding protein that specifically binds to *Klebsiella pneumoniae O*2 antigen comprising a VH comprising SEQ ID NO:202.

In one instance, provided herein is an isolated antigen binding protein that specifically binds to *Klebsiella pneumoniae O*2 antigen comprising a VL comprising SEQ ID NO:9.

In one instance, provided herein is an isolated antigen binding protein that specifically binds to *Klebsiella pneumoniae O*2 antigen comprising a VL comprising SEQ ID NO:203.

In one instance, provided herein is an isolated antigen binding protein that specifically binds to the same epitope in the *Klebsiella pneumoniae* O2 antigen as an antibody comprising a VH comprising SEQ ID NO:8 and a VL comprising SEQ ID NO:9.

In one instance, provided herein is an isolated antigen binding protein that specifically binds to the same epitope in the *Klebsiella pneumoniae* O2 antigen as an antibody comprising a VH comprising SEQ ID NO:202 and a VL comprising SEQ ID NO:203.

In one instance, provided herein is an isolated antigen binding protein that competitively inhibits the binding to *Klebsiella pneumoniae O*2 antigen of an antibody comprising a VH comprising SEQ ID NO:8 and a VL comprising SEQ ID NO:9.

In one instance, provided herein is an isolated antigen binding protein that competitively inhibits the binding to *Klebsiella pneumoniae O*2 antigen of an antibody comprising a VH comprising SEQ ID NO:202 and a VL comprising SEQ ID NO:203.

In one instance, provided herein is an isolated antigen binding protein that specifically binds to *Klebsiella pneumoniae* O2 antigen comprising a set of Complementarity-Determining Regions (CDRs): HCDR1, HCDR2, HCDR3, LCDR1, LCDR2, and LCDR3 wherein the HCDR1, HCDR2, HCDR3, LCDR1, LCDR2, and LCDR3 comprise the amino acid sequences of: SEQ. ID. NOs: 10-13, DVN or SEQ. ID. NO: 15, and SEQ. ID. NO: 16, respectively; SEQ. ID. NOs: 19-22, DVN or SEQ. ID. NO: 24, and SEQ. ID. NO: 25, respectively; SEQ. ID. NOs: 28-31, DAS or SEQ. ID. NO: 33, and SEQ. ID. NO: 34, respectively; SEQ. ID. NOs: 37-40, DMS or SEQ. ID. NO: 42, and SEQ. ID. NO: 43, respectively; SEQ. ID. NOs: 46-49, DVN or SEQ. ID. NO: 51, and SEQ. ID. NO: 52, respectively; SEQ. ID. NOs: 166-168, 175, DVN or SEQ. ID. NO: 177, and SEQ. ID. NO: 178, respectively; SEQ. ID. NOs: 169-171, 179, DVN or SEQ. ID. NO: 181, and SEQ. ID. NO: 182, respectively; SEQ. ID. NOs: 55-58, DMS or SEQ. ID. NO: 60, and SEQ. ID. NO: 61, respectively; SEQ. ID. NOs: 64-67, AAS or SEQ. ID. NO: 69, and SEQ. ID. NO: 70, respectively; SEQ. ID. NOs: 73-78, respectively; SEQ. ID. NOs: 82-85, EVS or SEQ. ID. NO: 87, and SEQ. ID. NO: 88, respectively; SEQ. ID. NOs: 91-94, DNN or SEQ. ID. NO: 96, and SEQ. ID. NO: 97, respectively; SEQ. ID. NOs: 100-103, ENN or SEQ. ID. NO: 105, and SEQ. ID. NO: 106, respectively; SEQ. ID. NOs: 109-112, ENN or SEQ. ID. NO: 114, and SEQ. ID. NO: 115, respectively; SEQ. ID. NOs: 118-121, EVN or SEQ. ID. NO: 123, and SEQ. ID. NO: 124, respectively; SEQ. ID. NOs: 127-130, GAS or SEQ. ID. NO: 132, and SEQ. ID. NO: 133, respectively; SEQ. ID.

NOs: 172-174, 183, EVN or SEQ. ID. NO: 185, and SEQ. ID. NO: 186, respectively; or SEQ ID NOs: 109-111, 199, 112-115, 200 and 201.

In one instance, provided herein is an isolated antigen binding protein that specifically binds to *Klebsiella pneumoniae* O2 antigen, wherein the antigen binding protein comprises a VH and VL at least 95%, 96%, 97%, 98%, or 99% identical to: SEQ. ID. NO: 17 and SEQ ID NO:18, respectively; SEQ. ID. NO: 26 and SEQ ID NO:27, respectively; SEQ. ID. NO: 35 and SEQ ID NO:36, respectively; SEQ. ID. NO: 44 and SEQ ID NO:45, respectively; SEQ. ID. NO: 53 and SEQ ID NO:54, respectively; SEQ. ID. NO: 187 and SEQ ID NO:190, respectively; SEQ. ID. NO: 188 and SEQ ID NO:191, respectively; SEQ. ID. NO: 62 and SEQ ID NO:63, respectively; SEQ. ID. NO: 71 and SEQ ID NO: 72, respectively; SEQ. ID. NO: 80 and SEQ ID NO:81, respectively; SEQ. ID. NO: 89 and SEQ ID NO:90, respectively; SEQ. ID. NO: 98 and SEQ ID NO:99, respectively; SEQ. ID. NO: 107 and SEQ ID NO:108, respectively; SEQ. ID. NO: 116 and SEQ ID NO:117, respectively; SEQ. ID. NO: 125 and SEQ ID NO:126, respectively; SEQ. ID. NO: 134 and SEQ ID NO:135, respectively; SEQ. ID. NO:189 and SEQ ID NO:192, respectively; or SEQ ID NOs 116 and 202-205.

In one instance, the antigen binding protein comprises a VH and a VL comprising: SEQ. ID. NO: 17 and SEQ ID NO:18, respectively; SEQ. ID. NO: 26 and SEQ ID NO:27, respectively; SEQ. ID. NO: 35 and SEQ ID NO:36, respectively; SEQ. ID. NO: 44 and SEQ ID NO:45, respectively; SEQ. ID. NO: 53 and SEQ ID NO:54, respectively; SEQ. ID. NO: 187 and SEQ ID NO:190, respectively; SEQ. ID. NO: 188 and SEQ ID NO:191, respectively; SEQ. ID. NO: 62 and SEQ ID NO:63, respectively; SEQ. ID. NO: 71 and SEQ ID NO:72, respectively; SEQ. ID. NO: 80 and SEQ ID NO:81, respectively; SEQ. ID. NO: 89 and SEQ ID NO:90, respectively; SEQ. ID. NO: 98 and SEQ ID NO:99, respectively; SEQ. ID. NO: 107 and SEQ ID NO:108, respectively; SEQ. ID. NO: 116 and SEQ ID NO:117, respectively; SEQ. ID. NO: 125 and SEQ ID NO:126, respectively; SEQ. ID. NO: 134 and SEQ ID NO:135, respectively; SEQ. ID. NO: 189 and SEQ ID NO:192, respectively; SEQ ID NOs 116 and 202-205; SEQ ID NO:273 and SEQ ID NO:247, respectively; SEQ ID NO:273 and SEQ ID NO:257, respectively; SEQ ID NO:273 and SEQ ID NO:217, respectively; SEQ ID NO:273 and SEQ ID NO:227, respectively; SEQ ID NO:274 and SEQ ID NO:247, respectively; SEQ ID NO:274 and SEQ ID NO:257, respectively; SEQ ID NO:274 and SEQ ID NO:217, respectively; and SEQ ID NO:274 and SEQ ID NO:227, respectively.

In one instance, provided herein is an isolated antigen binding protein that specifically binds to *Klebsiella pneumoniae* O2 antigen comprising a VH comprising SEQ ID NO:17, SEQ ID NO:26, SEQ ID NO: 35, SEQ ID NO:44, SEQ ID NO:53, SEQ ID NO:187, SEQ ID NO:188, SEQ ID NO:62, SEQ ID NO:71, SEQ ID NO:80, SEQ ID NO:89, SEQ ID NO:98, SEQ ID NO:107, SEQ ID NO:116, SEQ ID NO:125, SEQ ID NO:134, SEQ ID NO:189; or SEQ ID NO: 116; SEQ ID NO:202; SEQ ID NO:213; SEQ ID NO:223; SEQ ID NO:233; SEQ ID NO:243; SEQ ID NO:253; SEQ ID NO:263; SEQ ID NO:273; or SEQ ID NO:274.

In one instance, provided herein is an isolated antigen binding protein that specifically binds to *Klebsiella pneumoniae* O2 antigen comprising a VL comprising SEQ ID NO:18, SEQ ID NO:27, SEQ ID NO: 36, SEQ ID NO:45, SEQ ID NO:54, SEQ ID NO:190, SEQ ID NO:191, SEQ ID NO:63, SEQ ID NO:72, SEQ ID NO:81, SEQ ID NO:90, SEQ ID NO:99, SEQ ID NO:108, SEQ ID NO:117, SEQ ID NO:126, SEQ ID NO:135, SEQ ID NO: 192; SEQ ID NO: 203; SEQ ID NO:204; SEQ ID NO:205; SEQ ID NO:217; SEQ ID NO:227; SEQ ID NO:237; SEQ ID NO:247; SEQ ID NO:257; or SEQ ID NO:267.

In one instance, provided herein is an isolated antigen binding protein that specifically binds to the same epitope in the *Klebsiella pneumoniae* O2 antigen as an antibody comprising a VH and a VL comprising: SEQ. ID. NO: 17 and SEQ ID NO:18, respectively; SEQ. ID. NO: 26 and SEQ ID NO:27, respectively; SEQ. ID. NO: 35 and SEQ ID NO:36, respectively; SEQ. ID. NO: 44 and SEQ ID NO:45, respectively; SEQ. ID. NO: 53 and SEQ ID NO:54, respectively; SEQ. ID. NO: 187 and SEQ ID NO:190, respectively; SEQ. ID. NO: 188 and SEQ ID NO:191, respectively; SEQ. ID. NO: 62 and SEQ ID NO:63, respectively; SEQ. ID. NO: 71 and SEQ ID NO:72, respectively; SEQ. ID. NO: 80 and SEQ ID NO:81, respectively; SEQ. ID. NO: 89 and SEQ ID NO:90, respectively; SEQ. ID. NO: 98 and SEQ ID NO:99, respectively; SEQ. ID. NO: 107 and SEQ ID NO:108, respectively; SEQ. ID. NO: 116 and SEQ ID NO:117, respectively; SEQ. ID. NO: 125 and SEQ ID NO:126, respectively; SEQ. ID. NO: 134 and SEQ ID NO:135, respectively; SEQ. ID. NO: 189 and SEQ ID NO:192; or SEQ ID NOs 116 and 202-205.

In one instance, provided herein is an isolated antigen binding protein that competitively inhibits the binding to *Klebsiella pneumoniae* O2 antigen of an antibody comprising a VH and a VL comprising: SEQ. ID. NO: 17 and SEQ ID NO:18, respectively; SEQ. ID. NO: 26 and SEQ ID NO:27, respectively; SEQ. ID. NO: 35 and SEQ ID NO:36, respectively; SEQ. ID. NO: 44 and SEQ ID NO:45, respectively; SEQ. ID. NO: 53 and SEQ ID NO:54, respectively; SEQ. ID. NO: 187 and SEQ ID NO:190, respectively; SEQ. ID. NO: 188 and SEQ ID NO:191, respectively; SEQ. ID. NO: 62 and SEQ ID NO:63, respectively; SEQ. ID. NO: 71 and SEQ ID NO:72, respectively; SEQ. ID. NO: 80 and SEQ ID NO:81, respectively; SEQ. TD. NO: 89 and SEQ ID NO:90, respectively; SEQ. ID. NO: 98 and SEQ ID NO:99, respectively; SEQ. ID. NO: 107 and SEQ ID NO:108, respectively; SEQ TD NO 116 and SEQ ID NO: 117, respectively; SEQ. ID. NO: 125 and SEQ TD NO: 126, respectively, SEQ. ID. NO: 134 and SEQ ID NO:135, respectively; SEQ. ID. NO: 189 and SEQ ID NO:192; or SEQ ID NOs 116 and 202-205.

In one instance, the antigen binding protein that specifically binds to *Klebsiella pneumoniae* O2 antigen is murine, non-human, humanized, chimeric, resurfaced, or human.

In one instance, the antigen binding protein that specifically binds to *Klebsiella pneumoniae* O2 antigen is an antibody. In one instance, the antigen binding protein that specifically binds to *Klebsiella pneumoniae* O2 antigen is an antigen binding fragment of an antibody. In one instance, the antigen binding protein that specifically binds to *Klebsiella pneumoniae* O2 antigen is a monoclonal antibody, a recombinant antibody, a human antibody, a humanized antibody, a chimeric antibody, or an antigen binding fragment thereof In one instance, the antigen binding protein that specifically binds to *Klebsiella pneumoniae* O2 antigen comprises a Fab, Fab', F(ab')2, Fd, single chain Fv or scFv, disulfide linked Fv, V-NAR domain, IgNar, intrabody, IgGACH2, minibody, F(ab')3, single-domain antibody, DVD-Ig, Fcab, mAb2, (scFv)2, or scFv-Fc.

In one instance, the antigen binding protein (e.g. an antibody or antigen-binding fragment thereof that specifically binds to *Klebsiella pneumoniae* O2 antigen) binds to *Klebsiella* O2 antigen with an affinity constant of about 4.5E-09 or about 7.8E-09M. In one instance, the binding affinity is measured by octet binding, flow cytometry, Biacore, KinExa, or radioimmunoassay. In one instance, the antigen binding protein (e.g. an antibody or antigen-binding fragment thereof that specifically binds to *Klebsiella pneumoniae* O2 antigen) induces OPK of *Klebsiella*. In one instance, the antigen binding protein (e.g. an antibody or antigen-binding fragment thereof that specifically binds to *Klebsiella pneumoniae* O2 antigen) induces OPK of O1 serotype *Klebsiella* and O2 serotype *Klebsiella*. In one instance, the antigen binding protein (e.g. an antibody or antigen-binding fragment thereof that specifically binds to *Klebsiella pneumoniae* O2 antigen) induces OPK of O2 serotype *Klebsiella*, but does not induce OPK of O1 serotype *Klebsiella*. In one instance, the antigen binding protein (e.g. an antibody or antigen-binding fragment thereof that specifically binds to Klebsiellapneumoniae O2 antigen) protects mice from a lethal *Klebsiella* challenge.

In one instance, the antigen binding protein (e.g. an antibody or antigen-binding fragment thereof that specifically binds to *Klebsiella pneumoniae* O2 antigen) neutralizes LPS. In one instance, the antigen binding protein (e.g. an antibody or antigen-binding fragment thereof) inhibits, reduces, or prevents NF-kB activation induced by LPS. In one instance, the antigen binding protein (e.g. an antibody or antigen-binding fragment thereof that specifically binds to *Klebsiella pneumoniae* O2 antigen) inhibits, reduces, or prevents NF-kB activation induced by both *Klebsiella pneumoniae* O1 LPS and *Klebsiella pneumoniae* O2 LPS. In one instance, the antigen binding protein (e.g. an antibody or antigen-binding fragment thereof that specifically binds to *Klebsiella pneumoniae* O2 antigen) inhibits, reduces, or prevents NF-kB activation induced by *Klebsiella pneumoniae* O2 LPS, but does not inhibit, reduce, or prevent NF-kB activation induced by *Klebsiella pneumoniae* O1 LPS. In one instance, the antigen binding protein (e.g. an antibody or antigen-binding fragment thereof that specifically binds to *Klebsiella pneumoniae* O2 antigen) does not neutralize O1 LPS and induces OPK of O2 serotype *Klebsiella* but does not induce OPK of O1 serotype *Klebsiella*.

In one instance, the antigen binding protein (e.g. an antibody or antigen-binding fragment thereof that specifically binds to *Klebsiella pneumoniae* O2 antigen): (i) neutralizes O1 and/or O2 LPS and induces OPK of O2 serotype *Klebsiella* but does not induce OPK of O1 serotype *Klebsiella*; (ii) neutralizes O1 and/or O2 LPS and induces OPK of O1 serotype *Klebsiella* and O2 serotype *Klebsiella*; or (iii) does not neutralize O1 LPS and induces OPK of O2 serotype *Klebsiella* but does not induce OPK of O1 serotype *Klebsiella*.

In one instance, the antigen binding protein (e.g. an antibody or antigen-binding fragment thereof that specifically binds to *Klebsiella pneumoniae* O2 antigen) induces OPK of *K. pneumoniae, K. oxytoca, K. granulomatis*, K. ozaenae, K. rhinosclermoatis and/or *K. planticola*. In one instance, the antigen binding protein (e.g. an antibody or antigen-binding fragment thereof that specifically binds to *Klebsiella pneumoniae* O2 antigen) induces OPK of *K. pneumoniae.*

In one instance, the antigen binding protein (e.g. an antibody or antigen-binding fragment thereof that specifically binds to *Klebsiella pneumoniae* O2 antigen) binds to *Klebsiella pneumoniae* O1 antigen. In one instance, the antigen binding protein (e.g. an antibody or antigen-binding fragment thereof that specifically binds to Klebsiellapneumoniae O2 antigen): a) induces OPK in a multi-drug resistant *Klebsiella, b*) protects mice from a lethal multi-drug resistant *Klebsiella* challenge, or c) induces OPK of a multi-drug resistant *Klebsiella* and protects mice from a lethal multi-drug resistant *Klebsiella* challenge. In one instance, the multi-drug resistant *Klebsiella* is strain Kp961842 or Kp977778. In one instance, the multi-drug resistant *Klebsiella* is a strain listed in one of rows 1-226 of Table 8. In one instance, the antigen binding protein (e.g. an antibody or antigen-binding fragment thereof that specifically binds to *Klebsiella pneumoniae* O2 antigen) renders a multi-drug resistant *K. pneumoniae* strain sensitive to at least one antibiotic.

In one instance, the antigen binding protein (e.g. an antibody or antigen-binding fragment thereof that specifically binds to *Klebsiella pneumoniae* O2 antigen): a) induces OPK in a *Klebsiella* that is susceptible to antibiotics, b) protects mice from a lethal *Klebsiella* challenge, wherein the *Klebsiella* is susceptible to antibiotics, or c) induces OPK in a *Klebsiella* that is susceptible to antibiotics and protects mice from a lethal *Klebsiella* challenge, wherein the *Klebsiella* is susceptible to antibiotics. In one instance, the *Klebsiella* is a strain listed in one of rows 227-254 of Table 8.

In one instance, the antigen binding protein (e.g. an antibody or antigen-binding fragment thereof that specifically binds to *Klebsiella pneumoniae* O2 antigen) binds to gml-*Klebsiella*. In one instance, the antigen binding protein (e.g. an antibody or antigen-binding fragment thereof that specifically binds to *Klebsiella pneumoniae* O2 antigen) binds to gml+*Klebsiella*. In one instance, the antigen binding protein (e.g. an antibody or antigen-binding fragment thereof that specifically binds to *Klebsiella pneumoniae* O2 antigen) binds to the D-Galactan I domain of *K. pneumoniae O*2 antigen.

In one instance, the antigen binding protein (e.g. an antibody or antigen-binding fragment thereof that specifically binds to *Klebsiella pneumoniae* O2 antigen) comprises a heavy chain immunoglobulin constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain.

In one instance, the antigen binding protein (e.g. an antibody or antigen-binding fragment thereof that specifically binds to *Klebsiella pneumoniae* O2 antigen) comprises a light chain immunoglobulin constant domain selected from the group consisting of: (a) an Ig kappa constant domain; and (b) an Ig lambda constant domain.

In one instance, the antigen binding protein (e.g. an antibody or antigen-binding fragment thereof that specifically binds to *Klebsiella pneumoniae* O2 antigen) comprises a human IgG1 constant domain and a human lambda constant domain.

In one instance, provided herein is an isolated nucleic acid molecule encoding an antigen binding protein provided herein, including e.g., an antibody or antigen-binding fragment thereof that specifically binds to *Klebsiella pneumoniae* O2 antigen. In one instance, the nucleic acid molecule is operably linked to a control sequence.

In one instance, provided herein is a vector comprising a nucleic acid molecule provided herein.

In one instance, provided herein is a host cell transformed with a nucleic acid molecule provided herein or a vector provided herein. In one instance, the host cell is a mammalian host cell. In one instance, the host cell is a HEK293 cell, CHO cell, COS-7 cell, a HeLa cell, a NSO murine myeloma cell, or a PER.C6® human cell.

In one instance, provided herein is a hybridoma producing an antigen binding protein provided herein, including e.g., an antibody or antigen-binding fragment thereof that specifically binds to *Klebsiella pneumoniae* O2 antigen. In one instance provided herein is an isolated host cell producing an antigen binding protein provided herein, including e.g., an antibody or antigen-binding fragment thereof that specifically binds to Klebsiellapneumoniae O2 antigen. In one instance, provided herein is a method of making an antigen binding protein provided herein (e.g. an antibody or antigen-binding fragment thereof that specifically binds to *Klebsiella pneumoniae* O2 antigen) comprising (a) culturing a host cell expressing the antigen binding protein or culturing a host cell provided herein or a hybridoma provided herein; and (b) isolating the antigen binding protein thereof from the cultured host cell or hybridoma. In one instance, provided herein is an antigen binding protein (e.g. an antibody or antigen-binding fragment thereof that specifically binds to *Klebsiella pneumoniae* O2 antigen) produced using a method provided herein.

In one instance, provided herein is a pharmaceutical composition comprising an antigen binding provided herein (e.g. an antibody or antigen-binding fragment thereof that specifically binds to *Klebsiella pneumoniae* O2 antigen) and a pharmaceutically acceptable excipient. In one instance, the pharmaceutically acceptable excipient is a preservative, stabilizer, or antioxidant. In one instance, the pharmaceutical composition is for use as a medicament.

In one instance, the antigen binding protein provided herein or the pharmaceutical composition provided herein (e.g. an antibody or antigen-binding fragment thereof that specifically binds to *Klebsiella pneumoniae* O2 antigen) further comprises a labeling group or an effector group. In one instance, the labeling group is selected from the group consisting of: isotopic labels, magnetic labels, redox active moieties, optical dyes, biotinylated groups, fluorescent moieties such as biotin signaling peptides, Green Fluorescent Proteins (GFPs), blue fluorescent proteins (BFPs), cyan fluorescent proteins (CFPs), yellow fluorescent proteins (YFPs), polypeptide epitopes recognized by a secondary reporter such as histidine peptide (his), hemagglutinin (HA), gold binding peptide, and Flag. In one instance, the effector group is selected from the group consisting of a radioisotope, radionuclide, a toxin, a therapeutic and a chemotherapeutic agent.

In one instance, provided herein is the use of an antigen binding protein or pharmaceutical composition provided herein (e.g. an antibody or antigen-binding fragment thereof that specifically binds to *Klebsiella pneumoniae* O2 antigen) for treating a condition associated with a *Klebsiella* infection.

In one instance, provided herein is a method for treating, preventing, or ameliorating a condition associated with a *Klebsiella* infection in a subject in need thereof comprising administering to the subject an effective amount of an antigen binding protein provided herein or a pharmaceutical composition provided herein (e.g. an antibody or antigen-binding fragment thereof that specifically binds to *Klebsiella pneumoniae* O2 antigen).

In one instance, provided herein is a method for inhibiting the growth of *Klebsiella*, or reducing the number of *Klebsiella* in a subject infected with *Klebsiella* comprising administering to a subject in need thereof an antigen binding protein provided herein or a pharmaceutical composition provided herein.

In one instance, provided herein is a method for treating, preventing, or ameliorating a condition associated with a *Klebsiella* infection in a subject in need thereof comprising administering to the subject an effective amount of antigen binding protein that that specifically binds to *Klebsiella pneumoniae* O2 antigen.

In one instance, provided herein is a method for inhibiting the growth of *Klebsiella*, or reducing the number of *Klebsiella* in a subject infected with *Klebsiella* comprising administering to a subject an effective amount of an antigen binding protein that specifically binds to *Klebsiella pneumoniae* O2 antigen.

In one instance, the *Klebsiella* is antibiotic-resistant. In one instance, the *Klebsiella* is resistant to cephalosporin, quinolone, carbapnem, meroprem, fluoroquinolone, tetracycline, chloramphenicol, trimethoprim, sulfonamide, and/or colistin.

In one instance, provided herein is a method for sensitizing an antibiotic-resistant *Klebsiella* strain to antibiotics comprising contacting the antibody-resistant *Klebsiella* strain with an antigen binding protein that that specifically binds to *Klebsiella pneumoniae* O2 antigen.

In one instance, the method further comprises administering an antibiotic. In one instance, the antigen binding protein and the antibiotic provide a synergistic therapeutic effect.

In one instance, provided herein is a method of preventing or treating a condition associated with a *Klebsiella* infection in a subject infected with an antibiotic-resistant *Klebsiella* strain, comprising co-administering to a subject an antibiotic and an antigen binding protein that specifically binds to *Klebsiella pneumoniae* O2 antigen, wherein the co-administration provides a therapeutic effect greater than the sum of the individual effects of administration of equal molar quantities of the antigen binding protein (e.g. an antibody or antigen-binding fragment thereof) or the antibiotic. In one instance, the therapeutic effect results in greater percent survival than the additive percent survival of subjects to which only one of the antigen binding protein (e.g. an antibody or antigen-binding fragment thereof that specifically binds to *Klebsiella pneumoniae* O2 antigen) or the antibiotic was administered. In one instance, the antibiotic is meropenem, carbapenems, fluoroquinolone, tetracycline, chloramphenicol, trimethoprim, sulfonamide, and/or colistin. In one instance, the antigen binding protein also specifically binds *Klebsiella pneumoniae* O1 antigen.

In one instance, the antigen binding protein that specifically binds to *Klebsiella pneumoniae* O2 antigen is an antibody or antigen binding fragment thereof. In one instance, the antigen binding protein that specifically binds to *Klebsiella pneumoniae* O2 antigen is an antigen binding protein provided herein or a pharmaceutical composition provided herein.

In one instance, the *Klebsiella* is *K. pneumoniae, K. oxytoca, K. planticola,* K. ozaenae, K. rhinosclermoatis and/or *K. granulomatis*. In one instance, the *Klebsiella* is *K. pneumoniae*.

In one instance, the condition is selected from the group consisting of pneumonia, urinary tract infection, septicemia/sepsis, neonatal septicemia/sepsis, diarrhea, soft tissue infection, infection following an organ transplant, surgery infection, wound infection, lung infection, pyogenic liver abscesses (PLA), endophthalmitis, meningitis, necrotizing meningitis, ankylosing spondylitis, and spondyloarthropathies. In one instance, the condition is a nosocomial infection.

BRIEF DESCRIPTION OF THE DRAWINGS/FIGURES

FIGS. 1A-B show the expansion of the O2 LPS serotype in multi-drug resistant (MDR) strains of *Klebsiella pneu-*

*moniae*. FIG. 1A shows 0 serotype determining antigens for *Klebsiella pneumoniae* O1/O2 LPS and a western blot analysis of seven purified *Klebsiella* LPS serotypes probed with an isolated anti-O2 monoclonal antibody (mAb). FIG. 1B shows the prevalence of the O1 and O2 serotypes in recent *Klebsiella pneumoniae* clinical isolates.

FIGS. 2A-C show the characterization of anti-O2 LPS monoclonal antibodies (mAbs) by enzyme-linked immunosorbent assay (ELISA). FIG. 2A shows the binding of representative mAbs from each antibody class to O1 LPS. FIG. 2B shows the binding of representative mAbs from each class to O2 LPS. FIG. 2C shows the half maximal effective concentration ($EC_{50}$) of each mAb binding to LPS-O1 or LPS-O2.

FIGS. 3A-3O show the results of an octet binding assay with anti-O2 monoclonal antibodies (mAbs). FIGS. 3A-3F show a sensorgram trace of anti-O2 mAbs interacting with O1 LPS. FIGS. 3G-3L show a sensorgram trace of anti-O2 mAbs interacting with O2 LPS. FIGS. 3M-3O show affinity measurements of the Class III mAbs KPN42 and KPN179.

FIGS. 6A-6B show the protection conferred by Class III monoclonal antibodies (mAbs) in lethal pneumonia models. The % survival of mice challenged with *K. pneumoniae* Carbanpenemase (KPC) strain Kp961842_O2 is shown in the graph in FIG. 6A, and the % survival of mice challenged with KPC strain Kp977778_O2 is shown in the graph in FIG. 6B.

Figure 8A:
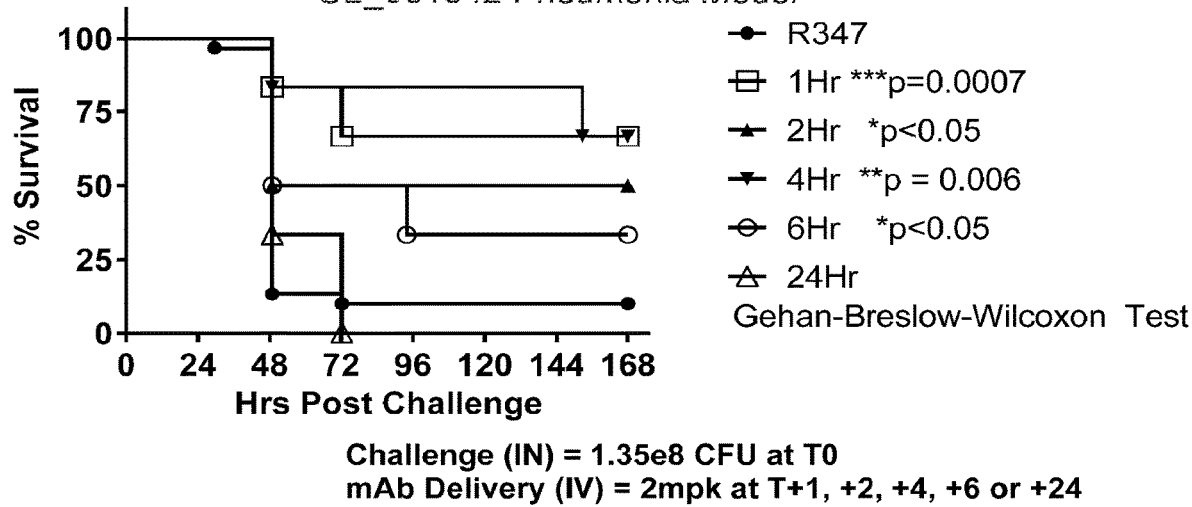
Figure 8B:
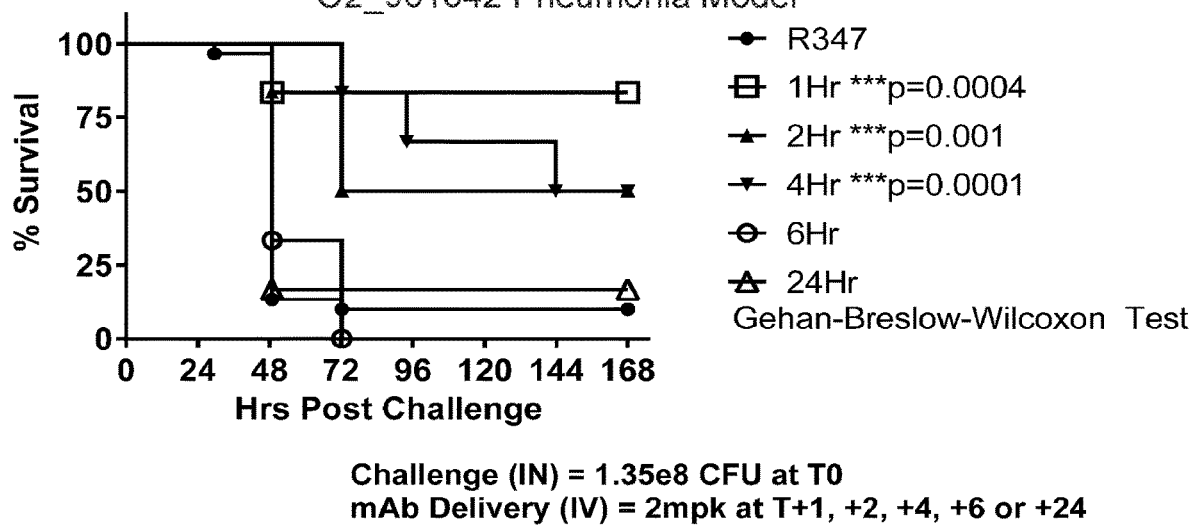

FIGS. 8A-8B show that select anti-O2 monoclonal antibodies (mAbs) protect mice for up to 6 hours post infection in conjunction with Meropenem. For mice treated with KPN42 in conjunction with meropenem, the % survival at various time points post challenge is shown in the graph in FIG. 8A. For mice treated with KPN179 in conjunction with meropenem, the % survival at various time points post challenge is shown in the graph in FIG. 8B.

FIGS. 9A-9C show the sequence optimization of KPN42 and KPN179. The binding of optimized versions of KPN42 and KPN179 to O2 LPS is shown in the graph in FIG. 9C.

Figure 10A:
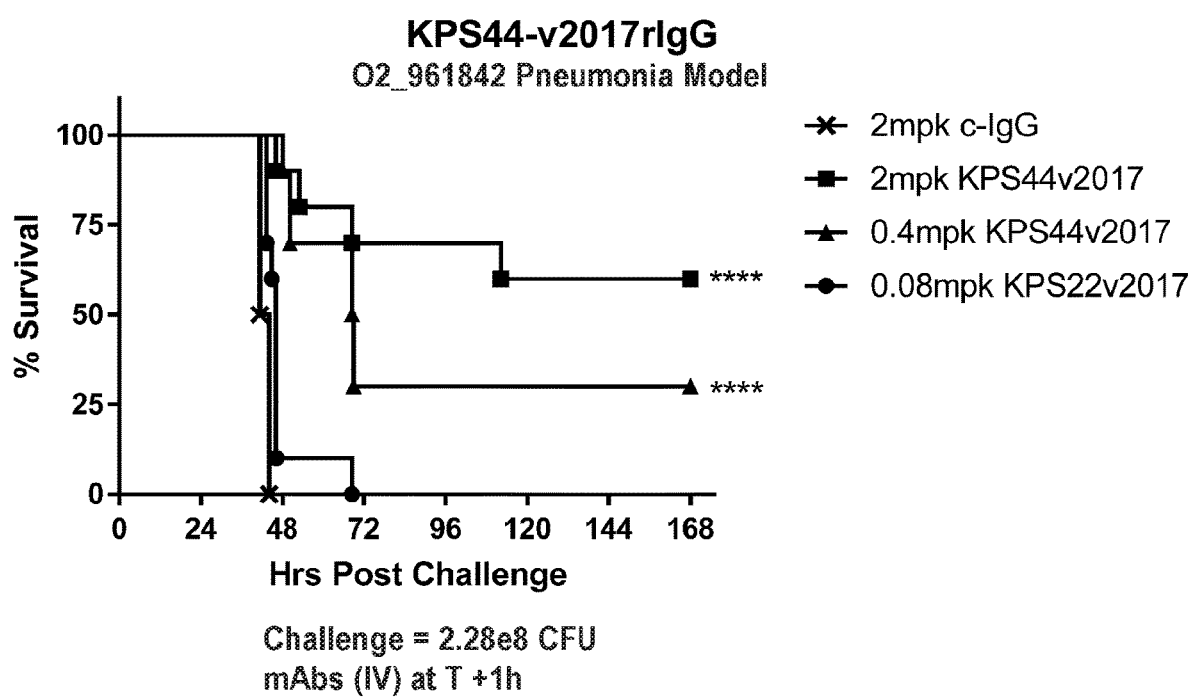
Figure 10B:
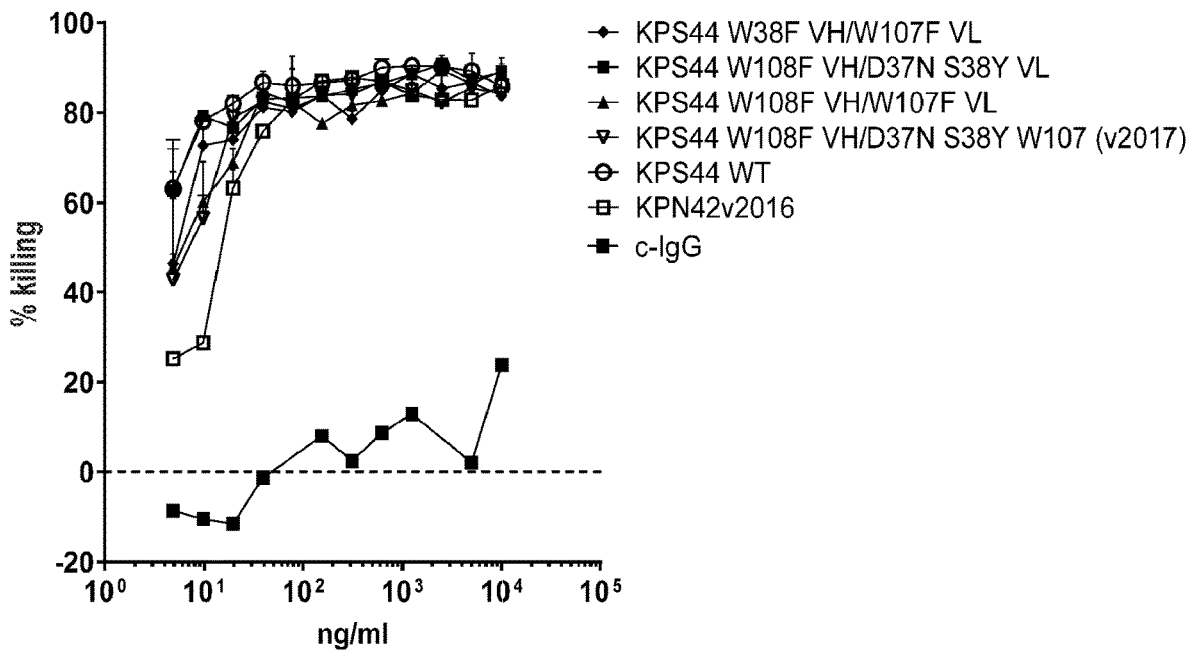
Figure 10C:
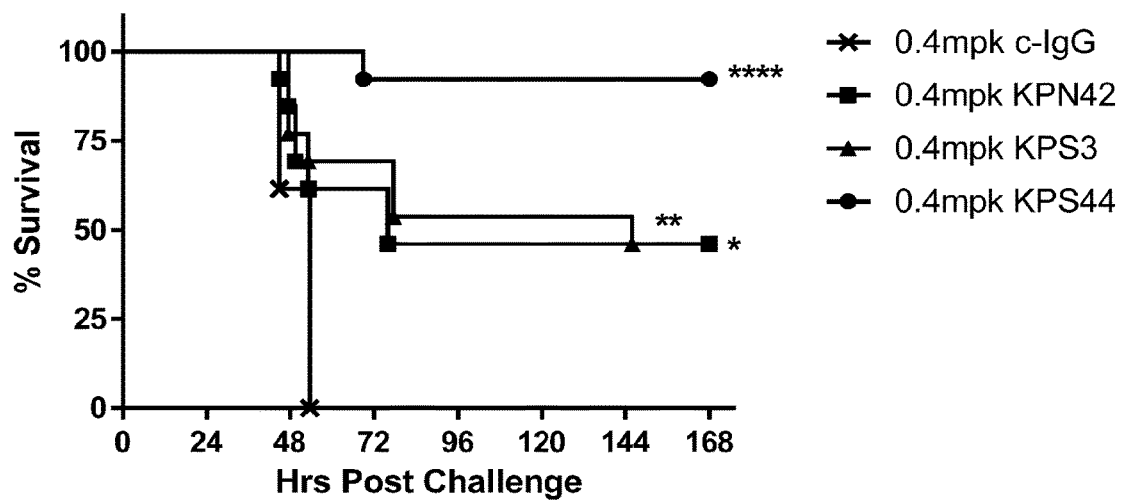

FIGS. 10A-C shows the protection conferred by Class III monoclonal antibodies KPS44 and KPS44v2017 in an opsonophagocytic killing (OPK) assay against an O2 strain of *K. pneumoniae* (FIG. 10B) and lethal pneumonia models against the KPS ST258 O2 strain 961842 (FIGS. 10A and 10C).

Figures 11A, 11B:
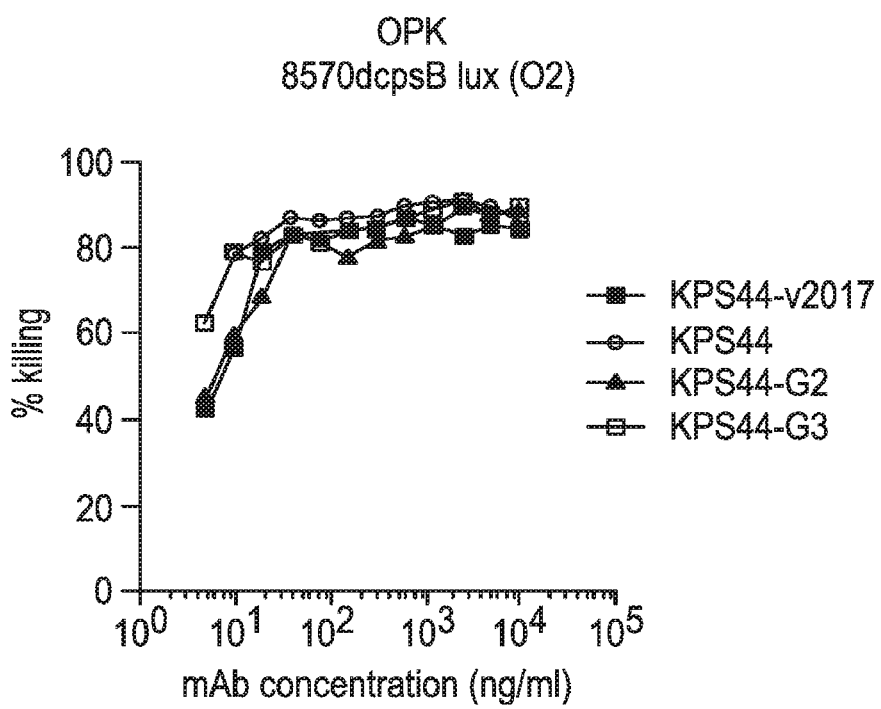

FIG. 11A shows the binding affinities from an octet binding assay with anti-O2 monoclonal antibodies (mAbs). FIG. 11B shows the protection conferred by Class III monoclonal antibodies KPS44, KPS44v2017, KPS44-G2, and KPS44-G3 in an opsonophagocytic killing (OPK) assay against an O2 strain of *K. pneumoniae*

DETAILED DESCRIPTION OF THE INVENTION

The data provided herein shows that a high prevalence of multidrug resistant *Klebsiella pneumoniae* strains are of the O2 serotype (see Example 1). Thus, there is a particularly great need to identify and develop antibodies that have protective effect against *Klebsiella* of the O2 serotype. Accordingly, the present disclosure provides isolated binding proteins, including antibodies or antigen binding fragments thereof, that bind to *Klebsiella pneumoniae* O2 antigen. Related polynucleotides, vectors, host cells, and pharmaceutical compositions comprising the *Klebsiella pneumoniae* O2 binding proteins, including antibodies or antigen binding fragments thereof, are also provided. Also provided are methods of making and using the O2 binding proteins, including antibodies or antigen binding fragments, disclosed herein. The present disclosure also provides methods of preventing and/or treating a condition associated with a *Klebsiella* infection (e.g., *K. pneumoniae* such as O2 serotype *K. pneumoniae*) by administering the O2 binding proteins, including antibodies or antigen binding fragments, disclosed herein.

In order that the present disclosure can be more readily understood, certain terms are first defined. Additional definitions are set forth throughout the detailed description.

I. Definitions

The terms "a," "an," and "the" include plural referents unless the context clearly dictates otherwise. For example, "an antigen binding protein" is understood to represent one or more antigen binding proteins. The terms "a" (or "an"), as well as the terms "one or more," and "at least one" can be used interchangeably herein. Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "comprise" is generally used in the sense of include, that is to say permitting the presence of one or more features or components. Wherever aspects are described herein with the language "comprising," otherwise analogous aspects described in terms of "consisting of," and/or "consisting essentially of" are also provided.

The term "about" as used in connection with a numerical value throughout the specification and the claims denotes an interval of accuracy, familiar and acceptable to a person skilled in the art. In general, such interval of accuracy is ±10%.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

The term "antigen binding protein" refers to a molecule comprised of one or more polypeptides that recognizes and specifically binds to a target, e.g., *K. pneumoniae* O2 antigen, such as an anti-O2 antibody or antigen-binding fragment thereof.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" or "antibody fragment thereof" refers to a portion of an intact antibody. An "antigen-binding fragment" or "antigen-binding fragment thereof" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, scFvs, and single chain antibodies.

It is possible to take monoclonal and other antibodies or fragments thereof and use techniques of recombinant DNA technology to produce other antibodies or chimeric molecules or fragments thereof that retain the specificity of the original antibody or fragment. Such techniques can involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A, or EP-A-239400, and a large body of subsequent literature. A hybridoma or other cell producing an antibody can be subject to genetic mutation or other changes, which may or may not alter the binding specificity of antibodies or fragments thereof produced.

Further techniques available in the art of antibody engineering have made it possible to isolate human and humanized antibodies or fragments thereof. For example, human hybridomas can be made as described by Kontermann and Sefan. Antibody Engineering, Springer Laboratory Manuals (2001). Phage display, another established technique for generating antigen binding proteins has been described in detail in many publications such as Kontermann and Sefan. Antibody Engineering, Springer Laboratory Manuals (2001) and WO92/01047. Transgenic mice in which the mouse antibody genes are inactivated and functionally replaced with human antibody genes while leaving intact other components of the mouse immune system, can be used for isolating human antibodies to human antigens.

Synthetic antibodies or fragments thereof can be created by expression from genes generated by means of oligonucleotides synthesized and assembled within suitable expression vectors, for example as described by Knappik et al. J. Mol. Biol. (2000) 296, 57-86 or Krebs et al. Journal of Immunological Methods 254 2001 67-84.

It has been shown that fragments of a whole antibody can perform the function of binding antigens. Examples of binding fragments are (i) the Fab fragment consisting of VL, VH, CL, and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989), McCafferty et al (1990) Nature, 348, 552-554) which consists of a VH domain; (v) isolated CDR regions; (vi) F(ab')2 fragments, a bivalent fragment comprising two linked Fab fragments; and (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); Fv or scFv molecules may be stabilized by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

The phrase "effector function" refers to the activities of antibodies that result from the interactions of their Fc components with Fc receptors or components of complement. These activities include, for example, antibody-dependent cell-mediated cytotoxicity (ADCC), complement-dependent cytotoxicity (CDC), and antibody-dependent cell phagocytosis (ADCP). Thus an antigen binding protein (e.g., an antibody or antigen binding fragment thereof) with altered effector function refers to an antigen binding protein (e.g., an antibody or antigen binding fragment thereof) that contains an alteration in an Fc region (e.g., amino acid substitution, deletion, or addition or change in oligosaccharide) that changes the activity of at least one effector function (e.g., ADCC, CDC, and/or ADCP). An antigen binding protein (e.g., an antibody or antigen binding fragment thereof) with improved effector function refers to an antigen binding protein (e.g., an antibody or antigen binding fragment thereof) that contains an alteration in an Fc region (e.g., amino acid substitution, deletion, or addition or change in oligosaccharide) that increases the activity of at least one effector function (e.g., ADCC, CDC, and/or ADCP).

The term "specific" can be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the antigen binding protein carrying the antigen binding domain will be able to bind to the various antigens carrying the epitope.

By "specifically binds" it is generally meant that an antigen binding protein including an antibody or antigen binding fragment thereof binds to an epitope via its antigen binding domain, and that the binding entails some complementarity between the antigen binding domain and the epitope. According to this definition, an antibody is said to "specifically bind" to an epitope when it binds to that epitope via its antigen binding domain more readily than it would bind to a random, unrelated epitope. As used herein, an antigen binding protein that "specifically binds" to *Klebsiella pneumoniae* O2 antigen may or may not also bind to other *Klebsiella pneumoniae* O antigens, including, for example, *Klebsiella pneumoniae* O1 antigen. In some embodiments, the antigen binding proteins disclosed herein specifically bind both *Klebsiella pneumoniae* O2 antigen and *Klebsiella pneumoniae* O1 antigen, while in other embodiments the antigen binding proteins disclosed herein specifically bind *Klebsiella pneumoniae* O2 antigen but do not specifically bind *Klebsiella pneumoniae* O1 antigen.

"Affinity" is a measure of the intrinsic binding strength of a ligand binding reaction. For example, a measure of the strength of the antibody (Ab)-antigen (Ag) interaction is measured through the binding affinity, which may be quantified by the dissociation constant, $k_d$. The dissociation constant is the binding affinity constant and is given by:

$$K_d = \frac{[Ab][Ag]}{[AbAg \text{ complex}]}$$

Affinity may, for example, be measured using a BIAcore®, a KinExA affinity assay, flow cytometry, and/or radioimmunoassay.

"Potency" is a measure of pharmacological activity of a compound expressed in terms of the amount of the compound required to produce an effect of given intensity. It refers to the amount of the compound required to achieve a defined biological effect; the smaller the dose required, the more potent the drug. Potency of an antigen binding protein that binds O2 can, for example, be determined using an OPK assay, as described herein.

"Opsonophagocytic killing" or "OPK" refers to the death of a cell, e.g., a *Klebsiella*, that occurs as a result of phagocytosis by an immune cell. OPK activity is measured according to the bioluminescent assay used in Example 8. An antigen binding protein (e.g., an antibody or antigen-binding fragment thereof) can induce OPK where the percentage of killing is 40% or greater. An antigen binding protein (e.g., an antibody or antigen-binding fragment thereof) can strongly induce OPK where the percentage of killing is 80% or greater.

An antigen binding protein including an antibody or antigen binding fragment thereof is said to competitively inhibit binding of a reference antibody or antigen binding fragment thereof to a given epitope or "compete" with a reference antibody or antigen binding fragment if it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope or compete with a reference antibody or antigen binding fragment thereof by at least 90%, at least 80%, at least 70%, at least 60%, or at least 50%.

The term "compete" when used in the context of antigen binding proteins (e.g., neutralizing antigen binding proteins or neutralizing antibodies) means competition between antigen binding proteins as determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., an O2 polysaccharide or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 92:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein.

Competitive inhibition can be measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 91%, 92%, 93%, 94%, 95%, 96%, 97%, 98%, 99% or more.

Antigen binding proteins, antibodies or antigen binding fragments thereof disclosed herein can be described or specified in terms of the epitope(s) or portion(s) of an antigen, e.g., a target polypeptide that they recognize or specifically bind. For example, the portion of O2 that specifically interacts with the antigen binding domain of the antigen binding polypeptide or fragment thereof disclosed herein is an "epitope". Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. A conformational epitope can be composed of discontinuous sections of the antigen's amino acid sequence. A linear epitope is formed by a continuous sequence of amino acids from the antigen. Epitope determinants may include chemically active surface groupings of molecules such as amino acids, sugar side chains, phosphoryl or sulfonyl groups, and can have specific three dimensional structural characteristics, and/or specific charge characteristics. An epitope typically includes at least 3, 4, 5, 6, 3, 4, 5, 6, 7, 8, 9, 10, 11, 12, 13, 14, 15, 16, 17, 18, 19, 20, 25, 30, 35 amino acids in a unique spatial conformation. Epitopes can be determined using methods known in the art.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "polypeptide" refers to a molecule composed of monomers (amino acids) linearly linked by amide bonds (also known as peptide bonds). The term "polypeptide" refers to any chain or chains of two or more amino acids, and does not refer to a specific length of the product. As used herein the term "protein" is intended to encompass a molecule comprised of one or more polypeptides, which can in some instances be associated by bonds other than amide bonds. On the other hand, a protein can also be a single polypeptide chain. In this latter instance the single polypeptide chain can in some instances comprise two or more polypeptide subunits fused together to form a protein. The terms "polypeptide" and "protein" also refer to the products of post-expression modifications, including without limitation glycosylation, acetylation, phosphorylation, amidation, derivatization by known protecting/blocking groups, proteolytic cleavage, or modification by non-naturally occurring amino acids. A polypeptide or protein can be derived from a natural biological source or produced by recombinant technology, but is not necessarily translated from a designated nucleic acid sequence. It can be generated in any manner, including by chemical synthesis.

The term "isolated" refers to the state in which antigen binding proteins of the disclosure, or nucleic acid encoding such binding proteins, will generally be in accordance with the present disclosure. Isolated proteins and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Proteins and nucleic acid may be formulated with diluents or adjuvants and still for practical purposes be isolated—for example the proteins will normally be mixed with gelatin or other carriers if used to coat microtitre plates for use in immunoassays, or will be mixed with pharmaceutically acceptable carriers or diluents when used in diagnosis or therapy. Antigen binding proteins may be glycosylated, either naturally or by systems of heterologous eukaryotic cells (e.g. CHO or NS0 (ECACC 85110503) cells, or they may be (for example if produced by expression in a prokaryotic cell) unglycosylated.

A polypeptide, antigen binding protein, antibody, polynucleotide, vector, cell, or composition which is "isolated" is a polypeptide, antigen binding protein, antibody, polynucleotide, vector, cell, or composition which is in a form not found in nature. Isolated polypeptides, antigen binding proteins, antibodies, polynucleotides, vectors, cells, or compositions include those which have been purified to a degree that they are no longer in a form in which they are found in nature. In some embodiments, an antigen binding protein, antibody, polynucleotide, vector, cell, or composition which is isolated is substantially pure.

A "recombinant" polypeptide, protein or antibody refers to a polypeptide or protein or antibody produced via recombinant DNA technology. Recombinant polypeptides, proteins and antibodies expressed in host cells are considered isolated for the purpose of the present disclosure, as are native or recombinant polypeptides which have been separated, fractionated, or partially or substantially purified by any suitable technique.

Also included in the present disclosure are fragments, variants, or derivatives of polypeptides, and any combination thereof. The term "fragment" when referring to polypeptides and proteins of the present disclosure include any polypeptides or proteins which retain at least some of the properties of the reference polypeptide or protein. Fragments of polypeptides include proteolytic fragments, as well as deletion fragments.

The term "variant" as used herein refers to an antibody or polypeptide sequence that differs from that of a parent antibody or polypeptide sequence by virtue of at least one amino acid modification. Variants of antibodies or polypeptides of the present disclosure include fragments, and also antibodies or polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "derivatives" as applied to antibodies or polypeptides refers to antibodies or polypeptides which have been altered so as to exhibit additional features not found on the native polypeptide or protein. An example of a "derivative" antibody is a fusion or a conjugate with a second polypeptide or another molecule (e.g., a polymer such as PEG, a chromophore, or a fluorophore) or atom (e.g., a radioisotope).

The terms "polynucleotide" or "nucleotide" as used herein are intended to encompass a singular nucleic acid as well as plural nucleic acids, and refers to an isolated nucleic acid molecule or construct, e.g., messenger RNA (mRNA), complementary DNA (cDNA), or plasmid DNA (pDNA). In certain aspects, a polynucleotide comprises a conventional phosphodiester bond or a non-conventional bond (e.g., an amide bond, such as found in peptide nucleic acids (PNA)).

The term "nucleic acid" refers to any one or more nucleic acid segments, e.g., DNA, cDNA, or RNA fragments, present in a polynucleotide. When applied to a nucleic acid or polynucleotide, the term "isolated" refers to a nucleic acid molecule, DNA or RNA, which has been removed from its native environment, for example, a recombinant polynucleotide encoding an antigen binding protein contained in a vector is considered isolated for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include such molecules produced synthetically. In addition, a polynucleotide or a nucleic acid can include regulatory elements such as promoters, enhancers, ribosome binding sites, or transcription termination signals.

As used herein, the term "host cell" refers to a cell or a population of cells harboring or capable of harboring a recombinant nucleic acid. Host cells can be a prokaryotic cells (e.g., *E. coli*), or alternatively, the host cells can be eukaryotic, for example, fungal cells (e.g., yeast cells such as *Saccharomyces* cerivisiae, *Pichia pastoris*, or *Schizosaccharomyces pombe*), and various animal cells, such as insect cells (e.g., Sf-9) or mammalian cells (e.g., HEK293F, CHO, COS-7, NIH-3T3, a NS0 murine myeloma cell, a PER.C6® human cell, a Chinese hamster ovary (CHO) cell or a hybridoma).

The term "amino acid substitution" refers to replacing an amino acid residue present in a parent sequence with another amino acid residue. An amino acid can be substituted in a parent sequence, for example, via chemical peptide synthesis or through recombinant methods known in the art. Accordingly, references to a "substitution at position X" or "substitution at position X" refer to the substitution of an amino acid present at position X with an alternative amino acid residue. In some embodiments, substitution patterns can described according to the schema AXY, wherein A is the single letter code corresponding to the amino acid naturally present at position X, and Y is the substituting amino acid residue. In other aspects, substitution patterns can described according to the schema XY, wherein Y is the single letter code corresponding to the amino acid residue substituting the amino acid naturally present at position X.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala, Ser) or no side chain (e.g., Gly).

Other substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term "amino acid insertion" refers to introducing a new amino acid residue between two amino acid residues present in the parent sequence. An amino acid can be inserted in a parent sequence, for example, via chemical peptide synthesis or through recombinant methods known in the art. Accordingly as used herein, the phrases "insertion between positions X and Y," "insertion between IMGT positions X and Y," or "insertion between Kabat positions X and Y," wherein X and Y correspond to amino acid positions (e.g., a cysteine amino acid insertion between positions 239 and 240), refers to the insertion of an amino acid between the X and Y positions, and also to the insertion in a nucleic acid sequence of a codon encoding an amino acid between the codons encoding the amino acids at positions X and Y. Insertion patterns can be described according to the schema AXins, wherein A is the single letter code corresponding to the amino acid being inserted, and X is the position preceding the insertion.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software programs. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at ebi.ac.uk/Tools/psa.

"Specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. The present disclosure is concerned with antigen-antibody type reactions.

The term "IgG" as used herein refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, and IgG3.

The term "antigen binding domain" describes the part of an antibody that comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). An antigen binding domain may comprise an antibody light chain variable region (VL) and an antibody heavy chain variable region (VH).

The term "antigen binding protein fragment" or "antibody fragment" refers to a portion of an intact antigen binding protein or antibody and refers to the antigenic determining variable regions of an intact antigen binding protein or antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides. The term "humanized antibody" refers to an antibody derived from a non-human (e.g., murine) immunoglobulin, which has been engineered to contain minimal non-human (e.g., murine) sequences.

The term "chimeric antibody" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The term "antibody binding site" refers to a region in the antigen (e.g., O2) comprising a continuous or discontinuous site (i.e., an epitope) to which a complementary antibody specifically binds. Thus, the antibody binding site can contain additional areas in the antigen which are beyond the epitope and which can determine properties such as binding affinity and/or stability, or affect properties such as antigen enzymatic activity or dimerization. Accordingly, even if two antibodies bind to the same epitope within an antigen, if the antibodies establish distinct intermolecular contacts with amino acids outside of the epitope, such antibodies are considered to bind to distinct antibody binding sites.

The IMGT numbering system is generally used when referring to a residue in the variable domain (approximately residues 1-107 of the light chain and residues 1-113 of the heavy chain) (e.g. Lefranc, M.-P. et al. Dev. Comp. Immunol. 27: 55-77 (2003)).

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The IMGT (Lefranc, M.-P. et al. Dev. Comp. Immunol. 27: 55-77 (2003)) classification of CDRs can also be used.

The term "EU index as in Kabat" refers to the numbering system of the human IgG1 EU antibody described in Kabat et al., Sequences of Immunological Interest, 5th Ed. Public Health Service, National Institutes of Health, Bethesda, Md. (1991). All amino acid positions referenced in the present application refer to IMGT unique numbering unless indicated otherwise. For example, C105 is defined according to IMGT unique numbering. For example, KPN42-C105 and KPN179-C105 correspond to Kabat position 89.

The terms "Fc domain," "Fc Region," and "IgG Fc domain" as used herein refer to the portion of an immunoglobulin, e.g., an IgG molecule, that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor. For example, an Fc domain contains the entire second constant domain CH2 (residues at EU positions 231-340 of human IgG1) and the third constant domain CH3 (residues at EU positions 341-447 of human IgG1).

Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358. Thus, a "wild type IgG Fc domain" or "WT IgG Fc domain" refers to any naturally occurring IgG Fc region (i.e., any allele). Myriad Fc mutants, Fc fragments, Fc variants, and Fc derivatives are described, e.g., in U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008; U.S. Patent publication 2004/0002587; and PCT Publication Nos. WO 99/058572, WO 2011/069164 and WO 2012/006635.

The sequences of the heavy chains of human IgG1, IgG2, IgG3 and IgG4 can be found in a number of sequence databases, for example, at the Uniprot database (uniprot.org) under accession numbers P01857 (IGHG1_HUMAN), P01859 (IGHG2_HUMAN), P01860 (IGHG3_HUMAN), and P01861 (IGHG1_HUMAN), respectively.

The terms "YTE" or "YTE mutant" refer to a set of mutations in an IgG1 Fc domain that results in an increase in the binding to human FcRn and improves the serum half-life of the antibody having the mutation. A YTE mutant comprises a combination of three "YTE mutations": M252Y, S254T, and T256E, wherein the numbering is according to the EU index as in Kabat, introduced into the heavy chain of an IgG. See U.S. Pat. No. 7,658,921, which is incorporated by reference herein. The YTE mutant has been shown to increase the serum half-life of antibodies compared to wild-type versions of the same antibody. See, e.g., Dall'Acqua et al., J. Biol. Chem. 281:23514-24 (2006) and U.S. Pat. No. 7,083,784, which are hereby incorporated by reference in their entireties. A "Y" mutant comprises only the M256Y mutations; similarly a "YT" mutation comprises only the M252Y and S254T; and a "YE" mutation comprises only the M252Y and T256E. It is specifically contemplated that other mutations may be present at EU positions 252 and/or 256. In certain aspects, the mutation at EU position 252 may be M252F, M252S, M252W or M252T and/or the mutation at EU position 256 may be T256S, T256R, T256Q or T256D.

The term "N3" or "N3 mutant" refers to a set of mutations in an IgG1 Fc domain that results in an increase in the binding to FcRn and improves the serum half-life of the antibody having the mutation. The N3 mutant comprises the sequence Cys-Ser-Trp-His-Leu-Cys at positions 432-437 (no insertion between positions 437 and 438). incorporated into a wild type IgG1 constant domain base structure. See WO2015175874, which is hereby incorporated by reference.

The term "naturally occurring O2" generally refers to a state in which the O2 polysaccharide or a fragment thereof can occur. Naturally occurring O2 means O2 polysaccharide which is naturally produced by a cell, without prior introduction of encoding nucleic acid using recombinant technology. Thus, naturally occurring O2 can be as produced naturally by for example *K. pneumoniae* and/or as isolated from different members of the *Klebsiella* genus.

The term "recombinant O2" refers to a state in which the O2 polysaccharide or fragments thereof may occur. Recombinant O2 means O2 polysaccharide or fragments thereof produced by recombinant DNA, e.g., in a heterologous host.

Recombinant proteins expressed in prokaryotic bacterial expression systems are not glycosylated while those expressed in eukaryotic systems such as mammalian or insect cells are glycosylated. Proteins expressed in insect cells however differ in glycosylation from proteins expressed in mammalian cells.

The terms "half-life" or "in vivo half-life" as used herein refer to the biological half-life of a particular type of antibody, antigen binding protein, or polypeptide of the present disclosure in the circulation of a given animal and is represented by a time required for half the quantity administered in the animal to be cleared from the circulation and/or other tissues in the animal.

The term "subject" as used herein refers to any animal (e.g., a mammal), including, but not limited to humans, non-human primates, rodents, sheep, dogs, cats, horses, cows, bears, chickens, amphibians, reptiles, and the like, which is to be the recipient of a particular treatment. The terms "subject" and "patient" as used herein refer to any subject, particularly a mammalian subject, for whom diagnosis, prognosis, or therapy of a condition associated with a *Klebsiella* infection. As used herein, phrases such as "a patient having a condition associated with a *Klebsiella* infection" includes subjects, such as mammalian subjects, that would benefit from the administration of a therapy, imaging or other diagnostic procedure, and/or preventive treatment for that condition associated with a *Klebsiella* infection.

"*Klebsiella*" refers to a genus of gram-negative, facultatively anaerobic, rod-shaped bacteria in the Enterobacteriaceae family. *Klebsiella* include, for example, *K. pneumoniae, K. oxytoca, K. planticola K. granulomatis*, K. ozaenae, and K. rhinoscleromatis.

Members of the *Klebsiella* genus typically express 2 types of antigens on their cell surface: an O antigen and a K antigen. The O antigen is a lipopolysaccharide, and the K antigen is a capsular polysaccharide. The structural variability of these antigens forms the basis for their classification in into *Klebsiella* "serotypes." Thus, the ability of an O2 binding protein (e.g., an antibody or an antigen binding fragment thereof) to bind to multiple serotypes refers to its ability to bind to *Klebsiella* with different O and/or K antigens. In some embodiments, provided herein, the *Klebsiella* is of the O2 serotype. In some embodiments, provided herein, the *Klebsiella* is of the O1 serotype.

The term "pharmaceutical composition" as used herein refers to a preparation which is in such form as to permit the biological activity of the active ingredient to be effective, and which contains no additional components which are unacceptably toxic to a subject to which the composition would be administered. Such composition can be sterile.

An "effective amount" of an antigen binding protein (including an antibody or antigen binding fragment thereof), as disclosed herein is an amount sufficient to carry out a specifically stated purpose. An "effective amount" can be determined empirically and in a routine manner, in relation to the stated purpose. The term "therapeutically effective amount" as used herein refers to an amount of a polypeptide, e.g., an antigen binding protein including an antibody, or other drug effective to "treat" a disease or condition in a subject or mammal and provides some improvement or benefit to a subject having a *Klebsiella*-mediated disease or condition. Thus, a "therapeutically effective" amount is an amount that provides some alleviation, mitigation, and/or decrease in at least one clinical symptom of the *Klebsiella*-mediated disease or condition. Clinical symptoms associated with the *Klebsiella*-mediated disease or condition that can be treated by the methods and systems of the disclosure are well known to those skilled in the art. Further, those skilled in the art will appreciate that the therapeutic effects need not be complete or curative, as long as some benefit is provided to the subject. In some embodiments, the term "therapeutically effective" refers to an amount of a therapeutic agent that is capable of reducing *Klebsiella* (e.g., *K. pneumoniae*) or *Klebsiella* (e.g., *K. pneumoniae*) activity in a patient in need thereof. The actual amount administered and rate and time-course of administration, will depend on the nature and severity of what is being treated. Prescription of treatment, e.g. decisions on dosage etc., is within the responsibility of general practitioners and other medical doctors. Appropriate doses of antibodies and antigen binding fragments thereof are well known in the art; see Ledermann J.A. et al. (1991) Int. J. Cancer 47: 659-664; Bagshawe K. D. et al. (1991) Antibody, Immunoconjugates and Radiopharmaceuticals 4: 915-922.

As used herein, a "sufficient amount" or "an amount sufficient to" achieve a particular result in a patient having a *Klebsiella*-mediated disease or condition refers to an amount of a therapeutic agent (e.g., an antigen binding protein including an antibody, as disclosed herein) that is effective to produce a desired effect, which is optionally a therapeutic effect (i.e., by administration of a therapeutically effective amount). In some embodiments, such particular result is a reduction in *Klebsiella* (e.g., *K. pneumoniae*) or *Klebsiella* (e.g., *K. pneumoniae*) activity in a patient in need thereof.

The term "label" when used herein refers to a detectable compound or composition which is conjugated directly or indirectly to a polypeptide, e.g., an antigen binding protein including an antibody, so as to generate a "labeled" polypeptide or antibody. The label can be detectable by itself (e.g., radioisotope labels or fluorescent labels) or, in the case of an enzymatic label, can catalyze chemical alteration of a substrate compound or composition which is detectable.

Terms such as "treating" or "treatment" or "to treat" or "alleviating" or "to alleviate" or "ameliorating" or "or ameliorate" refer to therapeutic measures that cure, slow down, lessen symptoms of, and/or halt progression of a diagnosed pathologic condition or disorder. Terms such as "preventing" refer to prophylactic or preventative measures that prevent and/or slow the development of a targeted pathologic condition or disorder. Thus, those in need of treatment include those already with the disease or condition. Those in need of prevention include those prone to have the disease or condition and those in whom the disease or condition is to be prevented. For example, the phrase "treating a patient having a *Klebsiella*-mediated disease or condition" refers to reducing the severity of the *Klebsiella*-mediated disease or condition, preferably, to an extent that the subject no longer suffers discomfort and/or altered function due to it (for example, a relative reduction in asthma exacerbations when compared to untreated patients). The phrase "preventing a *Klebsiella*-mediated disease or condition" refers to reducing the potential for a *Klebsiella*-mediated disease or condition and/or reducing the occurrence of the *Klebsiella*-mediated disease or condition.

As used herein, the term "a condition associated with a *Klebsiella* infection" refers to any pathology caused by (alone or in association with other mediators), exacerbated by, associated with, or prolonged by *Klebsiella* infection (e.g. infection with *K. pneumoniae, K. oxytoca, K. planticola*, K. ozaenae, K. rhinosclermoatis and/or *K. granulomatis*) in the subject having the disease or condition. Non-limiting examples of conditions associated with a *Klebsiella* infection include pneumonia, urinary tract infection, septicemia/sepsis, neonatal septicemia, diarrhea, soft tissue infections, infections following an organ transplant, surgery infection, wound infection, lung infection, pyogenic liver abscesses, endophthalmitis, meningitis, necrotizing meningitis, ankylosing spondylitis and spondyloarthropathies. In some embodiments, the *Klebsiella* infection is a nosocomial infection. In some embodiments, the *Klebsiella* infection is an opportunistic infection. In some embodiments, the *Klebsiella* infection follows an organ transplant. In some embodiments, the subject is exposed to a *Klebsiella* contaminated medical device, including, e.g., a ventilator, a catheter, or an intravenous catheter.

The structure for carrying a CDR or a set of CDRs will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. (US Department of Health and Human Services. 1987, and updates thereof, now available on the Internet (immuno.bme.nwu.edu or find "Kabat" using any search engine), herein incorporated by reference. CDRs can also be carried by other scaffolds such as fibronectin or cytochrome B.

A CDR amino acid sequence substantially as set out herein can be carried as a CDR in a human variable domain or a substantial portion thereof. The HCDR3 sequences substantially as set out herein represent embodiments of the present disclosure and each of these may be carried as a HCDR3 in a human heavy chain variable domain or a substantial portion thereof.

Variable domains employed in the disclosure can be obtained from any germ-line or rearranged human variable domain, or can be a synthetic variable domain based on consensus sequences of known human variable domains. A CDR sequence (e.g. CDR3) can be introduced into a repertoire of variable domains lacking a CDR (e.g. CDR3), using recombinant DNA technology.

For example, Marks et al. (Bio/Technology, 1992, 10:779-783; which is incorporated herein by reference) provide methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire can be combined with a CDR3 of a particular antibody. Using analogous techniques, the CDR3-derived sequences of the present disclosure can be shuffled with repertoires of VH or VL domains lacking a CDR3, and the shuffled complete VH or VL domains combined with a cognate VL or VH domain to provide antigen binding proteins. The repertoire can then be displayed in a suitable host system such as the phage display system of WO92/01047 or any of a subsequent large body of literature, including Kay, B. K., Winter, J., and McCafferty, J. (1996) Phage Display of Peptides and Proteins: A Laboratory Manual, San Diego: Academic Press, so that suitable antigen binding proteins may be selected. A repertoire can consist of from anything from 104 individual members upwards, for example from 106 to 108 or 1010 members. Other suitable host systems include yeast display, bacterial display, T7 display, ribosome display and so on. For a review of ribosome display for see Lowe D and Jermutus L, 2004, Curr. Pharm. Biotech, 517-27, also WO92/01047, which are herein incorporated by reference.

Analogous shuffling or combinatorial techniques are also disclosed by Stemmer (Nature, 1994, 370:389-391, which is herein incorporated by reference), who describes the technique in relation to a β-lactamase gene but observes that the approach may be used for the generation of antibodies.

A further alternative is to generate novel VH or VL regions carrying CDR-derived sequences of the disclosure using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. In some embodiments, one or two amino acid substitutions are made within a set of HCDRs and/or LCDRs.

Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

The methods and techniques of the present disclosure are generally performed according to conventional methods well known in the art and as described in various general and more specific references that are cited and discussed throughout the present specification unless otherwise indicated. See, e.g., Sambrook et al., *Molecular Cloning*: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), all of which are herein incorporated by reference.

The skilled person will be able to use such techniques described above to provide antigen binding proteins of the present disclosure using routine methodology in the art.

II. O2 Antigen Binding Molecules

The present disclosure provides O2 antigen binding molecules, e.g., antigen binding proteins, antibodies, and antigen binding fragments thereof, that specifically bind *K. pneumoniae* O2 antigen. Collectively, these agents are referred to herein as "O2 binding molecules" or "O2 binding agents." In some instances, an O2 binding agent (e.g., an antibody or antigen-binding fragment thereof) binds to *K. pneumoniae* O1 antigen in addition to binding to *K. pneumoniae* O2 antigen. In some instances, an O2 binding agent (e.g., an antibody or antigen-binding fragment thereof) binds to *K. pneumoniae* O1 antigen, but binds preferentially to *K. pneumoniae* O2 antigen. In some instances, an O2 binding agent (e.g., an antibody or antigen-binding fragment thereof) binds to *K. pneumoniae* O2 antigen but does not bind *K. pneumoniae* O1 antigen.

The O2 antigen of *Klebsiella* lipopolysaccharide (LPS) contains repeating D-galactan I (D-Gal I) units as major structural components. In the O2 antigen, the D-Gal I polymers are directly linked to the core oligosaccharide and are composed of repeat units of the structure→3)-β-D-Galf-(1→3)-α-D-Galp-(1→. In contrast, the O1 antigen of *Klebsiella* lipopolysaccharide (LPS) contains two structural domains composed of the repeat units D-galactan I and D-galactan II. For both the O1 antigen and the O2 antigen of *Klebsiella*, 0-antigen biosynthesis is performed by products of the wb (rfb) gene cluster, which is composed of six genes (wzm, wzt, glf, wbbM, wbbN, and wbbO) (Whitfield, C. et al. 1991. Expression of two structurally distinct D-Galactan O antigens in the lipopolysaccharide of *Klebsiella pneumoniae* serotype O2. J. Bacteriology. 1420-1431; Clarke, B. R. and Whitfield C. 1992. Molecular cloning of the rfb region of *Klebsiella pneumoniae* serotype O2:K20. J. Bacteriology. 174: 4614-4621). D-Gal I domain is also the major O-antigen component for *Klebsiella* O2 LPS. See FIG. 1A.

Several O2 sub-serotypes have been discussed in the literature. (Kelly, R. F., et al. 1996. Clonally diverse rfb gene clusters are involved in expression of a family of related D-Galactan O antigens in *Klebsiella* species. J. Bacteriology. 5205-5214.) Structural analyses showed that sub-serotype O2 (2a) expresses only the D-Gal I moiety, while other sub-serotypes, such as O2 (2a, 2c), O2 (2a, 2e), O2 (2a, 2e, 2h), etc. contain additional modifications on the D-Gal I backbone. Recently, →3)-β-D-Galf-(1→3)-[-α-D-Galp-(1→4)]-α-D-Galp-(1→trisaccharide repeating unit of sub-serotype O2 (2a, 2f, 2g) were defined as D-Galactan III domain that was expressed in a subset of highly resistant CRE strains (clonal complex 258). The Galactan I modifying locus (gml) gene was responsible for the Galactan III domain, which has an additional galactose attached to D-galactopyranose on D-Gal I repeating units. (Szijarto, V. et. al. *Int J Med Microbiol*. 306(2):89-98 (2016)).

As used herein, the phrase "O2 antigen" includes both gml+ and gml-O2 LPS and does not include the D-galactose side chain of D-galactan III (D-Gal III) units. Accordingly, an "O2 binding agent" (e.g., an antibody or antigen-binding fragment thereof) as defined herein does not bind specifically to D-Gal III. Thus, in some embodiments, an O2 binding agent (e.g., an antibody or antigen-binding fragment thereof) can bind to an O2 antigen regardless of D-Gal III expression (Table 8). In some embodiments, an O2 binding agent (e.g., an antibody or antigen-binding fragment thereof) can bind to an O2 antigen that contains both D-Gal I and D-Gal III, e.g., by binding to the common carbohydrate moieties expressed in all O2 strains.

In some embodiments, the disclosure provides an isolated antigen binding protein that is an antibody or polypeptide that specifically binds to *K. pneumoniae* O2 antigen. In some embodiments, the antigen binding protein is an antigen binding fragment of an antibody that specifically binds to *K. pneumoniae* O2 antigen.

In certain embodiments, the O2 binding molecules are antibodies or polypeptides. In some embodiments, the disclosure provides an isolated antigen binding protein that is a murine, non-human, humanized, chimeric, resurfaced, or human antigen binding protein that specifically binds to *K. pneumoniae* O2 antigen. In some embodiments, the O2 binding molecules are humanized antibodies or antigen binding fragment thereof. In some embodiments, the O2 binding molecule is a human antibody or antigen binding fragment thereof.

The disclosure provides an isolated antigen binding protein (including an antibody or antigen binding fragment thereof) that specifically binds to *K. pneumoniae* O2 antigen, wherein said antigen binding protein (e.g., an antibody or antigen binding fragment thereof): a) induces opsonophagocytic killing (OPK) of a *Klebsiella*, b) protects mice from a lethal *Klebsiella* challenge or c) induces OPK of a *Klebsiella* and protects mice from a lethal *Klebsiella* challenge. In certain embodiments, the isolated antigen binding protein (including an antibody or antigen binding fragment thereof) does not have LPS neutralization activity (e.g., as determined using the assay described in Example 7). In certain embodiments, the isolated antigen binding protein (including an antibody or antigen binding fragment thereof) has LPS neutralization activity against O2 LPS (e.g., as determined using the assay described in Example 7). In certain embodiments, the isolated antigen binding protein (including an antibody or antigen binding fragment thereof) has LPS neutralization activity against both O1 and O2 LPS (e.g., as determined using the assay described in Example 7). In certain embodiments, the isolated antigen binding protein (including an antibody or antigen binding fragment thereof) does not inhibit, reduce, or prevent NF-kB activation induced by LPS. In certain embodiments, the isolated antigen binding protein (including an antibody or antigen binding fragment thereof) inhibits, reduces, or prevents NF-kB activation induced by O2 LPS. In certain embodiments, the isolated antigen binding protein (including an antibody or antigen binding fragment thereof) inhibits, reduces, or prevents NF-kB activation induced by both O1 and O2 LPS.

The O2-binding agents include anti-O2 antigen antibodies KPN42, KPN42-FR-1-2-4-GL-VH/KPN42-FR-GL-C105A-VL (KPN42-v2016), KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, KPD1, and antigen-binding fragments thereof. The O2-binding agents also include O2-binding agents (e.g., anti-O2 antigen antibodies or antigen-binding fragments thereof) that specifically bind to the same K. pneumoniae O2 epitope as KPN42, KPN42-FR-1-2-4-GL-VH/KPN42-FR-GL-C105A-VL, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1. In some embodiments, the O2-binding agents disclosed herein include anti-O2 antigen antibodies or antigen binding fragments thereof that bind to the D-Galactan I domain of K. pneumoniae O2 antigen.

The O2-binding agents (e.g. anti-O2 antigen antibodies or antigen binding fragments thereof) also include O2-binding agents that competitively inhibit binding of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 to K. pneumoniae O2 antigen. In some embodiments, an anti-O2 antibody or antigen-binding fragment thereof competitively inhibits binding of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 to K. pneumoniae O2 antigen in a competition ELISA assay. In some embodiments, an anti-O2 antibody or antigen-binding fragment thereof competitively inhibits binding of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 to K. pneumoniae in a competition ELISA assay.

The O2-binding agents (e.g. anti-O2 antigen antibodies or antigen binding fragments thereof) also include O2-binding agents that bind Klebsiella of the O2 serotype, independent of gml gene expression. The effect of gml gene expression can be assessed, for example, using the methods provided in Szijártó et al., *International Journal of Medical Microbiology* 306: 89-98 (2016), which is herein incorporated by reference in its entirety. In some embodiments, the O2-binding agents disclosed herein include anti-O2 antigen antibodies or antigen binding fragments thereof that bind Klebsiella of the O2 serotype that do not express the gml gene (i.e., gml-Klebsiella). In some embodiments, the O2-binding agents disclosed herein include anti-O2 antigen antibodies or antigen binding fragments thereof that bind Klebsiella of the O2 serotype that express the gml gene (i.e., gml+ Klebsiella).

The O2-binding agents (e.g. anti-O2 antigen antibodies or antigen binding fragments thereof) also include O2-binding agents that comprise the heavy and light chain complementarity determining region (CDR) sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1. The CDR sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS30, and KPD1 are described in Tables 1 and 2 below.

TABLE 1

Variable heavy chain CDR amino acid sequences

| Antibody | VH-CDR1 | VH-CDR2 | VH-CDR3 |
| --- | --- | --- | --- |
| KPN42 | GFTFNDAW (SEQ ID NO: 1) | IKKKHEGVTT (SEQ ID NO: 2) | TTRIVTTNDY (SEQ ID NO: 3) |
| KPN42-FR-1-2-4-GL-VH/KPN42-FR-GL-C105A-VL (KPN42-v2016) | GFTFNDAW (SEQ ID NO: 10) | IKKKHEGVTT (SEQ ID NO: 11) | TTRIVTTNDY (SEQ ID NO: 12) |
| KPN42-FR-GL-VH/KPN42-FR-GL-C105A-VL | GFTFNDAW (SEQ ID NO: 19) | IKKKHEGVTT (SEQ ID NO: 20) | TTRIVTTNDY (SEQ ID NO: 21) |
| KPS3 | GFSFRDYG (SEQ ID NO: 28) | ISYDGRDQ (SEQ ID NO: 29) | GPFYNPSLYYPP (SEQ ID NO: 30) |
| KPN70 | GGSISTYY (SEQ ID NO: 37) | IHQSGTT (SEQ ID NO: 38) | ARESDDGYKWNYFDY (SEQ ID NO: 39) |
| KPN179 | GFTFNNAW (SEQ ID NO: 46) | IKRKADGETT (SEQ ID NO: 47) | TTRIVTTNDY (SEQ ID NO: 48) |
| KPN179-FR-1-2-4-GL-N35S-VH/KPN179-FR-GL-C105A-VL | GFTFSNAW (SEQ ID NO: 166) | IKRKADGETT (SEQ ID NO: 167) | TTRIVTTNDY (SEQ ID NO: 168) |
| KPN179-FR-GL N35S-VH/KPN179-FR-GL-C105A-VL | GFTFSNAW (SEQ ID NO: 169) | IKRKADGETT (SEQ ID NO: 170) | TTRIVTTNDY (SEQ ID NO: 171) |
| KPN44 | GGSTSSYY (SEQ ID NO: 55) | IHHGGTT (SEQ ID NO: 56) | ARESDDGYRWNYFDY (SEQ ID NO: 57) |
| KPN17 | GFTFSHFW (SEQ ID NO: 64) | IDGSVTNL (SEQ ID NO: 65) | ARDLVGIGTPAGYGMDV (SEQ ID NO: 66) |
| 6F6 | PIAYMG (SEQ ID NO: 73) | DILPNIGRTIYGEKFED (SEQ ID NO: 74) | RGTSGAMDY (SEQ ID NO: 75) |
| KPL26 | GFIFGSSW (SEQ ID NO: 82) | INPDGSAT (SEQ ID NO: 83) | TRNKAYNALDY (SEQ ID NO: 84) |
| KPS18 | GFTFKNAW (SEQ ID NO: 91) | VKNEVDGGTI (SEQ ID NO: 92) | RAFWSGFPAGY (SEQ ID NO: 93) |
| KPS24 | GFTFKNAW (SEQ ID NO: 100) | VKSEVDGGTT (SEQ ID NO: 101) | RAFWSDFQTGY (SEQ ID NO: 102) |
| KPS44 | GFTFKNAW (SEQ ID NO: 109) | VKSEVDGGTI (SEQ ID NO: 110) | RAFWSGFPTGY (SEQ ID NO: 111) |
| KPS44-v2017 | GFTFKNAW (SEQ ID NO: 109) | VKSEVDGGTI (SEQ ID NO: 110) | RAFFSGFPTGY (SEQ ID NO: 199) |
| KPS44-G1 | GFTFKNAW (SEQ ID NO: 109) | VKSEVDGGTI (SEQ ID NO: 110) | RAFWSGFPTGY (SEQ ID NO: 111) |
| KPS44-G2 | GFTFKNAW (SEQ ID NO: 109) | VKSEVDGGTI (SEQ ID NO: 110) | RAFFSGFPTGY (SEQ ID NO: 199) |
| KPS44-G3 | GFTFKNAW (SEQ ID NO: 109) | VKSEVDGGTI (SEQ ID NO: 110) | RAFFSGFPTGY (SEQ ID NO: 199) |
| KPS30 | GFSFSTSW (SEQ ID NO: 118) | IDPDGSTR (SEQ ID NO: 119) | ARDYAYNRFDY (SEQ ID NO: 120) |

TABLE 1-continued

Variable heavy chain CDR amino acid sequences

| Antibody | VH-CDR1 | VH-CDR2 | VH-CDR3 |
| --- | --- | --- | --- |
| KPD1 | GVSITSNTYW (SEQ ID NO: 127) | LSYSGDT (SEQ ID NO: 128) | ARDPDIIRNFQFDY (SEQ ID NO: 129) |
| KPL36 | GFTFISSW (SEQ ID NO: 172) | INPDGTET (SEQ ID NO: 173) | ARNKAYNAHDF (SEQ ID NOT 74) |
| KPS44-G4 | GFTFKNAW (SEQ ID NO: 109) | VKSEVDAGTI (SEQ ID NO: 215) | RAFYSGFPTGY (SEQ ID NO: 216) |
| KPS44-G6 | GFTFKNAW (SEQ ID NO: 109) | VKSEVDAGTI (SEQ ID NO: 215) | RAFYSGFPTGY (SEQ ID NO: 216) |
| KPS44-G8 | GFTFKNAW (SEQ ID NO: 109) | VKSEVDAGTI (SEQ ID NO: 215) | RAFYSGFPTGY (SEQ ID NO: 216) |
| KPS44-G10 | GFTFKNAW (SEQ ID NO: 109) | VKSEVDAGTI (SEQ ID NO: 215) | RAFYSGFPTGY (SEQ ID NO: 216) |
| KPS44-G11 | GFTFKNAW (SEQ ID NO: 109) | VKSEVDAGTI (SEQ ID NO: 215) | RAFYSGFPTGY (SEQ ID NO: 216) |
| KPS44-G14 | GFTFKNAW (SEQ ID NO: 109) | VKSEVDAGTI (SEQ ID NO: 215) | RAFYSGFPTGY (SEQ ID NO: 216) |

TABLE 2

Variable light chain CDR amino acid sequences

| Antibody | VL-CDR1 | VL-CDR2 | VL-CDR3 |
| --- | --- | --- | --- |
| KPN42 | SSDVGAYDY (SEQ ID NO: 4) | DVN (SEQ ID NO: 5) or IIYDVNERP (SEQ ID NO: 6) | CSYAGGDIFV (SEQ ID NO: 7) |
| KPN42-FR-1-2-4-GL-VH/KPN42-FR-GL-C105A-VL (KPN42-v2016) | SSDVGAYDY (SEQ ID NO: 13) | DVN (SEQ ID NO: 14) or MIYDVNKRP (SEQ ID NO: 15) | ASYAGGDIFV (SEQ ID NO: 16) |
| KPN42-FR-GL-VH/KPN42-FR-GL-C105A-VL | SSDVGAYDY (SEQ ID NO: 22) | DVN (SEQ ID NO: 23) or MIYDVNKRP (SEQ ID NO: 24) | ASYAGGDIFV (SEQ ID NO: 25) |
| KPS3 | QSISSQ (SEQ ID NO: 31) | DAS (SEQ ID NO: 32) or LIHDASNRD (SEQ ID NO: 33) | LQRNNWPPWT (SEQ ID NO: 34) |
| KPN70 | QIVTNY (SEQ ID NO: 40) | DMS (SEQ ID NO: 41) or LIFDMSIRA (SEQ ID NO: 42) | QHRSNWPLFT (SEQ ID NO: 43) |
| KPN179 | SSDVGYYDY (SEQ ID NO: 49) | DVN (SEQ ID NO: 50) or MIYDVNKRP (SEQ ID NO: 51) | CSYAGGDTFV (SEQ ID NO: 52) |
| KPN179-FR-1-2-4-GL-N35S-VH/KPN179-FR-GL-C105A-VL | SSDVGYYDY (SEQ ID NO: 175) | DVN (SEQ ID NO: 176) or MIYDVNKRP (SEQ ID NO: 177) | ASYAGGDTFV (SEQ ID NO: 178) |

TABLE 2-continued

Variable light chain CDR amino acid sequences

| Antibody | VL-CDR1 | VL-CDR2 | VL-CDR3 |
|---|---|---|---|
| KPN179-FR-GL N35S-VH/KPN179-FR-GL-C105A-VL | SSDVGYYDY (SEQ ID NO: 179) | DVN (SEQ ID NO: 180) or MIYDVNKRP (SEQ ID NO: 181) | ASYAGGDTFV (SEQ ID NO: 182) |
| KPN44 | QTITNY (SEQ ID NO: 58) | DMS (SEQ ID NO: 59) or LIFDMSKRA (SEQ ID NO: 60) | QHRSNWPLFT (SEQ ID NO: 61) |
| KPN17 | QGISTY (SEQ ID NO: 67) | AAS (SEQ ID NO: 68) or LIYAASTLQ (SEQ ID NO: 69) | QQLTSHLYT (SEQ ID NO: 70) |
| 6F6 | RSSQGLVHSTGNTFLH (SEQ ID NO: 76) | KVSNRFS (SEQ ID NO: 77) | SQSTHIPYT (SEQ ID NO: 78) |
| KPL26 | SSDVGGNNY (SEQ ID NO: 85) | EVS (SEQ ID NO: 86) or IIYEVSKRP (SEQ ID NO: 87) | SSFGGSKM (SEQ ID NO: 88) |
| KPS18 | RSNIGSDS (SEQ ID NO: 94) | DNN (SEQ ID NO: 95) or LMYDNNKRP (SEQ ID NO: 96) | ATWDSSLSAYV (SEQ ID NO: 97) |
| KPS24 | SSNIGSDS (SEQ ID NO: 103) | ENN (SEQ ID NO: 104) or LMYENNKRP (SEQ ID NO: 105) | AAWDSSLRAYV (SEQ ID NO: 106) |
| KPS44 | SSNIGSDS (SEQ ID NO: 112) | ENN (SEQ ID NO: 113) or LIYENNKRP (SEQ ID NO: 114) | ATWDSSLSAYV (SEQ ID NO: 115) |
| KPS44-v2017 | SSNIGSNY (SEQ ID NO: 200) | ENN (SEQ ID NO: 113) or LIYENNKRP (SEQ ID NO: 114) | ATFDSSLSAYV (SEQ ID NO: 201) |
| KPS44-G1 | SSNIGSNY (SEQ ID NO: 200) | ENN (SEQ ID NO: 113) or LIYENNKRP (SEQ ID NO: 114) | ATFDSSLSAYV (SEQ ID NO: 201) |
| KPS44-G2 | SSNIGSDS (SEQ ID NO: 112) | ENN (SEQ ID NO: 113) or LIYENNKRP (SEQ ID NO: 114) | ATFDSSLSAYV (SEQ ID NO: 201) |
| KPS44-G3 | SSNIGSNY (SEQ ID NO: 200) | ENN (SEQ ID NO: 113) or LIYENNKRP (SEQ ID NO: 114) | ATWDSSLSAYV (SEQ ID NO: 115) |
| KPS30 | SSDIGANNY (SEQ ID NO: 121) | EVN (SEQ ID NO: 122) or LLYEVNKRP (SEQ ID NO: 123) | CGYGGGRV (SEQ ID NO: 124) |
| KPD1 | QILYMSH (SEQ ID NO: 130) | GAS (SEQ ID NO: 131) or LIYGASIRA (SEQ ID NO: 132) | QQYGASPT (SEQ ID NO: 133) |
| KPL36 | SSDVGGNNF (SEQ ID NO: 183) | EVN (SEQ ID NO: 184) or IIYEVNKRP (SEQ ID NO: 185) | GAFGGSKM (SEQ ID NO: 186) |
| KPS44-G4 | SSNIGSDA (SEQ ID NO: 218) | ENN (SEQ ID NO: 113) or LIYENNKRP (SEQ ID NO: 114) | ATFESSLSAYV (SEQ ID NO: 230) |
| KPS44-G6 | SSNIGSES (SEQ ID NO: 228) | ENN (SEQ ID NO: 113) or LIYENNKRP (SEQ ID NO: 114) | ATFESSLSAYV (SEQ ID NO: 230) |
| KPS44-G8 | SSNIGSDS (SEQ ID NO: 238) | ENN (SEQ ID NO: 113) or LIYENNKRP (SEQ ID NO: 114) | ATFESSLSAYV (SEQ ID NO: 230) |

TABLE 2-continued

Variable light chain CDR amino acid sequences

| Antibody | VL-CDR1 | VL-CDR2 | VL-CDR3 |
|---|---|---|---|
| KPS44-G10 | SSNIGSDS (SEQ ID NO: 238) | ENN (SEQ ID NO: 113) or LIYENNKRP (SEQ ID NO: 114) | ATFESSLSAYV (SEQ ID NO: 230) |
| KPS44-G11 | SSNIGSDS (SEQ ID NO: 238) | ENN (SEQ ID NO: 113) or LIYENNKRP (SEQ ID NO: 114) | ATFESSLSAYV (SEQ ID NO: 230) |
| KPS44-G14 | SSNIGSDS (SEQ ID NO: 238) | ENN (SEQ ID NO: 113) or LIYENNKRP (SEQ ID NO: 114) | ATFESSLSAYV (SEQ ID NO: 230) |

Antigen binding proteins (including anti-O2 antigen antibodies or antigen binding fragments thereof) described herein can comprise one of the individual variable light chains or variable heavy chains described herein. Antigen binding proteins (including anti-O2 antigen antibodies or antigen binding fragments thereof) described herein can also comprise both a variable light chain and a variable heavy chain. The variable light chain and variable heavy chain sequences of anti-O2 antigen KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, and KPD1 antibodies are provided in Tables 3 and 4 below.

TABLE 3

Variable heavy chain amino acid sequences

| Antibody | VH Amino Acid Sequence (SEQ ID NO) |
|---|---|
| KPN42 | EVQLVESGGGLVKPGGSLRLSCAASGFTFNDAWMNWVRQAPGKGLEWVARIKKKHEGVTTDYPASVRGRFTISRDDSKNTVYLQMGRLRIEDTAIYYCTTRIVTTNDYWGQGTLVTVSS (SEQ ID NO: 8) |
| KPN42-v2016 | EVQLVESGGGLVKPGGSLRLSCAASGFTFNDAWMNWVRQAPGKGLEWVGRIKKKHEGVTTDYPASVRGRFTISRDDSKNTVYLQMGRLRIEDTAIYYCTTRIVTTNDYWGQGTLVTVSS (SEQ ID NO: 17) |
| KPN42-FR-GL-VH/KPN42-FR-GL-C105A-VL | EVQLVESGGGLVKPGGSLRLSCAASGFTFNDAWMNWVRQAPGKGLEWVGRIKKKHEGVTTDYAAPVKGRFTISRDDSKNTLYLQMNSLKTEDTAVYYCTTRIVTTNDYWGQGTLVTVSS (SEQ ID NO: 26) |
| KPS3 | QGQLVDSGGGVVQRGGSQRLSCAASGFSFRDYGMHWVRQAPGKGLEWVAFISYDGRDQYYADSVKGRFIISRDNSKNTLSLQMNSLRPEDTAVYYCGPFYNPSLYYPPWGHGLPVIVSS (SEQ ID NO: 35) |
| KPN70 | QVQLQESGPGLVKPSETLSLTCTVSGGSISTYYWNWIRQSPGKELEWIANIHQSGTTYYNPSLKSRVTMSVDTSKNQFSLKVISVTAADTAVYYCARESDDGYKWNYFDYWGQGTLVTVSS (SEQ ID NO: 44) |
| KPN179 | EVQVVESGGGLVKPGGSLRLSCAASGFTFNNAWMNWVRQAPGKGLEWVGRIKRKADGETTDYPASVKGRFTVSRDDSKNTIYLQMNSLKTEDTAIYYCTTRIVTTNDYWGQGTLVTVSS (SEQ ID NO: 53) |
| KPN179-FR-1-2-4-GL-N35S-VH/KPN179-FR-GL-C105A-VL | EVQLVESGGGLVKPGGSLRLSCAASGFTFSNAWMNWVRQAPGKGLEWVGRIKRKADGETTDYPASVKGRFTVSRDDSKNTIYLQMNSLKTEDTAIYYCTTRIVTTNDYWGQGTLVTVSS (SEQ ID NO: 187) |

TABLE 3-continued

Variable heavy chain amino acid sequences

| Antibody | VH Amino Acid Sequence (SEQ ID NO) |
|---|---|
| KPN179-FR-GL N35S-VH/KPN179-FR-GL-C105A-VL | EVQLVESGGGLVKPGGSLRLSCAASGFTFSNAWMNWVRQAPGKGLEWVGRIKRK ADGETTDYAAPVKGRFTISRDDSKNTLYLQMNSLKTEDTAVYYCTTRIVTTNDYW GQGTLVTVSS (SEQ ID NO: 188) |
| KPN44 | QVQLQESGPGLVKPSETLSLTCTVSGGSTSSYYWNWIRQAPGKPLQWIANIHHGGT TYYNPSLRSRVTMSLDTSNNQFSLKLTSVTAADTAVYFCARESDDGYRWNYFDY WGQGVLVTVSS (SEQ ID NO: 62) |
| KPN17 | EVQLVESGGGLVQPGGSLRLSCAASGFTFSHFWMHWVRQAPGQGLVWVARIDGS VTNLRYAGSVEGRFTISRDNAKNTLYLQMNSLRDEDTAVYYCARDLVGIGTPAGY GMDVWGQGTTVTVSS (SEQ ID NO: 71) |
| 6F6 | QVHLQQSGSELRSPGSSVKLSCKDFDSDVFPIAYMGWIRQQPGHGFDWIGDILPNI GRTIYGEKFEDKATLDADTVSNTAYLELSSLTSEDSAIYYCARRGTSGAMDYWGQ GTSVTVSS (SEQ ID NO: 80) |
| KPL26 | EVQLVESGGGLVQSGGSLRLSCETSGFIFGSSWMTWVRQAPGKGLEWVATINPDG SATSYEDSVRGRFAVSRDNAKNSVYLQMNSLRAEDTAVYFCTRNKAYNALDYW GQGTLVTVSS (SEQ ID NO: 89) |
| KPS18 | EVRLVESGGGLVKPGGSLRLSCAASGFTFKNAWMSWIRQAPGKGLEWVGRVKNE VDGGTIDYGVPVRGRFTISRDDSQGTLSLEMNSLREDDTGIYYCRAFWSGFPAGY WGQGTLVSVSS (SEQ ID NO: 98) |
| KPS24 | ELHLVESGGGLVKPGGSLRLSCAASGFTFKNAWMSWIRQAPGKGLEWVGRVKSE VDGGTTDYGVPVRGRFTISRDDSQSTLSLEMSSLQDDDTGVYYCRAFWSDFQTGY WGQGTLVTVSS (SEQ ID NO: 107) |
| KPS44 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFWSGFPTGY WGQGALVSVSS (SEQ ID NO: 116) |
| KPS44-v2017 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFFSGFPTGY WGQGALVSVSS (SEQ ID NO: 202) |
| KPS44-G1 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFWSGFPTGY WGQGALVSVSS (SEQ ID NO: 116) |
| KPS44-G2 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFFSGFPTGY WGQGALVSVSS (SEQ ID NO: 202) |
| KPS44-G3 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFFSGFPTGY WGQGALVSVSS (SEQ ID NO: 202) |
| KPS30 | EMQLVESGGGLVQPGVSLRLSCVDSGFSFSTSWLAWVRQAPGKGLEWLANIDPD GSTRNHVDSVRGRFTISRDNAKNSLYLQMNSLRAEDTAVYYCARDYAYNRFDYW GQGTMVTVSS (SEQ ID NO: 125) |
| KPD1 | QVQLQESDPRLVKPSETLSLTCSVSGVSITSNTYWWAWIRQPPGKKLEWIGSLSYS GDTYYNPSLTSRVTISRDIHQNQFFLELNSVTAADTAMYYCARDPDIIRNFQFDYW GRGTLVTVSS (SEQ ID NO: 134) |
| KPL36 | EVQLVESGGGVVQSGGSLRLSCETSGFTFISSWMSWVRQAPGTGLEWVATINPDG TETPYADSLKGRFTISRDNTKKSLYLQIHSLRADDTAVYFCARNKAYNAHDFWGQ GTLVMVSS (SEQ ID NO: 189) |
| KPS44-G4 | QVQLVESGGGLVKPGGSLRLSCAASGFTFKNAWMSWIRQAPGKGLEWVGRVKSE VDAGTIDYGVPVRGRFTISRDDSKNTLYLQMNSLKTEDTAVYYCRAFYSGFPTGY WGQGTLVTVSS (SEQ ID NO: 213) |
| KPS44-G6 | QVQLVESGGGLVKPGGSLRLSCAASGFTFKNAWMSWIRQAPGKGLEWVGRVKSE VDAGTIDYGVPVRGRFTISRDDSKNTLYLQMNSLKTEDTAVYYCRAFYSGFPTGY WGQGTLVTVSS (SEQ ID NO: 223) |
| KPS44-G8 | QVQLVESGGGLVKPGGSLRLSCAASGFTFKNAWMSWIRQAPGKGLEWVGRVKSE VDAGTIDYGVPVRGRFTISRDDSKNTLYLQMNSLKTEDTAVYYCRAFYSGFPTGY WGQGTLVTVSS (SEQ ID NO: 233) |

TABLE 3-continued

Variable heavy chain amino acid sequences

| Antibody | VH Amino Acid Sequence (SEQ ID NO) |
|---|---|
| KPS44-G10 | EVHLVESGGGLVKPGGSLRLSCAASGFTFKNAWMSWIRQAPGKGLEWVGRVKSE VDAGTIDYGVPVRGRFTISRDDSQGTLSLEMNSLKDDDTGVYYCRAFYSGFPTGY WGQGALVSVSS (SEQ ID NO: 243) |
| KPS44-G11 | EVHLVESGGGLVKPGGSLRLSCAASGFTFKNAWMSWIRQAPGKGLEWVGRVKSE VDAGTIDYGVPVRGRFTISRDDSQGTLSLEMNSLKDDDTGVYYCRAFYSGFPTGY WGQGALVSVSS (SEQ ID NO: 253) |
| KPS44-G14 | QVQLVESGGGLVKPGGSLRLSCAASGFTFKNAWMSWIRQAPGKGLEWVGRVKSE VDAGTIDYGVPVRGRFTISRDDSKNTLYLQMNSLKTEDTAVYYCRAFYSGFPTGY WGQGTLVTVSS (SEQ ID NO: 263) |
| KPS44-G8-HCvFW1 | QVQLVESGGGLVKPGGSLRLSCAASGFTFKNAWMSWIRQAPGKGLEWVGRVKSE VDAGTIDYGVPVRGRFTISRDDSQGTLYLQMNSLKTEDTGVYYCRAFYSGFPTGY WGQGTLVTVSS (SEQ ID NO: 273) |
| KPS44-G8-HCvFW2 | QVHLVESGGGLVKPGGSLRLSCAASGFTFKNAWMSWIRQAPGKGLEWVGRVKSE VDAGTIDYGVPVRGRFTISRDDSQGTLYLQMNSLKTEDTGVYYCRAFYSGFPTGY WGQGTLVTVSS (SEQ ID NO: 274) |

TABLE 4

Variable light chain amino acid sequences

| Antibody | VL Amino Acid Sequence (SEQ ID NO) |
|---|---|
| KPN42 | QSALTQPPSVSGSPGQSVTISCTGTSSDVGAYDYVSWYQQYAGKVPKHIIYDVNER PSGVPDRFSGSKSGNTAALTISGLQAEDEADYYCCSYAGGDIFVFGTGTQVTVL (SEQ ID NO: 9) |
| KPN42-v2016 | QSALTQPRSVSGSPGQSVTISCTGTSSDVGAYDYVSWYQQHPGKAPKLMIYDVNK RPSGVPDRFSGSKSGNTASLTISGLQAEDEADYYCASYAGGDIFVFGTGTKVTVL (SEQ ID NO: 18) |
| KPN42-FR-GL-VH/KPN42-FR-GL-C105A-VL | QSALTQPRSVSGSPGQSVTISCTGTSSDVGAYDYVSWYQQHPGKAPKLMIYDVNK RPSGVPDRFSGSKSGNTASLTISGLQAEDEADYYCASYAGGDIFVFGTGTKVTVL (SEQ ID NO: 27) |
| KPS3 | EVVLTQSPATLSLSPGERATLSCRASQSISSQLAWYQQKPGQAPRLLIHDASNRDTG VPDRFSGSGSGTDFTLTISSLEPEDFAMYYCLQRNNWPPWTFGQGTKVEIK (SEQ ID NO: 36) |
| KPN70 | EIVLTQSPASLSLSPGERATLSCRASQIVTNYLAWYQHKPGQAPRLLIFDMSIRAAGI PARFSGSGSGTDFTLTISSLEPEDFAVYYCQHRSNWPLFTFGPGTKVDIK (SEQ ID NO: 45) |
| KPN179 | QSALTQPPSVSGSPGQSVTISCTGTSSDVGYYDYVSWYQQHPGKAPKHMIYDVN KRPSGVPDRFSGSKSGNTASLTISGLQAEDEADYYCCSYAGGDTFVFGTGTKVTVL (SEQ ID NO: 54) |
| KPN179-FR-1-2-4-GL-N35S-VH/KPN179-FR-GL-C105A-VL | QSALTQPRSVSGSPGQSVTISCTGTSSDVGYYDYVSWYQQHPGKAPKLMIYDVNK RPSGVPDRFSGSKSGNTASLTISGLQAEDEADYYCASYAGGDTFVFGTGTKVTVL (SEQ ID NO: 190) |
| KPN179-FR-GL N35S-VH/KPN179-FR-GL-C105A-VL | QSALTQPRSVSGSPGQSVTISCTGTSSDVGYYDYVSWYQQHPGKAPKLMIYDVNK RPSGVPDRFSGSKSGNTASLTISGLQAEDEADYYCASYAGGDTFVFGTGTKVTVL (SEQ ID NO: 191) |

TABLE 4-continued

Variable light chain amino acid sequences

| Antibody | VL Amino Acid Sequence (SEQ ID NO) |
|---|---|
| KPN44 | EIVLTQSPASLSLSPGDRATLSCRASQTITNYLAWYQHKPGQAPRLLIFDMSKRATG IPARFSGSGSGTDFTLTISSLEPEDFAVYYCQHRSNWPLFTFGPGTNVDIK (SEQ ID NO: 63) |
| KPN17 | DIQLTQSPSFLSASVGDRVTITCRASQGISTYLAWYQQKPGKAPKLLIYAASTLQSG VPSRFSGSGSGTEFTLTINSLQSEDFATYYCQQLTSHLYTFGQGTKLEIK (SEQ ID NO: 72) |
| 6F6 | DVVMTQTPLFLPVSLGDQASISCRSSQGLVHSTGNTFLHWYLQKPGQSPKLLIYKV SNRFSGVPDRFSGSGSGTDFTLKISRVEAEDLGIYFCSQSTHIPYTFGGGTKLEIK (SEQ ID NO: 81) |
| KPL26 | QSALTQPPSASGSPGQSVTLSCTGTSSDVGGNNYVSWYQQHPGKAPKLIIYEVSKR PSGVPNRFSGSKSGNTASLTVSGLQAEDEADYYCSSFGGSKMFGGGTKLTVL (SEQ ID NO: 90) |
| KPS18 | QSVLTQPPSLSAAPGQTVTIACSGSRSNIGSDSVSWFQQFPGTAPRVLMYDNNKRP SGISDRFSGSKSGTSVTLDITGLQTGDEADYYCATWDSSLSAYVFGSGTKVTVL (SEQ ID NO: 99) |
| KPS24 | QSVLTQPPSVSAAPGQTVTIACSGSSSNIGSDSVSWFQQLPGTAPRVLMYENNKRPS GISDRFSGSKSGTSVTLGITGLQTGDEADYYCAAWDSSLRAYVFGSGTKVTVL (SEQ ID NO: 108) |
| KPS44 | QSVLTQPPSLSAAPGQTITIACSGTSSNIGSDSVSWFQQFPGTAPRVLIYENNKRPSGI SDRFSGSKSGTSVTLGITGLQTGDEADYYCATWDSSLSAYVFGSGTKVTVL (SEQ ID NO: 117) |
| KPS44-v2017 | QSVLTQPPSLSAAPGQTITIACSGTSSNIGSNYVSWFQQFPGTAPRVLIYENNKRPSG ISDRFSGSKSGTSVTLGITGLQTGDEADYYCATFDSSLSAYVFGSGTKVTVL (SEQ ID NO: 203) |
| KPS44-G1 | QSVLTQPPSLSAAPGQTITIACSGTSSNIGSNYVSWFQQFPGTAPRVLIYENNKRPSG ISDRFSGSKSGTSVTLGITGLQTGDEADYYCATFDSSLSAYVFGSGTKVTVL (SEQ ID NO: 203) |
| KPS44-G2 | QSVLTQPPSLSAAPGQTITIACSGTSSNIGSNYVSWFQQFPGTAPRVLIYENNKRPSGI SDRFSGSKSGTSVTLGITGLQTGDEADYYCATFDSSLSAYVFGSGTKVTVL (SEQ ID NO: 204) |
| KPS44-G3 | QSVLTQPPSLSAAPGQTITIACSGTSSNIGSNYVSWFQQFPGTAPRVLIYENNKRPSG ISDRFSGSKSGTSVTLGITGLQTGDEADYYCATWDSSLSAYVFGSGTKVTVL (SEQ ID NO: 205) |
| KPS30 | QSALTQPPSASGSPGQSVVISCTGTSSDIGANNYVSWYQQHPGKAPKLLLYEVNKR PSGVPDRFSASKSGNTASLTVSGLLAEDEADYYCCGYGGGRVFGGGTKLTVL (SEQ ID NO: 126) |
| KPD1 | EIVLTQSPGILSLSPGERATLSCRVSQILYMSHLAWYQHKPGQAPRLLIYGASIRAT GVPDRFSGSGSGTDFTLTISRLEPEDFAVYYCQQYGASPTFGQGTMVEIK (SEQ ID NO: 135) |
| KPL36 | QSALTQPPSASGSPGQSVTISCTGTSSDVGGNNFVSWYQQYPGKAPKLIIYEVNKRP SGVPDRFSGSKSGNTASLTVSGLQAEDEADYYCGAFGGSKMFGGGTKLTVL (SEQ ID NO: 192) |
| KPS44-G4 | QSVLTQPPSVSAAPGQKVTIACSGTSSNIGSDAVSWFQQLPGTAPKLLIYENNKRPS GISDRFSGSKSGTSVTLGITGLQTGDEADYYCATFESSLSAYVFGTGTKVTVL (SEQ ID NO: 217) |
| KPS44-G6 | QSVLTQPPSVSAAPGQKVTIACSGTSSNIGSESVSWFQQLPGTAPKLLIYENNKRPS GISDRFSGSKSGTSVTLGITGLQTGDEADYYCATFESSLSAYVFGTGTKVTVL (SEQ ID NO: 227) |
| KPS44-G8 | QSVLTQPPSVSAAPGQKVTIACSGTSSNIGSDSVSWFQQLPGTAPKLLIYENNKRPS GISDRFSGSKSGTSVTLGITGLQTGDEADYYCATFESSLSAYVFGTGTKVTVL (SEQ ID NO: 237) |
| KPS44-G10 | QSVLTQPPSLSAAPGQTITIACSGTSSNIGSDSVSWFQQFPGTAPRVLIYENNKRPSGI SDRFSGSKSGTSVTLGITGLQTGDEADYYCATFESSLSAYVFGSGTKVTVL (SEQ ID NO: 247) |
| KPS44-G11 | QSVLTQPPSVSAAPGQKVTIACSGTSSNIGSDSVSWFQQLPGTAPKLLIYENNKRPS GISDRFSGSKSGTSVTLGITGLQTGDEADYYCATFESSLSAYVFGTGTKVTVL (SEQ ID NO: 257) |

TABLE 4-continued

Variable light chain amino acid sequences

| Antibody | VL Amino Acid Sequence (SEQ ID NO) |
|---|---|
| KPS44-G14 | QSVLTQPPSLSAAPGQTITIACSGTSSNIGSDSVSWFQQFPGTAPRVLIYENNKRPSGI SDRFSGSKSGTSVTLGITGLQTGDEADYYCATFESSLSAYVFGSGTKVTVL (SEQ ID NO: 267) |

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a heavy chain variable region (VH) at least 95, 96, 97, 98, or 99% identical to SEQ ID NO: 8, 17, 26, 35, 44, 53, 187, 188, 62, 71, 80, 89, 98, 107, 116, 125, 134, or 189 and a light chain variable region (VL) at least 95, 96, 97, 98, or 99% identical to SEQ ID NOs: 9, 18, 27, 36, 45, 54, 190, 191, 63, 72, 81, 90, 99, 108, 117, 126, 135, or 192. In some embodiments, the isolated antigen binding protein (including, e.g., anti-O2 antigen antibodies or antigen-binding fragments thereof) that specifically binds to *K. pneumoniae* O2 antigen comprises a heavy chain variable region comprising the sequences of SEQ ID NO: 8, 17, 26, 35, 44, 53, 187, 188, 62, 71, 80, 89, 98, 107, 116, 125, 134, or 189 and a light chain variable region comprising the sequences of SEQ ID NOs: 9, 18, 27, 36, 45, 54, 190, 191, 63, 72, 81, 90, 99, 108, 117, 126, 135, or 192. In some embodiments, the isolated antigen binding protein (including, e.g., anti-O2 antigen antibodies or antigen-binding fragments thereof) having least 95, 96, 97, 98, or 99% sequence identity to SEQ ID NO: 8, 9, 17, 18, 26, 27, 35, 36, 44, 45, 53, 54, 187, 190, 188, 191, 62, 63, 71, 72, 80, 81, 89, 90, 98, 99, 107, 108, 116, 117, 125, 126, 134, 135, 189, or 192 differs from SEQ ID NO: 8, 9, 17, 18, 26, 27, 35, 36, 44, 45, 53, 54, 187, 190, 188, 191, 62, 63, 71, 72, 80, 81, 89, 90, 98, 99, 107, 108, 116, 117, 125, 126, 134, 135, 189, or 192 by conservative amino acid substitutions only.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 95% identical to SEQ ID NOs:8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135 or 189 and 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 95% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90,98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 95% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 95% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192 respectively, and wherein the antigen binding protein act synergistically with an antibiotic (e.g., meropenem, carbapenems, or colistin).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 96% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90,98 and 99, 107 and 108, 116 and 117, 125 and 126, 134 and 135, or 189 and 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 96% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90,98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 96% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90,98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 96% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90,98 and 99, 107 and 108, 116 and 117, 125 and 126, 134 and 135, or 189 and 192, respectively, and wherein the antigen binding protein act synergistically with an antibiotic (e.g., meropenem, carbapenems, or colistin).

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 97% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90,98 and 99, 107 and 108, 116 and 117, 125 and 126, 134 and 135, or 189 and 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 97% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90,98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 97% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 97% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, 189 and 192, respectively, and wherein the antigen binding protein act synergistically with an antibiotic (e.g., meropenem, carbapenems, or colistin).

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 98% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, 189 or 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 98% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 98% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 98% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90,98 and 99, 107 and 108, 116 and 117, 125 and 126, 134 and 135, or 189 and 192, respectively, and wherein the antigen binding protein act synergistically with an antibiotic (e.g., meropenem, carbapenems, or colistin).

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 99% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 99% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae O*2 antigen, wherein said antigen binding protein comprises a VH and VL at least 99% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 99% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein act synergistically with an antibiotic (e.g., meropenem, carbapenems, or colistin).

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the *K. pneumoniae* O2 antigen is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to *K. pneumoniae* O2 antigen is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2008, J. Mol. Bio., 376: 1182-200 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

According to the present disclosure, techniques can be adapted for the production of single-chain antibodies specific to *K. pneumoniae* O2 antigen (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for O2 antigen, or fragments thereof. Antibody fragments can be produced by techniques in the art including, but not limited to: (a) a F(ab')2 fragment produced by pepsin digestion of an antibody; (b) a Fab fragment generated by reducing the disulfide bridges of an F(ab')2 fragment, (c) a Fab fragment generated by the treatment of the antibody with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antigen binding proteins of the present disclosure (including, e.g., anti-O2 antigen antibodies or antigen-binding fragments thereof) can further comprise antibody constant regions or parts thereof. For example, a VL domain can be attached at its C-terminal end to antibody light chain constant domains including human Cx or Cv chains. Similarly, an antigen binding protein based on a VH domain can be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. For example, the immunoglobulin heavy chain can be derived from the antibody isotype sub-class, IgG1. Any synthetic or other constant region variant that has these properties and stabilizes variable regions is also contemplated for use in embodiments of the present disclosure. The antibody constant region can be an Fc region with a YTE mutation, such that the Fc region comprises the following amino acid substitutions: M252Y/S254T/T256E. This residue numbering is based on Kabat numbering. The YTE mutation in the Fc region increases serum persistence of the antigen-binding protein (see Dall'Acqua, W. F. et al. (2006) The Journal of Biological Chemistry, 281, 23514-23524).

In some embodiments herein, the antigen binding protein, e.g., antibody or antigen-binding fragment thereof, is modified to improve effector function, e.g., so as to enhance antigen-dependent cell-mediated cytotoxicity (ADCC) and/or complement dependent cytotoxicity (CDC). This can be achieved by making one or more amino acid substitutions or by introducing cysteine in the Fc region. Variants of the Fc region (e.g., amino acid substitutions and/or additions and/or deletions) that can enhance or diminish effector function of an antibody and/or alter the pharmacokinetic properties (e.g., half-life) of the antibody are disclosed, for example in U.S. Pat. No. 6,737,056B1, U.S. Patent Application Publication No. 2004/0132101A1, U.S. Pat. Nos. 6,194,551, and 5,624,821 and 5,648,260. One particular set of substitutions, the triple mutation L234F/L235E/P331S ("TM") causes a profound decrease in the binding activity of human IgG1 molecules to human C1q, CD64, CD32A and CD16. See, e.g., Oganesyan et al., Acta Crystallogr D Biol Crystallogr. 64:700-704 (2008). In other cases it can be that constant region modifications increase serum half-life. The serum half-life of proteins comprising Fc regions can be increased by increasing the binding affinity of the Fc region for FcRn.

When the antigen-binding protein is an antibody or an antigen-binding fragment thereof, it can further comprise a heavy chain immunoglobulin constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain. In some embodiments, the antigen-binding protein is an antibody or an antigen-binding fragment thereof that comprises an IgG1 heavy chain immunoglobulin constant domain. In some embodiments, the antigen-binding protein is an antibody or an antigen-binding fragment thereof that comprises an IgG1/IgG3 chimeric heavy chain immunoglobulin constant domain.

The antigen-binding protein of the disclosure (including, e.g., anti-O2 antigen antibodies or antigen-binding fragments thereof) can further comprise a light chain immunoglobulin constant domain selected from the group consisting of: (a) an Ig kappa constant domain; and (b) an Ig lambda constant domain.

The antigen-binding protein of the disclosure (including, e.g., anti-O2 antigen antibodies or antigen-binding fragments thereof) can further comprise a human IgG1 constant domain and a human lambda constant domain. The antigen-binding protein of the disclosure (including, e.g., anti-O2 antigen antibodies or antigen-binding fragments thereof) can further comprise a human IgG2 constant domain and a human lambda constant domain.

The antigen-binding protein of the disclosure can comprise an IgG1 Fc domain containing a mutation at positions 252, 254 and 256, wherein the position numbering is according to the EU index as in Kabat. For example, the IgG1 Fc domain can contain a mutation of M252Y, S254T, and T256E, wherein the position numbering is according to the EU index as in Kabat.

The present disclosure also relates to an isolated VH domain of the antigen-binding protein of the disclosure and/or an isolated VL domain of the antigen-binding protein of the disclosure.

Antigen-binding proteins (including antibodies or antigen binding fragments thereof) of the disclosure can be labeled with a detectable or functional label. Detectable labels include radiolabels such as 131I or 99Tc, which may be attached to antibodies of the present disclosure using conventional chemistry known in the art of antibody imaging. Labels also include enzyme labels such as horseradish peroxidase. Labels further include chemical moieties such as biotin which may be detected via binding to a specific cognate detectable moiety, e.g., labeled avidin. Non-limiting examples of other detectable or functional labels which may be attached to the antigen-binding proteins (including antibodies or antigen binding fragments thereof) of the disclosure include: isotopic labels, magnetic labels, redox active moieties, optical dyes, biotinylated groups, fluorescent moieties such as biotin signaling peptides, Green Fluorescent Proteins (GFPs), blue fluorescent proteins (BFPs), cyan fluorescent proteins (CFPs), and yellow fluorescent proteins (YFPs), and polypeptide epitopes recognized by a secondary reporter such as histidine peptide (his), hemagglutinin (HA), gold binding peptide, Flag; a radioisotope, radionuclide, a toxin, a therapeutic and a chemotherapeutic agent.

III. Pharmaceutical Compositions

The disclosure also provides a pharmaceutical composition comprising one or more of the O2-binding agents (including, e.g., anti-O2 antigen antibodies or antigen binding fragments) described herein. In certain embodiments, the pharmaceutical compositions further comprise a pharmaceutically acceptable vehicle or pharmaceutically acceptable excipient. In certain embodiments, these pharmaceutical compositions find use in treating, preventing or ameliorating a condition associated with a *Klebsiella* (e.g., *K. pneumoniae*) infection in human patients. In certain embodiments, these pharmaceutical compositions find use in inhibiting growth of *Klebsiella* (e.g., *K. pneumoniae*). In some embodiments, the *Klebsiella* (e.g., *K. pneumoniae*) is of the O2 serotype. In some embodiments, the *Klebsiella* (e.g., *K. pneumoniae*) is of the O1 serotype. In some embodiments, the pharmaceutical composition comprising an O2-binding agent include an anti-O2 antigen antibody or antigen binding fragments thereof that comprise the heavy and light chain complementarity determining region (CDR) sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS30, or KPD1. The CDR sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/

KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 antibody as described in Tables 1 and 2 or comprise the variable light chain and variable heavy chain sequences of an anti-O2 antigen KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 antibody as described in Tables 3 and 4.

In certain embodiments, formulations are prepared for storage and use by combining an antibody or anti-O2 binding agent described herein with a pharmaceutically acceptable vehicle (e.g., carrier, excipient) (see, e.g., Remington, The Science and Practice of Pharmacy 20th Edition Mack Publishing, 2000, herein incorporated by reference). In some embodiments, the formulation comprises a preservative.

The pharmaceutical compositions of the present disclosure can be administered in any number of ways for either local or systemic treatment.

In some embodiments, a pharmaceutical composition comprising one or more of the O2-binding agents (e.g., anti-O2 antigen antibodies or antigen binding fragments) described herein is used for treating pneumonia, urinary tract infection, septicemia/sepsis, neonatal septicemia/sepsis, diarrhea, soft tissue infection, infection following an organ transplant, surgery infection, wound infection, lung infection, pyogenic liver abscesses (PLA), endophthalmitis, meningitis, necrotizing meningitis, ankylosing spondylitis, or spondyloarthropathies. In some embodiments, a pharmaceutical composition comprising one or more of the O2-binding agents (e.g., anti-O2 antigen antibodies or antigen binding fragments) described herein is useful in nosocomial infections, opportunistic infections, infections following organ transplants, and other conditions associated with a Klebsiella infection (e.g. infection with K. pneumoniae, K. oxytoca, K. planticola, K. ozaenae, K. rhinosclermoatis, and/or K. granulomatis). In some embodiments, a pharmaceutical composition comprising one or more of the O2-binding agents (including, e.g., anti-O2 antigen antibodies or antigen binding fragments) described herein is useful in subjects exposed to a Klebsiella contaminated device, including, e.g., a ventilator, a catheter, or an intravenous catheter.

In some embodiments, the pharmaceutical composition comprises an amount of an O2-binding agent (e.g., an anti-O2 antigen antibody or antigen-binding fragment thereof) that is effective to inhibit growth of the Klebsiella in a subject. In some embodiments, the Klebsiella is K. pneumoniae, K. oxytoca, K. planticola, K. ozaenae, K. rhinosclermoatis, and/or K. granulomatis. In some embodiments, the Klebsiella is K. pneumoniae, K. oxytoca, and/or K. granulomatis. In some embodiments, the Klebsiella is K. pneumoniae. In some embodiments, the Klebsiella (e.g., K. pneumoniae) is of the O2 serotype. In some embodiments, the Klebsiella (e.g., K. pneumoniae) is of the O1 serotype.

In some embodiments, the methods of treating, preventing and/or ameliorating a condition associated with a Klebsiella infection comprises contacting a subject infected with a Klebsiella with a pharmaceutical composition comprising an O2-binding agent (e.g., an anti-O2 antigen antibody or antigen-binding fragment thereof) in vivo. In some embodiments, a pharmaceutical composition comprising an O2-binding agent is administered at the same time or shortly after a subject has been exposed to bacteria to prevent infection. In some embodiments, the pharmaceutical composition comprising an O2-binding agent is administered as a therapeutic after infection.

In certain embodiments, the method of treating, preventing, and/or ameliorating Klebsiella infections comprises administering to a subject a pharmaceutical composition comprising an O2-binding agent (e.g., an anti-O2 antigen antibody or antigen-binding fragment thereof). In certain embodiments, the subject is a human. In some embodiments, the pharmaceutical composition comprising an O2-binding agent (e.g., an anti-O2 antigen antibody or antigen-binding fragment thereof) is administered before the subject is infected with Klebsiella. In some embodiments, the pharmaceutical composition comprising an O2-binding agent (e.g., an anti-O2 antigen antibody or antigen-binding fragment thereof) is administered after the subject is infected with a Klebsiella.

In certain embodiments, the pharmaceutical composition comprising an O2-binding agent (e.g., an anti-O2 antigen antibody or antigen-binding fragment thereof) is administered to a subject on a ventilator. In certain embodiments, the subject has a catheter (e.g., a urinary catheter or an intravenous catheter). In certain embodiments, the subject is receiving antibiotics (e.g., meropenem, carbapenems, fluoroquinolone, tetracycline, chloramphenicol, trimethoprim, sulfonamide, and/or colistin).

In certain embodiments, a pharmaceutical composition comprising an O2-binding agent (e.g., an anti-O2 antigen antibody or antigen-binding fragment thereof) is for the treatment or prevention of a nosocomial Klebsiella infection. In certain embodiments, a pharmaceutical composition comprising an O2-binding agent (e.g., an anti-O2 antigen antibody or antigen-binding fragment thereof) is for the treatment or prevention of an opportunistic Klebsiella infection. In certain embodiments, a pharmaceutical composition comprising an O2-binding agent (e.g., an anti-O2 antigen antibody or antigen-binding fragment thereof) is for the treatment or prevention of a Klebsiella infection following an organ transplant.

In certain embodiments, a pharmaceutical composition comprising an O2-binding 9agent (e.g., an anti-O2 antigen antibody or antigen-binding fragment thereof) is for the treatment or prevention of a Klebsiella infection, wherein the Klebsiella is an extended spectrum beta-lactamase (ESBL) producing Klebsiella. In certain embodiments, a pharmaceutical composition comprising an O2-binding agent (e.g., an anti-O2 antigen antibody or antigen-binding fragment thereof) is for the treatment or prevention of a Klebsiella infection, wherein the Klebsiella is a non-extended spectrum beta-lactamase (ESBL) producing Klebsiella. In certain embodiments, a pharmaceutical composition comprising an O2-binding agent (e.g., an anti-O2 antigen antibody or antigen-binding fragment thereof) is for the treatment or prevention of a Klebsiella infection, wherein the Klebsiella is a Klebsiella pneumoniae carbapenemase (KPC) producing Klebsiella.

In certain embodiments, a pharmaceutical composition comprising an O2-binding agent (e.g., an anti-O2 antigen antibody or antigen-binding fragment thereof) is for the treatment or prevention of a cephalosporin resistant Klebsiella infection. In certain embodiments, a pharmaceutical composition comprising an O2-binding agent (e.g., an anti-O2 antibody or antigen-binding fragment thereof) is for the treatment or prevention of an aminoglycoside resistant *Klebsiella* infection. In certain embodiments, a pharmaceutical composition comprising an O2-binding agent (e.g., an anti-O2 antigen antibody or antigen-binding fragment thereof) is for the treatment or prevention of a quinolone resistant *Klebsiella* infection. In certain embodiments, a pharmaceutical composition comprising an O2-binding agent (e.g., an anti-O2 antigen antibody or antigen-binding fragment thereof) is for the treatment or prevention of a carbapenem resistant *Klebsiella* infection. In certain embodiments, a pharmaceutical composition comprising an O2-binding agent (e.g., an anti-O2 antigen antibody or antigen-binding fragment thereof) is for the treatment or prevention of a colistin resistant *Klebsiella* infection. In certain embodiments, a pharmaceutical composition comprising an O2-binding agent (e.g., an anti-O2 antigen antibody or antigen-binding fragment thereof) is for the treatment or prevention of a cephalosporin, aminoglycoside, quinolone, fluoroquinolone, tetracycline, chloramphenicol, trimethoprim, sulfonamide, carbapenem, and colistin resistant *Klebsiella* infection. In certain embodiments, a pharmaceutical composition comprising an O2-binding agent (e.g., an anti-O2 antigen antibody or antigen-binding fragment thereof) is for the treatment or prevention of an infection with a *Klebsiella* that is susceptible to antibiotics.

For the treatment, prevention and/or amelioration of a condition associated with a *Klebsiella* infection, the appropriate dosage of a pharmaceutical composition, antibody, or anti-O2 binding agent described herein depends on the type of condition, the severity and course of the condition, the responsiveness of the condition, whether the pharmaceutical composition, antibody, or anti-O2 binding agent is administered for therapeutic or preventative purposes, previous therapy, patient's clinical history, and so on all at the discretion of the treating physician. The pharmaceutical composition, antibody, or anti-O2 binding agent can be administered one time or over a series of treatments lasting from several days to several months, or until a cure is effected or a diminution of the condition is achieved. Optimal dosing schedules can be calculated from measurements of drug accumulation in the body of the patient and will vary depending on the relative potency of an individual antibody or agent. The administering physician can easily determine optimum dosages, dosing methodologies and repetition rates. The O2-binding agents and/or pharmaceutical compositions useful to treat, prevent, and/or amelioration of a condition associated with a *Klebsiella* infection include an anti-O2 antigen antibody or antigen binding fragments thereof that comprise the heavy and light chain complementarity determining region (CDR) sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS30, or KPD1. The CDR sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 antibody as described in Tables 1 and 2 or comprise the variable light chain and variable heavy chain sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 antibody as described in Tables 3 and 4.

IV. Methods of Use

The O2-binding agents (including anti-O2 antigen antibodies and antigen-binding fragments thereof) described herein are useful in a variety of applications including, but not limited to, pneumonia, urinary tract infection, septicemia/sepsis, neonatal septicemia/sepsis, diarrhea, soft tissue infection, infection following an organ transplant, surgery infection, wound infection, lung infection, pyogenic liver abscesses (PLA), endophthalmitis, meningitis, necrotizing meningitis, ankylosing spondylitis, and spondyloarthropathies. In some embodiments, the O2-binding agents (including anti-O2 antigen antibodies and antigen-binding fragments thereof) described herein are useful in nosocomial infections, opportunistic infections, infections following organ transplants, and other conditions associated with a *Klebsiella* infection (e.g. infection with *K. pneumoniae*, *K. oxytoca*, *K. planticola*, K. ozaenae, K. rhinosclermoatis, and/or *K. granulomatis*). In some embodiments, the O2-binding agents (including anti-O2 antigen antibodies and antigen-binding fragments thereof) described herein are useful in subjects exposed to a *Klebsiella* contaminated device, including, e.g., a ventilator, a catheter, or an intravenous catheter.

In some embodiments, the disclosure provides methods of treating, preventing and/or ameliorating a condition associated with a *Klebsiella* infection comprising administering an effective amount of an O2-binding agent (e.g., an anti-O2 antigen antibody or antigen-binding fragment thereof) to a subject. In some embodiments, the amount is effective to inhibit growth of the *Klebsiella* in the subject. In some embodiments, the *Klebsiella* is *K. pneumoniae, K. oxytoca, K. planticola*, K. ozaenae, K. rhinosclermoatis, and/or *K. granulomatis*. In some embodiments, the *Klebsiella* is *K. pneumoniae, K. oxytoca*, and/or *K. granulomatis*. In some embodiments, the *Klebsiella* is *K. pneumoniae*. In some embodiments, the *Klebsiella* (e.g., *K. pneumoniae*) is of the O2 serotype. In some embodiments, the *Klebsiella* (e.g., *K. pneumoniae*) is of the O1 serotype. In some embodiments, the subject has been exposed to *Klebsiella*. In some embodiments, *Klebsiella* has been detected in the subject. In some embodiments, the subject is suspected of being infected with *Klebsiella*, e.g., based on symptoms.

In some embodiments, the disclosure further provides methods of inhibiting growth of *Klebsiella* comprising administering an O2-binding agent (e.g., an anti-O2 antigen antibody or antigen-binding fragment thereof) to a subject. In some embodiments, the *Klebsiella* is *K. pneumoniae, K. oxytoca, K. planticola*, K. ozaenae, K. rhinosclermoatis, and/or *K. granulomatis*. In some embodiments, the *Klebsiella* is *K. pneumoniae, K. oxytoca*, and/or *K. granulomatis*. In some embodiments, the *Klebsiella* is *K. pneumoniae*. In some embodiments, the *Klebsiella* (e.g., *K. pneumoniae*) is of the O2 serotype. In some embodiments, the *Klebsiella* (e.g., *K. pneumoniae*) is of the O1 serotype. In some embodiments, the subject has been exposed to *Klebsiella*. In some embodiments, *Klebsiella* has been detected in the subject. In some embodiments, the subject is suspected of being infected with a *Klebsiella*, e.g., based on symptoms.

In some embodiments, the methods of treating, preventing and/or ameliorating a condition associated with a *Klebsiella* infection comprises contacting a subject infected with a *Klebsiella* with the O2-binding agent (e.g., an anti-O2 antigen antibody or antigen-binding fragment thereof) in vivo. In certain embodiments, contacting a cell with an O2-binding agent is undertaken in an animal model. For example, O2-binding agents can be administered to murine *Klebsiella* infection models to reduce bacterial burden. In some embodiments, the O2-binding agent (e.g., an anti-O2 antigen antibody or antigen-binding fragment thereof) is administered before introduction of bacteria to the animal to prevent infections. In some embodiments, the O2-binding agent (e.g., an anti-O2 antigen antibody or antigen-binding fragment thereof) is administered at the same time or shortly after the animal has been exposed to bacteria to prevent infection. In some embodiments, the O2-binding agent (e.g., an anti-O2 antigen antibody or antigen-binding fragment thereof) is administered as a therapeutic after infection.

In certain embodiments, the method of treating, preventing, and/or ameliorating *Klebsiella* infections comprises administering to a subject an effective amount of an O2-binding agent (e.g., an anti-O2 antigen antibody or antigen-binding fragment thereof). In certain embodiments, the subject is a human. In some embodiments, the effective amount of an O2-binding agent (e.g., an anti-O2 antigen antibody or antigen-binding fragment thereof) is administered before the subject is infected with Klebsiella. In some embodiments, the effective amount of an O2-binding agent (e.g., an anti-O2 antigen antibody or antigen-binding fragment thereof) is administered after the subject is infected with a *Klebsiella*.

In certain embodiments, the subject is on a ventilator. In certain embodiments, the subject has a catheter (e.g., a urinary catheter or an intravenous catheter). In certain embodiments, the subject is receiving antibiotics (e.g., meropenem, carbapenems, or colistin).

In certain embodiments, the *Klebsiella* infection is a nosocomial infection. In certain embodiments, the *Klebsiella* infection is an opportunistic infection. In certain embodiments, the *Klebsiella* infection follows an organ transplant.

In certain embodiments, the *Klebsiella* is an extended spectrum beta-lactamase (ESBL) producing *Klebsiella*. In certain embodiments, the *Klebsiella* is a non-ESBL producing *Klebsiella*. In certain embodiments, the *Klebsiella* is a *Klebsiella pneumoniae* carbapenemase (KPC) producing *Klebsiella*.

In certain embodiments, the *Klebsiella* is cephalosporin resistant. In certain embodiments, the *Klebsiella* is aminoglycoside resistant. In certain embodiments, the *Klebsiella* is quinolone resistant. In certain embodiments, the *Klebsiella* is carbapenem resistant. In certain embodiments, the *Klebsiella* is cephalosporin, aminoglycoside, quinolone, and carbapenem resistant. In certain embodiments, the *Klebsiella* is cephalosporin, aminoglycoside, and quinolone resistant. In certain embodiments, the *Klebsiella* is susceptible to antibiotics.

In certain embodiments, the method of treating, preventing, and/or ameliorating *Klebsiella* infections comprises administering to a subject an effective amount of an O2-binding agent (e.g., an anti-O2 antigen antibody or antigen-binding fragment thereof) and an antibiotic. The O2-binding agent (e.g., an anti-O2 antigen antibody or antigen-binding fragment thereof) and the antibiotic can be administered simultaneously or sequentially. The O2-binding agent (e.g., an anti-O2 antigen antibody or antigen-binding fragment thereof) and the antibiotic can be administered in the same pharmaceutical composition. The O2-binding agent (e.g., an anti-O2 antigen antibody or antigen-binding fragment thereof) and the antibiotic can be administered in separate pharmaceutical compositions simultaneously or sequentially. In certain embodiments, the antibiotic is an antibiotic suitable to treat a *Klebsiella* infection. In certain embodiments, the antibiotic is meropenem. In certain embodiments, the antibiotic is a carbapanem or colistin. In certain embodiments, the antibiotic is a cephalosporin, aminoglycoside, quinolone, fluoroquinolone, tetracycline, chloramphenicol, trimethoprim, sulfonamide, carbapenem, and/or colistin.

The present disclosure also provides methods of detecting O2 lipopolysaccharide or *Klebsiella* containing O2 antigen. In some embodiments, a method of detecting O2 or *Klebsiella* containing O2 antigen comprises contacting a sample with an O2 binding agent (e.g., an anti-O2 antigen antibody or antigen-binding fragment thereof) provided herein and assaying for binding of the binding agent (e.g., an antibody or antigen-binding fragment thereof) to the sample. Methods of assessing binding are well known in the art. In some embodiments, the methods comprise detecting O1 lipopolysaccharide or *Klebsiella* containing O1 antigen and O2 lipopolysaccharide or *Klebsiella* containing O2 antigen. In some embodiments, a method of detecting O1 and O2 or *Klebsiella* containing O1 or O2 antigen comprises contacting a sample with an O2 binding agent (e.g., an anti-O2 antigen antibody or antigen-binding fragment thereof) provided herein and assaying for binding of the binding agent (e.g., an antibody or antigen-binding fragment thereof) to the sample. Methods of assessing binding are well known in the art.

V. Kits

A kit comprising an isolated antigen-binding protein (e.g. an anti-O2 antigen antibody or antigen-binding fragment thereof) according to any aspect or embodiment of the present disclosure is also provided as an aspect of the present disclosure. In a kit, the antigen-binding protein, antibody, or antigen-binding fragment thereof can be labeled to allow its reactivity in a sample to be determined, e.g., as described further below. Components of a kit are generally sterile and in sealed vials or other containers. Kits can be employed in diagnostic analysis or other methods for which antibodies are useful. A kit can contain instructions for use of the components in a method, e.g., a method in accordance with the present disclosure. Ancillary materials to assist in or to enable performing such a method may be included within a kit of the disclosure. O2-binding agents suitable for use in a kit include an anti-O2 antigen antibodies or antigen binding fragments thereof that comprise the heavy and light chain complementarity determining region (CDR) sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1. The CDR sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS30, and KPD1 antibodies as described in Tables 1 and 2 or comprise the variable light chain and variable heavy chain sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, and KPD1 antibodies as described in Tables 3 and 4.

The reactivities of antibodies or antigen-binding fragments thereof in a sample can be determined by any appropriate means. Radioimmunoassay (RIA) is one possibility. Radioactive labeled antigen is mixed with unlabeled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay can also be used with non-radioactive antigen, using antigen or an analogue linked to a reporter molecule. The reporter molecule can be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules can be enzymes which catalyze reactions that develop or change colors or cause changes in electrical properties, for example. They can be molecularly excitable, such that electronic transitions between energy states result in characteristic spectral absorptions or emissions. They can include chemical entities used in conjunction with biosensors. Biotin/avidin or biotin/streptavidin and alkaline phosphatase detection systems can be employed.

The signals generated by individual antibody-reporter conjugates can be used to derive quantifiable absolute or relative data of the relevant antibody binding in samples (normal and test).

The present disclosure also provides the use of an antigen-binding protein as described above for measuring antigen levels in a competition assay, including methods of measuring the level of O2 antigen or *Klebsiella* containing O2 antigen in a sample by employing an antigen-binding protein provided by the present disclosure in a competition assay. In some embodiments, the physical separation of bound from unbound antigen is not required. In some embodiments, a reporter molecule is linked to the antigen-binding protein so that a physical or optical change occurs on binding. The reporter molecule can directly or indirectly generate detectable, and preferably measurable, signals. In some embodiments, the linkage of reporter molecules is direct or indirect, or covalent, e.g., via a peptide bond or non-covalent interaction. Linkage via a peptide bond can be as a result of recombinant expression of a gene fusion encoding antibody and reporter molecule.

The present disclosure also provides methods of measuring levels of O2 antigen directly, by employing an antigen-binding protein (e.g., an anti-O2 antigen antibody or antigen-binding fragment thereof) according to the disclosure. In some embodiments, these methods utilize a biosensor system. In some embodiments, the methods comprise detecting O1 and O2 antigen by employing an antigen-binding protein (e.g., an anti-O2 antigen antibody or antigen-binding fragment thereof) according to the disclosure. In some embodiments, these methods utilize a biosensor system.

VI. Polynucleotides and Host Cells

In further aspects, the present disclosure provides an isolated nucleic acid comprising a nucleic acid sequence encoding an antigen-binding protein (e.g. an anti-O2 antigen antibody or antigen-binding fragment thereof), VH domain and/or VL domain according to the present disclosure. In some aspects the present disclosure provides methods of making or preparing an antigen-binding protein (e.g. an anti-O2 antigen antibody or antigen-binding fragment thereof), a VH domain and/or a VL domain described herein, comprising expressing said nucleic acid under conditions to bring about production of said antigen-binding protein, VH domain and/or VL domain and, optionally, recovering the antigen-binding protein, VH domain and/or VL domain.

A nucleic acid provided by the present disclosure includes DNA and/or RNA. In one aspect, the nucleic acid is cDNA. In one aspect, the present disclosure provides a nucleic acid which codes for a CDR or set of CDRs or VH domain or VL domain or antibody antigen-binding site or antibody, e.g., scFv, IgG1, or IgG2, as described above (see, e.g., Tables 1-4).

One aspect of the present disclosure provides a nucleic acid, generally isolated, optionally a cDNA, encoding a VH CDR or VL CDR sequence described herein. In some embodiments, the VH CDR sequence is selected from the SEQ ID NOs provided in Table 1. In some embodiments, the VL CDR sequence is selected from the SEQ ID NOs provided in Table 2. A nucleic acid encoding the KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 set of HCDRs and nucleic acid encoding the KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 set of LCDRs are also provided, as are nucleic acids encoding individual CDRs, HCDRs, LCDRs and sets of CDRs, HCDRs, LCDRs as described in Tables 1 and 2. In some embodiments, the nucleic acids of the present disclosure encode a VH and/or VL domain of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 as described in Tables 3 and 4.

The invention further provides a polynucleotide comprising a sequence selected from those shown in Tables 5 and 6 below.

Table 5: Variable heavy chain polynucleotide sequences Antibody VH Pol nucleotide Sequence (SEQ ID NO)

TABLE 5

| Variable heavy chain polynucleotide sequences | |
|---|---|
| Antibody | VH Polynucleotide Sequence (SEQ ID NO) |
| KPN42 | GAGGTGCAGCTGGTGGAGTCTGGGGGAGGCTTGGTAAAGCCGGGGGG TCCCTTAGACTCTCCTGTGCAGCCTCTGGTTTCACTTTCAATGACGCCTGG ATGAACTGGGTCCGCCAGGCTCCAGGAAAGGGGCTGGAGTGGGTCGCCC GCATTAAAAAGAAACATGAAGGTGTTACGACAGACTACCCTGCATCCGT GAGAGGCAGATTCACCATCTCAAGAGATGATTCTAAAAACACAGTGTAT CTGCAGATGGGCAGACTGAGAATCGAGGACACTGCCATATATTACTGTA CCACAAGGATAGTGACTACCAATGACTACTGGGGCCAGGGAACCCTGGT CACCGTCTCCTCAG (SEQ ID NO: 136) |
| KPN42-v2016 | GAGGTGCAGCTGGTCGAATCTGGCGGGGACTGGTGAAACCTGGCGGCT CTCTGAGGCTGAGTTGCGCCGCTTCAGGCTTCACCTTCAACGACGCATGG ATGAATTGGGTGCGACAGGCACCTGGAAAGGGACTGGAGTGGGTCGGCC GGATCAAGAAAAAGCACGAAGGGGTGACCACAGATTACCCTGCTAGCGT CCGGGGAAGATTCACTATTAGCAGAGACGATTCCAAAAACACCGTGTAT CTGCAGATGGGCAGGCTGCGCATCGAGGACACCGCCATCTACTATTGTA CTACCCGCATCGTGACAACTAATGATTACTGGGGCAGGGAACCCTGGT GACAGTCAGCTCC (SEQ ID NO: 137) |
| KPN42-FR-GL-VH/KPN42-FR-GL-C105A-VL | GAGGTGCAGCTGGTCGAATCTGGCGGGGACTGGTGAAGCCTGGCGGCT CTCTGCGACTGAGTTGCGCCGCTTCAGGCTTCACCTTTAACGACGCTTGG ATGAATTGGGTGAGGCAGGCACCTGGAAAAGGACTGGAGTGGGTGGGA CGCATCAAGAAAAAGCACGAAGGGGTGACCACAGATTACGCAGCCCCT GTCAAAGGCCGGTTCACAATTAGCAGAGACGATTCCAAGAACACTCTGT ATCTGCAGATGAATAGCCTGAAAACCGAGGACACAGCCGTGTACTATTG TACTACCAGAATCGTCACAACTAACGATTACTGGGGGCAGGGAACTCTG GTGACCGTCAGCTCC (SEQ ID NO: 138) |
| KPS3 | CAGGGACAGTTGGTGGACTCTGGGGGAGGCGTGGTCCAGCGGGGGGG TCTCAGAGACTCTCCTGCGCAGCGTCTGGATTCAGCTTCAGAGACTATGG CATGCACTGGGTCCGCCAGGCTCCAGGCAAGGGGCTGGAGTGGGTGGCC TTTATATCATATGATGGGAGAGATCAATACTATGCAGACTCCGTGAAGG GCCGATTCATCATCTCCAGAGACAATTCCAAGAACACGCTGTCTCTGCAA ATGAACAGCCTGAGACCTGAGGACACGGCTGTCTATTACTGTGGGCCTTT TTATAACCCCAGTCTCTACTACCCCCCCTGGGGCCACGGACTTCCGGTCA TCGTCTCCTCAG (SEQ ID NO: 139) |
| KPN70 | CAGGTGCAGCTGCAGGAGTCGGGCCCGGGACTGGTGAAGCCTTCGGAGA CCCTGTCTCTCACCTGCACTGTCTCTGGTGGCTCCATCAGTACTTACTACT GGAACTGGATCCGGCAGTCCCCAGGGAAGGAATTGGAGTGGATTGCAAA TATACATCAAAGTGGGACCACCTACTACAACCCTCCCTCAAGAGTCGA GTCACCATGTCAGTAGACACGTCCAAGAACCAGTTCTCCCTGAAGGTGA TCTCTGTGACTGCTGCGGACACGGCCGTGTATTACTGTGCGAGAGAGTCC GACGATGGCTACAAGTGGAACTACTTTGACTACTGGGGCCAGGGAACCC TAGTCACCGTCTCCTCAG (SEQ ID NO: 140) |
| KPN179 | GAGGTGCAGGTGGTGGAGTCTGGGGGAGGCTTGGTAAAGCCGGGGGGG TCCCTTAGACTCTCCTGTGCAGCCTCTGGTTTCACTTTCAATAACGCCTGG ATGAACTGGGTCCGCCAGGCTCCAGGGAAGGGGCTGGAGTGGGTCGGCC GTATTAAAAGGAAAGCTGATGGTGAGACAACAGACTACCCTGCATCCGT GAAAGGCAGATTCACCGTCTCAAGAGATGATTCAAAAAACACGATATAT CTGCAGATGAACAGCCTGAAAACCGAGGACACAGCCATATATTACTGTA CCACAAGGATAGTGACTACCAATGACTACTGGGGCCAGGGAACCCTGGT CACCGTCTCCTCAG (SEQ ID NO: 141) |
| KPN179-FR-1-2-4-GL-N35S-VH/KPN179-FR-GL-C105A-VL | GAGGTGCAGCTGGTCGAATCCGGCGGGGACTGGTGAAACCTGGCGGCT CTCTGCGACTGAGTTGCGCCGCTTCAGGCTTCACCTTTAGCAACGCATGG ATGAATTGGGTGAGACAGGCACCTGGAAAGGGACTGGAGTGGGTCGGC CGGATCAAGAGAAAAGCTGACGGGGAAACCACAGATTACCCTGCATCTG TGAAGGGCAGGTTCACAGTCAGCCGCGACGATTCCAAAAACACTATCTA CCTGCAGATGAATAGTCTGAAGACCGAGGACACAGCCATCTACTATTGT ACTACCCGGATTGTGACAACTAACGATTACTGGGGGCAGGGAACTCTGG TGACCGTCAGCTCC (SEQ ID NO: 193) |

TABLE 5-continued

Variable heavy chain polynucleotide sequences

| Antibody | VH Polynucleotide Sequence (SEQ ID NO) |
| --- | --- |
| KPN179-FR-GL N35S-VH/KPN179-FR-GL-C105A-VL | GAGGTGCAGCTGGTCGAATCTGGCGGGGGACTGGTGAAACCTGGCGGCT CTCTGCGACTGAGTTGCGCCGCTTCAGGCTTCACCTTTAGCAACGCTTGG ATGAATTGGGTGAGACAGGCACCTGGAAAGGGACTGGAGTGGGTGGGA CGGATCAAGAGAAAAGCCGACGGGGAAACCACAGATTACGCAGCCCCT GTGAAGGGCAGGTTCACAATTAGCCGCGACGATTCCAAAAACACTCTGT ATCTGCAGATGAATAGCCTGAAGACCGAGGACACAGCCGTGTACTATTG TACTACCCGGATCGTCACAACTAACGATTACTGGGGGCAGGGAACTCTG GTGACCGTCAGCTCC (SEQ ID NO: 194) |
| KPN44 | CAGGTGCAGCTGCAGGAGTCGGGCCCGGGACTGGTGAAGCCTTCGGAGA CCCTGTCTCTCACCTGCACTGTGTCCGGTGGCTCCACCAGTAGTTACTAC TGGAACTGGATCCGGCAGGCCCCAGGGAAGCCATTGCAGTGGATTGCAA ATATACATCACGGTGGGACCACTTATTACAACCCCTCCCTCAGGAGTCGG GTCACCATGTCTCTGGACACTTCCAATAACCAGTTCTCCCTGAAGCTGAC CTCTGTGACTGCTGCGGACACGGCCGTCTATTTCTGTGCGAGAGAGTCCG ACGATGGCTACAGGTGGAACTACTTTGACTACTGGGGCCAGGGAGTCCT GGTCACCGTCTCCTCAG (SEQ ID NO: 142) |
| KPN17 | GAGGTGCAGCTGGTGGAGTCCGGGGGAGGCTTGGTTCAGCCTGGGGGGT CCCTGAGACTCTCCTGTGCAGCCTCTGGATTCACCTTCAGTCACTTCTGG ATGCACTGGGTCCGCCAAGCTCCAGGGCAGGGGCTGGTGTGGGTCGCAC GTATTGATGGTTCTGTGACAAACTTGAGGTACGCGGGCTCCGTGGAGGG GCGATTCACCATCTCCAGAGACAACGCCAAGAACACGCTGTATTTGCAA ATGAACAGTCTGAGAGACGAGGACACGGCTGTATATTACTGTGCAAGAG ATTTGGTAGGAATTGGCACGCCGGCCGGGTACGGTATGGACGTCTGGGG CCAAGGGACCACGGTCACCGTCTCCTCAG (SEQ ID NO: 143) |
| 6F6 | CAGGTTCACCTACAACAGTCTGGTTCTGAACTGAGGAGTCCTGGGTCTTC AGTAAAGCTTTCATGCAAGGATTTTGATTCAGACGTCTTCCCTATTGCTT ATATGGGTTGGATTAGGCAGCAGCCTGGGCATGGATTTGACTGGATTGG GGACATACTCCCAAATATTGGTAGAACAATCTATGGAGAGAAGTTTGAG GACAAAGCCACACTGGATGCAGACACAGTGTCCAACACAGCCTACTTGG AGCTCAGCAGTCTGACATCTGAGGACTCTGCTATCTACTATTGTCAAGG AGGGGGACGTCGGGGGCTATGGACTACTGGGGTCAAGGAACCTCAGTCA CCGTCTCCTCA (SEQ ID NO: 144) |
| KPL26 | GAGGTGCAGCTGGTGGAGTCTGGGGGAGGCTTGGTCCAGTCGGGGGGT CCCTGAGACTCTCCTGTGAAACCTCTGGATTCATTTTTGGTAGTTCTTGG ATGACCTGGGTCCGCCAGGCTCCAGGGAAAGGGCTGGAGTGGGTGGCCA CCATAAACCCTGATGGAAGTGCGACAAGCTATGAGGACTCTGTGAGGGG CCGATTCGCCGTCTCCAGAGACAACGCCAAGAACTCAGTGTATCTGCAA ATGAACAGCCTGAGAGCCGAGGACACGGCCGTGTACTTCTGTACAAGGA ATAAGGCATACAATGCCCTTGACTACTGGGGCCAGGGAACCCTGGTCAC CGTCTCCTCAG (SEQ ID NO: 145) |
| KPS18 | GAGGTTCGCCTGGTGGAGTCTGGGGGAGGCTTGGTAAAGCCTGGGGGGT CCCTAAGACTCTCCTGTGCAGCCTCAGGATTCACTTTCAAAAACGCCTGG ATGAGCTGGATCCGCCAGGCTCCAGGGAAGGGGCTGGAGTGGGTTGGCC GTGTTAAAAACGAAGTTGATGGGGGGACAATAGACTACGGTGTGCCCGT GAGAGGCAGATTCACCATCTCAAGAGACGATTCACAAGGCACGCTGTCT CTGGAGATGAACAGCCTGAGAGAGGATGACACAGGGATTTATTACTGTC GGGCTTTTTGGAGTGGTTTTCCTGCCGGATACTGGGGCCAGGGAACCCTG GTCAGCGTCTCCTCAG (SEQ ID NO: 146) |
| KPS24 | GAGCTGCACCTGGTGGAGTCTGGGGGAGGCTTGGTAAAGCCTGGGGGGT CCCTTAGACTCTCCTGTGCAGCCTCAGGATTCACTTTCAAAAACGCCTGG ATGAGCTGGATCCGCCAGGCTCCAGGGAAGGGGCTGGAGTGGGTTGGCC GTGTTAAAAAGCGAAGTTGATGGGGGGACAACAGACTACGGTGTGCCCGT GAGAGGCAGATTCACCATCTCAAGAGATGATTCACAAAGCACGCTGTCT CTGGAGATGAGCAGCCTGCAAGACGATGACACAGGCGTTTATTACTGTC GGGCTTTTTGGAGTGATTTTCAAACCGGCTACTGGGGCCAGGGAACCCT GGTCACCGTCTCCTCAG (SEQ ID NO: 147) |
| KPS44 | GAGGTGCACCTGGTGGAGTCTGGGGGAGGCTTGGTAAAGCCTGGGGGGT CCCTTAGACTCTCCTGTGCAGCCTCAGGATTCACTTTCAAAAACGCCTGG ATGAGCTGGATCCGCCAGGCTCCAGGGAAGGGGCTGGAGTGGGTTGGCC GTGTTAAAAAGCGAAGTTGATGGGGGGACAATAGACTACGGTGTGCCCGT GAGAGGCAGATTCACCATCTCAAGAGATGATTCACAAGGCACACTGTCT CTGGAGATGAACAGCCTGAAAGACGATGACACAGGCGTTTATTATTGTC GGGCTTTTTGGAGTGGTTTTCCTACCGGATACTGGGGCCAGGGAGCCCTG GTCAGCGTCTCCTCAG (SEQ ID NO: 148) |
| KPS44-v2017 | GAGGTGCACCTGGTCGAATCCGGCGGGGGACTGGTGAAACCAGGCGGGT CTCTGAGACTGAGTTGCGCCGCTTCAGGCTTCACCTTCAAGAACGCATGG ATGAGCTGGATTAGACAGGCACCTGGAAGGGACTGGAGTGGGTGGGC CGCGTCAAATCTGAAGTGGATGGAGGCACCATCGACTACGGGGTGCCTG |

TABLE 5-continued

Variable heavy chain polynucleotide sequences

| Antibody | VH Polynucleotide Sequence (SEQ ID NO) |
|---|---|
| | TCCGGGAAGATTCACCATTAGCCGAGACGATTCCCAGGGCACACTGTC<br>TCTGGAGATGAATAGTCTGAAGGACGATGACACTGGGGTGTACTATTGT<br>AGAGCTTTCTTTTCAGGATTTCCTACCGGCTATTGGGGACAGGGGCCCT<br>GGTGAGCGTCAGCTCC (SEQ ID NO: 206) |
| KPS44-G1 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGGGGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTGGAGTGGCTTCCCGACTGGGTACTGGGGGCAAGGTGCTC<br>TTGTCTCAGTGTCATCC (SEQ ID NO: 207) |
| KPS44-G2 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGGGGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTTTAGTGGCTTCCCGACTGGGTACTGGGGGCAAGGTGCTCT<br>TGTCTCAGTGTCATCC (SEQ ID NO: 208) |
| KPS44-G3 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGGGGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTTTAGTGGCTTCCCGACTGGGTACTGGGGGCAAGGTGCTCT<br>TGTCTCAGTGTCATCC (SEQ ID NO: 208) |
| KPS30 | GAGATGCAGTTGGTAGAGTCTGGGGGAGGCTTGGTCCAGCCTGGGGTGT<br>CCCTGAGACTCTCCTGTGTAGACTCTGGATTCAGTTTTAGTACCTCTTGGT<br>TGGCCTGGGTCCGCCAGGCTCCAGGGAAGGGGCTGGAGTGGCTGGCCAA<br>CATAGATCCAGATGGAAGCACGAGAAATCATGTGGACTCTGTGAGGGGC<br>CGATTCACCATCTCCAGAGACAACGCCAAGAATTCACTGTATCTCCAGAT<br>GAACAGCCTGAGAGCCGAGGACACGGCCGTCTATTACTGTGCGAGAGAC<br>TATGCCTACAATCGCTTTGACTACTGGGGCCAGGGAACCATGGTCACCGT<br>CTCCTCAG (SEQ ID NO: 149) |
| KPD1 | CAGGTGCAGCTGCAGGAGTCGGACCCACGACTGGTGAAGCCTTCGGAGA<br>CCCTGTCCCTCACCTGTAGTGTCTCTGGTGTCTCCATCACCAGTAACACTT<br>ACTGGTGGGCCTGGATCCGCCAGCCCCAGGGAAGAAACTGGAGTGGAT<br>TGGGAGTCTCTCTTACAGTGGGGACACCTACTACAACCCGTCCCTCACGA<br>GTCGCGTCACCATATCAAGAGATATCCATCAGAACCAATTTTTCCTGGAG<br>TTGAACTCTGTGACCGCCGCCGACACGGCCATGTATTACTGTGCGAGAG<br>ATCCCGACATCATTCGCAATTTCCAGTTTGACTACTGGGGCCGGGGAACC<br>CTGGTCACCGTCTCCTCGG (SEQ ID NO: 150) |
| KPL36 | GAGGTGCAGCTGGTGGAGTCTGGGGGAGGCGTGGTCCAGTCTGGGGGGT<br>CCCTGAGACTCTCCTGTGAGACTTCTGGATTCACCTTTATAAGTTCTTGG<br>ATGAGTTGGGTCCGCCAGGCTCCAGGGACAGGACTGGAGTGGGTGGCCA<br>CCATTAACCCTGATGGAACTGAGACACCCTACGCGGACTCGCTGAAGGG<br>CCGCTTCACCATCTCCAGAGACAACACCAAGAAGTCACTTTATCTGCAA<br>ATCCATAGCCTGAGAGCCGACGACACGGCCGTCTATTTCTGTGCAAGGA<br>ATAAGGCATACAATGCCCATGACTTCTGGGGCCAGGGAACCCTGGTCAC<br>CGTCTCCTCAG (SEQ ID NO: 195) |
| KPS44-G4 | CAGGTACAGCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCCGGGACGATAGATTACGGTGTTCCCG<br>TGCGCGGCAGATTCACGATAAGTCGAGACGACTCTAAGAATACACTTTA<br>CCTCCAGATGAATAGCCTCAAAACCGAGGATACAGCCGTTTATTATTGCC<br>GCGCATTCTATAGTGGCTTCCCGACTGGGTACTGGGGGCAAGGTACTCTT<br>GTCACAGTGTCATCC (SEQ ID NO: 221) |
| KPS44-G6 | CAGGTACAGCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCCGGGACGATAGATTACGGTGTTCCCG<br>TGCGCGGCAGATTCACGATAAGTCGAGACGACTCTAAGAATACACTTTA<br>CCTCCAGATGAATAGCCTCAAAACCGAGGATACAGCCGTTTATTATTGCC<br>GCGCATTCTATAGTGGCTTCCCGACTGGGTACTGGGGGCAAGGTACTCTT<br>GTCACAGTGTCATCC (SEQ ID NO: 231) |

TABLE 5-continued

Variable heavy chain polynucleotide sequences

| Antibody | VH Polynucleotide Sequence (SEQ ID NO) |
| --- | --- |
| KPS44-G8 | CAGGTACAGCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCCGGGACGATAGATTACGGTGTTCCCG<br>TGCGCGGCAGATTCACGATAAGTCGAGACGACTCTAAGAATACACTTTA<br>CCTCCAGATGAATAGCCTCAAAACCGAGGATACAGCCGTTTATTATTGCC<br>GCGCATTCTATAGTGGCTTCCCGACTGGGTACTGGGGCAAGGTACTCTT<br>GTCACAGTGTCATCC (SEQ ID NO: 241) |
| KPS44-G10 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTACAGTGGCTTCCCGACTGGGTACTGGGGGCAAGGTGCTCT<br>TGTCTCAGTGTCATCC (SEQ ID NO: 251) |
| KPS44-G11 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTACAGTGGCTTCCCGACTGGGTACTGGGGGCAAGGTGCTCT<br>TGTCTCAGTGTCATCC (SEQ ID NO: 261) |
| KPS44-G14 | CAGGTACAGCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCCGGGACGATAGATTACGGTGTTCCCG<br>TGCGCGGCAGATTCACGATAAGTCGAGACGACTCTAAGAATACACTTTA<br>CCTCCAGATGAATAGCCTCAAAACCGAGGATACAGCCGTTTATTATTGCC<br>GCGCATTCTATAGTGGCTTCCCGACTGGGTACTGGGGGCAAGGTACTCTT<br>GTCACAGTGTCATCC (SEQ ID NO: 271) |

TABLE 6

Variable light chain polynucleotide sequences

| Antibody | VL Polynucleotide Sequence (SEQ ID NO) |
| --- | --- |
| KPN42 | CAGTCTGCCCTGACTCAGCCTCCCTCAGTGTCCGGGTCTCCTGGACAGTC<br>AGTCACCATCTCCTGCACTGGAACCAGCAGTGATGTTGGTGCTTACGACT<br>ATGTCTCCTGGTACCAACAGTACGCAGGCAAAGTCCCCAAACACATAAT<br>TTATGATGTCAATGAGCGGCCCTCAGGGGTCCCTGATCGCTTCTCTGGCT<br>CCAAGTCTGGCAACACGGCCGCCCTGACCATCTCTGGGCTCCAGGCTGA<br>GGATGAGGCTGATTATTATTGCTGCTCATATGCAGGCGGTGACATCTTTG<br>TCTTCGGAACTGGGACTCAGGTCACCGTCCTA (SEQ ID NO: 151) |
| KPN42-v2016 | CAGTCTGCCCTGACCCAGCCTAGGTCTGTGAGTGGGTCACCCGGACAGA<br>GTGTCACAATCTCATGCACCGGAACAAGCTCCGACGTGGGCGCTTACGA<br>TTATGTCTCTTGGTACCAGCAGCACCCCGGGAAGGCACCTAAACTGATG<br>ATCTACGACGTGAACAAGCGGCCAAGTGGCGTCCCCGATAGATTCAGCG<br>GCTCCAAATCTGGGAATACAGCTAGCCTGACTATCTCCGGCCTGCAGGC<br>AGAGGACGAAGCCGATTACTATTGTGCCAGCTACGCTGGCGGGACATT<br>TTCGTGTTTGGAACTGGCACCAAGGTGACCGTCCTG (SEQ ID NO: 152) |
| KPN42-FR-GL-<br>VH/KPN42-FR-<br>GL-C105A-VL | CAGTCTGCCCTGACCCAGCCTAGGTCTGTGAGTGGGTCACCCGGACAGA<br>GTGTCACAATCTCATGCACCGGAACAAGCTCCGACGTGGGCGCTTACGA<br>TTATGTCTCTTGGTACCAGCAGCACCCCGGGAAGGCACCTAAACTGATG<br>ATCTACGACGTGAACAAGCGGCCAAGTGGCGTCCCCGATAGATTCAGCG<br>GCTCCAAATCTGGGAATACAGCTAGCCTGACTATCTCCGGCCTGCAGGC<br>AGAGGACGAAGCCGATTACTATTGTGCCAGCTACGCTGGCGGGACATT<br>TTCGTGTTTGGAACTGGCACCAAGGTGACCGTCCTG (SEQ ID NO: 153) |

TABLE 6-continued

Variable light chain polynucleotide sequences

| Antibody | VL Polynucleotide Sequence (SEQ ID NO) |
|---|---|
| KPS3 | GAGGTTGTCTTGACACAGTCTCCAGCCACTCTGTCTTTGTCTCCAGGGGA<br>AAGAGCCACCCTCTCCTGTAGGGCCAGTCAGAGCATTAGCAGCCAATTA<br>GCGTGGTACCAACAGAAACCTGGCCAGGCTCCCAGGCTCCTCATCCATG<br>ATGCATCCAACAGGGACACTGGCGTCCCAGACAGGTTCAGTGGCAGTGG<br>GTCTGGGACAGACTTCACTCTCACCATCAGCAGCCTAGAGCCTGAAGAT<br>TTTGCTATGTATTACTGTCTCCAGCGTAACAACTGGCCTCCGTGGACGTT<br>CGGCCAAGGGACCAAGGTGGAAATCAAAC (SEQ ID NO: 154) |
| KPN70 | GAAATTGTGTTGACACAGTCTCCAGCCTCCCTGTCTTTGTCTCCAGGGGA<br>AAGAGCCACCCTCTCCTGCAGGGCCAGTCAGATTGTTACCAACTACTTAG<br>CCTGGTATCAACATAAACCTGGCCAGGCTCCCAGGCTCCTCATCTTTGAT<br>ATGTCCATTAGGGCCGCTGGCATCCCAGCCAGGTTCAGTGGCAGTGGGT<br>CTGGGACAGACTTCACTCTCACCATCAGCAGCCTTGAGCCTGAAGATTTT<br>GCAGTTTATTACTGTCAACACCGTAGCAACTGGCCTCTATTCACTTTCGG<br>CCCTGGGACCAAAGTGGATATCAAAC (SEQ ID NO: 155) |
| KPN179 | CAGTCTGCCCTGACTCAGCCTCCCTCAGTGTCCGGGTCTCCTGGACAGTC<br>AGTCACCATCTCCTGCACTGGAACCAGCAGTGATGTTGGTTATTACGACT<br>ATGTCTCCTGGTACCAACAGCACCACCCAGGCAAAGCCCCCAAACACAT<br>GATTTATGATGTCAATAAGCGGCCCTCAGGGGTCCCTGATCGCTTCTCTG<br>GCTCCAAGTCTGGCAACACGGCCTCCCTGACCATCTCTGGGCTCCAGGCT<br>GAGGATGAGGCTGATTATTATTGCTGTTCATATGCAGGCGGTGACACTTT<br>TGTCTTCGGAACTGGGACCAAGGTCACCGTCCTAG (SEQ ID NO: 156) |
| KPN179-FR-1-2-<br>4-GL-N35S-<br>VH/KPN179-FR-<br>GL-C105A-VL | CAGTCTGCCCTGACTCAGCCTAGGTCTGTGAGTGGGTCACCCGGACAGA<br>GTGTCACAATCTCATGCACCGGAACAAGCTCCGACGTGGGCTACTATGA<br>TTACGTCTCTTGGTATCAGCAGCACCCCGGGAAGGCTCCTAAACTGATGA<br>TCTACGACGTGAACAAGCGGCCAAGTGGCGTCCCCGATAGATTCAGCGG<br>CTCCAAATCTGGGAATACAGCAAGCCTGACTATTTCCGGCCTGCAGGCA<br>GAGGACGAAGCCGATTACTATTGTGCCAGCTATGCTGGCGGGGACACCT<br>TCGTGTTTGGAACTGGCACCAAGGTGACAGTCCTG (SEQ ID NO: 196) |
| KPN179-FR-GL<br>N35S-<br>VH/KPN179-FR-<br>GL-C105A-VL | CAGTCTGCCCTGACTCAGCCTAGGTCTGTGAGTGGGTCACCCGGACAGA<br>GTGTCACAATCTCATGCACCGGAACAAGCTCCGACGTGGGCTACTATGA<br>TTACGTCTCTTGGTATCAGCAGCACCCCGGGAAGGCTCCTAAACTGATGA<br>TCTACGACGTGAACAAGCGGCCAAGTGGCGTCCCCGATAGATTCAGCGG<br>CTCCAAATCTGGGAATACAGCAAGCCTGACTATTTCCGGCCTGCAGGCA<br>GAGGACGAAGCCGATTACTATTGTGCCAGCTATGCTGGCGGGGACACCT<br>TCGTGTTTGGAACTGGCACCAAGGTGACAGTCCTG (SEQ ID NO: 197) |
| KPN44 | GAAATTGTGTTGACACAGTCTCCAGCCTCCCTGTCTTTGTCTCCAGGGGA<br>CAGAGCCACCCTCTCCTGCAGGGCCAGTCAGACGATTACCAACTACTTA<br>GCCTGGTACCAACATAAACCTGGCCAGGCTCCCAGACTCCTCATCTTTGA<br>TATGTCGAAAAGGGCCACTGGCATCCCAGCCAGGTTCAGTGGCAGTGGG<br>TCTGGGACAGACTTCACTCTCACCATCAGCAGCCTTGAGCCTGAAGATTT<br>TGCAGTTTACTACTGTCAACACCGTAGCAACTGGCCTCTATTCACTTTCG<br>GCCCTGGGACCAACGTGGATATCAAAC (SEQ ID NO: 157) |
| KPN17 | GACATCCAGTTGACCCAGTCTCCATCCTTCCTGTCTGCCTCTGTAGGAGA<br>CAGAGTCACCATCACTTGCCGGGCCAGTCAGGGCATTAGCACTTATTTAG<br>CCTGGTATCAACAAAAACCAGGGAAAGCCCCTAAGCTCCTGATCTATGC<br>TGCATCCACTTTGCAAAGTGGGGTCCCATCAAGGTTCAGCGGCAGTGGA<br>TCTGGGACAGAATTCACTCTCACAATCAACAGCCTGCAGTCTGAAGATTT<br>TGCAACTTACTACTGTCAGCAGCTTACTAGTCACCTCTACACTTTTGGCC<br>AGGGGACCAAGCTGGAGATCAAAC (SEQ ID NO: 158) |
| 6F6 | GATGTTGTGATGACCCAAACTCCACTCTTCCTGCCTGTCAGTCTTGGAGA<br>TCAAGCCTCCATCTCTTGCAGATCTAGTCAGGGCCTTGTACACAGTACTG<br>GAAACACCTTTTTACATTGGTACCTGCAGAAGCCAGGCCAGTCTCCAAA<br>GCTCCTGATCTACAAAGTTTCCAACCGATTTTCTGGGGTCCCAGACAGGT<br>TCAGTGGCAGTGGATCAGGGACAGATTTCACACTCAAGATCAGCAGAGT<br>GGAGGCTGAGGATCTGGGAATTTATTTCTGCTCTCAAAGTACACATATTC<br>CGTACACGTTCGGAGGGGGGACCAAGCTGGAAATAAAA (SEQ ID<br>NO: 159) |
| KPL26 | CAGTCTGCCCTGACTCAGCCTCCCTCCGCGTCCGGGTCTCCTGGACAATC<br>AGTCACCCTCTCCTGCACTGGAACCAGCAGTGACGTTGGTGGTAATAACT<br>ATGTCTCCTGGTACCAACAGCACCCAGGCAAAGCCCCCAAACTCATCAT<br>TTATGAGGTCAGTAAGCGGCCCTCAGGGGTCCCTAATCGTTTCTCTGGCT<br>CCAAGTCTGGCAACACGGCCTCCCTGACCGTCTCTGGGCTCCAGGCTGA<br>GGATGAGGCTGATTATTACTGCAGCTCATTTGGAGGTAGTAAGATGTTCG<br>GCGGAGGGACCAAGCTGACCGTCCTAG (SEQ ID NO: 160) |
| KPS18 | CAGTCTGTGTTGACGCAGCCGCCCTCACTGTCTGCGGCCCCAGGACAGA<br>CGGTCACCATCGCCTGCTCTGGAAGTAGATCCAACATTGGGAGTGATTCC<br>GTCTCCTGGTTCCAGCAGTTCCCAGGAACAGCCCCCAGAGTCCTCATGTA |

TABLE 6-continued

Variable light chain polynucleotide sequences

| Antibody | VL Polynucleotide Sequence (SEQ ID NO) |
|---|---|
| | TGACAATAATAAGCGACCCTCAGGCATTTCTGACCGATTCTCTGGCTCCA<br>AGTCTGGCACGTCAGTCACCCTGGACATCACCGGACTCCAGACTGGGGA<br>CGAGGCCGATTATTACTGCGCAACATGGGATAGCAGCCTGAGTGCTTAT<br>GTCTTCGGATCTGGGACCAAGGTCACCGTCCTAA (SEQ ID NO: 161) |
| KPS24 | CAGTCTGTGTTGACGCAGCCGCCCTCAGTGTCTGCGGCCCCAGGACAGA<br>CGGTCACCATCGCCTGCTCTGGAAGTAGCTCCAACATTGGGAGTGATTCC<br>GTATCCTGGTTCCAGCAGCTCCCAGGAACAGCCCCCAGAGTCCTCATGTA<br>TGAAAATAATAAGCGACCCTCAGGGATTTCTGACCGATTCTCTGGCTCCA<br>AGTCTGGCACGTCAGTCACCCTGGGCATCACCGGACTCCAGACTGGGGA<br>CGAGGCCGATTATTACTGCGCAGCATGGGATAGCAGCCTACGTGCTTAT<br>GTCTTCGGATCTGGGACCAAGGTCACCGTCCTAG (SEQ ID NO: 162) |
| KPS44 | CAGTCTGTGTTGACGCAGCCGCCCTCACTGTCTGCGGCCCCTGGACAGAC<br>GATCACCATCGCCTGCTCTGGAACTAGTTCCAACATTGGGAGTGATTCCG<br>TATCCTGGTTCCAGCAATTCCCAGGAACAGCCCCCAGAGTCCTCATATAT<br>GAGAATAATAAGCGACCCTCAGGCATTTCTGACCGATTCTCTGGCTCCAA<br>GTCTGGCACGTCAGTCACACTGGGCATCACCGGACTCCAGACTGGGGAC<br>GAGGCCGATTATTACTGCGCAACATGGGATAGCAGCCTGAGTGCTTATG<br>TCTTCGGATCTGGGACCAAGGTCACCGTCCTAG (SEQ ID NO: 163) |
| KPS44-v2017 | CAGAGCGTGCTGACACAGCCCCCTTCACTGAGCGCCGCTCCTGGACAGA<br>CCATCACAATTGCTTGCTCCGGCACTAGCTCCAACATCGGGTCCAATTAC<br>GTGTCTTGGTTCCAGCAGTTTCCAGGAACCGCACCCAGGGTCCTGATCTA<br>TGAGAACAATAAGCGGCCCTCAGGCATTAGCGACAGATTCTCCGGGTCT<br>AAAAGTGGAACTAGCGTGACCCTGGGAATTACCGGCCTGCAGACAGGCG<br>ACGAAGCAGATTACTATTGTGCCACCTTCGATTCTAGTCTGAGTGCCTAC<br>GTCTTTGGCTCTGGGACAAAAGTGACTGTCCTG (SEQ ID NO: 209) |
| KPS44-G1 | CAGTCCGTTTTGACGCAACCCCCGTCACTGAGTGCTGCGCCTGGGCAGAC<br>CATAACGATCGCCTGCTCAGGGACCAGCAGTAATATAGGCTCTAATTAT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTTTGATAGCTCTCTTTCAGCTTAC<br>GTGTTTGGTTCCGGGACCAAAGTGACAGTCCTC (SEQ ID NO: 210) |
| KPS44-G2 | CAGTCCGTTTTGACGCAACCCCCGTCACTGAGTGCTGCGCCTGGGCAGAC<br>CATAACGATCGCCTGCTCAGGGACCAGCAGTAATATAGGCTCTGATTCT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTTTGATAGCTCTCTTTCAGCTTAC<br>GTGTTTGGTTCCGGGACCAAAGTGACAGTCCTC (SEQ ID NO: 211) |
| KPS44-G3 | CAGTCCGTTTTGACGCAACCCCCGTCACTGAGTGCTGCGCCTGGGCAGAC<br>CATAACGATCGCCTGCTCAGGGACCAGCAGTAATATAGGCTCTAATTAT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTGGGATAGCTCTCTTTCAGCTTAC<br>GTGTTTGGTTCCGGGACCAAAGTGACAGTCCTC (SEQ ID NO: 212) |
| KPS30 | CAGTCTGCCCTGACTCAGCCTCCCTCCGCGTCCGGGTCTCCTGGACAGTC<br>AGTCGTCATCTCCTGCACTGGAACCAGCAGTGACATTGGGGCTAATAAC<br>TATGTCTCCTGGTACCAACAACACCCAGGCAAAGCCCCCAAACTCTTGCT<br>TTATGAGGTCAATAAGCGGCCCTCAGGGGTCCCTGATCGCTTCTCTGCCT<br>CCAAGTCTGGCAACACGGCCTCCCTGACCGTCTCTGGGCTCCTGGCTGAG<br>GATGAGGCTGATTATTACTGCTGCGGATATGGAGGCGGGAGGGTGTTCG<br>GCGGAGGGACCAAGCTGACCGTCCTAC (SEQ ID NO: 164) |
| KPD1 | GAAATTGTGTTGACGCAGTCTCCAGGCATCCTGTCTTTGTCTCCAGGGGA<br>GAGAGCCACCCTCTCTTGCAGGGTCAGTCAGATTCTTTACATGTCTCATT<br>TGGCCTGGTATCAGCATAAACCTGGACAGGCTCCCAGACTCCTCATCTAT<br>GGTGCGTCCATCAGGGCCACTGGCGTCCCAGACAGGTTCAGTGGCAGTG<br>GGTCCGGGACAGACTTCACTCTCACCATCAGCAGACTGGAGCCTGAAGA<br>TTTTGCAGTGTATTACTGTCAGCAGTATGCGCCTCACCGACGTTCGGCC<br>AAGGGACAATGGTGGAAATCAAAC (SEQ ID NO: 165) |
| KPL36 | CAGTCTGCCCTGACTCAGCCTCCCTCCGCGTCCGGGTCTCCTGGACAATC<br>AGTCACCATCTCCTGCACTGGAACCAGTAGTGACGTAGGTGGTAATAAC<br>TTTGTCTCCTGGTACCAACAGTATCCAGGCAAAGCCCCCAAACTCATTAT<br>TTATGAGGTCAATAAGCGGCCCTCAGGGGTCCCTGATCGTTTCTCTGGCT<br>CCAAGTCTGGCAACACGGCCTCCCTGACCGTCTCTGGGCTCCAGGCTGA<br>GGATGAGGCTGATTATTACTGCGGCGCATTTGGAGGTAGCAAGATGTTC<br>GGCGGAGGGACCAAGCTGACCGTCCTAG (SEQ ID NO: 198) |

TABLE 6-continued

Variable light chain polynucleotide sequences

| Antibody | VL Polynucleotide Sequence (SEQ ID NO) |
|---|---|
| KPS44-G4 | CAGTCCGTTTTGACGCAACCCCCGTCAGTGAGTGCTGCGCCTGGGCAGA<br>AGGTGACGATCGCCTGCTCAGGGACCAGCAGTAATATAGGCTCTGATGC<br>TGTATCATGGTTCCAGCAACTGCCTGGCACGGCACCTAAACTGCTGATCT<br>ACGAAAATAATAAGCGGCCCTCAGGCATTTCAGATAGGTTCTCTGGGAG<br>CAAGAGTGGTACAAGCGTAACGCTCGGTATCACCGGTCTCCAGACAGGT<br>GATGAAGCTGATTACTACTGCGCTACTTTTGAGAGCTCTCTTTCAGCTTA<br>CGTGTTTGGTACCGGGACCAAAGTGACAGTCCTC (SEQ ID NO: 222) |
| KPS44-G6 | CAGTCCGTTTTGACGCAACCCCCGTCAGTGAGTGCTGCGCCTGGGCAGA<br>AGGTGACGATCGCCTGCTCAGGGACCAGCAGTAATATAGGCTCTGAGTC<br>TGTATCATGGTTCCAGCAACTGCCTGGCACGGCACCTAAACTGCTGATCT<br>ACGAAAATAATAAGCGGCCCTCAGGCATTTCAGATAGGTTCTCTGGGAG<br>CAAGAGTGGTACAAGCGTAACGCTCGGTATCACCGGTCTCCAGACAGGT<br>GATGAAGCTGATTACTACTGCGCTACTTTTGAGAGCTCTCTTTCAGCTTA<br>CGTGTTTGGTACCGGGACCAAAGTGACAGTCCTC (SEQ ID NO: 232) |
| KPS44-G8 | CAGTCCGTTTTGACGCAACCCCCGTCAGTGAGTGCTGCGCCTGGGCAGA<br>AGGTGACGATCGCCTGCTCAGGGACCAGCAGTAATATAGGCTCTGATTC<br>TGTATCATGGTTCCAGCAACTGCCTGGCACGGCACCTAAACTGCTGATCT<br>ACGAAAATAATAAGCGGCCCTCAGGCATTTCAGATAGGTTCTCTGGGAG<br>CAAGAGTGGTACAAGCGTAACGCTCGGTATCACCGGTCTCCAGACAGGT<br>GATGAAGCTGATTACTACTGCGCTACTTTTGAGAGCTCTCTTTCAGCTTA<br>CGTGTTTGGTACCGGGACCAAAGTGACAGTCCTC (SEQ ID NO: 242) |
| KPS44-G10 | CAGTCCGTTTTGACGCAACCCCCGTCACTGAGTGCTGCGCCTGGGCAGAC<br>CATAACGATCGCCTGCTCAGGGACCAGCAGTAATATAGGCTCTGATTCT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTTTGAGAGCTCTCTTTCAGCTTAC<br>GTGTTTGGTTCCGGGACCAAAGTGACAGTCCTC (SEQ ID NO: 252) |
| KPS44-G11 | CAGTCCGTTTTGACGCAACCCCCGTCAGTGAGTGCTGCGCCTGGGCAGA<br>AGGTGACGATCGCCTGCTCAGGGACCAGCAGTAATATAGGCTCTGATTC<br>TGTATCATGGTTCCAGCAACTGCCTGGCACGGCACCTAAACTGCTGATCT<br>ACGAAAATAATAAGCGGCCCTCAGGCATTTCAGATAGGTTCTCTGGGAG<br>CAAGAGTGGTACAAGCGTAACGCTCGGTATCACCGGTCTCCAGACAGGT<br>GATGAAGCTGATTACTACTGCGCTACTTTTGAGAGCTCTCTTTCAGCTTA<br>CGTGTTTGGTACCGGGACCAAAGTGACAGTCCTC (SEQ ID NO: 262) |
| KPS44-G14 | CAGTCCGTTTTGACGCAACCCCCGTCACTGAGTGCTGCGCCTGGGCAGAC<br>CATAACGATCGCCTGCTCAGGGACCAGCAGTAATATAGGCTCTGATTCT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTTTGAGAGCTCTCTTTCAGCTTAC<br>GTGTTTGGTTCCGGGACCAAAGTGACAGTCCTC (SEQ ID NO: 272) |

Also provided is a polynucleotide having at least about 9500, at least about 9600, at least about 97% o, at least about 98% o, or at least about 99% o sequence identity to any one of the SEQ TD NOs provided in Table 5 or 6. Thus, in certain embodiments, the polynucleotide comprises (a) a polynucleotide having at least about 9500 sequence identity to any one of the SEQ ID NOs provided in Table 5, and/or (b) a polynucleotide having at least about 95% sequence identity to any one of the SEQ ID NOs provided in Table 6. In certain embodiments, the polynucleotide comprises: (a) a polynucleotide having the sequence of a SEQ ID NO provided in Table 5; and/or (b) a polynucleotide having the sequence of a SEQ ID NO provided in Table 6.

The present disclosure provides an isolated polynucleotide or cDNA molecule sufficient for use as a hybridization probe, PCR primer or sequencing primer that is a fragment of a nucleic acid molecule disclosed herein or its complement. The nucleic acid molecule can, for example, be operably linked to a control sequence.

The present disclosure also provides constructs in the form of plasmids, vectors, transcription or expression cassettes which comprise at least one polynucleotide as described above (see, e.g., Tables 5 and 6).

The present disclosure also provides a recombinant host cell which comprises one or more nucleic acids, plasmids, vectors or as described above (see, e.g., Tables 5 and 6). A nucleic acid encoding any CDR or set of CDRs or VH domain or VL domain or antibody antigen-binding site, antibody, e.g., scFv, IgG1, or IgG2 as provided (see, e.g., Tables 1-4) itself forms an aspect of the present disclosure, as does a method of production of the encoded product, which method comprises expression from the nucleic acid encoding the product (e.g. the antigen binding protein, including, e.g., an anti-O2 antigen antibody or antigen-binding fragment thereof, disclosed herein). Expression can conveniently be achieved by culturing under appropriate conditions recombinant host cells containing a nucleic acid described herein. Following production by expression a CDR, set of CDRs, VH or VL domain, an antigen-binding protein can be isolated and/or purified using any suitable technique.

In some instances, the host cell is a mammalian host cell, such as a HEK293 cell, a HeLa cell, NS0 murine myeloma cell, a PER.C6® human cell, or a Chinese hamster ovary (CHO) cell.

Antigen-binding proteins, VH and/or VL domains and encoding nucleic acid molecules and vectors can be isolated and/or purified, e.g., from their natural environment, in substantially pure or homogeneous form, or, in the case of nucleic acid, free or substantially free of nucleic acid or genes origin other than the sequence encoding a polypeptide with the required function. Nucleic acids according to the present disclosure can comprise DNA or RNA and can be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, plant cells, yeast and baculovirus systems and transgenic plants and animals. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others. A common bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of an antigen-binding protein for example Chadd H E and Chamow S M (2001) 110 Current Opinion in Biotechnology 12: 188-194, Andersen D C and Krummen L (2002) Current Opinion in Biotechnology 13: 117, Larrick J W and Thomas D W (2001) Current opinion in Biotechnology 12:411-418.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 3rd edition, Sambrook and Russell, 2001, Cold Spring Harbor Laboratory Press. Many known techniques and protocols for manipulation of nucleic acids, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1988, *Short Protocols in Molecular Biology: A Compendium of Methods from Current Protocols in Molecular Biology*, Ausubel et al. eds., John Wiley & Sons, 4$^{th}$ edition 1999. The disclosures of Sambrook et al. and Ausubel et al. (both) are incorporated herein by reference.

Thus, a further aspect of the present disclosure provides a host cell containing nucleic acid as disclosed herein. For example, the disclosure provides a host cell transformed with nucleic acid comprising a nucleotide sequence (see, e.g., Tables 5 and 6) encoding an antigen-binding protein of the present disclosure or antibody CDR, set of CDRs, or VH and/or VL domain of an antigen-binding protein of the present disclosure (see, e.g., Tables 1-4). In some embodiments, the host cell comprises the expressed antigen-binding protein of the present disclosure or antibody CDR, set of CDRs, or VH and/or VL domain of an antigen-binding protein of the present disclosure (see, e.g., Tables 1-4).

Such a host cell can be in vitro and can be in culture. Such a host cell can be an isolated host cell. Such a host cell can be in vivo.

A still further aspect provided herein is a method comprising introducing such nucleic acid into a host cell. The introduction can employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. Introducing nucleic acid in the host cell, in particular a eukaryotic cell can use a viral or a plasmid based system. The plasmid system can be maintained episomally or may incorporated into the host cell or into an artificial chromosome. Incorporation can be either by random or targeted integration of one or more copies at single or multiple loci. For bacterial cells, suitable techniques may include calcium chloride transformation, electroporation, and transfection using bacteriophage.

The introduction can be followed by causing or allowing expression from the nucleic acid, e.g., by culturing host cells under conditions for expression of the gene.

In one embodiment, the nucleic acid of the present disclosure is integrated into the genome (e.g. chromosome) of the host cell. Integration can be promoted by inclusion of sequences which promote recombination with the genome, in accordance with standard techniques.

The present disclosure also provides a method which comprises using a construct (e.g. plasmid, vector, etc. as described above) in an expression system in order to express an antigen-binding protein or polypeptide as described above.

In another aspect, the disclosure provides a hybridoma producing the antigen-binding protein (e.g. anti-O2 antigen antibodies or antigen binding fragments thereof) of the disclosure.

A yet further aspect of the disclosure provides a method of production of an antibody binding protein (e.g. anti-O2 antigen antibodies or antigen binding fragments thereof) of the disclosure, the method including causing expression from encoding nucleic acid. Such a method can comprise culturing host cells under conditions suitable for production of said antigen-binding protein.

In some embodiments, the method of production further comprises isolating and/or purifying the antigen binding protein (including anti-O2 antigen antibodies or antigen binding fragments thereof) produced from the host cell or hybridoma.

EXAMPLES

Materials and Methods

Unless otherwise stated, all *K. pneumoniae* isolates were purchased from America Type Culture Collection, Eurofin collection, or IHMA collection, and cultures were maintained in 2×YT media at 37° C. supplemented with antibiotics when appropriate.

All statistical analysis was performed in GraphPad Prism version 6. For comparing bacterial burden, anti-O2 antigen antibody treated animals were compared with human isotype control antibody treated animals by unpaired t test. Survival results were plotted as Kaplan-Meier curves and analyzed as Log-rank (Mental-Cox) tests.

Unless otherwise specified, all antibodies used in the examples were in the human IgG1 format.

Example 1: Expansion of O2 Serotype in Multi-Drug Resistant (MDR) Strains

Highly purified LPS was generated from *Klebsiella pneumoniae* LPS serotype reference strains (Staten Serum Institute), which do not express capsular polysaccharides. SDS-PAGE analysis followed by Silver Stain confirmed the purity of LPS. Human antibodies against O2 serotypes were then identified based on the reactivity of human B cells against the respective purified LPS. The anti-O2 LPS antibodies (such as KPD1) showed cross-reactivity with O1 LPS, likely due to the common D-galactan I subunit shared between O1 and O2 LPS. (FIG. 1A).

Western blots were performed on 709 *Klebsiella* clinical isolates collected between 2012 and 2014 from various geographical locations spanning six continents and various sites of infection. The KPD1 antibody was used to assess the propensity of O2 isolates. Contrary to historical literature demonstrating the propensity of O1 isolates (Trautmann, M, et. al. 2004. O antigen seroepidemiology of *Klebsiella* clinical isolates and implications for immunoprophylaxis of *Klebsiella* infections. Vaccine. 22: 818-821.), O2 was the most prevalent LPS serotype (35.8%, FIG. 1*i*). Isolates were further categorized into three different drug susceptibility groups to determine if the increased incidence of O2 may be attributed to an overall increase in multi-drug resistant (MDR) isolates. The susceptibility groups were based on minimum inhibitory concentration (MIC) information provided by IHMA. Extended spectrum beta-lactamase producing (ESBL) strains are resistant to ceftazidime, but susceptible to carbanpenem. Carbapenem-Resistant Enterobacteriaceae (CRE) strains are resistant to carbanpenems. Interestingly, steady increases were observed in the O2 prevalence in multi-drug resistant isolates. The increases of O2 serotype were even more pronounced in CRE strains, suggesting the unique expansion of O2 MDR strains (see FIG. 1B).

Example 2: Isolation of *K. pneumoniae* O2 Specific Hybridomas

BALB/c mice were immunized weekly with O2 lipopolysaccharide (LPS) via subcutaneous route for four weeks. At the end of the immunization, lymph node and splenic B cells were harvested and fused with P3X myelomas. Supernatants from the resulting hybridomas were then screened for binding to *Klebsiella pneumoniae* 43816DM by whole bacterial enzyme-linked immunosorbent assay (ELISA). Positive hybridomas were sub-cultured in antibiotic-free medium, and the supernatants were subjected to ELISA binding and opsonophagocytic killing (OPK) assay to select for potentially protective hybridomas against *K. pneumoniae* O2 LPS. The 6F6 antibody was obtained from this method.

Example 3: Isolation of *K. pneumoniae* O2 Specific Antibodies from Tonsil and Patient B Cells Peripheral blood mononuclear cells (PBMC) and sera were separated from buffy coats from healthy blood donors or convalescent patients after *K. pneumoniae* infection as described in Beltramello M. et al., Cell Host Microbe. 8, 271-283 (2010). PMBC were stored in liquid nitrogen whereas the plasma was stored at 4° C. Alternatively lymphocytes were obtained from tonsils or adenoids after tissue homogenization in the presence of DNAaseI and collagenase. Memory B cells were isolated from cryopreserved PMBC or from lymphocytes isolated from tonsils or adenoids using CD19 microbeads, followed by depletion of cells carrying IgM, IgD, and IgA by cell sorting. Memory B cells were immortalized as described in Traggiai, E. et al., Nature Medicine 10: 871-875 (2004).

For PBMC donor selection the corresponding plasmas were diluted in PBS and used to determine the presence of antibodies binding to different pools of bacterial strains or to purified bacterial antigens (e.g. LPS or other polysaccharides, bacterial proteins) by ELISA.

For tonsil and adenoid donor selection, tonsillar lymphocytes were polyclonally stimulated as described in Pinna, D., et al., European Journal of Immunology 39: 1260-1270 (2009). Supernatants containing polyclonal antibody mixtures were used to determine the presence of antibodies binding to different pools of bacterial strains or to purified bacterial antigens (e.g. LPS or other polysaccharides, bacterial proteins) by enzyme-linked immunosorbent assay (ELISA).

The antibody KPD1 was isolated by screening B cells from peripheral blood mononuclear cells (PBMC) of a healthy donor in ELISA with plates coated with different *K. pneumoniae* strains. In secondary screenings, KPD1 showed binding to LPS-O1 and O2, neutralized LPS-O1 and O2, and showed OPK activity against an O2 capsule mutant. KPD1 was isolated as a human IgG2 antibody.

The antibodies KPS3, KPS24, KPS18, KPS30, and KPS44 were obtained by screening B cells of a convalescent donor in ELISA with plates coated with LPS-O2. In secondary screening KPS30 bound LPS-O1 and -O2, whereas KPS3, KPS18 and KPS24 bound specifically to LPS-O2. KPS3, 18, 24, 30, and 44 showed strong OPK activity against an O2 capsule mutant strain, but not the O1 capsule mutant strain. KPS3, KPS24, KPS18 neutralized LPSO2, KPS30 neutralized both LPS-O1 and LPS-O2. KPS3, KPS18, KPS24, KPS30 and KPS44 were isolated as human IgG2 antibodies.

The antibodies KPN17, KPN42, KPN44, KPN70, and KPN179 were isolated by interrogating sorted IgG2 B cells from tonsil 21 in ELISA with LPS-O2. KPN17, KPN42, KPN44 and KPN179 were shown to bind LPS-O1 and —O2 in secondary screening by ELISA. KPN17 and KPN42 neutralize LPS-O2, KPN44 and KPN70 neutralize both LPS-O2 and LPS-O1. KPN179 did not show LPS-neutralizing activity. KPN17, KPN42 and KPN44 showed OPK activity against an O2 capsule mutant.

The antibodies KPL26 and KPL36 were isolated by interrogating sorted IgG2 B cells from tonsil 14 in high content flow cytometry for binding to O2 strains. In secondary screening they were confirmed to bind to LPS-O1 and LPS-O2 in ELISA and KPL26 to neutralize LPS-O1 and LPS-O2, KPL36 to neutralize LPS-O2. KPL26 showed OPK activity against O1 and O2 capsule mutants.

Example 4: Summary of Three Classes of O2 LPS mAbs

As described in more detail in below, anti-O2 LPS mAbs were tested for: 1) binding to O1 and O2 LPS (see Example 5); 2) LPS neutralization (LPS-Neut) against O1 and O2 LPS (see Example 7); 3) OPK against capsule mutant strain 43816ΔcpsB lux (O1) and 8570ΔcpsB lux (O2) (see Example 8); and 4) protective activity in pneumonia models (see Example 9). O2 LPS mAbs were subsequently divided into three classes based on their in vitro activities. Class I mAbs were characterized as Binding (O1+O2+)/OPK (O1−O2+); Class 2 mAbs were characterized as Binding (O1+O2+)/OPK (O1+O2+); and Class III mAbs were characterized as Binding (O1±O2+)/OPK (O1−O2+). Table 7 summarizes the binding characteristics of the three classes of Anti-O2 LPS mAbs.

TABLE 7

Summary of Anti-O2 Antigen Antibodies.

| Catagory | mAb | Original Isotype | LPS binding | LPS Neut O1 | LPS Neut O2 | D Capsule OPK O1 | D Capsule OPK O2 | Mouse protection models |
|---|---|---|---|---|---|---|---|---|
| Class I | KPD1 | Hu rIgG2 | O1/O2 | ++ | ++ | − | ++ | − (O1/O2) |
| | 6F6 | Ms IgM | | NT | NT | − | + | − (O2) |
| | KPN17 | Hu rIgG2 | | − | +/− | − | + | − (O2) |
| | KPN70 | Hu rIgG2 | | ++ | ++ | − | +++ | +/− (O1/O2) |
| | KPS30 | Hu rIgG2 | | ++ | ++ | − | +++ | NT |
| Class II | KPL26 | Hu rIgG2 | O1/O2 | + | + | + | + | + (O1) |
| | KPL36 | Hu rIgG2 | | − | + | + | + | NT |
| Class III | KPN42 | Hu rIgG2 | O2, | − | +/− | − | +++ | +++ (O2) |
| | KPN179 | Hu rIgG2 | weak O1 | − | +/− | − | +++ | +++ (O2) |
| | KPS3 | Hu rIgG2 | | − | +/− | − | +++ | NT |
| | KPS18 | Hu rIgG2 | | − | +/− | − | +++ | NT |
| | KPS24 | Hu rIgG2 | | − | +/− | − | +++ | NT |
| | KPS44v2017 | Hu rIgG2 | | − | +/− | − | +++ | +++ (O2) |
| | KPS44 | Hu rIgG2 | | − | +/− | − | +++ | +++ (O2) |

NT: not tested
+++: Strongly positive activity
+: Positive activity
+/−: Somewhat positive depending upon the test conditions Notably, significant LPS neutralization activity is not required for high levels of in vivo protection.

Example 5: Enzyme-Linked Immunosorbent Assay (ELISA)

For screening by ELISA, spectraplate-384 with high protein binding treatment (custom made from Perkin Elmer, CUSG83093) were coated overnight at 4° C. with 5 g/ml O1 or O2 LPS in phosphate-buffered saline (PBS), pH 7.2, and plates were subsequently blocked with PBS-B, i.e. PBS supplemented with 1% endotoxin free BSA (Sigma, #A9430). The coated plates were incubated with cell culture supernatants from polyclonally stimulated lymphocytes (AMVBRA) or from monoclonal immortalized B cells (donor interrogations) containing fully human antibodies or with diluted plasma samples (PBMC donor selections) for 1 hour at room temperature. The plates were then washed with PBS containing 0.1% Tween-20 (PBS-T). Secondary antibody was added; either Alkaline Phosphatase-conjugated Goat Anti-Human IgG-AP (Southern Biotech, 2040-04, 1:1000 in PBS-B) or Peroxidase AffiniPure F(ab')$_2$ Fragment Goat Anti-Human IgG, Fc Fragment Specific (Jackson ImmunoResearch #309 036 098, 1:5000 in PBS-B) were used. Secondary antibodies were typically incubated for 1 h. Plates were washed three times with PBS-T, and P-NitroPhenyl Phosphate (pNPP, Sigma-Aldrich, cat #N2765-100TAB) or Sureblue (KPL, 53-00-03) substrates were added and incubated for 10 min or until the development of a colorimetric reaction. In the case of the HRP substrate Sureblue, the reaction was stopped by adding an equal volume of 0.2N HCl. The absorbance at 405 nm (pNPP) or 450 nm (Sureblue) was measured by a microplate reader (Biotek, Elx808).

To determine binding EC50 values ELISA was performed in 96 well plates (Maxi sorp, Nunc #442404) coated overnight at 4° C. with 5 μg/ml O1 or O2 LPS in phosphate-buffered saline (PBS), pH 7.2, and plates were subsequently blocked with PBS-B, i.e. PBS supplemented with 1% endotoxin free BSA (Sigma, #A9430). The coated plates were incubated with serial dilutions of the monoclonal antibodies for 1 hour at room temperature. The plates were then washed with PBS containing 0.1% Tween-20 (PBS-T). Alkaline Phosphatase-conjugated Goat Anti-Human IgG (Southern Biotech, 2040-04, 1:1000 in PBS-B) was added. The secondary antibody reactions were incubated for 1 h. Plates were washed three times with PBS-T, and P-NitroPhenyl Phosphate (pNPP, Sigma-Aldrich, cat #N2765-100TAB) substrate was added and incubated for 30 min or until the development of a colorimetric reaction. The absorbance at 405 nm was measured by a microplate reader (Biotek, Elx808). The data was plotted with Graphpad Prism software. Representative mAbs from each class were tested for their binding to O1 LPS (FIG. 2A) and O2 LPS (FIG. 2B), and EC50 values were obtained (FIG. 2C). The majority of the anti-O2 LPS mAbs bound to both O1 and O2 LPS by ELISA. Among these, KPN42 showed lower affinity to O1 than O2. None of these LPS mAbs bound to the O3, O4, O5, O7, or O12 LPS serotypes (see e.g., FIG. 1A).

Example 6: Octet Binding Assay with Anti-O2 mAbs

The interaction of anti-O2 LPS mAbs with O1 and O2 LPS was further tested in solution phase by Octet platform. This platform provides a powerful tool to measure the rate of biomolecular complex formation and complex stability in a more biologically meaningful setting. Briefly, Protein A coated sensors were coated with 0.2 μg/mL anti-O2 LPS mAbs for 10 minutes before being dipped into solution containing 2 μg/mL O1 or O2 LPS in Kinetics buffer (ForteBio, dilute 10× to 1× with PBS). Changes in the number of molecules bound to the biosensor caused a shift in the interference pattern that was recorded in real time. As shown in FIGS. 3A and 3B, Class I and Class II mAbs bound to both O1 and O2 LPS, while Class III mAb (KPN42) showed no binding to O1 LPS. The affinity constant ($K_D$) of Class III mAbs to O2 LPS was calculated based on the on-rate and off-rate from Octet sensorgram. Both KPN42 and KPN179 showed comparable affinity constant at the average of 4.8E-09 and 7.98E-09M, respectively (FIG. 3C).

Example 7: LPS Neutralization Assays

Activation of TLR4 receptors by bacterial LPS leads to downstream activation of the NF-κB transcriptional regulator. A decrease in induction of NF-κB-responsive luciferase activity was used to quantify LPS neutralization activity by LPS mAbs. A murine RAW264.7 macrophage cell line was engineered to carry a firefly luciferase reporter gene under the control of an NF-κB-responsive promoter (RAW264.7-lux). Serially diluted antibody stocks were mixed with LPS in a 1:1 ratio and incubated at 4° C. for 1 hr. Antibody/LPS mixtures were then diluted 1:10 into assay plates containing pre-seeded RAW264.7-lux cells (4e5 cells/well), which were then placed at 37° C. with 5% CO2 for 2.5 hours. Following incubations, Steady Glo solution (Promega) was added to each well and incubated for another 20 min protected from light. The relative light units (RLUs) were measured using a multi-mode microplate reader (Synergy 2, Biotek or envision multilabel plate reader, Perkin Elmer). The percentage of inhibition was determined by comparing RLU derived from assays with no antibodies to RLU derived from assays with anti-*K. pneumoniae* mAbs and assays performed with a negative control mAb. Results from these neutralization assays are shown in FIG. 4. The KPD1, KPN44, KPN70, and KPL26 blocked O1 and O2 LPS activation of NF-κB, while KPN42, KPN17, KPL36, KPS3, KPS18, KPS24, and KPS44 showed moderate neutralizing activity against O2 LPS, but no activity against O1 LPS. All mAbs were tested in human IgG1 format.

Example 8: OPK Activity of Selected O2 mAbs

Figure 4A:
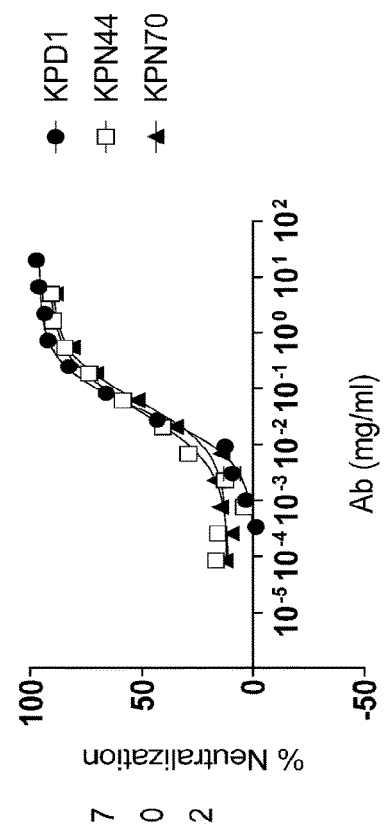
FIGS. 4A-4F shows LPS neutralization assays performed with selected monoclonal antibodies (mAbs). The % neutralization of the mAbs against LPS-O1 is shown in FIGS. 4A-4C, and the % neutralization of the mAbs against LPS-O2 is shown in FIGS. 4D-4F.
Figure 4B:
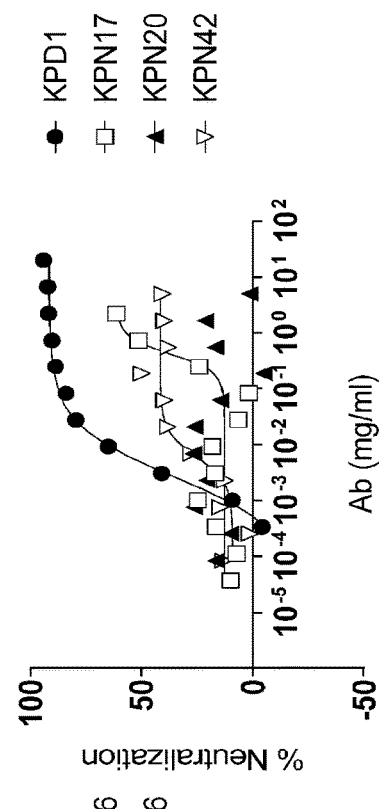
Figure 4C:
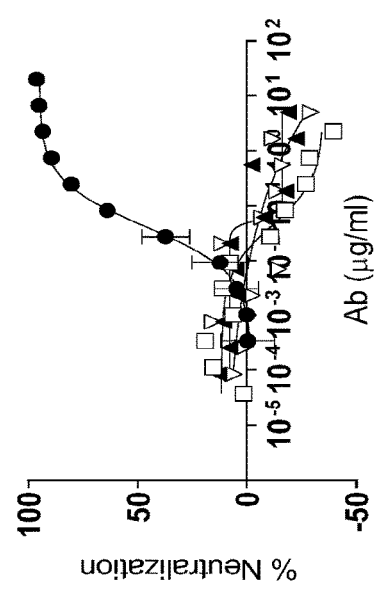
Figure 4D:
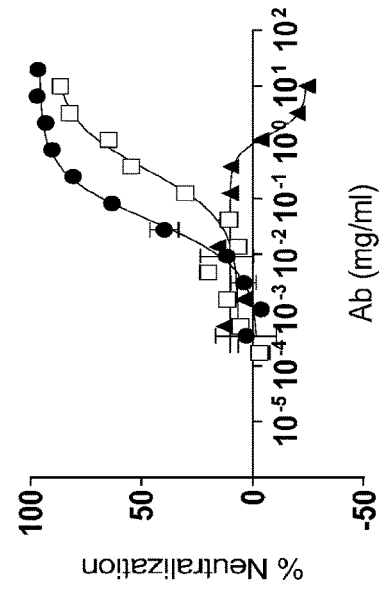
Figure 4E:
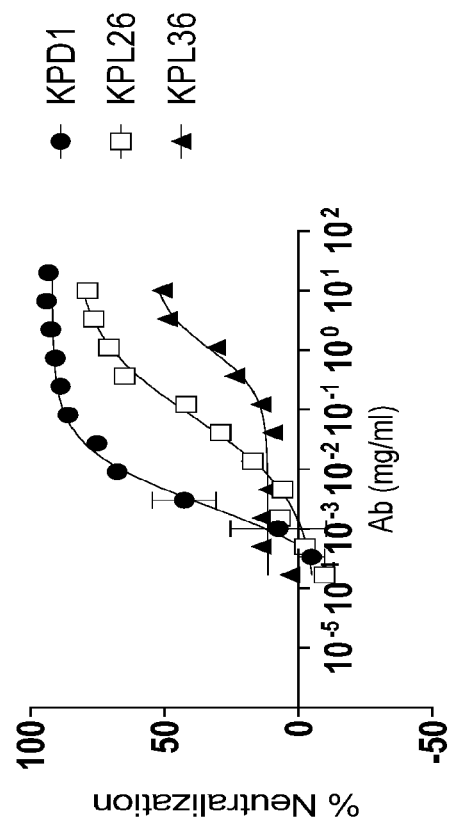
Figure 4F:
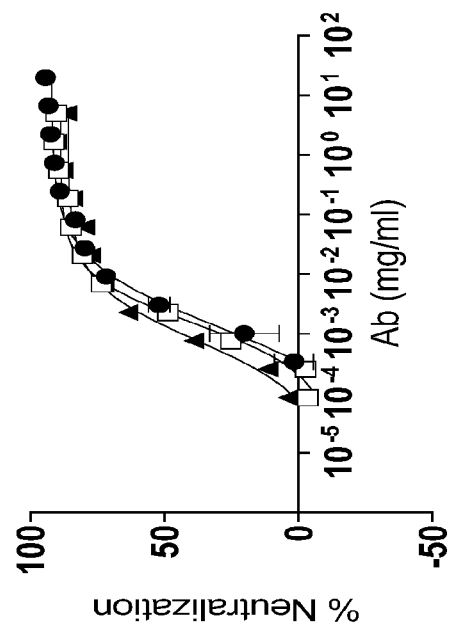
Figures 5A, 5B:
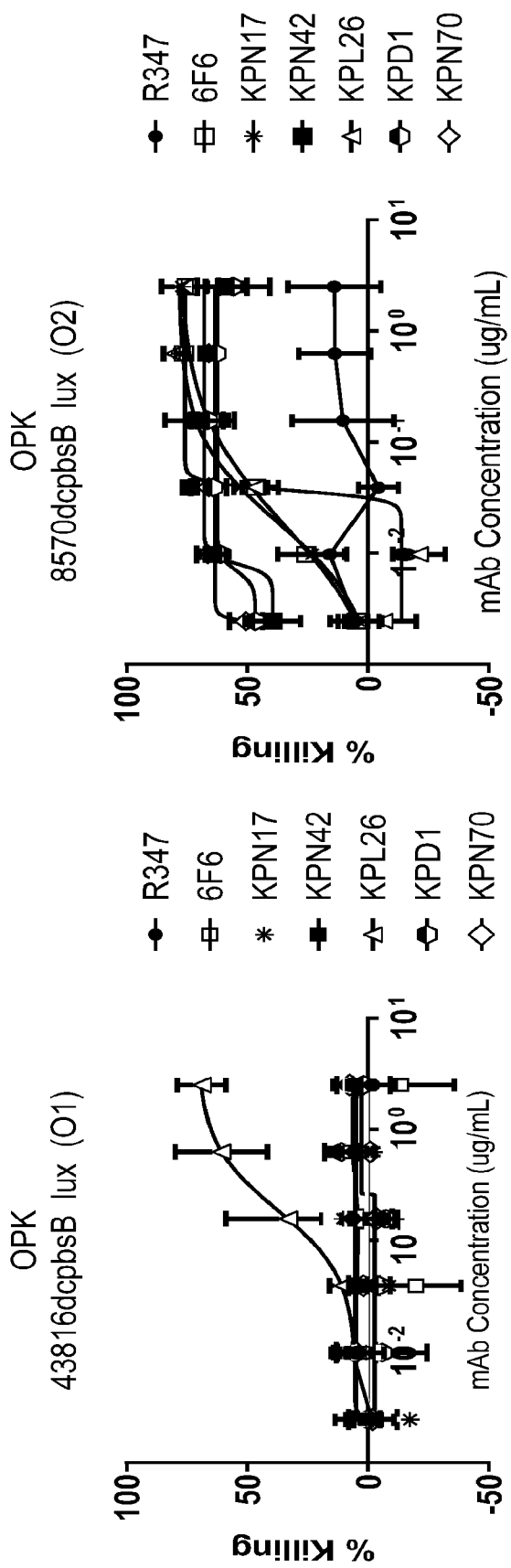
FIGS. 5A-5B show the opsonophagocytic killing (OPK) activity of selected anti-O2 monoclonal antibodies (mAbs). The OPK of these mAbs against an O1 strain of *K. pneumoniae* is shown in the graph in FIG. 5A, and the OPK of these mAbs against an O2 strain of *K. pneumoniae* is shown in the graph in FIG. 5B.

OPK activity of anti-O2 LPS mAbs was tested against O1 and O2 strains. Briefly, log phase cultures of luminescent *K. pneumoniae* strains 8570ΔcpsBLux (O2) and 43816ΔcpsBLux (O1) were diluted to ~2×10$^6$ cells/ml. *K. pneumoniae* cells, 5e5/well dimethylformamide (DMF) differentiated HL-60 cells, cleared baby rabbit serum (1:10 Cedarlane), and a series dilution of antibodies (2 ng-2.5 µg/mL) were mixed in 96-well plates and incubated at 37° C. for two hours with shaking (250 rpm). The relative light units (RLUs) were then measured using a multi-mode microplate reader (Synergy 2, Biotek or envision multilabel plate reader, Perkin Elmer). The percentage of killing was determined by comparing RLU derived from assays with no antibodies to RLU derived from assays with anti-*K. pneumoniae* mAbs and assays performed with a negative control mAb. Positive killing was determined where the percentage of killing is above 40%. All anti-O2 IgG1 mAbs tested showed strong OPK activity (80-100% killing) against O2 capsule mutant strains (FIG. 5 and FIG. 10). KPL26 induced OPK activity to both O1 and O2 strains (FIG. 5).

Example 9: Class III mAbs Protect in Lethal Pneumonia Models

C57/BL6 mice were obtained from Jackson Laboratories and maintained in a special pathogen-free facility. All animal experiments were conducted in accordance with Institutional Animal Care and Use Committee (IACUC) protocol and guidance. *K. pneumoniae* strains were grown on agar plates overnight and diluted in saline at proper concentration. The inoculum titer was determined by plating a serial dilution of bacteria onto agar plates prior to and post challenge. In acute pneumonia models, C57/BL6 mice were inoculated with 1e4 to 2e8 colony-forming units (CFU) of *K. pneumoniae* clinical isolates in 50 µl saline intranasally. Anti-*K pneumoniae* monoclonal antibodies (mAbs) and human IgG1 control antibodies were given 1-24 hour post bacterial challenge (therapeutic dosing). Mouse survival was monitored daily until up to day 8. Survival data of representative experiments were plotted in Graphpad Prism software.

Mice were challenged with 2e8 CFU of *Klebsiella pneumoniae* Carbanpenemase (KPC) strain Kp961842_O2 or with 3e8 CFU of KPC strain Kp977778_O2, followed by the administration of anti-O2 mAbs. When administered at a concentration of 2 mg/kg 1 hour post bacterial infection, Class III anti-O2 LPS mAbs KPN42, KPN179-IgG1, and KPS44v2017 protected mice from lethal bacterial challenge with the multi-drug resistant KPC strains Kp961842_O2 (FIG. 6, left panel, and FIG. 10) and Kp977778_O2 (FIG. 6B, right panel). KPN179-IgG3 also conferred protection, while the Class I mAb KPN70-hIgG1 or KPD1-IgG1 did not protect in these two models. Class II mAb KPL26 conferred moderate protection in a lethal O1 pneumonia model, while did not show protection in Kp961842_O2 pneumonia model.

Figure 7A:
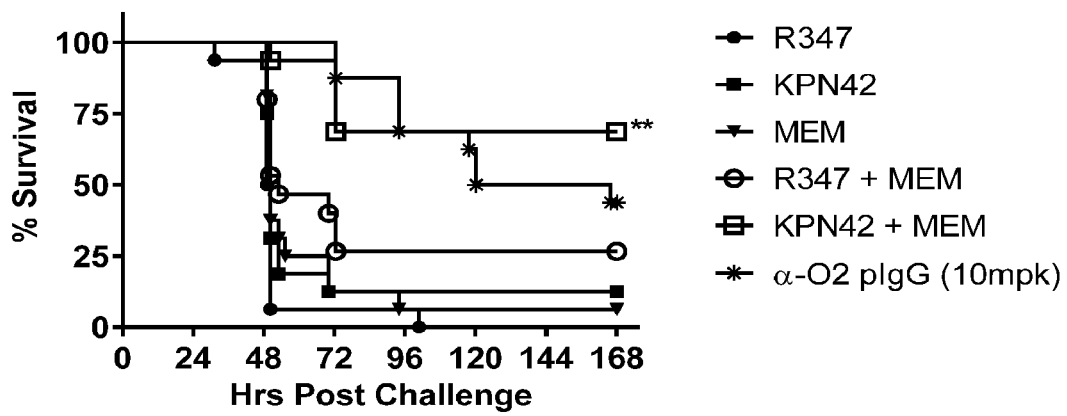
FIGS. 7A-7B show that the anti-O2 LPS monoclonal antibodies (mAbs) KPN42 and KPN179 have strong synergy with meropenem in a lethal pneumonia model, as measured by the % survival of mice at various time points post challenge.
Figure 7B:
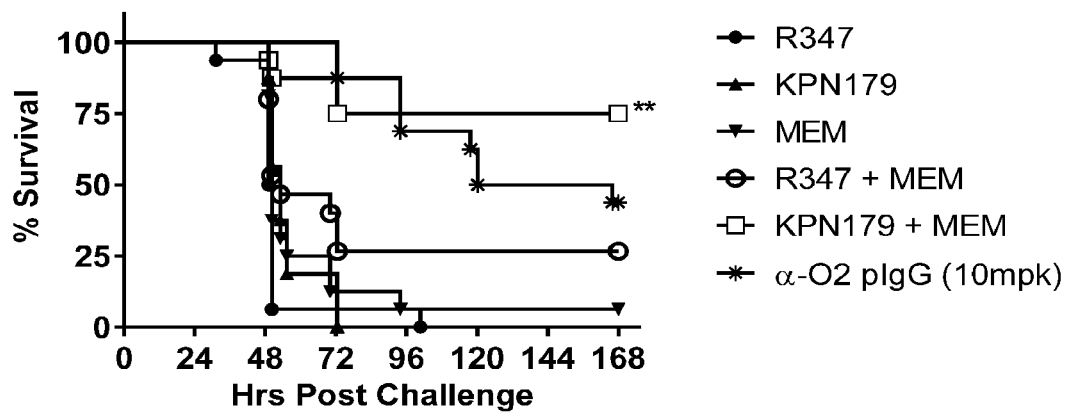

Example 10: Anti-O2 LPS mAbs KPN42 and KPN179 Show Strong Synergy with Antibiotic Meropenem in Lethal Pneumonia Model The lethal pneumonia model as described in Example 9 was used to assess the activity of anti-O2 LPS antibodies in combination with an antibiotic. Both antibiotic and antibody were administered 1 hour after bacterial infection. The combination of meropenem human equivalent dosage (50 mpk) with sub-therapeutic dosages (0.2 mpk) of KPN42 or KPN179 showed significantly improved protection compared to antibody or antibiotic monotherapy (FIG. 7). These results illustrate that administration of an anti-O2 antibody, including KPN42 or KPN179, sensitizes antibiotic resistant *Klebsiella pneumoniae* strains to antibiotic therapy and that sub-therapeutic doses of the anti-O2 antibodies KPN42 or KPN179 show strong synergy with antibiotics in antibiotic resistant *Klebsiella pneumoniae* strains.

Example 11: KPN42 Protects Up to 6 Hour Post Infection in Conjunction with Meropenem 50 mg/kg of meropenem and 2 mg/kg of antibody were administered at 1, 2, 4, 6, and 24 hour after bacterial infection, as described for the antibody and antibiotic combination studies in Examples 9 and 10. The combination of meropenem and KPN42 showed significantly better protection than a combination of a control mAb and meropenem up to 6 hours post infection (FIG. 8). The combination of KPN179 and meropenem conferred better protection than a combination of a control mAb and meropenem up to 4 hours post infection (FIG. 8). Together with Example 10, these results illustrate the efficacy of administering an anti-O2 antibody, including KPN42 or KPN179, after bacterial infection (i.e., therapeutic administration).

Example 12: KPN42 and KPN179 Sequence Optimization

In order to reduce sequence liability for mAb development and potential anti-drug antibody, an unpaired cysteine in the light chain CDR3 of KPN42 was exchanged with alanine (see FIG. 9, antibody A (KPN42-FR-GL-VH/KPN42-FR-GL-C105A-VL) and antibody B (KPN42-FR-1-2-4-GL-VH/KPN42-FR-GL-C105A-VL)), and somatic mutations in the frameworks of KPN42 (see FIG. 9, antibody A) or in the frameworks 1, 2, and 4 of KPN42 (see FIG. 9, antibody B) were replace with germline residues. Similarly an unpaired cysteine in the light chain CDR3 of KPN179 was exchanged with alanine, and an asparagine residue forming a deamidation motif in the KPN179 heavy chain CDR1 was replaced with the germline residue serine (see FIG. 9, antibody C (KPN179-FR-GL-N35S-VH/KPN179-FR-GL-C105A-VL) and antibody D (KPN179-FR-1-2-4-GL-N35S-VH/KPN179-FR-GL-C105A-VL)), somatic mutations in the frameworks of KPN179 (see FIG. 9, antibody C) or in frameworks 1, 2 and 4 of KPN179 were replaced with germline residues (see FIG. 9, antibody D). Replacement of all somatic mutations in KPN179 VH and VL frameworks with germline residues (see FIG. 9, antibody C) significantly reduced binding to O2 LPS. The rest of the mutations showed comparable binding to parent antibodies (see, e.g., FIG. 9, antibodies A, B and D).

Example 13: Anti-O2 Antigen Antibodies Bind to Clinically Relevant *Klebsiella*

In order to determine if anti-O2 antigen antibodies bind to clinically relevant *Klebsiella* strains, the binding of anti-O2 mAbs to clinical isolates was determined by western blot assay. Briefly, purified LPS or bacterial lysates were subjected to sodium dodecyl sulfate-polyacrylaminde gel electrophoresis (SDS-PAGE). Separated proteins and LPS were transferred from gels to nitrocellulose membranes with an iBlot apparatus based on the manufacturer's recommendation. (Life Technology). Membranes were then blocked with Casein blocking buffer before being probed with O2 (KPD1) monoclonal antibodies or antibodies specific for other LPS serotypes. After three washes with 0.05% Tween in PBS buffer (PBS-T), blots were incubated with JRDye680 or 800 fluorescent $2^{nd}$ antibodies (Licor). Blots were visualized with an Odyssey Image Station. Distinct laddering patterns were observed for LPS blots. Assays were repeated at least twice. In some circumstances, bacterial lysates were treated with Protease K to remove protein components before the western blot analysis. Strains that bind to KPD1, but not to other LPS serotype specific mAbs were characterized as O2 strains. A summary of the clinically relevant *Klebsiella* strains to which anti-O2 mAbs KPD1 and KPN42 bind is shown in Table 8.

TABLE 8

Summary of clinical *Klebsiella* strains to which anti-O2 mAbs bind.

|  | Region | Country | IHMA Number | Body Location | Facility Name | Molecular Summary |
|---|---|---|---|---|---|---|
| 1 | Latin America | Chile | 847204 | INT: Wound | Surgery General | SHV-11(b); TEM-1(b); KPC-2; |
| 2 | Latin America | Argentina | 847378 | Respiratory: Endotracheal aspirate | Medicine ICU | KPC-2; |
| 3 | Latin America | Argentina | 847383 | Respiratory: Bronchoalveolar lavage | Medicine ICU | SHV-11(b); TEM-1(b); CTX-M-15; NDM-1; |
| 4 | Latin America | Argentina | 847387 | Respiratory: Bronchoalveolar lavage | Medicine ICU | SHV-11(b); TEM-1(b); CTX-M-15; NDM-1; |
| 5 | Latin America | Argentina | 847694 | Unknown | Medicine ICU | SHV-11(b); KPC-2; |
| 6 | Latin America | Argentina | 847747 | Respiratory: Endotracheal aspirate | Medicine ICU | SHV-11(b); KPC-2; |
| 7 | Europe | Greece | 848832 | Respiratory: Sputum | General Unspecified ICU | SHV-1(b); CTX-M-15; KPC-2; |
| 8 | Europe | Greece | 848844 | Respiratory: Sputum | General Unspecified ICU | SHV-12(e); KPC-2; |
| 9 | Europe | Greece | 848876 | Respiratory: Bronchial brushing | Medicine General | SHV-1(b); TEM-1(b); CTX-M-2; |
| 10 | Middle East | Israel | 849156 | Bodily Fluids: Peritoneal | Medicine General | SHV-1(b); TEM-1(b); CTX-M-2; |
| 11 | Middle East | Israel | 849584 | INT: Abscess | Pediatric ICU | SHV- 11(b); TEM- 1(b); KPC-3; |
| 12 | Middle East | Israel | 849585 | INT: Wound | Medicine General | SHV-1(b); KPC-3; |
| 13 | North America | United States | 854022 | Respiratory: Endotracheal aspirate | General Unspecified ICU | SHV-11(b); TEM-1(b); CTX-M-15; OXA-48(c) |
| 14 | North America | United States | 857973 | Respiratory: Endotracheal aspirate | Other | SHV-11(b); TEM-1(b); CTX-M-15; OXA-48(c) |
| 15 | North America | United States | 857978 | Respiratory: Endotracheal aspirate | Medicine General | SHV-11(b); TEM-1(b); CTX-M-15; |
| 16 | North America | United States | 863890 | INT: Decubitus | None Given | SHV-11(b); TEM-1(b); KPC-2; |
| 17 | North America | United States | 863930 | Bodily Fluids: Peritoneal | Surgery ICU | SHV-11(b); TEM-1(b); KPC-2; |
| 18 | Europe | Italy | 867822 | Bodily Fluids: Peritoneal | Surgery General | SHV-11(b); TEM-1(b); KPC-3; |
| 19 | Middle East | Israel | 869311 | Respiratory: Bronchial brushing | Medicine ICU | SHV-11(b); KPC-3; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 20 | Europe | Romania | 869918 | Respiratory: Sputum | General Unspecified ICU | SHV-11(b); TEM-1(b); KPC-2; |
| 21 | Europe | Russia | 874316 | Respiratory: Sputum | General Unspecified ICU | SHV-11(b); CTX-M-55; OXA-48(c) |
| 22 | Europe | Russia | 874329 | Respiratory: Other | General Unspecified ICU | |
| 23 | Europe | Russia | 874876 | Respiratory: Sputum | Pediatric ICU | SHV-11(b); TEM-1(b); CTX-M-15; KPC-2; |
| 24 | Europe | Belgium | 875655 | Respiratory: Endotracheal aspirate | General Unspecified ICU | SHV-28(e); TEM-1(b); CTX-M-15; KPC-3; |
| 25 | Europe | Italy | 875926 | Respiratory: Sputum | Medicine General | SHV-11(b); KPC-3; |
| 26 | Europe | Italy | 875928 | Respiratory: Endotracheal aspirate | Medicine ICU | SHV-2(e); |
| 27 | Europe | Italy | 875931 | Respiratory: Bronchoalveolar lavage | Medicine General | SHV-11(b); KPC-3; |
| 28 | Latin America | Brazil | 900678 | Respiratory: Endotracheal aspirate | Medicine ICU | SHV-OSBL(u); TEM-OSBL(u); VEB-2; KPC-2; |
| 29 | Europe | Italy | 918904 | Respiratory: Bronchoalveolar lavage | Medicine General | SHV-OSBL(u); TEM-OSBL(u); KPC-3; |
| 30 | Europe | Greece | 921185 | Respiratory: Sputum | Medicine General | SHV-12(e); KPC-2; |
| 31 | Europe | Turkey | 926871 | Respiratory: Endotracheal aspirate | General Unspecified ICU | SHV-OSBL(u); CTX-M-15; OXA-48(c) |
| 32 | Europe | Turkey | 926901 | Respiratory: Sputum | Medicine General | SHV-OSBL(u); CTX-M-15; OXA-48(c) |
| 33 | Europe | Greece | 927850 | Respiratory: Endotracheal aspirate | Medicine ICU | SHV-OSBL(u); OXA-48(c) |
| 34 | Europe | Greece | 927897 | Respiratory: Endotracheal aspirate | General Unspecified ICU | SHV-OSBL(u); TEM-OSBL(u); CTX-M-2; |
| 35 | Europe | Greece | 927898 | Respiratory: Endotracheal aspirate | General Unspecified ICU | SHV-OSBL(u); KPC-2; |
| 36 | Europe | Greece | 927915 | Respiratory: Endotracheal aspirate | General Unspecified ICU | |
| 37 | Europe | Greece | 927952 | Respiratory: Endotracheal aspirate | General Unspecified ICU | |
| 38 | Europe | Greece | 927963 | Respiratory: Endotracheal aspirate | General Unspecified ICU | |
| 39 | Europe | Greece | 927964 | Respiratory: Endotracheal aspirate | General Unspecified ICU | TEM-OSBL(u); CTX-M-15; CTX-M-27; NDM-1; |
| 40 | Middle East | Israel | 937433 | Respiratory: Sputum | Medicine General | SHV-OSBL(u); KPC-3; |
| 41 | Europe | Romania | 938940 | INT: Wound | Medicine General | SHV-OSBL(u); TEM-OSBL(u); KPC-2; |
| 42 | Europe | Romania | 939003 | Respiratory: Endotracheal aspirate | Medicine ICU | SHV-OSBL(u); TEM-OSBL(u); KPC-2; |
| 43 | Latin America | Argentina | 939866 | Respiratory: Lungs | Surgery ICU | SHV-OSBL(u); TEM-OSBL(u); CTX-M-15; OXA-48(c) |
| 44 | Latin America | Argentina | 939929 | Respiratory: Bronchial brushing | General Unspecified ICU | SHV-12(e); TEM-OSBL(u); KPC-2; |
| 45 | Latin America | Argentina | 939943 | Respiratory: Bronchial brushing | General Unspecified ICU | SHV-12(e); TEM-OSBL(u); KPC-2; |
| 46 | Europe | Italy | 946889 | Respiratory: Bronchoalveolar lavage | General Unspecified ICU | SHV-OSBL(u); TEM-OSBL(u); KPC-2; |
| 47 | Europe | Italy | 946897 | Respiratory: Bronchial brushing | Medicine General | SHV-OSBL(u); KPC-3; |
| 48 | Europe | Italy | 946900 | Respiratory: Bronchial brushing | Surgery General | SHV-OSBL(u); TEM-OSBL(u); KPC-3; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 49 | Europe | Italy | 947475 | Respiratory: Lungs | Medicine General | SHV-OSBL(u); TEM-OSBL(u); CTX-M-65; KPC-2; |
| 50 | Latin America | Colombia | 960228 | INT: Wound | Medicine General | SHV-OSBL(u); TEM-OSBL(u); KPC-2; |
| 51 | Latin America | Colombia | 960249 | Respiratory: Other | Medicine General | SHV-OSBL(u); KPC-2; |
| 52 | North America | United States | 961842 | Respiratory: Bronchoalveolar lavage | Medicine ICU | SHV-12(e); TEM-OSBL(u); CTX-M-65; KPC-2; |
| 53 | Africa | South Africa | 963278 | Respiratory: Endotracheal aspirate | Medicine ICU | SHV-12(e); KPC-2; |
| 54 | South Pacific | Philippines | 966426 | Respiratory: Sputum | Medicine General | SHV-12(e); TEM-OSBL(u); CTX-M-15; NDM-7; |
| 55 | Europe | Italy | 971222 | Respiratory: Bronchial brushing | Medicine General | SHV-OSBL(u); TEM-OSBL(u); KPC-3; |
| 56 | Europe | Russia | 975977 | Respiratory: Endotracheal aspirate | Surgery ICU | SHV-12(e); TEM-OSBL(u); KPC-2; |
| 57 | Europe | Russia | 976037 | Respiratory: Endotracheal aspirate | Surgery ICU | SHV-OSBL(u); TEM-OSBL(u); CTX-M-15; OXA-244(c) |
| 58 | Europe | Russia | 976078 | Respiratory: Endotracheal aspirate | Surgery ICU | SHV-12(e); TEM-OSBL(u); KPC-2; |
| 59 | Latin America | Argentina | 977128 | INT: Wound | Medicine General | SHV-12(e); TEM-OSBL(u); KPC-2; |
| 60 | Latin America | Argentina | 977314 | Bodily Fluids: Peritoneal | Medicine General | SHV-12(e); KPC-2; |
| 61 | North America | United States | 977778 | GI: Abscess | Medicine General | SHV-OSBL(u); KPC-3; |
| 62 | North America | United States | 978960 | INT: Wound | Medicine General | SHV-12(e); TEM-OSBL(u); KPC-3; |
| 63 | North America | United States | 978971 | Respiratory: Sputum | Medicine ICU | SHV-OSBL(u); TEM-OSBL(u); KPC-3; |
| 64 | North America | United States | 979049 | Respiratory: Sputum | Medicine General | CTX-M-12; KPC-2; |
| 65 | North America | United States | 979288 | Respiratory: Sputum | Surgery General | SHV-OSBL(u); KPC-3; |
| 66 | North America | United States | 979290 | Respiratory: Sputum | Medicine ICU | SHV-12(e); TEM-OSBL(u); KPC-3; |
| 67 | Latin America | Brazil | 990976 | Bodily Fluids: Peritoneal | None Given | SHV-OSBL(u); CTX-M-2; KPC-2; |
| 68 | Latin America | Brazil | 991499 | Respiratory: Endotracheal aspirate | Medicine ICU | SHV-OSBL(u); TEM-OSBL(u); CTX-M-15; NDM-1; |
| 69 | Middle East | Israel | 994039 | Respiratory: Endotracheal aspirate | Medicine General | SHV-OSBL(u); CTX-M-15; NDM-1; |
| 70 | Asia | China | 995976 | Respiratory: Sputum | Pediatric ICU | SHV-OSBL(u); TEM-OSBL(u); CTX-M-15; OXA-48(c) |
| 71 | Europe | Greece | 1013421 | Respiratory: Sputum | Medicine General | |
| 72 | Europe | Greece | 1013442 | INT: Skin Ulcer | General Unspecified ICU | SHV-OSBL(u); CTX-M-15; OXA-48(c) |
| 73 | Africa | Nigeria | 1043242 | INT: Wound | Medicine General | SHV-55(e); TEM-OSBL(u); CTX-M-15; NDM-1; |
| 74 | Europe | Russia | 1049163 | Respiratory: Endotracheal aspirate | Medicine ICU | SHV-OSBL(u); TEM-OSBL(u); CTX-M-15; |
| 75 | Europe | Russia | 1049391 | Respiratory: Bronchoalveolar lavage | Surgery ICU | SHV-12(e); TEM-OSBL(u); KPC-2; |
| 76 | Europe | Russia | 1049400 | Respiratory: Bronchoalveolar lavage | Surgery ICU | SHV-OSBL(u); TEM-OSBL(u); CTX-M-15; |
| 77 | Europe | Russia | 1049474 | Respiratory: Bronchoalveolar lavage | Surgery General | SHV-12(e); TEM-OSBL(u); KPC-2; |
| 78 | Europe | Russia | 1049592 | Respiratory: Sputum | Medicine ICU | SHV-OSBL(u); CTX-M-3; OXA-48(c) |
| 79 | Europe | Spain | 1073956 | Respiratory: Bronchial brushing | Medicine ICU | SHV-OSBL(u); TEM-OSBL(u); KPC-3; |
| 80 | South Pacific | Philippines | 1079540 | CVS: Blood | Pediatric ICU | SHV-12(e); TEM-OSBL(u); KPC-3; |
| 81 | South Pacific | Philippines | 1079544 | Respiratory: Endotracheal aspirate | Medicine ICU | TEM-OSBL(u); KPC-3; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 82 | Europe | Italy | 1081144 | Respiratory: Sputum | Medicine ICU | |
| 83 | Europe | Greece | 1081949 | CVS: Blood | Medicine General | |
| 84 | Europe | Greece | 1081956 | CVS: Blood | Surgery General | SHV-OSBL(u); TEM-OSBL(u); KPC-3; |
| 85 | Europe | Greece | 1081997 | Respiratory: Bronchoalveolar lavage | General Unspecified ICU | SHV-OSBL(u); TEM-OSBL(u); KPC-3; |
| 86 | Europe | Greece | 1082051 | Respiratory: Bronchoalveolar lavage | General Unspecified ICU | SHV-12(e); TEM-OSBL(u); KPC-2; |
| 87 | Europe | Greece | 1082058 | CVS: Blood | Other | |
| 88 | Europe | Greece | 1082074 | CVS: Blood | General Unspecified ICU | |
| 89 | Europe | Greece | 1082098 | CVS: Blood | General Unspecified ICU | |
| 90 | Asia | Korea, South | 1085601 | Respiratory: Sputum | Medicine General | SHV-12(e); TEM-OSBL(u); KPC-2; |
| 91 | Europe | Hungary | 1090072 | Bodily Fluids: Peritoneal | Surgery General | |
| 92 | Africa | South Africa | 1093894 | Bodily Fluids: Peritoneal | General Unspecified ICU | SHV-OSBL(u); CTX-M-15; |
| 93 | Latin America | Argentina | 1093960 | Respiratory: Bronchoalveolar lavage | Medicine ICU | SHV-OSBL(u); CTX-M-15; KPC-2; |
| 94 | Latin America | Argentina | 1093976 | Respiratory: Bronchoalveolar lavage | Medicine ICU | SHV-OSBL(u); KPC-2; |
| 95 | Latin America | Argentina | 1093980 | Bodily Fluids: Peritoneal | Emergency Room | |
| 96 | North America | United States | 1105534 | Respiratory: Bronchoalveolar lavage | Medicine General | SHV-OSBL(u); TEM-OSBL(u); KPC-2; |
| 97 | North America | United States | 1105547 | Respiratory: Bronchoalveolar lavage | Medicine General | |
| 98 | Latin America | Colombia | 1109216 | Bodily Fluids: Peritoneal | Surgery General | SHV-OSBL(u); KPC-3; |
| 99 | Europe | Czech Republic | 1120042 | Respiratory: Sputum | Medicine ICU | SHV-OSBL(u); TEM-OSBL(u); CTX-M-15; |
| 100 | Europe | Austria | 1127552 | INT: Wound | Medicine ICU | |
| 101 | Europe | Italy | 1137983 | GI: Abscess | Surgery General | SHV-OSBL(u); |
| 102 | Europe | Italy | 1137984 | Respiratory: Bronchial brushing | Medicine ICU | SHV-12(e); TEM-OSBL(u); KPC-2; |
| 103 | Europe | Italy | 1137991 | Bodily Fluids: Peritoneal | Surgery General | |
| 104 | Latin America | Chile | 969740 | INT: Wound | Surgery General | SHV-OSBL(u); TEM-OSBL(u); CTX-M-15; |
| 105 | Latin America | Chile | 969743 | Respiratory: Endotracheal aspirate | Medicine General | SHV-OSBL(u); TEM-OSBL(u); CTX-M-15; CTX-M-2; |
| 106 | Latin America | Argentina | 977113 | Respiratory: Endotracheal aspirate | Medicine ICU | |
| 107 | North America | United States | 1094435 | INT: Wound | Medicine General | |
| 108 | North America | United States | 1147894 | Respiratory: Endotracheal aspirate | Medicine ICU | |
| 109 | Europe | Italy | 947566 | GU: Urine | Medicine General | SHV-12(e); VIM-New Variant; |
| 110 | Latin America | Argentina | 847700 | GU: Urine | Medicine General | TEM-1(b); KPC-2; |
| 111 | Latin America | Argentina | 847708 | GU: Urine | Medicine ICU | SHV-11(b); TEM-1(b); KPC-2; |
| 112 | Europe | Greece | 848827 | GU: Urine | Emergency Room | SHV-11(b); TEM-1(b); KPC-2; |
| 113 | Europe | Greece | 848828 | GU: Urine | General Unspecified ICU | SHV-11(b); TEM-1(b); KPC-2; |
| 114 | Europe | Greece | 848829 | GU: Urine | Other | SHV-11(b); KPC-2; |
| 115 | Europe | Greece | 848843 | GU: Urine | Medicine General | SHV-11(b); TEM-1(b); KPC-2; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 116 | Middle East | Israel | 869317 | GU: Urine | Other | SHV-11(b); TEM-1(b); KPC-3; |
| 117 | North America | United States | 872020 | GU: Urine | Medicine ICU | SHV-28(e); TEM-1(b); CTX-M-15; KPC-2; |
| 118 | Europe | Turkey | 889939 | GU: Urine | Surgery ICU | SHV-1(b); OXA-48(c) |
| 119 | North America | United States | 897067 | GU: Urine | Surgery ICU | SHV-11(b); KPC-3; |
| 120 | Latin America | Brazil | 900687 | GU: Urine | Surgery General | TEM-1(b); CTX-M-14; KPC-2; |
| 121 | Latin America | Brazil | 900765 | GU: Urine | Emergency Room | SHV-11(b); TEM-1(b); CTX-M-14; KPC-2; |
| 122 | Europe | Greece | 921177 | GU: Ureter | Medicine General | SHV-12(e); TEM-OSBL(u); CMY-13; KPC-2; VIM-1; |
| 123 | Europe | Greece | 927901 | GU: Urine | Medicine General | SHV-12(e); |
| 124 | Europe | Greece | 927949 | GU: Urine | Medicine General | SHV-12(e); TEM-OSBL(u); KPC-2; |
| 125 | Europe | Greece | 927981 | GU: Urine | Medicine General | SHV-12(e); TEM-OSBL(u); KPC-2; |
| 126 | Europe | Greece | 928020 | GU: Urine | Pediatric General | SHV-12(e); TEM-OSBL(u); KPC-2; |
| 127 | Europe | Russia | 976026 | GU: Urine | Surgery ICU | SHV-OSBL(u); TEM-OSBL(u); CTX-M-15; OXA-244(c) |
| 128 | North America | United States | 978959 | GU: Urine | Medicine General | SHV-OSBL(u); TEM-OSBL(u); KPC-3; |
| 129 | Europe | Belgium | 979620 | GU: Urine | Medicine General | SHV-OSBL(u); NDM-1; OXA-232(c) |
| 130 | Latin America | Brazil | 990975 | GU: Urine | Medicine General | SHV-OSBL(u); TEM-OSBL(u); CTX-M-15; KPC-2; |
| 131 | Latin America | Brazil | 991020 | GU: Urine | Medicine ICU | SHV-OSBL(u); TEM-OSBL(u); KPC-2; |
| 132 | Latin America | Brazil | 991969 | GU: Urine | Medicine ICU | SHV-OSBL(u); KPC-2; |
| 133 | Latin America | Colombia | 960227 | GU: Urine | Medicine General | SHV-OSBL(u); TEM-OSBL(u); KPC-3; |
| 134 | South Pacific | Australia | 1035778 | GU: Urine | Surgery General | SHV-OSBL(u); TEM-OSBL(u); IMP-4; |
| 135 | Europe | Russia | 1048991 | GU: Urine | Surgery General | SHV-OSBL(u); TEM-OSBL(u); CTX-M-15; OXA-48(c) |
| 136 | Latin America | Colombia | 1109206 | GU: Urine | Other | |
| 137 | Latin America | Mexico | 1138246 | GU: Urine | Medicine General | |
| 138 | Africa | Nigeria | 1143069 | GU: Urine | Emergency Room | |
| 139 | Africa | Nigeria | 1143099 | GU: Urine | Medicine General | |
| 140 | Middle East | Kuwait | 1143576 | GU: Urine | Emergency Room | |
| 141 | South Pacific | Philippines | 850792 | Bodily Fluids: Abcess/Pus | Other | SHV-1(b); TEM-1(b); CTX-M-15; |
| 142 | South Pacific | Philippines | 845353 | Respiratory: Sputum | Other | SHV-1(b); CTX-M-15; |
| 143 | South Pacific | Philippines | 845587 | Respiratory: Sputum | Medicine General | SHV-31(e); |
| 144 | Europe | Italy | 848597 | Respiratory: Sputum | Surgery ICU | SHV-12(e); |
| 145 | Europe | Czech Republic | 851661 | Respiratory: Sputum | Medicine ICU | SHV-5(e); |
| 146 | North America | United States | 851698 | GI: Stomach | Surgery General | SHV-11(b); DHA-1; |
| 147 | North America | United States | 851702 | GI: Small Colon | Surgery General | SHV-12(e); TEM-1(b); |
| 148 | Latin America | Mexico | 854739 | Respiratory: Other | Pediatric General | SHV-11(b); TEM-1(b); CTX-M-15; DHA-1; |
| 149 | South Pacific | Philippines | 855930 | Respiratory: Endotracheal aspirate | Surgery General | SHV-11(b); TEM-1(b); CTX-M-15; |
| 150 | Latin America | Venezuela | 858492 | Respiratory: Sputum | Emergency Room | SHV-5(e); CTX-M-3; |
| 151 | Latin America | Venezuela | 866356 | Bodily Fluids: Peritoneal | None Given | SHV-5(e); CTX-M-15; |
| 152 | Middle East | Israel | 869315 | GU: Urethra | Medicine General | SHV-11(b); TEM-1(b); CTX-M-15; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 153 | Europe | Russia | 870216 | Respiratory: Sputum | Medicine General | SHV-11(b); TEM-1(b); CTX-M-14; |
| 154 | Europe | Russia | 870245 | Respiratory: Sputum | Medicine General | SHV-11(b); TEM-1(b); CTX-M-15; |
| 155 | Europe | Russia | 870258 | INT: Wound | Surgery General | SHV-11(b); CTX-M-55; |
| 156 | Asia | China | 871354 | Respiratory: Sputum | Other | SHV-11(b); TEM-1(b); CTX-M-15; |
| 157 | North America | United States | 873464 | Respiratory: Endotracheal aspirate | Medicine General | SHV-1(b); TEM-1(b); CTX-M-15; |
| 158 | Europe | Russia | 874317 | Respiratory: Sputum | General Unspecified ICU | SHV-11(b); TEM-1(b); CTX-M-28; |
| 159 | Europe | Russia | 874882 | Respiratory: Bronchoalveolar lavage | Medicine ICU | SHV-1(b); TEM-1(b); CTX-M-15; |
| 160 | Europe | Russia | 874899 | Respiratory: Bronchoalveolar lavage | Surgery General | SHV-11(b); CTX-M-15; |
| 161 | Europe | Russia | 874907 | Respiratory: Bronchoalveolar lavage | Medicine General | SHV-11(b); TEM-1(b); CTX-M-15; CMY-2; |
| 162 | Europe | Russia | 874921 | Respiratory: Bronchoalveolar lavage | Medicine ICU | SHV-12(e); |
| 163 | Africa | South Africa | 884275 | Respiratory: Endotracheal aspirate | Pediatric ICU | SHV-11(b); TEM-1(b); CTX-M-15; CTX-M-2; |
| 164 | Africa | South Africa | 884335 | Respiratory: Sputum | Medicine General | SHV-OSBL(u); TEM-OSBL(u); CTX-M-15; |
| 165 | Latin America | Brazil | 900685 | Respiratory: Endotracheal aspirate | Medicine ICU | SHV-OSBL(u); TEM-12(e); CTX-M-15; |
| 166 | Europe | Greece | 921041 | INT: Wound | Medicine General | SHV-12(e); |
| 167 | Europe | France | 921564 | Respiratory: Endotracheal aspirate | Surgery ICU | SHV-OSBL(u); TEM-OSBL(u); CTX-M-15; |
| 168 | North America | United States | 928335 | Respiratory: Bronchoalveolar lavage | Medicine ICU | SHV-OSBL(u); TEM-OSBL(u); CTX-M-15; |
| 169 | North America | United States | 928336 | Respiratory: Bronchoalveolar lavage | Medicine ICU | SHV-OSBL(u); TEM-OSBL(u); CTX-M-15; |
| 170 | Europe | Portugal | 938166 | Respiratory: Sputum | Surgery General | SHV-OSBL(u); TEM-OSBL(u); CTX-M-15; OXA-48(c) |
| 171 | Europe | Portugal | 938170 | Respiratory: Endotracheal aspirate | Surgery ICU | SHV-12(e); TEM-OSBL(u); CTX-M-14; |
| 172 | Europe | Romania | 938937 | INT: Wound | Medicine General | SHV-OSBL(u); TEM-OSBL(u); CTX-M-15; |
| 173 | Asia | Taiwan | 949399 | Respiratory: Other | Medicine ICU | SHV-12(e); |
| 174 | Latin America | Mexico | 950099 | Respiratory: Sputum | Medicine General | SHV-12(e); |
| 175 | Latin America | Mexico | 950104 | Respiratory: Endotracheal aspirate | Surgery General | SHV-12(e); |
| 176 | South Pacific | Philippines | 957823 | Respiratory: Endotracheal aspirate | Medicine ICU | SHV-OSBL(u); TEM-OSBL(u); CTX-M-15; |
| 177 | South Pacific | Philippines | 957905 | Respiratory: Endotracheal aspirate | Medicine General | SHV-12(e); TEM-OSBL(u); CTX-M-15; DHA-1; |
| 178 | South Pacific | Philippines | 957920 | Respiratory: Endotracheal aspirate | Medicine ICU | SHV-OSBL(u); TEM-OSBL(u); CTX-M-15; |
| 179 | South Pacific | Philippines | 957921 | Respiratory: Sputum | Medicine General | SHV-OSBL(u); TEM-OSBL(u); CTX-M-15; |
| 180 | Asia | Taiwan | 958118 | Respiratory: Bronchoalveolar lavage | Medicine ICU | SHV-OSBL(u); TEM-OSBL(u); CTX-M-15; |
| 181 | Europe | Russia | 975237 | Respiratory: Bronchoalveolar lavage | Surgery ICU | SHV-OSBL(u); TEM-OSBL(u); CTX-M-15; |
| 182 | Europe | Russia | 975238 | Respiratory: Bronchoalveolar lavage | Pediatric ICU | SHV-5(e); CTX-M-15; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 183 | Europe | Russia | 975905 | Respiratory: Bronchoalveolar lavage | Surgery ICU | SHV-OSBL(u); TEM-OSBL(u); CTX-M-15; DHA-1; |
| 184 | Europe | Russia | 975906 | Respiratory: Bronchoalveolar lavage | Surgery ICU | SHV-12(e); |
| 185 | Europe | Russia | 977430 | GU: Urine | Surgery General | SHV-OSBL(u); TEM-OSBL(u); CTX-M-15; |
| 186 | Europe | Poland | 985195 | Respiratory: Sputum | Medicine General | SHV-12(e); TEM-OSBL(u); |
| 187 | Asia | Korea, South | 990759 | Respiratory: Sputum | Medicine General | SHV-OSBL(u); TEM-OSBL(u); CTX-M-15; |
| 188 | Asia | Korea, South | 990778 | Respiratory: Sputum | Medicine ICU | SHV-OSBL(u); |
| 189 | Asia | Malaysia | 993593 | GU: Urine | Pediatric General | SHV-OSBL(u); TEM-OSBL(u); CTX-M-15; |
| 190 | Middle East | Israel | 1007663 | Respiratory: Endotracheal aspirate | Medicine General | SHV-OSBL(u); TEM-OSBL(u); CTX-M-15; |
| 191 | Middle East | Israel | 1007677 | Bodily Fluids: Peritoneal | Surgery General | SHV-OSBL(u); TEM-OSBL(u); CTX-M-15; |
| 192 | Europe | Russia | 1049171 | Respiratory: Endotracheal aspirate | Medicine ICU | SHV-OSBL(u); TEM-OSBL(u); CTX-M-15; |
| 193 | Europe | Russia | 1049223 | Respiratory: Bronchoalveolar lavage | Surgery General | SHV-OSBL(u); CTX-M-15; |
| 194 | Europe | Russia | 1049540 | Respiratory: Sputum | Medicine General | |
| 195 | Europe | Russia | 1049545 | Respiratory: Bronchoalveolar lavage | Surgery General | |
| 196 | Europe | Russia | 1049870 | Respiratory: Bronchoalveolar lavage | Medicine General | SHV-2A(e); TEM-1(b); CTX-M-15; |
| 197 | Latin America | Venezuela | 1073801 | Respiratory: Endotracheal aspirate | Medicine ICU | SHV-36(u); |
| 198 | Asia | Korea, South | 1085618 | Respiratory: Sputum | Medicine General | CTX-M-15; |
| 199 | North America | United States | 873460 | Respiratory: Sputum | Medicine General | SHV-11(b); CTX-M-15; |
| 200 | Europe | Russia | 874383 | Respiratory: Endotracheal aspirate | General Unspecified ICU | SHV-28(e); TEM-1(b); CTX-M-15; DHA-1; |
| 201 | Europe | Russia | 875080 | Respiratory: Sputum | Surgery ICU | SHV-12(e); TEM-OSBL(u); |
| 202 | North America | United States | 882753 | INT: Wound | Medicine General | SHV-OSBL(u); TEM-OSBL(u); CTX-M-15; |
| 203 | Asia | Taiwan | 894334 | Respiratory: Other | Medicine ICU | SHV-12(e); |
| 204 | Europe | Czech Republic | 923859 | Respiratory: Endotracheal aspirate | Surgery ICU | SHV-12(e); |
| 205 | Europe | Portugal | 938167 | Bodily Fluids: Peritoneal | Emergency Room | SHV-OSBL(u); TEM-OSBL(u); CTX-M-15; |
| 206 | Latin America | Mexico | 950100 | Respiratory: Bronchoalveolar lavage | Medicine ICU | SHV-OSBL(u); CTX-M-14; |
| 207 | Latin America | Mexico | 950102 | Respiratory: Endotracheal aspirate | Surgery ICU | SHV-OSBL(u); TEM-OSBL(u); CTX-M-15; |
| 208 | Latin America | Mexico | 950107 | Respiratory: Endotracheal aspirate | Medicine ICU | SHV-OSBL(u); TEM-OSBL(u); CTX-M-15; |
| 209 | Latin America | Mexico | 951241 | Respiratory: Bronchial brushing | Pediatric ICU | SHV-OSBL(u); TEM-OSBL(u); CTX-M-15; |
| 210 | South Pacific | Philippines | 957918 | Respiratory: Sputum | Medicine ICU | |
| 211 | South Pacific | Philippines | 966430 | Respiratory: Sputum | Medicine General | |
| 212 | Europe | Russia | 975841 | Respiratory: Sputum | Surgery ICU | SHV-OSBL(u); TEM-OSBL(u); CTX-M-15; |
| 213 | Latin America | Mexico | 979791 | Respiratory: Bronchial brushing | Surgery ICU | SHV-OSBL(u); TEM-OSBL(u); CTX-M-15; |
| 214 | North America | United States | 981436 | Respiratory: Endotracheal aspirate | Medicine ICU | SHV-OSBL(u); TEM-OSBL(u); CTX-M-15; |
| 215 | Europe | Russia | 1049468 | Respiratory: Bronchoalveolar lavage | Medicine General | SHV-110(u); CTX-M-15; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 216 | Europe | Russia | 1050019 | INT: Wound | Surgery ICU | SHV-OSBL(u); TEM-OSBL(u); CTX-M-15; |
| 217 | Europe | Russia | 1050029 | INT: Wound | General Unspecified ICU | |
| 218 | Europe | Russia | 1050038 | INT: Wound | Medicine General | |
| 219 | Europe | Russia | 1050052 | Respiratory: Bronchoalveolar lavage | Medicine ICU | |
| 220 | North America | United States | 1073361 | Respiratory: Sputum | Medicine General | TEM-1(b); CTX-M-15; |
| 221 | Europe | Spain | 1073953 | Respiratory: Sputum | Medicine General | SHV-11(b); CTX-M-15; |
| 222 | Europe | United Kingdom | 1081745 | Respiratory: Endotracheal aspirate | Medicine ICU | SHV-11(b); TEM-1(b); CTX-M-15; |
| 223 | Latin America | Mexico | 950095 | Respiratory: Endotracheal aspirate | Surgery ICU | SHV-12(e); DHA-1; |
| 224 | Europe | Russia | 870321 | Respiratory: Other | Surgery General | SHV-OSBL(u); |
| 225 | Europe | Russia | 1050017 | INT: Wound | Surgery ICU | |
| 226 | Europe | Russia | 1050053 | Respiratory: Bronchoalveolar lavage | Medicine ICU | |
| 227 | Europe | Greece | 848879 | Respiratory: Sputum | General Unspecified ICU | |
| 228 | North America | United States | 855499 | INT: Wound | Outpatient | |
| 229 | Latin America | Colombia | 860723 | GI: Abscess | General Unspecified ICU | |
| 230 | Asia | Taiwan | 862260 | Respiratory: Sputum | Surgery General | |
| 231 | North America | United States | 863922 | GI: Gall Bladder | Other | |
| 232 | Latin America | Venezuela | 866365 | GU: Urine | Medicine ICU | |
| 233 | Europe | Austria | 896420 | INT: Wound | Surgery ICU | |
| 234 | North America | United States | 920265 | GI: Stomach | Medicine ICU | |
| 235 | Asia | Thailand | 949027 | Respiratory: Sputum | Medicine General | |
| 236 | Latin America | Brazil | 991831 | GU: Urine | Emergency Room | |
| 237 | Asia | Malaysia | 996710 | GI: Abscess | Surgery General | |
| 238 | North America | United States | 1072091 | GU: Urine | Medicine ICU | |
| 239 | Europe | United Kingdom | 1087502 | Respiratory: Sputum | Surgery General | |
| 240 | Africa | South Africa | 1088186 | INT: Wound | Medicine ICU | |
| 241 | Europe | Belgium | 1089861 | GU: Urine | Medicine General | |
| 242 | Europe | Czech Republic | 1097531 | Respiratory: Endotracheal aspirate | Medicine ICU | |
| 243 | Europe | Spain | 1098542 | INT: Wound | Medicine General | |
| 244 | Asia | Japan | 1132015 | Respiratory: Sputum | Medicine General | |
| 245 | Europe | France | 1149311 | Bodily Fluids: Peritoneal | Medicine ICU | |
| 246 | Asia | Hong Kong | 1151042 | GU: Urine | Medicine General | |
| 247 | South Pacific | Philippines | 845578 | INT: Wound | Medicine General | |
| 248 | Europe | Portugal | 845918 | INT: Wound | Medicine General | |
| 249 | Latin America | Chile | 847189 | GI: Abscess | Surgery ICU | |
| 250 | Latin America | Argentina | 847386 | GI: Abscess | Surgery General | |
| 251 | North America | United States | 857611 | Respiratory: Sputum | Surgery ICU | |

TABLE 8-continued

Summary of clinical *Klebsiella* strains to which anti-O2 mAbs bind.

| Region | Country | IHMA Number | Body Location | Facility Name | Molecular Summary |
|---|---|---|---|---|---|
| 252 Latin America | Colombia | 860724 | Respiratory: Sputum | Medicine General | |
| 253 Latin America | Venezuela | 866345 | Respiratory: Sputum | Medicine General | |
| 254 Latin America | Argentina | 867249 | Respiratory: Endotracheal aspirate | Surgery ICU | |

The isolates in rows 1-140 of Table 8 are *Klebsiella pneumoniae* carbapenamase (KPC) strains. The isolates in rows 141-226 of Table 8 are extended spectrum beta lactamase (ESBL) strains, and the isolates in rows 227-254 of Table 8 are antibiotic-susceptible strains.

These results demonstrate that anti-O2 mAbs bind not only to a large and diverse group of clinical strains, but also to antibiotic resistant clinically relevant strains. These results suggest that anti-O2 mAbs can be useful as a therapeutic and/or diagnostic as described herein, for example, for one or more of the *Klebsiella* strains disclosed in Table 8.

Example 14: Anti-O2 Antigen Antibodies Bind to O2 *Klebsiella* Strains Regardless of Gml Gene Expression Monoclonal antibodies that recognized Gal III structure have been reported to bind to gml+ *Klebsiella* ST258 strains. We obtained whole genome sequences from a number of O2 *Klebsiella* clinical isolates and performed experiments to (i) whether these strains express the gml gene; and (ii) whether anti-O2 mAbs bind to these strains by fluorescence activated cell sorting (FACS) or western blot analysis. In addition, we analyzed multi locus sequence type (MLST) and gml locus based on whole genome sequences. Table 9 lists FACS binding, MLST, and gml expression data of 31 O2 *Klebsiella* clinical isolates.

TABLE 9

Anti-O2 monoclonal antibodies binding to gml+ and gml− *Klebsiella* clinical isolates.

| | KPN42 | KPN70 | KPN179 | MLST | gml | comments |
|---|---|---|---|---|---|---|
| ARC2698 | + | + | + | 258 | + | |
| ARC2708 | + | + | + | 258 | + | |
| ARC2712 | + | + | + | 258 | + | |
| ARC2929 | + | + | + | 258 | + | |
| ARC2945 | + | + | + | 258 | + | |
| ARC3516 | + | + | + | 45 | | |
| ARC3797 | + | + | + | 147 | | |
| ARC4771 | + | + | + | 45 | | |
| ARC4773 | +/− | +/− | +/− | 45 | | KPN42+ by Western |
| ARC4778 | + | + | + | 70 | + | |
| ARC4780 | + | + | + | 11 | + | |
| ARC4784 | + | + | + | 218 | + | |
| ARC5109 | + | + | + | 258 | + | |
| ARC5113 | + | + | + | 1728 | | KPN42+ by Western |
| ARC5115 | + | + | + | 34 | | |
| ARC5116 | + | + | + | 258 | + | |
| ARC5117 | + | + | + | 258 | + | |
| ARC5121 | + | ++ | + | 258 | + | |
| ARC5372 | + | + | + | 258 | + | KPN42+ by Western |

TABLE 9-continued

Anti-O2 monoclonal antibodies binding to gml+ and gml− *Klebsiella* clinical isolates.

| | KPN42 | KPN70 | KPN179 | MLST | gml | comments |
|---|---|---|---|---|---|---|
| ARC5411 | + | + | + | 258 | + | |
| ARC5449 | + | + | + | 11* | | KPN42+ by Western |
| ARC6084 | + | + | + | 17 | + | KPN42+ by Western |
| ARC6086 | + | + | + | 11 | + | |
| ARC6093 | + | + | + | 11 | | |
| ARC6095 | + | + | + | 258 | + | KPN42+ by Western |
| ARC6099 | + | + | + | 437* | | |
| ARC6100 | + | + | + | 340 | | |
| ARC6102 | + | + | + | 20 | + | KPN42+ by Western |
| ARC6106 | + | + | + | 641 | | |
| ARC6114 | + | + | + | 45 | | |
| ARC6118 | + | + | + | 512 | + | |

As shown in Table 9, multiple ST types, including ST258, were present in this collection. Twelve of the non-ST258 strains did not express the gml gene. KPN42 bound to 9200 (11/12) gml− and 10000 (19/19) gmnl+ *Klebsiella* strains. These data suggest that anti-O2 antibodies such as KPN42 bind to O2 antigen, but do not bind to a Gal III epitope. Thus, such O2 antibodies confer broader coverage against O2 strains than Gal III-binding antibodies.

Example 15: KPS44 Sequence Optimization

In order to reduce sequence liability for mAb development, a tryptophan in the heavy chain CDR3 of KPS44 was exchanged with a phenylalanine (see heavy chain of KPS44-v2017, SEQ ID NO: 202, also known as KPS44-v2017-W108F-VH). Additionally, a tryptophan in the light chain CDR1 of KPS44 was exchanged with a phenylalanine, and an aspartic acid and a serine in the light chain CDR3 of KPS44 were substituted for an asparagine and a tyrosine, respectively (see light chain of KPS44v-2017, SEQ ID NO: 203, also known as KPS44-v2017-D37N-S38Y-W107F-VL). Collectively, this resulted in KPS44-v2017 (also known as KPS44-W108F-VH/KPS44-D37N-S38Y-W107F-VL.)

Combinations of the heavy chain CDRs and light chain CDRs of parental KPS44 and KPS44-v2017 were made, resulting in KPS44-D37N-S38Y-W107F-VL (KPS44-G1), KPS44-W108F-VH/KPS44-W107F-VL (KPS44-G2), and KPS44-W108F-VH/KPS44-D37N-S38Y-VL (KPS44-G3).

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 10

Additional Sequences

| SEQ ID NO in ST25 sequence listing filed in parent U.S. application No. 16/323,185 | Description of Sequence | Sequence: |
| --- | --- | --- |
| 219 | Synthetic KPS44-G4 VL-CDR2 peptide | ENN |
| 229 | Synthetic KPS44-G6 VL-CDR2 peptide | ENN |
| 239 | Synthetic KPS44-G8 VL-CDR2 peptide | ENN |
| 249 | Synthetic KPS44-G10 VL-CDR2 peptide | ENN |
| 259 | Synthetic KPS44-G11 VL-CDR2 peptide | ENN |
| 269 | Synthetic KPS44-G14 VL-CDR2 peptide | ENN |

What is claimed is:

1. A method for treating or ameliorating a *Klebsiella* infection in a subject in need thereof comprising administering to said subject an effective amount of an antigen binding protein that specifically binds to *Klebsiella pneumoniae* O2 antigen and comprises a set of Complementarity-Determining Regions (CDRs): HCDR1, HCDR2, HCDR3, LCDR1, LCDR2, and LCDR3 wherein the HCDR1, HCDR2, HCDR3, LCDR1, LCDR2, and LCDR3 comprise the amino acid sequences of:

SEQ. ID. NOs: 10-13, DVN or SEQ ID NO: 15, and SEQ ID NO:16, respectively;

SEQ. ID. NOs: 19-22, DVN or SEQ ID NO: 24, and SEQ ID NO: 25, respectively;

SEQ. ID. NOs: 28-31, DAS or SEQ ID NO: 33, and SEQ ID NO: 34, respectively;

SEQ. ID. NOs: 37-40, DMS or SEQ ID NO: 42, and SEQ ID NO: 43, respectively;

SEQ. ID. NOs: 46-49, DVN or SEQ ID NO: 51, and SEQ ID NO: 52, respectively;

SEQ. ID. NOs: 166-168, 175, DVN or SEQ ID NO: 177, and SEQ ID NO: 178, respectively;

SEQ. ID. NOs: 169-171, 179, DVN or SEQ ID NO: 181, and SEQ ID NO: 182, respectively;

SEQ. ID. NOs: 55-58, DMS or SEQ ID NO: 60, and SEQ ID NO: 61, respectively;

SEQ. ID. NOs: 64-67, AAS or SEQ ID NO: 69, and SEQ ID NO: 70, respectively;

SEQ. ID. NOs: 73-78, respectively;

SEQ. ID. NOs: 82-85, EVS or SEQ ID NO: 87, and SEQ ID NO: 88, respectively;

SEQ. ID. NOs: 91-94, DNN or SEQ ID NO: 96, and SEQ ID NO: 97, respectively;

SEQ. ID. NOs: 100-103, ENN or SEQ ID NO: 105, and SEQ ID NO: 106, respectively;

SEQ. ID. NOs: 109-112, ENN or SEQ ID NO: 114, and SEQ ID NO: 115, respectively;

SEQ. ID. NOs: 118-121, EVN or SEQ ID NO: 123, and SEQ ID NO: 124, respectively;

SEQ. ID. NOs: 127-130, GAS or SEQ ID NO: 132, and SEQ ID NO: 133, respectively; or SEQ. ID. NOs: 172-174, 183, EVN or SEQ ID NO: 185, and SEQ ID NO: 186, respectively.

2. A method for inhibiting the growth of *Klebsiella*, or reducing the number of *Klebsiella* in a subject infected with *Klebsiella* comprising administering to a subject in need thereof an antigen binding protein that specifically binds to *Klebsiella pneumoniae* O2 antigen and comprises a set of Complementarity-Determining Regions (CDRs): HCDR1, HCDR2, HCDR3, LCDR1, LCDR2, and LCDR3 wherein the HCDR1, HCDR2, HCDR3, LCDR1, LCDR2, and LCDR3 comprise the amino acid sequences of:

SEQ. ID. NOs: 10-13, DVN or SEQ ID NO: 15, and SEQ ID NO:16, respectively;

SEQ. ID. NOs: 19-22, DVN or SEQ ID NO: 24, and SEQ ID NO: 25, respectively;

SEQ. ID. NOs: 28-31, DAS or SEQ ID NO: 33, and SEQ ID NO: 34, respectively;

SEQ. ID. NOs: 37-40, DMS or SEQ ID NO: 42, and SEQ ID NO: 43, respectively;

SEQ. ID. NOs: 46-49, DVN or SEQ ID NO: 51, and SEQ ID NO: 52, respectively;

SEQ. ID. NOs: 166-168, 175, DVN or SEQ ID NO: 177, and SEQ ID NO: 178, respectively;

SEQ. ID. NOs: 169-171, 179, DVN or SEQ ID NO: 181, and SEQ ID NO: 182, respectively;

SEQ. ID. NOs: 55-58, DMS or SEQ ID NO: 60, and SEQ ID NO: 61, respectively;

SEQ. ID. NOs: 64-67, AAS or SEQ ID NO: 69, and SEQ ID NO: 70, respectively;

SEQ. ID. NOs: 73-78, respectively;

SEQ. ID. NOs: 82-85, EVS or SEQ ID NO: 87, and SEQ ID NO: 88, respectively;

SEQ. ID. NOs: 91-94, DNN or SEQ ID NO: 96, and SEQ ID NO: 97, respectively;

SEQ. ID. NOs: 100-103, ENN or SEQ ID NO: 105, and SEQ ID NO: 106, respectively;

SEQ. ID. NOs: 109-112, ENN or SEQ ID NO: 114, and SEQ ID NO: 115, respectively;

SEQ. ID. NOs: 118-121, EVN or SEQ ID NO: 123, and SEQ ID NO: 124, respectively;

SEQ. ID. NOs: 127-130, GAS or SEQ ID NO: 132, and SEQ ID NO: 133, respectively; or SEQ. ID. NOs: 172-174, 183, EVN or SEQ ID NO: 185, and SEQ ID NO: 186, respectively.

3. The method of claim 1, wherein the *Klebsiella* is antibiotic-resistant.

4. The method of claim 3, wherein the *Klebsiella* is resistant to cephalosporin, quinolone, carbapenem, meropenem, fluoroquinolone, tetracycline, chloramphenicol, trimethoprim, sulfonamide, and/or colistin.

5. The method of claim 1, further comprising administering an antibiotic.

6. The method of claim 5, wherein the antigen binding protein and the antibiotic provide a synergistic therapeutic effect.

7. The method of claim 5, wherein the antibiotic is meropenem, carbapenems, fluoroquinolone, tetracycline, chloramphenicol, trimethoprim, sulfonamide, and/or colistin.

8. The method of claim 3, wherein antigen binding protein also specifically binds *Klebsiella pneumoniae* O1 antigen.

9. The method of claim 3, wherein the antigen binding protein that specifically binds to *Klebsiella pneumoniae* O2 antigen is an antibody or antigen binding fragment thereof.

10. The method of claim 1, wherein the *Klebsiella* is *K. pneumoniae, K. oxytoca, K. planticola, K. ozaenae, K. rhinosclermoatis* and/or *K. granulomatis*.

11. The method of claim 10, wherein the *Klebsiella* is *K. pneumoniae*.

12. The method of claim 1, wherein the HCDR1, HCDR2, HCDR3, LCDR1, LCDR2, and LCDR3 comprise the amino acid sequences of: SEQ. ID. NOs: 109-112, ENN, and SEQ ID NO: 115, respectively; and wherein the antigen-binding protein is an antibody.

13. The method of claim 12, wherein the antibody comprises a VH comprising the amino acid sequence of SEQ ID NO: 116 and a VL comprising the amino acid sequence of SEQ ID NO: 117.

14. The method of claim 2, wherein the HCDR1, HCDR2, HCDR3, LCDR1, LCDR2, and LCDR3 comprise the amino acid sequences of: SEQ. ID. NOs: 109-112, ENN, and SEQ ID NO: 115, respectively; and wherein the antigen-binding protein is an antibody.

15. The method of claim 14, wherein the antibody comprises a VH comprising the amino acid sequence of SEQ ID NO: 116 and a VL comprising the amino acid sequence of SEQ ID NO: 117.

* * * * *

SEQUENCE LISTING

```
Sequence total quantity: 274
SEQ ID NO: 1            moltype = AA  length = 8
FEATURE                 Location/Qualifiers
REGION                  1..8
                        note = Description of Artificial Sequence: SyntheticKPN42
                        VH-CDR1 peptide
source                  1..8
                        mol_type = protein
                        organism = synthetic construct
SEQUENCE: 1
GFTFNDAW                                                                  8

SEQ ID NO: 2            moltype = AA  length = 10
FEATURE                 Location/Qualifiers
REGION                  1..10
                        note = Description of Artificial Sequence: SyntheticKPN42
                        VH-CDR2 peptide
source                  1..10
                        mol_type = protein
                        organism = synthetic construct
SEQUENCE: 2
IKKKHEGVTT                                                                10

SEQ ID NO: 3            moltype = AA  length = 10
FEATURE                 Location/Qualifiers
REGION                  1..10
                        note = Description of Artificial Sequence: SyntheticKPN42
                        VH-CDR3 peptide
source                  1..10
                        mol_type = protein
                        organism = synthetic construct
SEQUENCE: 3
TTRIVTTNDY                                                                10

SEQ ID NO: 4            moltype = AA  length = 9
FEATURE                 Location/Qualifiers
REGION                  1..9
                        note = Description of Artificial Sequence: SyntheticKPN42
                        VL-CDR1 peptide
source                  1..9
                        mol_type = protein
                        organism = synthetic construct
SEQUENCE: 4
SSDVGAYDY                                                                 9

SEQ ID NO: 5            moltype =     length =
SEQUENCE: 5
000

SEQ ID NO: 6            moltype = AA  length = 9
FEATURE                 Location/Qualifiers
REGION                  1..9
```

```
                        note = Description of Artificial Sequence: SyntheticKPN42
                            VL-CDR2 peptide
source                  1..9
                        mol_type = protein
                        organism = synthetic construct
SEQUENCE: 6
IIYDVNERP                                                                   9

SEQ ID NO: 7            moltype = AA   length = 10
FEATURE                 Location/Qualifiers
REGION                  1..10
                        note = Description of Artificial Sequence: SyntheticKPN42
                            VL-CDR3 peptide
source                  1..10
                        mol_type = protein
                        organism = synthetic construct
SEQUENCE: 7
CSYAGGDIFV                                                                  10

SEQ ID NO: 8            moltype = AA   length = 119
FEATURE                 Location/Qualifiers
REGION                  1..119
                        note = Description of Artificial Sequence: SyntheticKPN42
                            VH polypeptide
source                  1..119
                        mol_type = protein
                        organism = synthetic construct
SEQUENCE: 8
EVQLVESGGG LVKPGGSLRL SCAASGFTFN DAWMNWVRQA PGKGLEWVAR IKKKHEGVTT   60
DYPASVRGRF TISRDDSKNT VYLQMGRLRI EDTAIYYCTT RIVTTNDYWG QGTLVTVSS   119

SEQ ID NO: 9            moltype = AA   length = 110
FEATURE                 Location/Qualifiers
REGION                  1..110
                        note = Description of Artificial Sequence: SyntheticKPN42
                            VL polypeptide
source                  1..110
                        mol_type = protein
                        organism = synthetic construct
SEQUENCE: 9
QSALTQPPSV SGSPGQSVTI SCTGTSSDVG AYDYVSWYQQ YAGKVPKHII YDVNERPSGV   60
PDRFSGSKSG NTAALTISGL QAEDEADYYC CSYAGGDIFV FGTGTQVTVL             110

SEQ ID NO: 10           moltype = AA   length = 8
FEATURE                 Location/Qualifiers
REGION                  1..8
                        note = Description of Artificial Sequence:
                            SyntheticKPN42--FR-1-2-4-GL-VH/KPN42-FR-GL-C105A-VL
                            (KPN42-v2016)VH-CDR1 peptide
source                  1..8
                        mol_type = protein
                        organism = synthetic construct
SEQUENCE: 10
GFTFNDAW                                                                    8

SEQ ID NO: 11           moltype = AA   length = 10
FEATURE                 Location/Qualifiers
REGION                  1..10
                        note = Description of Artificial Sequence:
                            SyntheticKPN42--FR-1-2-4-GL-VH/KPN42-FR-GL-C105A-VL(KPN42-v
                            2016) VH-CDR2 peptide
source                  1..10
                        mol_type = protein
                        organism = synthetic construct
SEQUENCE: 11
IKKKHEGVTT                                                                  10

SEQ ID NO: 12           moltype = AA   length = 10
FEATURE                 Location/Qualifiers
REGION                  1..10
                        note = Description of Artificial Sequence:
                            SyntheticKPN42--FR-1-2-4-GL-VH/KPN42-FR-GL-C105A-VL(KPN42-v
                            2016) VH-CDR3 peptide
source                  1..10
                        mol_type = protein
                        organism = synthetic construct
SEQUENCE: 12
TTRIVTTNDY                                                                  10
```

```
SEQ ID NO: 13              moltype = AA  length = 9
FEATURE                    Location/Qualifiers
REGION                     1..9
                           note = Description of Artificial Sequence:
                           SyntheticKPN42--FR-1-2-4-GL-VH/KPN42-FR-GL-C105A-VL(KPN42-v
                           2016) VL-CDR1 peptide
source                     1..9
                           mol_type = protein
                           organism = synthetic construct
SEQUENCE: 13
SSDVGAYDY                                                                    9

SEQ ID NO: 14              moltype =    length =
SEQUENCE: 14
000

SEQ ID NO: 15              moltype = AA  length = 9
FEATURE                    Location/Qualifiers
REGION                     1..9
                           note = Description of Artificial Sequence:
                           SyntheticKPN42--FR-1-2-4-GL-VH/KPN42-FR-GL-C105A-VL(KPN42-v
                           2016) VL-CDR2 peptide
source                     1..9
                           mol_type = protein
                           organism = synthetic construct
SEQUENCE: 15
MIYDVNKRP                                                                    9

SEQ ID NO: 16              moltype = AA  length = 10
FEATURE                    Location/Qualifiers
REGION                     1..10
                           note = Description of Artificial Sequence:
                           SyntheticKPN42--FR-1-2-4-GL-VH/KPN42-FR-GL-C105A-VL(KPN42-v
                           2016) VL-CDR3 peptide
source                     1..10
                           mol_type = protein
                           organism = synthetic construct
SEQUENCE: 16
ASYAGGDIFV                                                                   10

SEQ ID NO: 17              moltype = AA  length = 119
FEATURE                    Location/Qualifiers
REGION                     1..119
                           note = Description of Artificial Sequence:
                           SyntheticKPN42-v2016 VH polypeptide
source                     1..119
                           mol_type = protein
                           organism = synthetic construct
SEQUENCE: 17
EVQLVESGGG LVKPGGSLRL SCAASGFTFN DAWMNWVRQA PGKGLEWVGR IKKKHEGVTT             60
DYPASVRGRF TISRDDSKNT VYLQMGRLRI EDTAIYYCTT RIVTTNDYWG QGTLVTVSS              119

SEQ ID NO: 18              moltype = AA  length = 110
FEATURE                    Location/Qualifiers
REGION                     1..110
                           note = Description of Artificial Sequence:
                           SyntheticKPN42-v2016 VL polypeptide
source                     1..110
                           mol_type = protein
                           organism = synthetic construct
SEQUENCE: 18
QSALTQPRSV SGSPGQSVTI SCTGTSSDVG AYDYVSWYQQ HPGKAPKLMI YDVNKRPSGV             60
PDRFSGSKSG NTASLTISGL QAEDEADYYC ASYAGGDIFV FGTGTKVTVL                        110

SEQ ID NO: 19              moltype = AA  length = 8
FEATURE                    Location/Qualifiers
REGION                     1..8
                           note = Description of Artificial Sequence:
                           SyntheticKPN42-FR-GL-VH/KPN42-FR-GL-C105A-VL VH-CDR1
                           peptide
source                     1..8
                           mol_type = protein
                           organism = synthetic construct
SEQUENCE: 19
GFTFNDAW                                                                     8

SEQ ID NO: 20              moltype = AA  length = 10
FEATURE                    Location/Qualifiers
REGION                     1..10
```

```
                        note = Description of Artificial Sequence:
                          SyntheticKPN42-FR-GL-VH/KPN42-FR-GL-C105A-VL VH-CDR2
                          peptide
source                  1..10
                        mol_type = protein
                        organism = synthetic construct
SEQUENCE: 20
IKKKHEGVTT                                                              10

SEQ ID NO: 21           moltype = AA  length = 10
FEATURE                 Location/Qualifiers
REGION                  1..10
                        note = Description of Artificial Sequence:
                          SyntheticKPN42-FR-GL-VH/KPN42-FR-GL-C105A-VL VH-CDR3
                          peptide
source                  1..10
                        mol_type = protein
                        organism = synthetic construct
SEQUENCE: 21
TTRIVTTNDY                                                              10

SEQ ID NO: 22           moltype = AA  length = 9
FEATURE                 Location/Qualifiers
REGION                  1..9
                        note = Description of Artificial Sequence:
                          SyntheticKPN42-FR-GL-VH/KPN42-FR-GL-C105A-VL VL-CDR1
                          peptide
source                  1..9
                        mol_type = protein
                        organism = synthetic construct
SEQUENCE: 22
SSDVGAYDY                                                               9

SEQ ID NO: 23           moltype =     length =
SEQUENCE: 23
000

SEQ ID NO: 24           moltype = AA  length = 9
FEATURE                 Location/Qualifiers
REGION                  1..9
                        note = Description of Artificial Sequence:
                          SyntheticKPN42-FR-GL-VH/KPN42-FR-GL-C105A-VL VL-CDR2
                          peptide
source                  1..9
                        mol_type = protein
                        organism = synthetic construct
SEQUENCE: 24
MIYDVNKRP                                                               9

SEQ ID NO: 25           moltype = AA  length = 10
FEATURE                 Location/Qualifiers
REGION                  1..10
                        note = Description of Artificial Sequence:
                          SyntheticKPN42-FR-GL-VH/KPN42-FR-GL-C105A-VL VL-CDR3
                          peptide
source                  1..10
                        mol_type = protein
                        organism = synthetic construct
SEQUENCE: 25
ASYAGGDIFV                                                              10

SEQ ID NO: 26           moltype = AA  length = 119
FEATURE                 Location/Qualifiers
REGION                  1..119
                        note = Description of Artificial Sequence:
                          SyntheticKPN42-FR-GL-VH/KPN42-FR-GL-C105A-VL VH polypeptide
source                  1..119
                        mol_type = protein
                        organism = synthetic construct
SEQUENCE: 26
EVQLVESGGG LVKPGGSLRL SCAASGFTFN DAWMNWVRQA PGKGLEWVGR IKKKHEGVTT       60
DYAAPVKGRF TISRDDSKNT LYLQMNSLKT EDTAVYYCTT RIVTTNDYWG QGTLVTVSS       119

SEQ ID NO: 27           moltype = AA  length = 110
FEATURE                 Location/Qualifiers
REGION                  1..110
                        note = Description of Artificial Sequence:
                          SyntheticKPN42-FR-GL-VH/KPN42-FR-GL-C105A-VL VL polypeptide
source                  1..110
```

```
                            mol_type = protein
                            organism = synthetic construct
SEQUENCE: 27
QSALTQPRSV SGSPGQSVTI SCTGTSSDVG AYDYVSWYQQ HPGKAPKLMI YDVNKRPSGV   60
PDRFSGSKSG NTASLTISGL QAEDEADYYC ASYAGGDIFV FGTGTKVTVL             110

SEQ ID NO: 28           moltype = AA  length = 8
FEATURE                 Location/Qualifiers
REGION                  1..8
                        note = Description of Artificial Sequence: SyntheticKPS3
                          VH-CDR1 peptide
source                  1..8
                        mol_type = protein
                        organism = synthetic construct
SEQUENCE: 28
GFSFRDYG                                                            8

SEQ ID NO: 29           moltype = AA  length = 8
FEATURE                 Location/Qualifiers
REGION                  1..8
                        note = Description of Artificial Sequence: SyntheticKPS3
                          VH-CDR2 peptide
source                  1..8
                        mol_type = protein
                        organism = synthetic construct
SEQUENCE: 29
ISYDGRDQ                                                            8

SEQ ID NO: 30           moltype = AA  length = 12
FEATURE                 Location/Qualifiers
REGION                  1..12
                        note = Description of Artificial Sequence: SyntheticKPS3
                          VH-CDR3 peptide
source                  1..12
                        mol_type = protein
                        organism = synthetic construct
SEQUENCE: 30
GPFYNPSLYY PP                                                       12

SEQ ID NO: 31           moltype = AA  length = 6
FEATURE                 Location/Qualifiers
REGION                  1..6
                        note = Description of Artificial Sequence: SyntheticKPS3
                          VL-CDR1 peptide
source                  1..6
                        mol_type = protein
                        organism = synthetic construct
SEQUENCE: 31
QSISSQ                                                              6

SEQ ID NO: 32           moltype =   length =
SEQUENCE: 32
000

SEQ ID NO: 33           moltype = AA  length = 9
FEATURE                 Location/Qualifiers
REGION                  1..9
                        note = Description of Artificial Sequence: SyntheticKPS3
                          VL-CDR2 peptide
source                  1..9
                        mol_type = protein
                        organism = synthetic construct
SEQUENCE: 33
LIHDASNRD                                                           9

SEQ ID NO: 34           moltype = AA  length = 10
FEATURE                 Location/Qualifiers
REGION                  1..10
                        note = Description of Artificial Sequence: SyntheticKPS3
                          VL-CDR3 peptide
source                  1..10
                        mol_type = protein
                        organism = synthetic construct
SEQUENCE: 34
LQRNNWPPWT                                                          10

SEQ ID NO: 35           moltype = AA  length = 119
FEATURE                 Location/Qualifiers
REGION                  1..119
```

```
                        note = Description of Artificial Sequence: SyntheticKPS3 VH
                         polypeptide
source                  1..119
                        mol_type = protein
                        organism = synthetic construct
SEQUENCE: 35
QGQLVDSGGG VVQRGGSQRL SCAASGFSFR DYGMHWVRQA PGKGLEWVAF ISYDGRDQYY   60
ADSVKGRFII SRDNSKNTLS LQMNSLRPED TAVYYCGPFY NPSLYYPPWG HGLPVIVSS   119

SEQ ID NO: 36           moltype = AA   length = 108
FEATURE                 Location/Qualifiers
REGION                  1..108
                        note = Description of Artificial Sequence: SyntheticKPS3 VL
                         polypeptide
source                  1..108
                        mol_type = protein
                        organism = synthetic construct
SEQUENCE: 36
EVVLTQSPAT LSLSPGERAT LSCRASQSIS SQLAWYQQKP GQAPRLLIHD ASNRDTGVPD   60
RFSGSGSGTD FTLTISSLEP EDFAMYYCLQ RNNWPPWTFG QGTKVEIK              108

SEQ ID NO: 37           moltype = AA   length = 8
FEATURE                 Location/Qualifiers
REGION                  1..8
                        note = Description of Artificial Sequence: SyntheticKPN70
                         VH-CDR1 peptide
source                  1..8
                        mol_type = protein
                        organism = synthetic construct
SEQUENCE: 37
GGSISTYY                                                             8

SEQ ID NO: 38           moltype = AA   length = 7
FEATURE                 Location/Qualifiers
REGION                  1..7
                        note = Description of Artificial Sequence: SyntheticKPN70
                         VH-CDR2 peptide
source                  1..7
                        mol_type = protein
                        organism = synthetic construct
SEQUENCE: 38
IHQSGTT                                                              7

SEQ ID NO: 39           moltype = AA   length = 15
FEATURE                 Location/Qualifiers
REGION                  1..15
                        note = Description of Artificial Sequence: SyntheticKPN70
                         VH-CDR3 peptide
source                  1..15
                        mol_type = protein
                        organism = synthetic construct
SEQUENCE: 39
ARESDDGYKW NYFDY                                                    15

SEQ ID NO: 40           moltype = AA   length = 6
FEATURE                 Location/Qualifiers
REGION                  1..6
                        note = Description of Artificial Sequence: SyntheticKPN70
                         VL-CDR1 peptide
source                  1..6
                        mol_type = protein
                        organism = synthetic construct
SEQUENCE: 40
QIVTNY                                                               6

SEQ ID NO: 41           moltype =     length =
SEQUENCE: 41
000

SEQ ID NO: 42           moltype = AA   length = 9
FEATURE                 Location/Qualifiers
REGION                  1..9
                        note = Description of Artificial Sequence: SyntheticKPN70
                         VL-CDR2 peptide
source                  1..9
                        mol_type = protein
                        organism = synthetic construct
SEQUENCE: 42
LIFDMSIRA                                                            9
```

```
SEQ ID NO: 43              moltype = AA   length = 10
FEATURE                    Location/Qualifiers
REGION                     1..10
                           note = Description of Artificial Sequence: SyntheticKPN70
                           VL-CDR3 peptide
source                     1..10
                           mol_type = protein
                           organism = synthetic construct
SEQUENCE: 43
QHRSNWPLFT                                                                      10

SEQ ID NO: 44              moltype = AA   length = 121
FEATURE                    Location/Qualifiers
REGION                     1..121
                           note = Description of Artificial Sequence: SyntheticKPN70
                           VH polypeptide
source                     1..121
                           mol_type = protein
                           organism = synthetic construct
SEQUENCE: 44
QVQLQESGPG LVKPSETLSL TCTVSGGSIS TYYWNWIRQS PGKELEWIAN IHQSGTTYYN               60
PSLKSRVTMS VDTSKNQFSL KVISVTAADT AVYYCARESD DGYKWNYFDY WGQGTLVTVS              120
S                                                                              121

SEQ ID NO: 45              moltype = AA   length = 108
FEATURE                    Location/Qualifiers
REGION                     1..108
                           note = Description of Artificial Sequence: SyntheticKPN70
                           VL polypeptide
source                     1..108
                           mol_type = protein
                           organism = synthetic construct
SEQUENCE: 45
EIVLTQSPAS LSLSPGERAT LSCRASQIVT NYLAWYQHKP GQAPRLLIFD MSIRAAGIPA               60
RFSGSGSGTD FTLTISSLEP EDFAVYYCQH RSNWPLFTFG PGTKVDIK                           108

SEQ ID NO: 46              moltype = AA   length = 8
FEATURE                    Location/Qualifiers
REGION                     1..8
                           note = Description of Artificial Sequence: SyntheticKPN179
                           VH-CDR1 peptide
source                     1..8
                           mol_type = protein
                           organism = synthetic construct
SEQUENCE: 46
GFTFNNAW                                                                        8

SEQ ID NO: 47              moltype = AA   length = 10
FEATURE                    Location/Qualifiers
REGION                     1..10
                           note = Description of Artificial Sequence: SyntheticKPN179
                           VH-CDR2 peptide
source                     1..10
                           mol_type = protein
                           organism = synthetic construct
SEQUENCE: 47
IKRKADGETT                                                                     10

SEQ ID NO: 48              moltype = AA   length = 10
FEATURE                    Location/Qualifiers
REGION                     1..10
                           note = Description of Artificial Sequence: SyntheticKPN179
                           VH-CDR3 peptide
source                     1..10
                           mol_type = protein
                           organism = synthetic construct
SEQUENCE: 48
TTRIVTTNDY                                                                     10

SEQ ID NO: 49              moltype = AA   length = 9
FEATURE                    Location/Qualifiers
REGION                     1..9
                           note = Description of Artificial Sequence: SyntheticKPN179
                           VL-CDR1 peptide
source                     1..9
                           mol_type = protein
                           organism = synthetic construct
SEQUENCE: 49
```

```
SSDVGYYDY                                                                                9

SEQ ID NO: 50           moltype =    length =
SEQUENCE: 50
000

SEQ ID NO: 51           moltype = AA   length = 9
FEATURE                 Location/Qualifiers
REGION                  1..9
                        note = Description of Artificial Sequence: SyntheticKPN179
                         VL-CDR2 peptide
source                  1..9
                        mol_type = protein
                        organism = synthetic construct
SEQUENCE: 51
MIYDVNKRP                                                                                9

SEQ ID NO: 52           moltype = AA   length = 10
FEATURE                 Location/Qualifiers
REGION                  1..10
                        note = Description of Artificial Sequence: SyntheticKPN179
                         VL-CDR3 peptide
source                  1..10
                        mol_type = protein
                        organism = synthetic construct
SEQUENCE: 52
CSYAGGDTFV                                                                               10

SEQ ID NO: 53           moltype = AA   length = 119
FEATURE                 Location/Qualifiers
REGION                  1..119
                        note = Description of Artificial Sequence: SyntheticKPN179
                         VH polypeptide
source                  1..119
                        mol_type = protein
                        organism = synthetic construct
SEQUENCE: 53
EVQVVESGGG LVKPGGSLRL SCAASGFTFN NAWMNWVRQA PGKGLEWVGR IKRKADGETT        60
DYPASVKGRF TVSRDDSKNT IYLQMNSLKT EDTAIYYCTT RIVTTNDYWG QGTLVTVSS         119

SEQ ID NO: 54           moltype = AA   length = 111
FEATURE                 Location/Qualifiers
REGION                  1..111
                        note = Description of Artificial Sequence: SyntheticKPN179
                         VL polypeptide
source                  1..111
                        mol_type = protein
                        organism = synthetic construct
SEQUENCE: 54
QSALTQPPSV SGSPGQSVTI SCTGTSSDVG YYDYVSWYQQ HHPGKAPKHM IYDVNKRPSG        60
VPDRFSGSKS GNTASLTISG LQAEDEADYY CCSYAGGDTF VFGTGTKVTV L                 111

SEQ ID NO: 55           moltype = AA   length = 8
FEATURE                 Location/Qualifiers
REGION                  1..8
                        note = Description of Artificial Sequence: SyntheticKPN44
                         VH-CDR1 peptide
source                  1..8
                        mol_type = protein
                        organism = synthetic construct
SEQUENCE: 55
GGSTSSYY                                                                                 8

SEQ ID NO: 56           moltype = AA   length = 7
FEATURE                 Location/Qualifiers
REGION                  1..7
                        note = Description of Artificial Sequence: SyntheticKPN44
                         VH-CDR2 peptide
source                  1..7
                        mol_type = protein
                        organism = synthetic construct
SEQUENCE: 56
IHHGGTT                                                                                  7

SEQ ID NO: 57           moltype = AA   length = 15
FEATURE                 Location/Qualifiers
REGION                  1..15
                        note = Description of Artificial Sequence: SyntheticKPN44
                         VH-CDR3 peptide
```

```
source                  1..15
                        mol_type = protein
                        organism = synthetic construct
SEQUENCE: 57
ARESDDGYRW NYFDY                                                        15

SEQ ID NO: 58           moltype = AA  length = 6
FEATURE                 Location/Qualifiers
REGION                  1..6
                        note = Description of Artificial Sequence: SyntheticKPN44
                         VL-CDR1 peptide
source                  1..6
                        mol_type = protein
                        organism = synthetic construct
SEQUENCE: 58
QTITNY                                                                   6

SEQ ID NO: 59           moltype =    length =
SEQUENCE: 59
000

SEQ ID NO: 60           moltype = AA  length = 9
FEATURE                 Location/Qualifiers
REGION                  1..9
                        note = Description of Artificial Sequence: SyntheticKPN44
                         VL-CDR2 peptide
source                  1..9
                        mol_type = protein
                        organism = synthetic construct
SEQUENCE: 60
LIFDMSKRA                                                                9

SEQ ID NO: 61           moltype = AA  length = 10
FEATURE                 Location/Qualifiers
REGION                  1..10
                        note = Description of Artificial Sequence: SyntheticKPN44
                         VL-CDR3 peptide
source                  1..10
                        mol_type = protein
                        organism = synthetic construct
SEQUENCE: 61
QHRSNWPLFT                                                              10

SEQ ID NO: 62           moltype = AA  length = 121
FEATURE                 Location/Qualifiers
REGION                  1..121
                        note = Description of Artificial Sequence: SyntheticKPN44
                         VH polypeptide
source                  1..121
                        mol_type = protein
                        organism = synthetic construct
SEQUENCE: 62
QVQLQESGPG LVKPSETLSL TCTVSGGSTS SYYWNWIRQA PGKPLQWIAN IHHGGTTYYN         60
PSLRSRVTMS LDTSNNQFSL KLTSVTAADT AVYFCARESD DGYRWNYFDY WGQGVLVTVS        120
S                                                                      121

SEQ ID NO: 63           moltype = AA  length = 108
FEATURE                 Location/Qualifiers
REGION                  1..108
                        note = Description of Artificial Sequence: SyntheticKPN44
                         VL polypeptide
source                  1..108
                        mol_type = protein
                        organism = synthetic construct
SEQUENCE: 63
EIVLTQSPAS LSLSPGDRAT LSCRASQTIT NYLAWYQHKP GQAPRLLIFD MSKRATGIPA         60
RFSGSGSGTD FTLTISSLEP EDFAVYYCQH RSNWPLFTFG PGTNVDIK                    108

SEQ ID NO: 64           moltype = AA  length = 8
FEATURE                 Location/Qualifiers
REGION                  1..8
                        note = Description of Artificial Sequence: SyntheticKPN17
                         VH-CDR1 peptide
source                  1..8
                        mol_type = protein
                        organism = synthetic construct
SEQUENCE: 64
GFTFSHFW                                                                 8
```

| | |
|---|---|
| SEQ ID NO: 65<br>FEATURE<br>REGION<br><br>source | moltype = AA   length = 8<br>Location/Qualifiers<br>1..8<br>note = Description of Artificial Sequence: SyntheticKPN17<br>  VH-CDR2 peptide<br>1..8<br>mol_type = protein<br>organism = synthetic construct |
| SEQUENCE: 65<br>IDGSVTNL | 8 |
| SEQ ID NO: 66<br>FEATURE<br>REGION<br><br>source | moltype = AA   length = 17<br>Location/Qualifiers<br>1..17<br>note = Description of Artificial Sequence: SyntheticKPN17<br>  VH-CDR3 peptide<br>1..17<br>mol_type = protein<br>organism = synthetic construct |
| SEQUENCE: 66<br>ARDLVGIGTP AGYGMDV | 17 |
| SEQ ID NO: 67<br>FEATURE<br>REGION<br><br>source | moltype = AA   length = 6<br>Location/Qualifiers<br>1..6<br>note = Description of Artificial Sequence: SyntheticKPN17<br>  VL-CDR1 peptide<br>1..6<br>mol_type = protein<br>organism = synthetic construct |
| SEQUENCE: 67<br>QGISTY | 6 |
| SEQ ID NO: 68<br>SEQUENCE: 68<br>000 | moltype =    length = |
| SEQ ID NO: 69<br>FEATURE<br>REGION<br><br>source | moltype = AA   length = 9<br>Location/Qualifiers<br>1..9<br>note = Description of Artificial Sequence: SyntheticKPN17<br>  VL-CDR2 peptide<br>1..9<br>mol_type = protein<br>organism = synthetic construct |
| SEQUENCE: 69<br>LIYAASTLQ | 9 |
| SEQ ID NO: 70<br>FEATURE<br>REGION<br><br>source | moltype = AA   length = 9<br>Location/Qualifiers<br>1..9<br>note = Description of Artificial Sequence: SyntheticKPN17<br>  VL-CDR3 peptide<br>1..9<br>mol_type = protein<br>organism = synthetic construct |
| SEQUENCE: 70<br>QQLTSHLYT | 9 |
| SEQ ID NO: 71<br>FEATURE<br>REGION<br><br>source | moltype = AA   length = 124<br>Location/Qualifiers<br>1..124<br>note = Description of Artificial Sequence: SyntheticKPN17<br>  VH polypeptide<br>1..124<br>mol_type = protein<br>organism = synthetic construct |
| SEQUENCE: 71<br>EVQLVESGGG LVQPGGSLRL SCAASGFTFS HFWMHWVRQA PGQGLVWVAR IDGSVTNLRY<br>AGSVEGRFTI SRDNAKNTLY LQMNSLRDED TAVYYCARDL VGIGTPAGYG MDVWGQGTTV<br>TVSS | 60<br>120<br>124 |
| SEQ ID NO: 72<br>FEATURE<br>REGION<br><br>source | moltype = AA   length = 107<br>Location/Qualifiers<br>1..107<br>note = Description of Artificial Sequence: SyntheticKPN17<br>  VL polypeptide<br>1..107<br>mol_type = protein |

```
                              organism = synthetic construct
SEQUENCE: 72
DIQLTQSPSF LSASVGDRVT ITCRASQGIS TYLAWYQQKP GKAPKLLIYA ASTLQSGVPS    60
RFSGSGSGTE FTLTINSLQS EDFATYYCQQ LTSHLYTFGQ GTKLEIK                 107

SEQ ID NO: 73             moltype = AA   length = 6
FEATURE                   Location/Qualifiers
REGION                    1..6
                          note = Description of Artificial Sequence: Synthetic6F6
                            VH-CDR1 peptide
source                    1..6
                          mol_type = protein
                          organism = synthetic construct
SEQUENCE: 73
PIAYMG                                                                6

SEQ ID NO: 74             moltype = AA   length = 17
FEATURE                   Location/Qualifiers
REGION                    1..17
                          note = Description of Artificial Sequence: Synthetic6F6
                            VH-CDR2 peptide
source                    1..17
                          mol_type = protein
                          organism = synthetic construct
SEQUENCE: 74
DILPNIGRTI YGEKFED                                                   17

SEQ ID NO: 75             moltype = AA   length = 9
FEATURE                   Location/Qualifiers
REGION                    1..9
                          note = Description of Artificial Sequence: Synthetic6F6
                            VH-CDR3 peptide
source                    1..9
                          mol_type = protein
                          organism = synthetic construct
SEQUENCE: 75
RGTSGAMDY                                                             9

SEQ ID NO: 76             moltype = AA   length = 16
FEATURE                   Location/Qualifiers
REGION                    1..16
                          note = Description of Artificial Sequence: Synthetic6F6
                            VL-CDR1 peptide
source                    1..16
                          mol_type = protein
                          organism = synthetic construct
SEQUENCE: 76
RSSQGLVHST GNTFLH                                                    16

SEQ ID NO: 77             moltype = AA   length = 7
FEATURE                   Location/Qualifiers
REGION                    1..7
                          note = Description of Artificial Sequence: Synthetic6F6
                            VL-CDR2 peptide
source                    1..7
                          mol_type = protein
                          organism = synthetic construct
SEQUENCE: 77
KVSNRFS                                                               7

SEQ ID NO: 78             moltype = AA   length = 9
FEATURE                   Location/Qualifiers
REGION                    1..9
                          note = Description of Artificial Sequence: Synthetic6F6
                            VL-CDR3 peptide
source                    1..9
                          mol_type = protein
                          organism = synthetic construct
SEQUENCE: 78
SQSTHIPYT                                                             9

SEQ ID NO: 79             moltype =      length =
SEQUENCE: 79
000

SEQ ID NO: 80             moltype = AA   length = 119
FEATURE                   Location/Qualifiers
REGION                    1..119
                          note = Description of Artificial Sequence: Synthetic6F6 VH
```

```
                            polypeptide
source                      1..119
                            mol_type = protein
                            organism = synthetic construct
SEQUENCE: 80
QVHLQQSGSE LRSPGSSVKL SCKDFDSDVF PIAYMGWIRQ QPGHGFDWIG DILPNIGRTI     60
YGEKFEDKAT LDADTVSNTA YLELSSLTSE DSAIYYCARR GTSGAMDYWG QGTSVTVSS     119

SEQ ID NO: 81               moltype = AA  length = 112
FEATURE                     Location/Qualifiers
REGION                      1..112
                            note = Description of Artificial Sequence: Synthetic6F6 VL
                             polypeptide
source                      1..112
                            mol_type = protein
                            organism = synthetic construct
SEQUENCE: 81
DVVMTQTPLF LPVSLGDQAS ISCRSSQGLV HSTGNTFLHW YLQKPGQSPK LLIYKVSNRF     60
SGVPDRFSGS GSGTDFTLKI SRVEAEDLGI YFCSQSTHIP YTFGGGTKLE IK            112

SEQ ID NO: 82               moltype = AA  length = 8
FEATURE                     Location/Qualifiers
REGION                      1..8
                            note = Description of Artificial Sequence: SyntheticKPL26
                             VH-CDR1 peptide
source                      1..8
                            mol_type = protein
                            organism = synthetic construct
SEQUENCE: 82
GFIFGSSW                                                               8

SEQ ID NO: 83               moltype = AA  length = 8
FEATURE                     Location/Qualifiers
REGION                      1..8
                            note = Description of Artificial Sequence: SyntheticKPL26
                             VH-CDR2 peptide
source                      1..8
                            mol_type = protein
                            organism = synthetic construct
SEQUENCE: 83
INPDGSAT                                                               8

SEQ ID NO: 84               moltype = AA  length = 11
FEATURE                     Location/Qualifiers
REGION                      1..11
                            note = Description of Artificial Sequence: SyntheticKPL26
                             VH-CDR3 peptide
source                      1..11
                            mol_type = protein
                            organism = synthetic construct
SEQUENCE: 84
TRNKAYNALD Y                                                          11

SEQ ID NO: 85               moltype = AA  length = 9
FEATURE                     Location/Qualifiers
REGION                      1..9
                            note = Description of Artificial Sequence: SyntheticKPL26
                             VL-CDR1 peptide
source                      1..9
                            mol_type = protein
                            organism = synthetic construct
SEQUENCE: 85
SSDVGGNNY                                                              9

SEQ ID NO: 86               moltype =     length =
SEQUENCE: 86
000

SEQ ID NO: 87               moltype = AA  length = 9
FEATURE                     Location/Qualifiers
REGION                      1..9
                            note = Description of Artificial Sequence: SyntheticKPL26
                             VL-CDR2 peptide
source                      1..9
                            mol_type = protein
                            organism = synthetic construct
SEQUENCE: 87
IIYEVSKRP                                                              9
```

```
SEQ ID NO: 88              moltype = AA  length = 8
FEATURE                    Location/Qualifiers
REGION                     1..8
                           note = Description of Artificial Sequence: SyntheticKPL26
                            VL-CDR3 peptide
source                     1..8
                           mol_type = protein
                           organism = synthetic construct
SEQUENCE: 88
SSFGGSKM                                                                   8

SEQ ID NO: 89              moltype = AA  length = 118
FEATURE                    Location/Qualifiers
REGION                     1..118
                           note = Description of Artificial Sequence: SyntheticKPL26
                            VH polypeptide
source                     1..118
                           mol_type = protein
                           organism = synthetic construct
SEQUENCE: 89
EVQLVESGGG LVQSGGSLRL SCETSGFIFG SSWMTWVRQA PGKGLEWVAT INPDGSATSY          60
EDSVRGRFAV SRDNAKNSVY LQMNSLRAED TAVYFCTRNK AYNALDYWGQ GTLVTVSS           118

SEQ ID NO: 90              moltype = AA  length = 108
FEATURE                    Location/Qualifiers
REGION                     1..108
                           note = Description of Artificial Sequence: SyntheticKPL26
                            VL polypeptide
source                     1..108
                           mol_type = protein
                           organism = synthetic construct
SEQUENCE: 90
QSALTQPPSA SGSPGQSVTL SCTGTSSDVG GNNYVSWYQQ HPGKAPKLII YEVSKRPSGV          60
PNRFSGSKSG NTASLTVSGL QAEDEADYYC SSFGGSKMFG GGTKLTVL                      108

SEQ ID NO: 91              moltype = AA  length = 8
FEATURE                    Location/Qualifiers
REGION                     1..8
                           note = Description of Artificial Sequence: SyntheticKPS18
                            VH-CDR1 peptide
source                     1..8
                           mol_type = protein
                           organism = synthetic construct
SEQUENCE: 91
GFTFKNAW                                                                   8

SEQ ID NO: 92              moltype = AA  length = 10
FEATURE                    Location/Qualifiers
REGION                     1..10
                           note = Description of Artificial Sequence: SyntheticKPS18
                            VH-CDR2 peptide
source                     1..10
                           mol_type = protein
                           organism = synthetic construct
SEQUENCE: 92
VKNEVDGGTI                                                                10

SEQ ID NO: 93              moltype = AA  length = 11
FEATURE                    Location/Qualifiers
REGION                     1..11
                           note = Description of Artificial Sequence: SyntheticKPS18
                            VH-CDR3 peptide
source                     1..11
                           mol_type = protein
                           organism = synthetic construct
SEQUENCE: 93
RAFWSGFPAG Y                                                              11

SEQ ID NO: 94              moltype = AA  length = 8
FEATURE                    Location/Qualifiers
REGION                     1..8
                           note = Description of Artificial Sequence: SyntheticKPS18
                            VL-CDR1 peptide
source                     1..8
                           mol_type = protein
                           organism = synthetic construct
SEQUENCE: 94
RSNIGSDS                                                                   8
```

| | |
|---|---|
| SEQ ID NO: 95<br>SEQUENCE: 95<br>000 | moltype =     length = |
| SEQ ID NO: 96<br>FEATURE<br>REGION<br><br><br>source<br><br><br>SEQUENCE: 96<br>LMYDNNKRP | moltype = AA   length = 9<br>Location/Qualifiers<br>1..9<br>note = Description of Artificial Sequence: SyntheticKPS18<br>VL-CDR2 peptide<br>1..9<br>mol_type = protein<br>organism = synthetic construct<br><br>9 |
| SEQ ID NO: 97<br>FEATURE<br>REGION<br><br><br>source<br><br><br>SEQUENCE: 97<br>ATWDSSLSAY V | moltype = AA   length = 11<br>Location/Qualifiers<br>1..11<br>note = Description of Artificial Sequence: SyntheticKPS18<br>VL-CDR3 peptide<br>1..11<br>mol_type = protein<br>organism = synthetic construct<br><br>11 |
| SEQ ID NO: 98<br>FEATURE<br>REGION<br><br><br>source<br><br><br>SEQUENCE: 98<br>EVRLVESGGG LVKPGGSLRL SCAASGFTFK NAWMSWIRQA PGKGLEWVGR VKNEVDGGTI   60<br>DYGVPVRGRF TISRDDSQGT LSLEMNSLRE DDTGIYYCRA FWSGFPAGYW GQGTLVSVSS  120 | moltype = AA   length = 120<br>Location/Qualifiers<br>1..120<br>note = Description of Artificial Sequence: SyntheticKPS18<br>VH polypeptide<br>1..120<br>mol_type = protein<br>organism = synthetic construct |
| SEQ ID NO: 99<br>FEATURE<br>REGION<br><br><br>source<br><br><br>SEQUENCE: 99<br>QSVLTQPPSL SAAPGQTVTI ACSGSRSNIG SDSVSWFQQF PGTAPRVLMY DNNKRPSGIS   60<br>DRFSGSKSGT SVTLDITGLQ TGDEADYYCA TWDSSLSAYV FGSGTKVTVL            110 | moltype = AA   length = 110<br>Location/Qualifiers<br>1..110<br>note = Description of Artificial Sequence: SyntheticKPS18<br>VL polypeptide<br>1..110<br>mol_type = protein<br>organism = synthetic construct |
| SEQ ID NO: 100<br>FEATURE<br>REGION<br><br><br>source<br><br><br>SEQUENCE: 100<br>GFTFKNAW | moltype = AA   length = 8<br>Location/Qualifiers<br>1..8<br>note = Description of Artificial Sequence: SyntheticKPS24<br>VH-CDR1 peptide<br>1..8<br>mol_type = protein<br>organism = synthetic construct<br><br>8 |
| SEQ ID NO: 101<br>FEATURE<br>REGION<br><br><br>source<br><br><br>SEQUENCE: 101<br>VKSEVDGGTT | moltype = AA   length = 10<br>Location/Qualifiers<br>1..10<br>note = Description of Artificial Sequence: SyntheticKPS24<br>VH-CDR2 peptide<br>1..10<br>mol_type = protein<br>organism = synthetic construct<br><br>10 |
| SEQ ID NO: 102<br>FEATURE<br>REGION<br><br><br>source<br> | moltype = AA   length = 11<br>Location/Qualifiers<br>1..11<br>note = Description of Artificial Sequence: SyntheticKPS24<br>VH-CDR3 peptide<br>1..11<br>mol_type = protein |

```
                        organism = synthetic construct
SEQUENCE: 102
RAFWSDFQTG Y                                                              11

SEQ ID NO: 103          moltype = AA  length = 8
FEATURE                 Location/Qualifiers
REGION                  1..8
                        note = Description of Artificial Sequence: SyntheticKPS24
                        VL-CDR1 peptide
source                  1..8
                        mol_type = protein
                        organism = synthetic construct
SEQUENCE: 103
SSNIGSDS                                                                   8

SEQ ID NO: 104          moltype =   length =
SEQUENCE: 104
000

SEQ ID NO: 105          moltype = AA  length = 9
FEATURE                 Location/Qualifiers
REGION                  1..9
                        note = Description of Artificial Sequence: SyntheticKPS24
                        VL-CDR2 peptide
source                  1..9
                        mol_type = protein
                        organism = synthetic construct
SEQUENCE: 105
LMYENNKRP                                                                  9

SEQ ID NO: 106          moltype = AA  length = 11
FEATURE                 Location/Qualifiers
REGION                  1..11
                        note = Description of Artificial Sequence: SyntheticKPS24
                        VL-CDR3 peptide
source                  1..11
                        mol_type = protein
                        organism = synthetic construct
SEQUENCE: 106
AAWDSSLRAY V                                                              11

SEQ ID NO: 107          moltype = AA  length = 120
FEATURE                 Location/Qualifiers
REGION                  1..120
                        note = Description of Artificial Sequence: SyntheticKPS24
                        VH polypeptide
source                  1..120
                        mol_type = protein
                        organism = synthetic construct
SEQUENCE: 107
ELHLVESGGG LVKPGGSLRL SCAASGFTFK NAWMSWIRQA PGKGLEWVGR VKSEVDGGTT          60
DYGVPVRGRF TISRDDSQST LSLEMSSLQD DDTGVYYCRA FWSDFQTGYW GQGTLVTVSS         120

SEQ ID NO: 108          moltype = AA  length = 110
FEATURE                 Location/Qualifiers
REGION                  1..110
                        note = Description of Artificial Sequence: SyntheticKPS24
                        VL polypeptide
source                  1..110
                        mol_type = protein
                        organism = synthetic construct
SEQUENCE: 108
QSVLTQPPSV SAAPGQTVTI ACSGSSSNIG SDSVSWFQQL PGTAPRVLMY ENNKRPSGIS          60
DRFSGSKSGT SVTLGITGLQ TGDEADYYCA AWDSSLRAYV FGSGTKVTVL                   110

SEQ ID NO: 109          moltype = AA  length = 8
FEATURE                 Location/Qualifiers
REGION                  1..8
                        note = Description of Artificial Sequence: SyntheticKPS44
                        VH-CDR1 peptide
source                  1..8
                        mol_type = protein
                        organism = synthetic construct
SEQUENCE: 109
GFTFKNAW                                                                   8

SEQ ID NO: 110          moltype = AA  length = 10
FEATURE                 Location/Qualifiers
REGION                  1..10
```

```
                        note = Description of Artificial Sequence: SyntheticKPS44
                         VH-CDR2 peptide
source                  1..10
                        mol_type = protein
                        organism = synthetic construct
SEQUENCE: 110
VKSEVDGGTI                                                                    10

SEQ ID NO: 111          moltype = AA   length = 11
FEATURE                 Location/Qualifiers
REGION                  1..11
                        note = Description of Artificial Sequence: SyntheticKPS44
                         VH-CDR3 peptide
source                  1..11
                        mol_type = protein
                        organism = synthetic construct
SEQUENCE: 111
RAFWSGFPTG Y                                                                  11

SEQ ID NO: 112          moltype = AA   length = 8
FEATURE                 Location/Qualifiers
REGION                  1..8
                        note = Description of Artificial Sequence: SyntheticKPS44
                         VL-CDR1 peptide
source                  1..8
                        mol_type = protein
                        organism = synthetic construct
SEQUENCE: 112
SSNIGSDS                                                                       8

SEQ ID NO: 113          moltype =    length =
SEQUENCE: 113
000

SEQ ID NO: 114          moltype = AA   length = 9
FEATURE                 Location/Qualifiers
REGION                  1..9
                        note = Description of Artificial Sequence: SyntheticKPS44
                         VL-CDR2 peptide
source                  1..9
                        mol_type = protein
                        organism = synthetic construct
SEQUENCE: 114
LIYENNKRP                                                                      9

SEQ ID NO: 115          moltype = AA   length = 11
FEATURE                 Location/Qualifiers
REGION                  1..11
                        note = Description of Artificial Sequence: SyntheticKPS44
                         VL-CDR3 peptide
source                  1..11
                        mol_type = protein
                        organism = synthetic construct
SEQUENCE: 115
ATWDSSLSAY V                                                                  11

SEQ ID NO: 116          moltype = AA   length = 120
FEATURE                 Location/Qualifiers
REGION                  1..120
                        note = Description of Artificial Sequence:
                         SyntheticKPS44/KPS44-G1 VH polypeptide
source                  1..120
                        mol_type = protein
                        organism = synthetic construct
SEQUENCE: 116
EVHLVESGGG LVKPGGSLRL SCAASGFTFK NAWMSWIRQA PGKGLEWVGR VKSEVDGGTI    60
DYGVPVRGRF TISRDDSQGT LSLEMNSLKD DDTGVYYCRA FWSGFPTGYW GQGALVSVSS   120

SEQ ID NO: 117          moltype = AA   length = 110
FEATURE                 Location/Qualifiers
REGION                  1..110
                        note = Description of Artificial Sequence: SyntheticKPS44
                         VL polypeptide
source                  1..110
                        mol_type = protein
                        organism = synthetic construct
SEQUENCE: 117
QSVLTQPPSL SAAPGQTITI ACSGTSSNIG SDSVSWFQQF PGTAPRVLIY ENNKRPSGIS    60
DRFSGSKSGT SVTLGITGLQ TGDEADYYCA TWDSSLSAYV FGSGTKVTVL              110
```

```
SEQ ID NO: 118          moltype = AA  length = 8
FEATURE                 Location/Qualifiers
REGION                  1..8
                        note = Description of Artificial Sequence: SyntheticKPS30
                         VH-CDR1 peptide
source                  1..8
                        mol_type = protein
                        organism = synthetic construct
SEQUENCE: 118
GFSFSTSW                                                                     8

SEQ ID NO: 119          moltype = AA  length = 8
FEATURE                 Location/Qualifiers
REGION                  1..8
                        note = Description of Artificial Sequence: SyntheticKPS30
                         VH-CDR2 peptide
source                  1..8
                        mol_type = protein
                        organism = synthetic construct
SEQUENCE: 119
IDPDGSTR                                                                     8

SEQ ID NO: 120          moltype = AA  length = 11
FEATURE                 Location/Qualifiers
REGION                  1..11
                        note = Description of Artificial Sequence: SyntheticKPS30
                         VH-CDR3 peptide
source                  1..11
                        mol_type = protein
                        organism = synthetic construct
SEQUENCE: 120
ARDYAYNRFD Y                                                                11

SEQ ID NO: 121          moltype = AA  length = 9
FEATURE                 Location/Qualifiers
REGION                  1..9
                        note = Description of Artificial Sequence: SyntheticKPS30
                         VL-CDR1 peptide
source                  1..9
                        mol_type = protein
                        organism = synthetic construct
SEQUENCE: 121
SSDIGANNY                                                                    9

SEQ ID NO: 122          moltype =    length =
SEQUENCE: 122
000

SEQ ID NO: 123          moltype = AA  length = 9
FEATURE                 Location/Qualifiers
REGION                  1..9
                        note = Description of Artificial Sequence: SyntheticKPS30
                         VL-CDR2 peptide
source                  1..9
                        mol_type = protein
                        organism = synthetic construct
SEQUENCE: 123
LLYEVNKRP                                                                    9

SEQ ID NO: 124          moltype = AA  length = 8
FEATURE                 Location/Qualifiers
REGION                  1..8
                        note = Description of Artificial Sequence: SyntheticKPS30
                         VL-CDR3 peptide
source                  1..8
                        mol_type = protein
                        organism = synthetic construct
SEQUENCE: 124
CGYGGGRV                                                                     8

SEQ ID NO: 125          moltype = AA  length = 118
FEATURE                 Location/Qualifiers
REGION                  1..118
                        note = Description of Artificial Sequence: SyntheticKPS30
                         VH polypeptide
source                  1..118
                        mol_type = protein
                        organism = synthetic construct
```

```
SEQUENCE: 125
EMQLVESGGG LVQPGVSLRL SCVDSGFSFS TSWLAWVRQA PGKGLEWLAN IDPDGSTRNH   60
VDSVRGRFTI SRDNAKNSLY LQMNSLRAED TAVYYCARDY AYNRFDYWGQ GTMVTVSS   118

SEQ ID NO: 126          moltype = AA   length = 108
FEATURE                 Location/Qualifiers
REGION                  1..108
                        note = Description of Artificial Sequence: SyntheticKPS30
                         VL polypeptide
source                  1..108
                        mol_type = protein
                        organism = synthetic construct
SEQUENCE: 126
QSALTQPPSA SGSPGQSVVI SCTGTSSDIG ANNYVSWYQQ HPGKAPKLLL YEVNKRPSGV   60
PDRFSASKSG NTASLTVSGL LAEDEADYYC CGYGGGRVFG GGTKLTVL   108

SEQ ID NO: 127          moltype = AA   length = 10
FEATURE                 Location/Qualifiers
REGION                  1..10
                        note = Description of Artificial Sequence: SyntheticKPD1
                         VH-CDR1 peptide
source                  1..10
                        mol_type = protein
                        organism = synthetic construct
SEQUENCE: 127
GVSITSNTYW                                                         10

SEQ ID NO: 128          moltype = AA   length = 7
FEATURE                 Location/Qualifiers
REGION                  1..7
                        note = Description of Artificial Sequence: SyntheticKPD1
                         VH-CDR2 peptide
source                  1..7
                        mol_type = protein
                        organism = synthetic construct
SEQUENCE: 128
LSYSGDT                                                             7

SEQ ID NO: 129          moltype = AA   length = 14
FEATURE                 Location/Qualifiers
REGION                  1..14
                        note = Description of Artificial Sequence: SyntheticKPD1
                         VH-CDR3 peptide
source                  1..14
                        mol_type = protein
                        organism = synthetic construct
SEQUENCE: 129
ARDPDIIRNF QFDY                                                    14

SEQ ID NO: 130          moltype = AA   length = 7
FEATURE                 Location/Qualifiers
REGION                  1..7
                        note = Description of Artificial Sequence: SyntheticKPD1
                         VL-CDR1 peptide
source                  1..7
                        mol_type = protein
                        organism = synthetic construct
SEQUENCE: 130
QILYMSH                                                             7

SEQ ID NO: 131          moltype =      length =
SEQUENCE: 131
000

SEQ ID NO: 132          moltype = AA   length = 9
FEATURE                 Location/Qualifiers
REGION                  1..9
                        note = Description of Artificial Sequence: SyntheticKPD1
                         VL-CDR2 peptide
source                  1..9
                        mol_type = protein
                        organism = synthetic construct
SEQUENCE: 132
LIYGASIRA                                                           9

SEQ ID NO: 133          moltype = AA   length = 8
FEATURE                 Location/Qualifiers
REGION                  1..8
                        note = Description of Artificial Sequence: SyntheticKPD1
```

```
                        VL-CDR3 peptide
source                  1..8
                        mol_type = protein
                        organism = synthetic construct
SEQUENCE: 133
QQYGASPT                                                            8

SEQ ID NO: 134          moltype = AA  length = 122
FEATURE                 Location/Qualifiers
REGION                  1..122
                        note = Description of Artificial Sequence: SyntheticKPD1 VH
                        polypeptide
source                  1..122
                        mol_type = protein
                        organism = synthetic construct
SEQUENCE: 134
QVQLQESDPR LVKPSETLSL TCSVSGVSIT SNTYWWAWIR QPPGKKLEWI GSLSYSGDTY    60
YNPSLTSRVT ISRDIHQNQF FLELNSVTAA DTAMYYCARD PDIIRNFQFD YWGRGTLVTV   120
SS                                                                 122

SEQ ID NO: 135          moltype = AA  length = 107
FEATURE                 Location/Qualifiers
REGION                  1..107
                        note = Description of Artificial Sequence: SyntheticKPD1 VL
                        polypeptide
source                  1..107
                        mol_type = protein
                        organism = synthetic construct
SEQUENCE: 135
EIVLTQSPGI LSLSPGERAT LSCRVSQILY MSHLAWYQHK PGQAPRLLIY GASIRATGVP    60
DRFSGSGSGT DFTLTISRLE PEDFAVYYCQ QYGASPTFGQ GTMVEIK                 107

SEQ ID NO: 136          moltype = DNA  length = 358
FEATURE                 Location/Qualifiers
misc_feature            1..358
                        note = Description of Artificial Sequence: SyntheticKPN42
                        VH polynucleotide
source                  1..358
                        mol_type = other DNA
                        organism = synthetic construct
SEQUENCE: 136
gaggtgcagc tggtggagtc tgggggaggc ttggtaaagc cggggggtc ccttagactc    60
tcctgtgcag cctctggttt cactttcaat gacgcctgga tgaactgggt ccgccaggct  120
ccaggaaagg ggctggagtg ggtcgcccgc attaaaaaga acatgaagg tgttacgaca   180
gactaccctg catccgtgag aggcagatta accatctcaa gagatgattc taaaaacaca  240
gtgtatctga gatgggcag actgagaatc gaggacactg ccatatatta ctgtaccaca   300
aggatagtga ctaccaatga ctactggggc cagggaaccc tggtcaccgt ctcctcag    358

SEQ ID NO: 137          moltype = DNA  length = 357
FEATURE                 Location/Qualifiers
misc_feature            1..357
                        note = Description of Artificial Sequence:
                        SyntheticKPN42-v2016 VH polynucleotide
source                  1..357
                        mol_type = other DNA
                        organism = synthetic construct
SEQUENCE: 137
gaggtgcagc tggtcgaatc tggcggggga ctggtgaaac ctggcggctc tctgaggctg    60
agttgcgccg cttcaggctt caccttcaac gacgcatgga tgaattgggt gcgacaggca  120
cctggaaagg gactggagtg ggtcggccgg atcaagaaaa agcacgaagg ggtgaccaca  180
gattaccctg ctagcgtccg gggaagattc actattagca gagacgattc caaaaacacc  240
gtgtatctgc agatgggcag gctgcgcatc gaggacaccg ccatctacta ttgtactacc  300
cgcatcgtga caactaatga ttactggggg cagggaaccc tggtgacagt cagctcc     357

SEQ ID NO: 138          moltype = DNA  length = 357
FEATURE                 Location/Qualifiers
misc_feature            1..357
                        note = Description of Artificial Sequence:
                        SyntheticKPN42-FR-GL-VH/KPN42-FR-GL-C105A-VL VH
                        polynucleotide
source                  1..357
                        mol_type = other DNA
                        organism = synthetic construct
SEQUENCE: 138
gaggtgcagc tggtcgaatc tggcggggga ctggtgaagc ctggcggctc tctgcgactg    60
agttgcgccg cttcaggctt caccttaac gacgcttgga tgaattgggt gaggcaggca   120
cctggaaaag gactggagtg ggtgggacgc atcaagaaaa agcacgaagg ggtgaccaca  180
gattacgcag cccctgtcaa ggccggttc acaattagca gagacgattc caagaacact   240
ctgtatctgc agatgaatag cctgaaaacc gaggacacag ccgtgtacta ttgtactacc  300
```

```
agaatcgtca caactaacga ttactggggg cagggaactc tggtgaccgt cagctcc      357
```

SEQ ID NO: 139          moltype = DNA   length = 358
FEATURE                 Location/Qualifiers
misc_feature            1..358
                        note = Description of Artificial Sequence: SyntheticKPS3 VH
                          polynucleotide
source                  1..358
                        mol_type = other DNA
                        organism = synthetic construct
SEQUENCE: 139
```
cagggacagt tggtggactc tgggggaggc gtggtccagc ggggggggtc tcagagactc   60
tcctgcgcag cgtctggatt cagcttcaga gactatggca tgcactgggt ccgccaggct  120
ccaggcaagg ggctggagtg ggtggccttt atatcatatg atggagagat caatactat  180
gcagactccg tgaagggccg attcatcatc tccagagaca attccaagaa cacgctgtct  240
ctgcaaatga acagcctgag acctgaggac acggctgtct attactgtgg gccttttat  300
aaccccagtc tctactaccc ccctggggc acggacttc cggtcatcgt ctcctcag     358
```

SEQ ID NO: 140          moltype = DNA   length = 364
FEATURE                 Location/Qualifiers
misc_feature            1..364
                        note = Description of Artificial Sequence: SyntheticKPN70
                          VH polynucleotide
source                  1..364
                        mol_type = other DNA
                        organism = synthetic construct
SEQUENCE: 140
```
caggtgcagc tgcaggagtc gggcccggga ctggtgaagc cttcggagac cctgtctctc   60
acctgcactg tctctggtgg ctccatcagt acttactact ggaactggat ccggcagtcc  120
ccagggaagg aattgcaaat atacatcaaa gtgggaccac ctactacaac              180
ccctccctca agagtcgagt caccatgtca gtagacacgt ccaagaacca gttctccctg  240
aaggtgatct ctgtgactgc tgcggacacg gccgtgtatt actgtgcgag agagtccgac  300
gatggctaca gtggaactca ctttgactac tggggccagg gaaccctagt caccgtctcc  360
tcag                                                               364
```

SEQ ID NO: 141          moltype = DNA   length = 358
FEATURE                 Location/Qualifiers
misc_feature            1..358
                        note = Description of Artificial Sequence: SyntheticKPN179
                          VH polynucleotide
source                  1..358
                        mol_type = other DNA
                        organism = synthetic construct
SEQUENCE: 141
```
gaggtgcagg tggtggagtc tgggggaggc ttggtaaagc cggggggtc ccttagactc    60
tcctgtgcag cctctggttt cactttcaat aacgcctgga tgaactgggt ccgccaggct  120
ccagggaagg ggctggagtg ggtcggccgt attaaaaagg aagctgatgg tgagacaaca  180
gactacctg catccgtgaa aggcagattc accgtctcaa gagatgattc aaaaaacacg  240
atatatctgc agatgaacag cctgaaaacc gaggacacag ccatatatta ctgtaccaca  300
aggatagtga ctaccaatga ctactggggc cagggaaccc tggtcaccgt ctcctcag    358
```

SEQ ID NO: 142          moltype = DNA   length = 364
FEATURE                 Location/Qualifiers
misc_feature            1..364
                        note = Description of Artificial Sequence: SyntheticKPN44
                          VH polynucleotide
source                  1..364
                        mol_type = other DNA
                        organism = synthetic construct
SEQUENCE: 142
```
caggtgcagc tgcaggagtc gggcccggga ctggtgaagc cttcggagac cctgtctctc   60
acctgcactg tgtccggtgg ctccaccagt agttactact ggaactggat ccggcaggcc  120
ccagggaagc cattgcagtg gattgcaaat atacatcacg gtgggaccac ttattacaac  180
ccctccctca ggagtcgggt caccatgtct ctggacactt ccaataacca gttctccctg  240
aagctgacct ctgtgactgc tgcggacacg gccgtctatt tctgtgcgag agagtccgac  300
gatggctaca ggtggaacta ctttgactac tggggccagg gagtcctggt caccgtctcc  360
tcag                                                               364
```

SEQ ID NO: 143          moltype = DNA   length = 373
FEATURE                 Location/Qualifiers
misc_feature            1..373
                        note = Description of Artificial Sequence: SyntheticKPN17
                          VH polynucleotide
source                  1..373
                        mol_type = other DNA
                        organism = synthetic construct
SEQUENCE: 143
```
gaggtgcagc tggtggagtc cggggaggc ttggttcagc ctgggggtc cctgagactc     60
tcctgtgcag cctctggatt caccttcagt cacttctgga tgcactgggt ccgccaagct  120
```

```
ccagggcagg ggctggtgtg ggtcgcacgt attgatggtt ctgtgacaaa cttgaggtac    180
gcgggctccg tggaggggcg attcaccatc tccagagaca acgccaagaa cacgctgtat    240
ttgcaaatga acagtctgag agacgaggac acgctgtat attactgtgc aagagatttg    300
gtaggaattg gcacgccggc cgggtacggt atggacgtct ggggccaagg gaccacggtc    360
accgtctcct cag                                                      373
```

```
SEQ ID NO: 144           moltype = DNA   length = 357
FEATURE                  Location/Qualifiers
misc_feature             1..357
                         note = Description of Artificial Sequence: Synthetic6F6 VH
                          polynucleotide
source                   1..357
                         mol_type = other DNA
                         organism = synthetic construct
SEQUENCE: 144
caggttcacc tacaacagtc tggttctgaa ctgaggagtc ctgggtcttc agtaaagctt     60
tcatgcaagg attttgattc agacgtcttc cctattgctt atatgggttg gattaggcag    120
cagcctgggc atggatttga ctggattggg gacatactcc aaatattgg tagaacaatc    180
tatggagaga agtttgagga caaagccaca ctggatgcag acacagtgtc caacacagcc    240
tacttggagc tcagcagtct gacatctgag gactctgcta tctactattg tgcaaggagg    300
gggacgtcgg gggctatgga ctactgggt caaggaacct cagtcaccgt ctcctca       357
```

```
SEQ ID NO: 145           moltype = DNA   length = 355
FEATURE                  Location/Qualifiers
misc_feature             1..355
                         note = Description of Artificial Sequence: SyntheticKPL26
                          VH polynucleotide
source                   1..355
                         mol_type = other DNA
                         organism = synthetic construct
SEQUENCE: 145
gaggtgcagc tggtggagtc tgggggaggc ttggtccagt cgggggggtc cctgagactc     60
tcctgtgaaa cctctggatt cattttggt agttcttgga tgacctgggt ccgccaggct    120
ccagggaaag ggctggagtg ggtggccacc ataaaccctg atggaagtgc gacaagctat    180
gaggactctg tgaggggccg attcgccgtc tccagaagca cgccaagaa ctcagtgtat    240
ctgcaaatga acagcctgag agccgaggac acgccgtgt acttctgtac aaggaataag    300
gcatacaatg cccttgacta ctggggccag ggaaccctgg tcaccgtctc ctcag        355
```

```
SEQ ID NO: 146           moltype = DNA   length = 361
FEATURE                  Location/Qualifiers
misc_feature             1..361
                         note = Description of Artificial Sequence: SyntheticKPS18
                          VH polynucleotide
source                   1..361
                         mol_type = other DNA
                         organism = synthetic construct
SEQUENCE: 146
gaggttcgcc tggtggagtc tgggggaggc ttggtaaagc ctgggggggtc cctaagactc    60
tcctgtgcag cctcaggatt cactttcaaa acgcctgga tgagctggat ccgccaggct    120
ccagggaagg ggctggagtg ggttggccgt gttaaaaacg aagttgatgg ggggacaata    180
gactacggtg tgcccgtgag aggcagattc accatctcaa gagacgattc acaaggcacg    240
ctgtctctgg agatgaacag cctgagagag gatgacacag ggatttatta ctgtcgggct    300
ttttggagtg gttttcctgc cggatactgg ggccagggaa ccctggtcag cgtctcctca    360
g                                                                  361
```

```
SEQ ID NO: 147           moltype = DNA   length = 361
FEATURE                  Location/Qualifiers
misc_feature             1..361
                         note = Description of Artificial Sequence: SyntheticKPS24
                          VH polynucleotide
source                   1..361
                         mol_type = other DNA
                         organism = synthetic construct
SEQUENCE: 147
gagctgcacc tggtggagtc tgggggaggc ttggtaaagc ctgggggggtc ccttagactc    60
tcctgtgcag cctcaggatt cactttcaaa acgcctgga tgagctggat ccgccaggct    120
ccagggaagg ggctggagtg ggttggccgt gttaaaagcg aagttgatgg ggggacaaca    180
gactacggtg tgcccgtgag aggcagattc accatctcaa gagatgattc acaaagcacg    240
ctgtctctgg agatgagcag cctgcaagac gatgacacag gcgtttatta ctgtcgggct    300
ttttggagtg attttcaaac cggctactgg ggccagggaa ccctggtcac cgtctcctca    360
g                                                                  361
```

```
SEQ ID NO: 148           moltype = DNA   length = 361
FEATURE                  Location/Qualifiers
misc_feature             1..361
                         note = Description of Artificial Sequence: SyntheticKPS44
                          VH polynucleotide
source                   1..361
                         mol_type = other DNA
```

```
                        organism = synthetic construct
SEQUENCE: 148
gaggtgcacc tggtggagtc tgggggaggc ttggtaaagc ctggggggtc ccttagactc   60
tcctgtgcag cctcaggatt cactttcaaa aacgcctgga tgagctggat ccgccaggct  120
ccagggaagg ggctggagtg ggttggccgt gttaaaagcg aagttgatgg ggggacaata  180
gactacggtg tgcccgtgag aggcagattc accatctcaa gagatgattc acaaggcaca  240
ctgtctctgg agatgaacag cctgaaagac gatgacacag gcgtttatta ttgtcgggct  300
ttttggagtg gtttttcctac cggatactgg ggccagggag ccctggtcag cgtctcctca  360
g                                                                  361

SEQ ID NO: 149          moltype = DNA   length = 355
FEATURE                 Location/Qualifiers
misc_feature            1..355
                        note = Description of Artificial Sequence: SyntheticKPS30
                         VH polynucleotide
source                  1..355
                        mol_type = other DNA
                        organism = synthetic construct
SEQUENCE: 149
gagatgcagt tggtagagtc tgggggaggc ttggtccagc ctggggtgtc cctgagactc   60
tcctgtgtag actctggatt cagttttagt acctcttggt tggcctgggt ccgccaggct  120
ccagggaagg ggctggagtg gctggccaac atagatccag atggaagcac gagaaatcat  180
gtggactctg tgaggggccg attcaccatc tccagagaca cgccaagaa ttcactgtat  240
ctccagatga acagcctgag agccgaggac acggccgtct attactgtgc gagagactat  300
gcctacaatc gctttgacta ctggggccag ggaaccatgg tcaccgtctc ctcag       355

SEQ ID NO: 150          moltype = DNA   length = 367
FEATURE                 Location/Qualifiers
misc_feature            1..367
                        note = Description of Artificial Sequence: SyntheticKPD1 VH
                         polynucleotide
source                  1..367
                        mol_type = other DNA
                        organism = synthetic construct
SEQUENCE: 150
caggtgcagc tgcaggagtc ggacccacga ctggtgaagc cttcggagac cctgtccctc   60
acctgtagtg tctctggtgt ctccatcacc agtaacactt actggtgggc ctggatccgc  120
cagccccag ggaagaaact ggagtggatt gggagtctct cttacagtgg ggacacctac  180
tacaaccgt ccctcacgag tcgcgtcacc atatcaagag atatccatca gaaccaattt  240
ttcctggagt tgaactctgt gaccgccgcc gacacggcca tgtattactg tgcgagagat  300
cccgacatca ttcgcaattt ccagtttgac tactggggcc ggggaaccct ggtcaccgtc  360
tcctcgg                                                            367

SEQ ID NO: 151          moltype = DNA   length = 330
FEATURE                 Location/Qualifiers
misc_feature            1..330
                        note = Description of Artificial Sequence: SyntheticKPN42
                         VL polynucleotide
source                  1..330
                        mol_type = other DNA
                        organism = synthetic construct
SEQUENCE: 151
cagtctgccc tgactcagcc tccctcagtg tccgggtctc ctggacagtc agtcaccatc   60
tcctgcactg gaaccagcag tgatgttggt gcttacgact atgtctcctg gtaccaacag  120
tacgcaggca aagtccccaa acacataatt tatgatgtca gtagcggccc ctcagggtc  180
cctgatcgct tctctggctc caagtctggc aacacggccg ccctgaccat ctctgggctc  240
caggctgagg atgaggctga ttattattgc tgctcatatg caggcggtga catctttgtc  300
ttcggaactg ggactcaggt caccgtccta                                   330

SEQ ID NO: 152          moltype = DNA   length = 330
FEATURE                 Location/Qualifiers
misc_feature            1..330
                        note = Description of Artificial Sequence:
                         SyntheticKPN42-v2016 VL polynucleotide
source                  1..330
                        mol_type = other DNA
                        organism = synthetic construct
SEQUENCE: 152
cagtctgccc tgacccagcc taggtctgtg agtgggtcac ccggacagag tgtcacaatc   60
tcatgcaccg gaacaagctc cgacgtgggc gcttacgatt atgtctcttg gtaccagcag  120
caccccggga aggcacctaa actgatgatc tacgacgtga acaagcggcc aagtggcgtc  180
cccgatagat tcagcggctc caaatctggg aatacagcta gcctgactat ctccggcctc  240
caggcagagg acgaagccga ttactattgt gccagctacg ctggcgggga cattttcgtg  300
tttggaactg gcaccaaggt gaccgtcctg                                   330

SEQ ID NO: 153          moltype = DNA   length = 330
FEATURE                 Location/Qualifiers
misc_feature            1..330
                        note = Description of Artificial Sequence:
```

```
                         SyntheticKPN42-FR-GL-VH/KPN42-FR-GL-C105A-VL VL
                         polynucleotide
source                   1..330
                         mol_type = other DNA
                         organism = synthetic construct
SEQUENCE: 153
cagtctgccc tgacccagcc taggtctgtg agtgggtcac ccggacagag tgtcacaatc    60
tcatgcaccg gaacaagctc cgacgtgggc gcttacgatt atgtctcttg gtaccagcag   120
caccccggga aggcacctaa actgatgatc tacgacgtga acaagcggcc aagtggcgtc   180
cccgatagat tcagcggctc caaatctggg aatacagcta gcctgactat ctccggcctg   240
caggcagagg acgaagccga ttactattgt gccagctacg ctggcgggga cattttcgtg   300
tttggaactg gcaccaaggt gaccgtcctg                                    330

SEQ ID NO: 154           moltype = DNA  length = 325
FEATURE                  Location/Qualifiers
misc_feature             1..325
                         note = Description of Artificial Sequence: SyntheticKPS3 VL
                         polynucleotide
source                   1..325
                         mol_type = other DNA
                         organism = synthetic construct
SEQUENCE: 154
gaggttgtct tgacacagtc tccagccact ctgtctttgt ctccagggga aagagccacc    60
ctctcctgta gggccagtca gagcattagc agccaattag cgtggtacca acagaaacct   120
ggccaggctc ccaggctcct catccatgat gcatccaaca gggacactgg cgtcccagac   180
aggttcagtg gcagtgggtc tgggacagac ttcactctca ccatcagcag cctagagcct   240
gaagattttg ctatgtatta ctgtctccag cgtaacaact ggcctccgtg gacgttcggc   300
caagggacca aggtggaaat caaac                                         325

SEQ ID NO: 155           moltype = DNA  length = 325
FEATURE                  Location/Qualifiers
misc_feature             1..325
                         note = Description of Artificial Sequence: SyntheticKPN70
                         VL polynucleotide
source                   1..325
                         mol_type = other DNA
                         organism = synthetic construct
SEQUENCE: 155
gaaattgtgt tgacacagtc tccagcctcc ctgtctttgt ctccagggga aagagccacc    60
ctctcctgca gggccagtca gattgttacc aactacttag cctggtatca acataaacct   120
ggccaggctc ccaggctcct catctttgat atgtccatta gggccgctgg catcccagcc   180
aggttcagtg gcagtgggtc tgggacagac ttcactctca ccatcagcag ccttgagcct   240
gaagattttg cagtttatta ctgtcaacac cgtagcaact ggcctctatt cactttcggc   300
cctgggacca agtggatat caaac                                          325

SEQ ID NO: 156           moltype = DNA  length = 334
FEATURE                  Location/Qualifiers
misc_feature             1..334
                         note = Description of Artificial Sequence: SyntheticKPN179
                         VL polynucleotide
source                   1..334
                         mol_type = other DNA
                         organism = synthetic construct
SEQUENCE: 156
cagtctgccc tgactcagcc tccctcagtg tccgggtctc ctggacagtc agtcaccatc    60
tcctgcactg gaaccagcag tgatgttggt tattacgact atgtctcctg gtaccaacag   120
caccacccag gcaaagcccc caaacacatg atttatgatg tcaataagcg gccctcaggg   180
gtccctgatc gcttctctgg ctccaagtct ggcaacacgg cctccctgac catctctggg   240
ctccaggctg aggatgaggc tgattattat tgctgttcat atgcaggcgg tgacactttt   300
gtcttcggaa ctgggaccaa ggtcaccgtc ctag                               334

SEQ ID NO: 157           moltype = DNA  length = 325
FEATURE                  Location/Qualifiers
misc_feature             1..325
                         note = Description of Artificial Sequence: SyntheticKPN44
                         VL polynucleotide
source                   1..325
                         mol_type = other DNA
                         organism = synthetic construct
SEQUENCE: 157
gaaattgtgt tgacacagtc tccagcctcc ctgtctttgt ctccagggga cagagccacc    60
ctctcctgca gggccagtca gacgattacc aactacttag cctggtacca acataaacct   120
ggccaggctc ccagactcct catctttgat atgtcgaaaa gggccactgg catcccagcc   180
aggttcagtg gcagtgggtc tgggacagac ttcactctca ccatcagcag ccttgagcct   240
gaagattttg cagtttacta ctgtcaacac cgtagcaact ggcctctcatt cactttcggc   300
cctgggacca acgtggatat caaac                                         325

SEQ ID NO: 158           moltype = DNA  length = 322
FEATURE                  Location/Qualifiers
```

```
misc_feature            1..322
                        note = Description of Artificial Sequence: SyntheticKPN17
                        VL polynucleotide
source                  1..322
                        mol_type = other DNA
                        organism = synthetic construct
SEQUENCE: 158
gacatccagt tgacccagtc tccatccttc ctgtctgcct ctgtaggaga cagagtcacc    60
atcacttgcc gggccagtca gggcattagc acttatttag cctggtatca acaaaaacca   120
gggaaagccc ctaagctcct gatctatgct gcatccactt tgcaaagtgg ggtcccatca   180
aggttcagcg gcagtggatc tgggacagaa ttcactctca caatcaacag cctgcagtct   240
gaagattttg caacttacta ctgtcagcag cttactagtc acctctacac ttttggccag   300
gggaccaagc tggagatcaa ac                                            322

SEQ ID NO: 159          moltype = DNA  length = 336
FEATURE                 Location/Qualifiers
misc_feature            1..336
                        note = Description of Artificial Sequence: Synthetic6F6 VL
                        polynucleotide
source                  1..336
                        mol_type = other DNA
                        organism = synthetic construct
SEQUENCE: 159
gatgttgtga tgacccaaac tccactcttc ctgcctgtca gtcttggaga tcaagcctcc    60
atctcttgca gatctagtca gggccttgta cacagtactg gaaacacctt tttacattgg   120
tacctgcaga agccaggcca gtctccaaag ctcctacaaa gtttccaaccgattt         180
tctggggtcc cagacaggtt cagtggcagt ggatcaggga cagatttcac actcaagatc   240
agcagagtgg aggctgagga tctgggaatt tatttctgct ctcaaagtac acatattccg   300
tacacgttcg gaggggggac caagctggaa ataaaa                             336

SEQ ID NO: 160          moltype = DNA  length = 325
FEATURE                 Location/Qualifiers
misc_feature            1..325
                        note = Description of Artificial Sequence: SyntheticKPL26
                        VL polynucleotide
source                  1..325
                        mol_type = other DNA
                        organism = synthetic construct
SEQUENCE: 160
cagtctgccc tgactcagcc tccctccgcg tccgggtctc ctggacaatc agtcaccctc    60
tcctgcactg gaaccagcag tgacgttggt ggtaataact atgtctcctg gtaccaacag   120
cacccaggca aagcccccaa actcatcatt tatgaggtca gtaagcggcc ctcagggggtc   180
cctaatcgtt tctctggctc caagtctggc aacacggcct ccctgaccgt ctctgggctc   240
caggctgagg atgaggctga ttattactgc agctcatttg gaggtagtaa gatgttcggc   300
ggagggacca gctgaccgt cctag                                          325

SEQ ID NO: 161          moltype = DNA  length = 331
FEATURE                 Location/Qualifiers
misc_feature            1..331
                        note = Description of Artificial Sequence: SyntheticKPS18
                        VL polynucleotide
source                  1..331
                        mol_type = other DNA
                        organism = synthetic construct
SEQUENCE: 161
cagtctgtgt tgacgcagcc gccctcactg tctgcggccc caggacagac ggtcaccatc    60
gcctgctctg gaagtagatc caacattggg agtgattccg tctcctggtt ccagcagttc   120
ccaggaacag cccccagagt cctcatgtat gacaataata gcgaccctc aggcatttct   180
gaccgattct ctggctccaa gtctggcacg tcagtcaccc tggacatcac cggactccag   240
actggggacg aggccgatta ttactgcgca acatgggata gcagcctgag tgcttatgtc   300
ttcggatctg ggaccaaggt caccgtccta a                                  331

SEQ ID NO: 162          moltype = DNA  length = 331
FEATURE                 Location/Qualifiers
misc_feature            1..331
                        note = Description of Artificial Sequence: SyntheticKPS24
                        VL polynucleotide
source                  1..331
                        mol_type = other DNA
                        organism = synthetic construct
SEQUENCE: 162
cagtctgtgt tgacgcagcc gccctcagtg tctgcggccc caggacagac ggtcaccatc    60
gcctgctctg gaagtagctc caacattggg agtgattccg tatcctggtt ccagcagctc   120
ccaggaacag cccccagagt cctcatgtat gaaaataata gcgaccctc agggattct    180
gaccgattct ctggctccaa gtctggcacg tcagtcaccc tggcatcac cggactccag   240
actggggacg aggccgatta ttactgcgca gcatgggata gcagcctacg tgcttatgtc   300
ttcggatctg ggaccaaggt caccgtccta g                                  331

SEQ ID NO: 163          moltype = DNA  length = 331
```

```
FEATURE              Location/Qualifiers
misc_feature         1..331
                     note = Description of Artificial Sequence: SyntheticKPS44
                     VL polynucleotide
source               1..331
                     mol_type = other DNA
                     organism = synthetic construct
SEQUENCE: 163
cagtctgtgt tgacgcagcc gcccctcactg tctgcggccc ctggacagac gatcaccatc    60
gcctgctctg gaactagttc aacattggg agtgattccg tatcctggtt ccagcaattc    120
ccaggaacag cccccagagt cctcatatat gagaataata agcgaccctc aggcatttct    180
gaccgattct ctggctccaa gtctggcacg tcagtcacac tgggcatcac cggactccag    240
actggggacg aggccgatta ttactgcgca acatgggata gcagcctgag tgcttatgtc    300
ttcggatctg ggaccaaggt caccgtccta g                                   331

SEQ ID NO: 164       moltype = DNA   length = 325
FEATURE              Location/Qualifiers
misc_feature         1..325
                     note = Description of Artificial Sequence: SyntheticKPS30
                     VL polynucleotide
source               1..325
                     mol_type = other DNA
                     organism = synthetic construct
SEQUENCE: 164
cagtctgccc tgactcagcc tccctccgcg tccgggtctc ctggacagtc agtcgtcatc    60
tcctgcactg gaaccagcag tgacattggg gctaataact atgtctcttg gtaccaacaa    120
cacccaggca aagcccccaa actcttgctt tatgaggtca ataagcggcc ctcaggggtc    180
cctgatcgct tctctgcctc caagtctggc aacacggcct ccctgaccgt ctctgggctc    240
ctggctgagg atgaggctga ttattactgc tgcggatatg gaggcgggag ggtgttcggc    300
ggagggacca agctgaccgt cctac                                          325

SEQ ID NO: 165       moltype = DNA   length = 322
FEATURE              Location/Qualifiers
misc_feature         1..322
                     note = Description of Artificial Sequence: SyntheticKPD1 VL
                     polynucleotide
source               1..322
                     mol_type = other DNA
                     organism = synthetic construct
SEQUENCE: 165
gaaattgtgt tgacgcagtc tccaggcatc ctgtctttgt ctccagggga gagagccacc    60
ctctcttgca gggtcagtca gattctttac atgtctcatt tggcctggta tcagcataaa    120
cctggacagg ctcccagact cctcatctat ggtgcgtcca tcagccgcca tggcgtccca    180
gacaggttca gtggcagtgg gtccgggaca gacttcactc tcaccatcag cagactggag    240
cctgaagatt ttgcagtgta ttactgtcag cagtatggcg cctcaccgac gttcggccaa    300
gggacaatgg tggaaatcaa ac                                             322

SEQ ID NO: 166       moltype = AA   length = 8
FEATURE              Location/Qualifiers
REGION               1..8
                     note = Description of Artificial Sequence:
                     SyntheticKPN179-FR-1-2-4-GL N35S-VH/KPN179-FR-GL-C105A-VL
                     VH-CDR1 peptide
source               1..8
                     mol_type = protein
                     organism = synthetic construct
SEQUENCE: 166
GFTFSNAW                                                               8

SEQ ID NO: 167       moltype = AA   length = 10
FEATURE              Location/Qualifiers
REGION               1..10
                     note = Description of Artificial Sequence:
                     SyntheticKPN179-FR-1-2-4-GL N35S-VH/KPN179-FR-GL-C105A-VL
                     VH-CDR2 peptide
source               1..10
                     mol_type = protein
                     organism = synthetic construct
SEQUENCE: 167
IKRKADGETT                                                            10

SEQ ID NO: 168       moltype = AA   length = 10
FEATURE              Location/Qualifiers
REGION               1..10
                     note = Description of Artificial Sequence:
                     SyntheticKPN179-FR-1-2-4-GL N35S-VH/KPN179-FR-GL-C105A-VL
                     VH-CDR3 peptide
source               1..10
                     mol_type = protein
```

```
                                    -continued

SEQUENCE: 168           organism = synthetic construct
TTRIVTTNDY                                                              10

SEQ ID NO: 169          moltype = AA   length = 8
FEATURE                 Location/Qualifiers
REGION                  1..8
                        note = Description of Artificial Sequence:
                          SyntheticKPN179-FR-GL N35S-VH/KPN179-FR-GL-C105A-VL
                          VH-CDR1 peptide
source                  1..8
                        mol_type = protein
                        organism = synthetic construct
SEQUENCE: 169
GFTFSNAW                                                                 8

SEQ ID NO: 170          moltype = AA   length = 10
FEATURE                 Location/Qualifiers
REGION                  1..10
                        note = Description of Artificial Sequence:
                          SyntheticKPN179-FR-GL N35S-VH/KPN179-FR-GL-C105A-VL
                          VH-CDR2 peptide
source                  1..10
                        mol_type = protein
                        organism = synthetic construct
SEQUENCE: 170
IKRKADGETT                                                              10

SEQ ID NO: 171          moltype = AA   length = 10
FEATURE                 Location/Qualifiers
REGION                  1..10
                        note = Description of Artificial Sequence:
                          SyntheticKPN179-FR-GL N35S-VH/KPN179-FR-GL-C105A-VL
                          VH-CDR3 peptide
source                  1..10
                        mol_type = protein
                        organism = synthetic construct
SEQUENCE: 171
TTRIVTTNDY                                                              10

SEQ ID NO: 172          moltype = AA   length = 8
FEATURE                 Location/Qualifiers
REGION                  1..8
                        note = Description of Artificial Sequence: SyntheticKPL36
                          VH-CDR1 peptide
source                  1..8
                        mol_type = protein
                        organism = synthetic construct
SEQUENCE: 172
GFTFISSW                                                                 8

SEQ ID NO: 173          moltype = AA   length = 8
FEATURE                 Location/Qualifiers
REGION                  1..8
                        note = Description of Artificial Sequence: SyntheticKPL36
                          VH-CDR2 peptide
source                  1..8
                        mol_type = protein
                        organism = synthetic construct
SEQUENCE: 173
INPDGTET                                                                 8

SEQ ID NO: 174          moltype = AA   length = 11
FEATURE                 Location/Qualifiers
REGION                  1..11
                        note = Description of Artificial Sequence: SyntheticKPL36
                          VH-CDR3 peptide
source                  1..11
                        mol_type = protein
                        organism = synthetic construct
SEQUENCE: 174
ARNKAYNAHD F                                                            11

SEQ ID NO: 175          moltype = AA   length = 9
FEATURE                 Location/Qualifiers
REGION                  1..9
                        note = Description of Artificial Sequence:
                          SyntheticKPN179-FR-1-2-4-GL N35S-VH/KPN179-FR-GL-C105A-VL
                          VL-CDR1 peptide
```

```
source                      1..9
                            mol_type = protein
                            organism = synthetic construct
SEQUENCE: 175
SSDVGYYDY                                                                      9

SEQ ID NO: 176              moltype =    length =
SEQUENCE: 176
000

SEQ ID NO: 177              moltype = AA   length = 9
FEATURE                     Location/Qualifiers
REGION                      1..9
                            note = Description of Artificial Sequence:
                             SyntheticKPN179-FR-1-2-4-GL N35S-VH/KPN179-FR-GL-C105A-VL
                             VL-CDR2 peptide
source                      1..9
                            mol_type = protein
                            organism = synthetic construct
SEQUENCE: 177
MIYDVNKRP                                                                      9

SEQ ID NO: 178              moltype = AA   length = 10
FEATURE                     Location/Qualifiers
REGION                      1..10
                            note = Description of Artificial Sequence:
                             SyntheticKPN179-FR-1-2-4-GL N35S-VH/KPN179-FR-GL-C105A-VL
                             VL-CDR3 peptide
source                      1..10
                            mol_type = protein
                            organism = synthetic construct
SEQUENCE: 178
ASYAGGDTFV                                                                    10

SEQ ID NO: 179              moltype = AA   length = 9
FEATURE                     Location/Qualifiers
REGION                      1..9
                            note = Description of Artificial Sequence:
                             SyntheticKPN179-FR-GL N35S-VH/KPN179-FR-GL-C105A-VL
                             VL-CDR1 peptide
source                      1..9
                            mol_type = protein
                            organism = synthetic construct
SEQUENCE: 179
SSDVGYYDY                                                                      9

SEQ ID NO: 180              moltype =    length =
SEQUENCE: 180
000

SEQ ID NO: 181              moltype = AA   length = 9
FEATURE                     Location/Qualifiers
REGION                      1..9
                            note = Description of Artificial Sequence:
                             SyntheticKPN179-FR-GL N35S-VH/KPN179-FR-GL-C105A-VL
                             VL-CDR2 peptide
source                      1..9
                            mol_type = protein
                            organism = synthetic construct
SEQUENCE: 181
MIYDVNKRP                                                                      9

SEQ ID NO: 182              moltype = AA   length = 10
FEATURE                     Location/Qualifiers
REGION                      1..10
                            note = Description of Artificial Sequence:
                             SyntheticKPN179-FR-GL N35S-VH/KPN179-FR-GL-C105A-VL
                             VL-CDR3 peptide
source                      1..10
                            mol_type = protein
                            organism = synthetic construct
SEQUENCE: 182
ASYAGGDTFV                                                                    10

SEQ ID NO: 183              moltype = AA   length = 9
FEATURE                     Location/Qualifiers
REGION                      1..9
                            note = Description of Artificial Sequence: SyntheticKPL36
                             VL-CDR1 peptide
```

| | |
|---|---|
| source | 1..9<br>mol_type = protein<br>organism = synthetic construct |

SEQUENCE: 183
SSDVGGNNF                                                                9

| | |
|---|---|
| SEQ ID NO: 184 | moltype =    length = |

SEQUENCE: 184
000

| | |
|---|---|
| SEQ ID NO: 185 | moltype = AA   length = 9 |
| FEATURE | Location/Qualifiers |
| REGION | 1..9<br>note = Description of Artificial Sequence: SyntheticKPL36<br>VL-CDR2 peptide |
| source | 1..9<br>mol_type = protein<br>organism = synthetic construct |

SEQUENCE: 185
IIYEVNKRP                                                                9

| | |
|---|---|
| SEQ ID NO: 186 | moltype = AA   length = 8 |
| FEATURE | Location/Qualifiers |
| REGION | 1..8<br>note = Description of Artificial Sequence: SyntheticKPL36<br>VL-CDR3 peptide |
| source | 1..8<br>mol_type = protein<br>organism = synthetic construct |

SEQUENCE: 186
GAFGGSKM                                                                 8

| | |
|---|---|
| SEQ ID NO: 187 | moltype = AA   length = 119 |
| FEATURE | Location/Qualifiers |
| REGION | 1..119<br>note = Description of Artificial Sequence:<br>SyntheticKPN179-FR-1-2-4-GL N35S-VH/KPN179-FR-GL-C105A-VL<br>VHpolypeptide |
| source | 1..119<br>mol_type = protein<br>organism = synthetic construct |

SEQUENCE: 187
EVQLVESGGG LVKPGGSLRL SCAASGFTFS NAWMNWVRQA PGKGLEWVGR IKRKADGETT    60
DYPASVKGRF TVSRDDSKNT IYLQMNSLKT EDTAIYYCTT RIVTTNDYWG QGTLVTVSS    119

| | |
|---|---|
| SEQ ID NO: 188 | moltype = AA   length = 119 |
| FEATURE | Location/Qualifiers |
| REGION | 1..119<br>note = Description of Artificial Sequence:<br>SyntheticKPN179-FR-GL N35S-VH/KPN179-FR-GL-C105A-VL<br>VHpolypeptide |
| source | 1..119<br>mol_type = protein<br>organism = synthetic construct |

SEQUENCE: 188
EVQLVESGGG LVKPGGSLRL SCAASGFTFS NAWMNWVRQA PGKGLEWVGR IKRKADGETT    60
DYAAPVKGRF TISRDDSKNT LYLQMNSLKT EDTAVYYCTT RIVTTNDYWG QGTLVTVSS    119

| | |
|---|---|
| SEQ ID NO: 189 | moltype = AA   length = 118 |
| FEATURE | Location/Qualifiers |
| REGION | 1..118<br>note = Description of Artificial Sequence: SyntheticKPL36<br>VH polypeptide |
| source | 1..118<br>mol_type = protein<br>organism = synthetic construct |

SEQUENCE: 189
EVQLVESGGG VVQSGGSLRL SCETSGFTFI SSWMSWVRQA PGTGLEWVAT INPDGTETPY    60
ADSLKGRFTI SRDNTKKSLY LQIHSLRADD TAVYFCARNK AYNAHDFWGQ GTLVMVSS     118

| | |
|---|---|
| SEQ ID NO: 190 | moltype = AA   length = 110 |
| FEATURE | Location/Qualifiers |
| REGION | 1..110<br>note = Description of Artificial Sequence:<br>SyntheticKPN179-FR-1-2-4-GL N35S-VH/KPN179-FR-GL-C105A-VL<br>VLpolypeptide |
| source | 1..110<br>mol_type = protein<br>organism = synthetic construct |

```
SEQUENCE: 190
QSALTQPRSV SGSPGQSVTI SCTGTSSDVG YYDYVSWYQQ HPGKAPKLMI YDVNKRPSGV    60
PDRFSGSKSG NTASLTISGL QAEDEADYYC ASYAGGDTFV FGTGTKVTVL              110

SEQ ID NO: 191          moltype = AA   length = 110
FEATURE                 Location/Qualifiers
REGION                  1..110
                        note = Description of Artificial Sequence:
                        SyntheticKPN179-FR-GL N35S-VH/KPN179-FR-GL-C105A-VL VL
                        polypeptide
source                  1..110
                        mol_type = protein
                        organism = synthetic construct
SEQUENCE: 191
QSALTQPRSV SGSPGQSVTI SCTGTSSDVG YYDYVSWYQQ HPGKAPKLMI YDVNKRPSGV    60
PDRFSGSKSG NTASLTISGL QAEDEADYYC ASYAGGDTFV FGTGTKVTVL              110

SEQ ID NO: 192          moltype = AA   length = 108
FEATURE                 Location/Qualifiers
REGION                  1..108
                        note = Description of Artificial Sequence: SyntheticKPL36
                        VL polypeptide
source                  1..108
                        mol_type = protein
                        organism = synthetic construct
SEQUENCE: 192
QSALTQPPSA SGSPGQSVTI SCTGTSSDVG GNNFVSWYQQ YPGKAPKLII YEVNKRPSGV    60
PDRFSGSKSG NTASLTVSGL QAEDEADYYC GAFGGSKMFG GGTKLTVL                108

SEQ ID NO: 193          moltype = DNA   length = 357
FEATURE                 Location/Qualifiers
misc_feature            1..357
                        note = Description of Artificial Sequence:
                        SyntheticKPN179-FR-1-2-4-GL N35S-VH/KPN179-FR-GL-C105A-VL
                        VH polynucleotide
source                  1..357
                        mol_type = other DNA
                        organism = synthetic construct
SEQUENCE: 193
gaggtgcagc tggtcgaatc cggcggggga ctggtgaaac ctggcggctc tctgcgactg    60
agttgcgccg cttcaggctt cacctttagc aacgcatgga tgaattgggt gagacaggca   120
cctggaaagg gactggagtg ggtcggccgg atcaagagaa aagctgacgg ggaaaccaca   180
gattaccctg catctgtgaa gggcaggttc acagtcagcc gcgacgattc caaaaacact   240
atctacctgc agatgaatag tctgaagacc gaggacacag ccatctacta ttgtactacc   300
cggattgtga caactaacga ttactggggg cagggaactc tggtgaccgt cagctcc      357

SEQ ID NO: 194          moltype = DNA   length = 357
FEATURE                 Location/Qualifiers
misc_feature            1..357
                        note = Description of Artificial Sequence:
                        SyntheticKPN179-FR-GL N35S-VH/KPN179-FR-GL-C105A-VL VH
                        polynucleotide
source                  1..357
                        mol_type = other DNA
                        organism = synthetic construct
SEQUENCE: 194
gaggtgcagc tggtcgaatc tggcggggga ctggtgaaac ctggcggctc tctgcgactg    60
agttgcgccg cttcaggctt cacctttagc aacgcttgga tgaattgggt gagacaggca   120
cctggaaagg gactggagtg ggtgggacgg atcaagagaa aagcgacgg ggaaaccaca   180
gattacgcag cccctgtgaa gggcaggttc acaattagcc gcgacgattc caaaaacact   240
ctgtatctgc agatgaatag cctgaagacc gaggacacag ccgtgtacta ttgtactacc   300
cggatcgtca caactaacga ttactggggg cagggaactc tggtgaccgt cagctcc      357

SEQ ID NO: 195          moltype = DNA   length = 355
FEATURE                 Location/Qualifiers
misc_feature            1..355
                        note = Description of Artificial Sequence: SyntheticKPL36
                        VH polynucleotide
source                  1..355
                        mol_type = other DNA
                        organism = synthetic construct
SEQUENCE: 195
gaggtgcagc tggtggagtc tgggggaggc gtggtccagt ctgggggtc cctgagactc    60
tcctgtgaga cttctggatt cacctttata agttcttgga tgagttgggt ccgccaggct   120
ccagggacag gactggagtg ggtggccacc attaaccctg atggaactga gacaccctac   180
gcggactcgc tgaagggccg cttcaccatc tccagagaca acaccaagaa gtcactttat   240
ctgcaaatcc atagcctgag agccgacgac acggccgtct atttctgtgc aaggaataag   300
gcatacaatg cccatgactt ctggggccag ggaaccctgg tcaccgtctc ctcag        355
```

| SEQ ID NO: 196 | moltype = DNA   length = 330 |
| FEATURE | Location/Qualifiers |
| misc_feature | 1..330 |
| | note = Description of Artificial Sequence: SyntheticKPN179-FR-1-2-4-GL N35S-VH/KPN179-FR-GL-C105A-VL VL polynucleotide |
| source | 1..330 |
| | mol_type = other DNA |
| | organism = synthetic construct |

SEQUENCE: 196

```
cagtctgccc tgactcagcc taggtctgtg agtgggtcac ccggacagag tgtcacaatc   60
tcatgcaccg gaacaagctc cgacgtgggc tactatgatt acgtctcttg gtatcagcag  120
caccccggga aggctcctaa actgatgatc tacgacgtga acaagcggcc aagtggcgtc  180
cccgatagat tcagcggctc caaatctggg aatacagcaa gcctgactat ttccggcctg  240
caggcagagg acgaagccga ttactattgt gccagctatg ctggcgggga ccttcgtg    300
tttggaactg gcaccaaggt gacagtcctg                                   330
```

| SEQ ID NO: 197 | moltype = DNA   length = 330 |
| FEATURE | Location/Qualifiers |
| misc_feature | 1..330 |
| | note = Description of Artificial Sequence: SyntheticKPN179-FR-GL N35S-VH/KPN179-FR-GL-C105A-VL VL polynucleotide |
| source | 1..330 |
| | mol_type = other DNA |
| | organism = synthetic construct |

SEQUENCE: 197

```
cagtctgccc tgactcagcc taggtctgtg agtgggtcac ccggacagag tgtcacaatc   60
tcatgcaccg gaacaagctc cgacgtgggc tactatgatt acgtctcttg gtatcagcag  120
caccccggga aggctcctaa actgatgatc tacgacgtga acaagcggcc aagtggcgtc  180
cccgatagat tcagcggctc caaatctggg aatacagcaa gcctgactat ttccggcctg  240
caggcagagg acgaagccga ttactattgt gccagctatg ctggcgggga ccttcgtg    300
tttggaactg gcaccaaggt gacagtcctg                                   330
```

| SEQ ID NO: 198 | moltype = DNA   length = 325 |
| FEATURE | Location/Qualifiers |
| misc_feature | 1..325 |
| | note = Description of Artificial Sequence: SyntheticKPL36 VL polynucleotide |
| source | 1..325 |
| | mol_type = other DNA |
| | organism = synthetic construct |

SEQUENCE: 198

```
cagtctgccc tgactcagcc tcccteegeg teegggtete ctggacaate agtcaccate   60
tcctgcactg gaaccagtag tgacgtaggt ggtaataact ttgtctcctg gtaccaacag  120
tatccaggca aagcccccaa actcattatt tatgaggtca ataagcggcc ctcagggtc   180
cctgatcgtt tctctggctc caagtctggc aacacggcct ccctgaccgt ctctgggctc  240
caggctgagg atgaggctga ttattactgc ggcgcatttg aggtagcaa gatgttcggc   300
ggagggacca gctgaccgt cctag                                         325
```

| SEQ ID NO: 199 | moltype = AA   length = 11 |
| FEATURE | Location/Qualifiers |
| REGION | 1..11 |
| | note = Description of Artificial Sequence: SyntheticKPS44-v2017/KPS-44-G2/KPS-44-G3 VH-CDR3 peptide |
| source | 1..11 |
| | mol_type = protein |
| | organism = synthetic construct |

SEQUENCE: 199
RAFFSGFPTG Y                                                        11

| SEQ ID NO: 200 | moltype = AA   length = 8 |
| FEATURE | Location/Qualifiers |
| REGION | 1..8 |
| | note = Description of Artificial Sequence: SyntheticKPS44-v2017/KPS-44-G1/KPS-44-G3 VL-CDR1 peptide |
| source | 1..8 |
| | mol_type = protein |
| | organism = synthetic construct |

SEQUENCE: 200
SSNIGSNY                                                             8

| SEQ ID NO: 201 | moltype = AA   length = 11 |
| FEATURE | Location/Qualifiers |
| REGION | 1..11 |
| | note = Description of Artificial Sequence: SyntheticKPS44-v2017/KPS-44-G1/KPS-44-G2 VL-CDR3 peptide |
| source | 1..11 |
| | mol_type = protein |

```
                         organism = synthetic construct
SEQUENCE: 201
ATFDSSLSAY V                                                           11

SEQ ID NO: 202           moltype = AA  length = 120
FEATURE                  Location/Qualifiers
REGION                   1..120
                         note = Description of Artificial Sequence:
                         SyntheticKPS44-v2017/KPS44-G2/KPS44-G3 VH polypeptide
source                   1..120
                         mol_type = protein
                         organism = synthetic construct
SEQUENCE: 202
EVHLVESGGG LVKPGGSLRL SCAASGFTFK NAWMSWIRQA PGKGLEWVGR VKSEVDGGTI    60
DYGVPVRGRF TISRDDSQGT LSLEMNSLKD DDTGVYYCRA FFSGFPTGYW GQGALVSVSS   120

SEQ ID NO: 203           moltype = AA  length = 110
FEATURE                  Location/Qualifiers
REGION                   1..110
                         note = Description of Artificial Sequence:
                         SyntheticKPS44-v2017/KPS44-G1 VL polypeptide
source                   1..110
                         mol_type = protein
                         organism = synthetic construct
SEQUENCE: 203
QSVLTQPPSL SAAPGQTITI ACSGTSSNIG SNYVSWFQQF PGTAPRVLIY ENNKRPSGIS    60
DRFSGSKSGT SVTLGITGLQ TGDEADYYCA TFDSSLSAYV FGSGTKVTVL              110

SEQ ID NO: 204           moltype = AA  length = 110
FEATURE                  Location/Qualifiers
REGION                   1..110
                         note = Description of Artificial Sequence:
                         SyntheticKPS44-G2 VL polypeptide
source                   1..110
                         mol_type = protein
                         organism = synthetic construct
SEQUENCE: 204
QSVLTQPPSL SAAPGQTITI ACSGTSSNIG SDSVSWFQQF PGTAPRVLIY ENNKRPSGIS    60
DRFSGSKSGT SVTLGITGLQ TGDEADYYCA TFDSSLSAYV FGSGTKVTVL              110

SEQ ID NO: 205           moltype = AA  length = 110
FEATURE                  Location/Qualifiers
REGION                   1..110
                         note = Description of Artificial Sequence:
                         SyntheticKPS44-G3 VL polypeptide
source                   1..110
                         mol_type = protein
                         organism = synthetic construct
SEQUENCE: 205
QSVLTQPPSL SAAPGQTITI ACSGTSSNIG SNYVSWFQQF PGTAPRVLIY ENNKRPSGIS    60
DRFSGSKSGT SVTLGITGLQ TGDEADYYCA TWDSSLSAYV FGSGTKVTVL              110

SEQ ID NO: 206           moltype = DNA  length = 360
FEATURE                  Location/Qualifiers
misc_feature             1..360
                         note = Description of Artificial Sequence:
                         SyntheticKPS44-v2017 VH polynucleotide
source                   1..360
                         mol_type = other DNA
                         organism = synthetic construct
SEQUENCE: 206
gaggtgcacc tggtcgaatc cggcggggga ctggtgaaac caggcgggtc tctgagactg    60
agttgcgccg cttcaggctt caccttcaag aacgcatgga tgagctggat tagacaggca   120
cctgggaagg gactggagtg ggtgggccgc gtcaaatctg aagtggatgg aggcaccatc   180
gactacgggg tgcctgtccg gggaagattc accattagcc gagacgattc ccagggcaca   240
ctgtctctgg agatgaatag tctgaaggac gatgacactg gggtgtacta ttgtagagct   300
ttcttttcag gatttcctac cggctattgg ggacaggggg ccctggtgag cgtcagctcc   360

SEQ ID NO: 207           moltype = DNA  length = 360
FEATURE                  Location/Qualifiers
misc_feature             1..360
                         note = Description of Artificial Sequence:
                         SyntheticKPS44-G1 VH polynucleotide
source                   1..360
                         mol_type = other DNA
                         organism = synthetic construct
SEQUENCE: 207
gaggtacacc ttgtagaaag tgggggtggg cttgtcaagc tgggggaag tttgagactg     60
agttgcgccg caagtggctt cacgtttaag aacgcatgga tgtcctggat tagacaagcc   120
```

```
cccggtaaag gtttggaatg ggtaggacga gttaagtctg aggttgacgg ggggacgata   180
gattacggtg ttcccgtgcg cggcagattc acgataagtc gagacgactc tcagggtaca   240
cttagcctcg aaatgaatag cctcaaagac gatgatacag gcgtttatta ttgccgcgca   300
ttctggagtg gcttcccgac tgggtactgg gggcaaggtg ctcttgtctc agtgtcatcc   360

SEQ ID NO: 208           moltype = DNA  length = 360
FEATURE                  Location/Qualifiers
misc_feature             1..360
                         note = Description of Artificial Sequence:
                         SyntheticKPS44-G2/KPS44-G3 VH polynucleotide
source                   1..360
                         mol_type = other DNA
                         organism = synthetic construct
SEQUENCE: 208
gaggtacacc ttgtagaaag tgggggtggg cttgtcaagc ctgggggaag tttgagactg    60
agttgcgccg caagtggctt cacgtttaag aacgcatgga tgtcctggat tagacaagcc   120
cccggtaaag gtttggaatg ggtaggacga gttaagtctg aggttgacgg ggggacgata   180
gattacggtg ttcccgtgcg cggcagattc acgataagtc gagacgactc tcagggtaca   240
cttagcctcg aaatgaatag cctcaaagac gatgatacag gcgtttatta ttgccgcgca   300
ttctttagtg gcttcccgac tgggtactgg gggcaaggtg ctcttgtctc agtgtcatcc   360

SEQ ID NO: 209           moltype = DNA  length = 330
FEATURE                  Location/Qualifiers
misc_feature             1..330
                         note = Description of Artificial Sequence:
                         SyntheticKPS44-v2017 VL polynucleotide
source                   1..330
                         mol_type = other DNA
                         organism = synthetic construct
SEQUENCE: 209
cagagcgtgc tgacacagcc cccttcactg agcgccgctc ctggacagac catcacaatt    60
gcttgctccg gcactagctc caacatcggg tccaattacg tgtcttggtt ccagcagttt   120
ccaggaaccg cacccagggt cctgatctat gagaacaata gcggccctc aggcattagc    180
gacagattct ccgggtctaa aagtggaact agcgtgaccc tgggaattac cggcctgcag   240
acaggcgacg aagcagatta ctattgtgcc accttcgatt ctagtctgag tgcctacgtc   300
tttggctctg ggacaaaagt gactgtcctg                                    330

SEQ ID NO: 210           moltype = DNA  length = 330
FEATURE                  Location/Qualifiers
misc_feature             1..330
                         note = Description of Artificial Sequence:
                         SyntheticKPS44-G1 VL polynucleotide
source                   1..330
                         mol_type = other DNA
                         organism = synthetic construct
SEQUENCE: 210
cagtccgttt tgacgcaacc cccgtcactg agtgctgcgc ctgggcagac cataacgatc    60
gcctgctcag ggaccagcag taatataggc tctaattatg tatcatggtt ccagcaattc   120
cctggcacgg cacctcgcgt actgatctac gaaaataata gcggccctc aggcatttca   180
gataggttct ctgggagcaa gagtggtaca agcgtaacgc tcggtatcac cggtctccag   240
acaggtgatg aagctgatta ctactgcgct acttttgata gctctctttc agcttacgtg   300
tttggttccg ggaccaaagt gacagtcctc                                    330

SEQ ID NO: 211           moltype = DNA  length = 330
FEATURE                  Location/Qualifiers
misc_feature             1..330
                         note = Description of Artificial Sequence:
                         SyntheticKPS44-G2 VL polynucleotide
source                   1..330
                         mol_type = other DNA
                         organism = synthetic construct
SEQUENCE: 211
cagtccgttt tgacgcaacc cccgtcactg agtgctgcgc ctgggcagac cataacgatc    60
gcctgctcag ggaccagcag taatataggc tctgattctg tatcatggtt ccagcaattc   120
cctggcacgg cacctcgcgt actgatctac gaaaataata gcggccctc aggcatttca   180
gataggttct ctgggagcaa gagtggtaca agcgtaacgc tcggtatcac cggtctccag   240
acaggtgatg aagctgatta ctactgcgct acttttgata gctctctttc agcttacgtg   300
tttggttccg ggaccaaagt gacagtcctc                                    330

SEQ ID NO: 212           moltype = DNA  length = 330
FEATURE                  Location/Qualifiers
misc_feature             1..330
                         note = Description of Artificial Sequence:
                         SyntheticKPS44-G3 VL polynucleotide
source                   1..330
                         mol_type = other DNA
                         organism = synthetic construct
SEQUENCE: 212
cagtccgttt tgacgcaacc cccgtcactg agtgctgcgc ctgggcagac cataacgatc    60
```

```
gcctgctcag ggaccagcag taatataggc tctaattatg tatcatggtt ccagcaattc   120
cctggcacgg cacctcgcgt actgatctac gaaaataata agcggccctc aggcatttca   180
gataggttct ctgggagcaa gagtggtaca agcgtaacgc tcggtatcac cggtctccag   240
acaggtgatg aagctgatta ctactgcgct acttgggata gctctctttc agcttacgtg   300
tttggttccg ggaccaaagt gacagtcctc                                     330

SEQ ID NO: 213          moltype = AA   length = 120
FEATURE                 Location/Qualifiers
REGION                  1..120
                        note = Description of Artificial Sequence:
                        SyntheticKPS44-G4 VH polypeptide
source                  1..120
                        mol_type = protein
                        organism = synthetic construct
SEQUENCE: 213
QVQLVESGGG LVKPGGSLRL SCAASGFTFK NAWMSWIRQA PGKGLEWVGR VKSEVDAGTI    60
DYGVPVRGRF TISRDDSKNT LYLQMNSLKT EDTAVYYCRA FYSGFPTGYW GQGTLVTVSS   120

SEQ ID NO: 214          moltype = AA   length = 8
FEATURE                 Location/Qualifiers
REGION                  1..8
                        note = Description of Artificial Sequence:
                        SyntheticKPS44-G4 VH-CDR1 peptide
source                  1..8
                        mol_type = protein
                        organism = synthetic construct
SEQUENCE: 214
GFTFKNAW                                                               8

SEQ ID NO: 215          moltype = AA   length = 10
FEATURE                 Location/Qualifiers
REGION                  1..10
                        note = Description of Artificial Sequence:
                        SyntheticKPS44-G4 VH-CDR2 peptide
source                  1..10
                        mol_type = protein
                        organism = synthetic construct
SEQUENCE: 215
VKSEVDAGTI                                                            10

SEQ ID NO: 216          moltype = AA   length = 11
FEATURE                 Location/Qualifiers
REGION                  1..11
                        note = Description of Artificial Sequence:
                        SyntheticKPS44-G4 VH-CDR3 peptide
source                  1..11
                        mol_type = protein
                        organism = synthetic construct
SEQUENCE: 216
RAFYSGFPTG Y                                                          11

SEQ ID NO: 217          moltype = AA   length = 110
FEATURE                 Location/Qualifiers
REGION                  1..110
                        note = Description of Artificial Sequence:
                        SyntheticKPS44-G4 VL polypeptide
source                  1..110
                        mol_type = protein
                        organism = synthetic construct
SEQUENCE: 217
QSVLTQPPSV SAAPGQKVTI ACSGTSSNIG SDAVSWFQQL PGTAPKLLIY ENNKRPSGIS    60
DRFSGSKSGT SVTLGITGLQ TGDEADYYCA TFESSLSAYV FGTGTKVTVL              110

SEQ ID NO: 218          moltype = AA   length = 8
FEATURE                 Location/Qualifiers
REGION                  1..8
                        note = Description of Artificial Sequence:
                        SyntheticKPS44-G4 VL-CDR1 peptide
source                  1..8
                        mol_type = protein
                        organism = synthetic construct
SEQUENCE: 218
SSNIGSDA                                                               8

SEQ ID NO: 219          moltype =    length =
SEQUENCE: 219
000

SEQ ID NO: 220          moltype = AA   length = 11
```

```
FEATURE              Location/Qualifiers
REGION               1..11
                     note = Description of Artificial Sequence:
                     SyntheticKPS44-G4 VL-CDR3 peptide
source               1..11
                     mol_type = protein
                     organism = synthetic construct
SEQUENCE: 220
ATFESSLSAY V                                                       11

SEQ ID NO: 221       moltype = DNA   length = 360
FEATURE              Location/Qualifiers
misc_feature         1..360
                     note = Description of Artificial Sequence:
                     SyntheticKPS44-G4 VH polynucleotide
source               1..360
                     mol_type = other DNA
                     organism = synthetic construct
SEQUENCE: 221
caggtacagc ttgtagaaag tgggggtggg cttgtcaagc ctgggggaag tttgagactg     60
agttgcgccg caagtggctt cacgtttaag aacgcatgga tgtcctggat tagacaagcc   120
cccggtaaag gtttggaatg ggtaggacga gttaagtctg aggttgacgc cgggacgata   180
gattacggtg ttcccgtgcg cggcagattc acgataagtc gagacgactc taagaataca   240
ctttacctcc agatgaatag cctcaaaacc gaggatacag ccgtttatta ttgccgcgca   300
ttctatagtg gcttcccgac tgggtactgg ggcaaggta ctcttgtcac agtgtcatcc    360

SEQ ID NO: 222       moltype = DNA   length = 330
FEATURE              Location/Qualifiers
misc_feature         1..330
                     note = Description of Artificial Sequence:
                     SyntheticKPS44-G4 VL polynucleotide
source               1..330
                     mol_type = other DNA
                     organism = synthetic construct
SEQUENCE: 222
cagtccgttt tgacgcaacc cccgtcagtg agtgctgcgc tgggcagaa ggtgacgatc     60
gcctgctcag ggaccagcag taatataggc tctgatgctg tatcatggtt ccagcaactg   120
cctggcacgg cacctaaact gctgatctac gaaaataata gcggccctc aggcatttca    180
gatggttct ctgggagcaa gagtggtaca agcgtaacgc tcggtatcac cggtctccag    240
acaggtgatg aagctgatta ctactgcgct acttttgaga gctctctttc agcttacgtg   300
tttggtaccg ggaccaaagt gacagtcctc                                    330

SEQ ID NO: 223       moltype = AA    length = 120
FEATURE              Location/Qualifiers
REGION               1..120
                     note = Description of Artificial Sequence:
                     SyntheticKPS44-G6 VH polypeptide
source               1..120
                     mol_type = protein
                     organism = synthetic construct
SEQUENCE: 223
QVQLVESGGG LVKPGGSLRL SCAASGFTFK NAWMSWIRQA PGKGLEWVGR VKSEVDAGTI    60
DYGVPVRGRF TISRDDSKNT LYLQMNSLKT EDTAVYYCRA FYSGFPTGYW GQGTLVTVSS   120

SEQ ID NO: 224       moltype = AA    length = 8
FEATURE              Location/Qualifiers
REGION               1..8
                     note = Description of Artificial Sequence:
                     SyntheticKPS44-G6 VH-CDR1 peptide
source               1..8
                     mol_type = protein
                     organism = synthetic construct
SEQUENCE: 224
GFTFKNAW                                                            8

SEQ ID NO: 225       moltype = AA    length = 10
FEATURE              Location/Qualifiers
REGION               1..10
                     note = Description of Artificial Sequence:
                     SyntheticKPS44-G6 VH-CDR2 peptide
source               1..10
                     mol_type = protein
                     organism = synthetic construct
SEQUENCE: 225
VKSEVDAGTI                                                         10

SEQ ID NO: 226       moltype = AA    length = 11
FEATURE              Location/Qualifiers
REGION               1..11
```

```
                        note = Description of Artificial Sequence:
                        SyntheticKPS44-G6 VH-CDR3 peptide
source                  1..11
                        mol_type = protein
                        organism = synthetic construct
SEQUENCE: 226
RAFYSGFPTG Y                                                                    11

SEQ ID NO: 227          moltype = AA   length = 110
FEATURE                 Location/Qualifiers
REGION                  1..110
                        note = Description of Artificial Sequence:
                        SyntheticKPS44-G6 VL polypeptide
source                  1..110
                        mol_type = protein
                        organism = synthetic construct
SEQUENCE: 227
QSVLTQPPSV SAAPGQKVTI ACSGTSSNIG SESVSWFQQL PGTAPKLLIY ENNKRPSGIS               60
DRFSGSKSGT SVTLGITGLQ TGDEADYYCA TFESSLSAYV FGTGTKVTVL                          110

SEQ ID NO: 228          moltype = AA   length = 8
FEATURE                 Location/Qualifiers
REGION                  1..8
                        note = Description of Artificial Sequence:
                        SyntheticKPS44-G6 VL-CDR1 peptide
source                  1..8
                        mol_type = protein
                        organism = synthetic construct
SEQUENCE: 228
SSNIGSES                                                                        8

SEQ ID NO: 229          moltype =   length =
SEQUENCE: 229
000

SEQ ID NO: 230          moltype = AA   length = 11
FEATURE                 Location/Qualifiers
REGION                  1..11
                        note = Description of Artificial Sequence:
                        SyntheticKPS44-G6 VL-CDR3 peptide
source                  1..11
                        mol_type = protein
                        organism = synthetic construct
SEQUENCE: 230
ATFESSLSAY V                                                                    11

SEQ ID NO: 231          moltype = DNA   length = 360
FEATURE                 Location/Qualifiers
misc_feature            1..360
                        note = Description of Artificial Sequence:
                        SyntheticKPS44-G6 VH polynucleotide
source                  1..360
                        mol_type = other DNA
                        organism = synthetic construct
SEQUENCE: 231
caggtacagc ttgtagaaag tgggggtggg cttgtcaagc ctgggggaag tttgagactg               60
agttgcgccg caagtggctt cacgtttaag aacgcatgga tgtcctggat tagacaagcc              120
cccggtaaag gtttggaatg ggtaggacga gttaagtctg aggttgacgc cgggacgata              180
gattacggtg ttcccgtgcg cggcagattc acgataagtc gagacgactc taagaataca              240
ctttacctcc agatgaatag cctcaaaacc gaggatacag ccgttattta ttgccgcgca              300
ttctatagtg gcttcccgac tgggtactgg gggcaaggta ctcttgtcac agtgtcatcc              360

SEQ ID NO: 232          moltype = DNA   length = 330
FEATURE                 Location/Qualifiers
misc_feature            1..330
                        note = Description of Artificial Sequence:
                        SyntheticKPS44-G6 VL polynucleotide
source                  1..330
                        mol_type = other DNA
                        organism = synthetic construct
SEQUENCE: 232
cagtccgttt tgacgcaacc cccgtcagtg agtgctgcgc tgggcagaa ggtgacgatc                60
gcctgctcag ggaccagcag taatataggc tctgagtctg tatcatggtt ccagcaactg              120
cctggcacgg caccctaaact gctgatctac gaaaataata agcgccctc aggcatttca              180
gataggttct ctgggagcaa gagtggtaca agcgtaacgc tcggtatcac cggtctccag              240
acaggtgatg aagctgatta ctactgcgct acttttgaga gctctctttc agcttacgtg              300
tttggtaccg ggaccaaagt gacagtcctc                                               330

SEQ ID NO: 233          moltype = AA   length = 120
```

```
FEATURE                 Location/Qualifiers
REGION                  1..120
                        note = Description of Artificial Sequence:
                        SyntheticKPS44-G8 VH polypeptide
source                  1..120
                        mol_type = protein
                        organism = synthetic construct
SEQUENCE: 233
QVQLVESGGG LVKPGGSLRL SCAASGFTFK NAWMSWIRQA PGKGLEWVGR VKSEVDAGTI    60
DYGVPVRGRF TISRDDSKNT LYLQMNSLKT EDTAVYYCRA FYSGFPTGYW GQGTLVTVSS   120

SEQ ID NO: 234          moltype = AA  length = 8
FEATURE                 Location/Qualifiers
REGION                  1..8
                        note = Description of Artificial Sequence:
                        SyntheticKPS44-G8 VH-CDR1 peptide
source                  1..8
                        mol_type = protein
                        organism = synthetic construct
SEQUENCE: 234
GFTFKNAW                                                              8

SEQ ID NO: 235          moltype = AA  length = 10
FEATURE                 Location/Qualifiers
REGION                  1..10
                        note = Description of Artificial Sequence:
                        SyntheticKPS44-G8 VH-CDR2 peptide
source                  1..10
                        mol_type = protein
                        organism = synthetic construct
SEQUENCE: 235
VKSEVDAGTI                                                           10

SEQ ID NO: 236          moltype = AA  length = 11
FEATURE                 Location/Qualifiers
REGION                  1..11
                        note = Description of Artificial Sequence:
                        SyntheticKPS44-G8 VH-CDR3 peptide
source                  1..11
                        mol_type = protein
                        organism = synthetic construct
SEQUENCE: 236
RAFYSGFPTG Y                                                         11

SEQ ID NO: 237          moltype = AA  length = 110
FEATURE                 Location/Qualifiers
REGION                  1..110
                        note = Description of Artificial Sequence:
                        SyntheticKPS44-G8 VL polypeptide
source                  1..110
                        mol_type = protein
                        organism = synthetic construct
SEQUENCE: 237
QSVLTQPPSV SAAPGQKVTI ACSGTSSNIG SDSVSWFQQL PGTAPKLLIY ENNKRPSGIS    60
DRFSGSKSGT SVTLGITGLQ TGDEADYYCA TFESSLSAYV FGTGTKVTVL              110

SEQ ID NO: 238          moltype = AA  length = 8
FEATURE                 Location/Qualifiers
REGION                  1..8
                        note = Description of Artificial Sequence:
                        SyntheticKPS44-G8 VL-CDR1 peptide
source                  1..8
                        mol_type = protein
                        organism = synthetic construct
SEQUENCE: 238
SSNIGSDS                                                              8

SEQ ID NO: 239          moltype =     length =
SEQUENCE: 239
000

SEQ ID NO: 240          moltype = AA  length = 11
FEATURE                 Location/Qualifiers
REGION                  1..11
                        note = Description of Artificial Sequence:
                        SyntheticKPS44-G8 VL-CDR3 peptide
source                  1..11
                        mol_type = protein
                        organism = synthetic construct
```

```
SEQUENCE: 240
ATFESSLSAY V                                                                          11

SEQ ID NO: 241          moltype = DNA   length = 360
FEATURE                 Location/Qualifiers
misc_feature            1..360
                        note = Description of Artificial Sequence:
                        SyntheticKPS44-G8 VH polynucleotide
source                  1..360
                        mol_type = other DNA
                        organism = synthetic construct
SEQUENCE: 241
caggtacagc ttgtagaaag tgggggtggg cttgtcaagc ctggggggaag tttgagactg    60
agttgcgccg caagtggctt cacgtttaag aacgcatgga tgtcctggat tagacaagcc   120
cccggtaaag gtttggaatg ggtaggacga gttaagtctg aggttgacgc cgggacgata   180
gattacggtg ttcccgtgcg cggcagattc acgataagtc gagacgactc taagaataca   240
ctttacctcc agatgaatag cctcaaaacc gaggatacag ccgttattta ttgccgcgca   300
ttctatagtg gcttcccgac tgggtactgg ggcaaggta ctcttgtcac agtgtcatcc    360

SEQ ID NO: 242          moltype = DNA   length = 330
FEATURE                 Location/Qualifiers
misc_feature            1..330
                        note = Description of Artificial Sequence:
                        SyntheticKPS44-G8 VL polynucleotide
source                  1..330
                        mol_type = other DNA
                        organism = synthetic construct
SEQUENCE: 242
cagtccgttt tgacgcaacc cccgtcagtg agtgctgcgc tgggcagaa ggtgacgatc     60
gcctgctcag ggaccagcag taatataggc tctgattctg tatcatggtt ccagcaactg   120
cctggcacgg cacctaaact gctgatctac gaaaataata gcggcccctc aggcatttca   180
gataggttct ctgggagcaa gagtggtaca agcgtaacgc tcggtatcac cggtctccag   240
acaggtgatg aagctgatta ctactgcgct acttttgaga gctctcttc agcttacgtg    300
tttggtaccg ggaccaaagt gacagtcctc                                     330

SEQ ID NO: 243          moltype = AA   length = 120
FEATURE                 Location/Qualifiers
REGION                  1..120
                        note = Description of Artificial Sequence:
                        SyntheticKPS44-G10 VH polypeptide
source                  1..120
                        mol_type = protein
                        organism = synthetic construct
SEQUENCE: 243
EVHLVESGGG LVKPGGSLRL SCAASGFTFK NAWMSWIRQA PGKGLEWVGR VKSEVDAGTI    60
DYGVPVRGRF TISRDDSQGT LSLEMNSLKD DDTGVYYCRA FYSGFPTGYW GQGALVSVSS   120

SEQ ID NO: 244          moltype = AA   length = 8
FEATURE                 Location/Qualifiers
REGION                  1..8
                        note = Description of Artificial Sequence:
                        SyntheticKPS44-G10 VH-CDR1 peptide
source                  1..8
                        mol_type = protein
                        organism = synthetic construct
SEQUENCE: 244
GFTFKNAW                                                                               8

SEQ ID NO: 245          moltype = AA   length = 10
FEATURE                 Location/Qualifiers
REGION                  1..10
                        note = Description of Artificial Sequence:
                        SyntheticKPS44-G10 VH-CDR2 peptide
source                  1..10
                        mol_type = protein
                        organism = synthetic construct
SEQUENCE: 245
VKSEVDAGTI                                                                            10

SEQ ID NO: 246          moltype = AA   length = 11
FEATURE                 Location/Qualifiers
REGION                  1..11
                        note = Description of Artificial Sequence:
                        SyntheticKPS44-G10 VH-CDR3 peptide
source                  1..11
                        mol_type = protein
                        organism = synthetic construct
SEQUENCE: 246
RAFYSGFPTG Y                                                                          11
```

```
SEQ ID NO: 247          moltype = AA  length = 110
FEATURE                 Location/Qualifiers
REGION                  1..110
                        note = Description of Artificial Sequence:
                         SyntheticKPS44-G10 VL polypeptide
source                  1..110
                        mol_type = protein
                        organism = synthetic construct
SEQUENCE: 247
QSVLTQPPSL SAAPGQTITI ACSGTSSNIG SDSVSWFQQF PGTAPRVLIY ENNKRPSGIS    60
DRFSGSKSGT SVTLGITGLQ TGDEADYYCA TFESSLSAYV FGSGTKVTVL              110

SEQ ID NO: 248          moltype = AA  length = 8
FEATURE                 Location/Qualifiers
REGION                  1..8
                        note = Description of Artificial Sequence:
                         SyntheticKPS44-G10 VL-CDR1 peptide
source                  1..8
                        mol_type = protein
                        organism = synthetic construct
SEQUENCE: 248
SSNIGSDS                                                              8

SEQ ID NO: 249          moltype =   length =
SEQUENCE: 249
000

SEQ ID NO: 250          moltype = AA  length = 11
FEATURE                 Location/Qualifiers
REGION                  1..11
                        note = Description of Artificial Sequence:
                         SyntheticKPS44-G10 VL-CDR3 peptide
source                  1..11
                        mol_type = protein
                        organism = synthetic construct
SEQUENCE: 250
ATFESSLSAY V                                                         11

SEQ ID NO: 251          moltype = DNA  length = 360
FEATURE                 Location/Qualifiers
misc_feature            1..360
                        note = Description of Artificial Sequence:
                         SyntheticKPS44-G10 VH polynucleotide
source                  1..360
                        mol_type = other DNA
                        organism = synthetic construct
SEQUENCE: 251
gaggtacacc ttgtagaaag tgggggtggg cttgtcaagc ctgggggaag tttgagactg     60
agttgcgccg caagtggctt cacgtttaag aacgcatgga tgtcctggat tagacaagcc   120
cccggtaaag gttttgaatg ggtaggacga gttaagtctg aggttgacgc ggggacgata   180
gattacggtg ttcccgtgcg cggcagattc acgataagtc gagacgactc tcagggtaca   240
cttagcctcg aaatgaatag cctcaaagac gatgatacag gcgtttatta ttgccgcgca   300
ttctacagtg gcttcccgac tgggtactgg gggcaaggtg ctcttgtctc agtgtcatcc   360

SEQ ID NO: 252          moltype = DNA  length = 330
FEATURE                 Location/Qualifiers
misc_feature            1..330
                        note = Description of Artificial Sequence:
                         SyntheticKPS44-G10 VL polynucleotide
source                  1..330
                        mol_type = other DNA
                        organism = synthetic construct
SEQUENCE: 252
cagtccgttt tgacgcaacc cccgtcactg agtgctgcgc ctgggcagac cataacgatc     60
gcctgctcag ggaccagcag taatataggc tctgattctg tatcatggtt ccagcaattc   120
cctggcacgg cacctcgcgt actgatctac gaaaataata gcggccctc aggcatttca    180
gataggttct ctgggagcaa gagtggtaca agcgtaacgc tcggtatcac cggtctccag   240
acaggtgatg aagctgatta ctactgcgct acttttgaga gctctctttc agcttacgtg   300
tttggttccg ggaccaaagt gacagtcctc                                    330

SEQ ID NO: 253          moltype = AA  length = 120
FEATURE                 Location/Qualifiers
REGION                  1..120
                        note = Description of Artificial Sequence:
                         SyntheticKPS44-G11 VH polypeptide
source                  1..120
                        mol_type = protein
                        organism = synthetic construct
```

```
SEQUENCE: 253
EVHLVESGGG LVKPGGSLRL SCAASGFTFK NAWMSWIRQA PGKGLEWVGR VKSEVDAGTI    60
DYGVPVRGRF TISRDDSQGT LSLEMNSLKD DDTGVYYCRA FYSGFPTGYW GQGALVSVSS   120

SEQ ID NO: 254          moltype = AA   length = 8
FEATURE                 Location/Qualifiers
REGION                  1..8
                        note = Description of Artificial Sequence:
                        SyntheticKPS44-G11 VH-CDR1 peptide
source                  1..8
                        mol_type = protein
                        organism = synthetic construct
SEQUENCE: 254
GFTFKNAW                                                              8

SEQ ID NO: 255          moltype = AA   length = 10
FEATURE                 Location/Qualifiers
REGION                  1..10
                        note = Description of Artificial Sequence:
                        SyntheticKPS44-G11 VH-CDR2 peptide
source                  1..10
                        mol_type = protein
                        organism = synthetic construct
SEQUENCE: 255
VKSEVDAGTI                                                           10

SEQ ID NO: 256          moltype = AA   length = 11
FEATURE                 Location/Qualifiers
REGION                  1..11
                        note = Description of Artificial Sequence:
                        SyntheticKPS44-G11 VH-CDR3 peptide
source                  1..11
                        mol_type = protein
                        organism = synthetic construct
SEQUENCE: 256
RAFYSGFPTG Y                                                         11

SEQ ID NO: 257          moltype = AA   length = 110
FEATURE                 Location/Qualifiers
REGION                  1..110
                        note = Description of Artificial Sequence:
                        SyntheticKPS44-G11 VL polypeptide
source                  1..110
                        mol_type = protein
                        organism = synthetic construct
SEQUENCE: 257
QSVLTQPPSV SAAPGQKVTI ACSGTSSNIG SDSVSWFQQL PGTAPKLLIY ENNKRPSGIS    60
DRFSGSKSGT SVTLGITGLQ TGDEADYYCA TFESSLSAYV FGTGTKVTVL              110

SEQ ID NO: 258          moltype = AA   length = 8
FEATURE                 Location/Qualifiers
REGION                  1..8
                        note = Description of Artificial Sequence:
                        SyntheticKPS44-G11 VL-CDR1 peptide
source                  1..8
                        mol_type = protein
                        organism = synthetic construct
SEQUENCE: 258
SSNIGSDS                                                              8

SEQ ID NO: 259          moltype =      length =
SEQUENCE: 259
000

SEQ ID NO: 260          moltype = AA   length = 11
FEATURE                 Location/Qualifiers
REGION                  1..11
                        note = Description of Artificial Sequence:
                        SyntheticKPS44-G11 VL-CDR3 peptide
source                  1..11
                        mol_type = protein
                        organism = synthetic construct
SEQUENCE: 260
ATFESSLSAY V                                                         11

SEQ ID NO: 261          moltype = DNA  length = 360
FEATURE                 Location/Qualifiers
misc_feature            1..360
                        note = Description of Artificial Sequence:
```

```
                        SyntheticKPS44-G11 VH polynucleotide
source                  1..360
                        mol_type = other DNA
                        organism = synthetic construct
SEQUENCE: 261
gaggtacacc ttgtagaaag tgggggtggg cttgtcaagc ctgggggaag tttgagactg    60
agttgcgccg caagtggctt cacgtttaag aacgcatgga tgtcctggat tagacaagcc   120
cccggtaaag gtttggaatg ggtaggacga gttaagtctg aggttgacgc ggggacgata   180
gattacggtg ttcccgtgcg cggcagattc acgataagtc gagacgactc tcagggtaca   240
cttagcctcg aaatgaatag cctcaaagac gatgatacag gcgtttatta ttgccgcgca   300
ttctacagtg gcttcccgac tgggtactgg gggcaaggtg ctcttgtctc agtgtcatcc   360

SEQ ID NO: 262          moltype = DNA  length = 330
FEATURE                 Location/Qualifiers
misc_feature            1..330
                        note = Description of Artificial Sequence:
                        SyntheticKPS44-G11 VL polynucleotide
source                  1..330
                        mol_type = other DNA
                        organism = synthetic construct
SEQUENCE: 262
cagtccgttt tgacgcaacc cccgtcagtg agtgctgcgc ctgggcagaa ggtgacgatc    60
gcctgctcag ggaccagcag taatataggc tctgattctg tatcatggtt ccagcaactg   120
cctggcacgg cacctaaact gctgatctac gaaaataata gcggccctc aggcatttca    180
gataggttct ctgggagcaa gagtggtaca agctaacgc tcggtatcac cggtctccag    240
acaggtgatg aagctgatta ctactgcgct acttttgaga gctctctttc agcttacgtg   300
tttggtaccg ggaccaaagt gacagtcctc                                    330

SEQ ID NO: 263          moltype = AA  length = 120
FEATURE                 Location/Qualifiers
REGION                  1..120
                        note = Description of Artificial Sequence:
                        SyntheticKPS44-G14 VH polypeptide
source                  1..120
                        mol_type = protein
                        organism = synthetic construct
SEQUENCE: 263
QVQLVESGGG LVKPGGSLRL SCAASGFTFK NAWMSWIRQA PGKGLEWVGR VKSEVDAGTI    60
DYGVPVRGRF TISRDDSKNT LYLQMNSLKT EDTAVYYCRA FYSGFPTGYW GQGTLVTVSS   120

SEQ ID NO: 264          moltype = AA  length = 8
FEATURE                 Location/Qualifiers
REGION                  1..8
                        note = Description of Artificial Sequence:
                        SyntheticKPS44-G14 VH-CDR1 peptide
source                  1..8
                        mol_type = protein
                        organism = synthetic construct
SEQUENCE: 264
GFTFKNAW                                                              8

SEQ ID NO: 265          moltype = AA  length = 10
FEATURE                 Location/Qualifiers
REGION                  1..10
                        note = Description of Artificial Sequence:
                        SyntheticKPS44-G14 VH-CDR2 peptide
source                  1..10
                        mol_type = protein
                        organism = synthetic construct
SEQUENCE: 265
VKSEVDAGTI                                                           10

SEQ ID NO: 266          moltype = AA  length = 11
FEATURE                 Location/Qualifiers
REGION                  1..11
                        note = Description of Artificial Sequence:
                        SyntheticKPS44-G14 VH-CDR3 peptide
source                  1..11
                        mol_type = protein
                        organism = synthetic construct
SEQUENCE: 266
RAFYSGFPTG Y                                                         11

SEQ ID NO: 267          moltype = AA  length = 110
FEATURE                 Location/Qualifiers
REGION                  1..110
                        note = Description of Artificial Sequence:
                        SyntheticKPS44-G14 VL polypeptide
source                  1..110
```

```
                              mol_type = protein
                              organism = synthetic construct
SEQUENCE: 267
QSVLTQPPSL SAAPGQTITI ACSGTSSNIG SDSVSWFQQF PGTAPRVLIY ENNKRPSGIS    60
DRFSGSKSGT SVTLGITGLQ TGDEADYYCA TFESSLSAYV FGSGTKVTVL             110

SEQ ID NO: 268                moltype = AA   length = 8
FEATURE                       Location/Qualifiers
REGION                        1..8
                              note = Description of Artificial Sequence:
                               SyntheticKPS44-G14 VL-CDR1 peptide
source                        1..8
                              mol_type = protein
                              organism = synthetic construct
SEQUENCE: 268
SSNIGSDS                                                              8

SEQ ID NO: 269                moltype =    length =
SEQUENCE: 269
000

SEQ ID NO: 270                moltype = AA   length = 11
FEATURE                       Location/Qualifiers
REGION                        1..11
                              note = Description of Artificial Sequence:
                               SyntheticKPS44-G14 VL-CDR3 peptide
source                        1..11
                              mol_type = protein
                              organism = synthetic construct
SEQUENCE: 270
ATFESSLSAY V                                                         11

SEQ ID NO: 271                moltype = DNA   length = 360
FEATURE                       Location/Qualifiers
misc_feature                  1..360
                              note = Description of Artificial Sequence:
                               SyntheticKPS44-G14 VH polynucleotide
source                        1..360
                              mol_type = other DNA
                              organism = synthetic construct
SEQUENCE: 271
caggtacagc ttgtagaaag tgggggtggg cttgtcaagc ctgggggaag tttgagactg    60
agttgcgccg caagtggctt cacgtttaag aacgcatgga gtgtcctggat tagacaagcc  120
cccggtaaag gtttggaatg ggtaggacga gttaagtctg aggttgacgc cgggacgata   180
gattacggtg ttcccgtgcg cggcagattc acgataagtc gagacgactc taagaataca   240
cttacctcc agatgaatag cctcaaaacc gaggatacag ccgtttatta ttgccgcgca    300
ttctatagtg gcttcccgac tgggtactgg gggcaaggta ctcttgtcac agtgtcatcc   360

SEQ ID NO: 272                moltype = DNA   length = 330
FEATURE                       Location/Qualifiers
misc_feature                  1..330
                              note = Description of Artificial Sequence:
                               SyntheticKPS44-G14 VL polynucleotide
source                        1..330
                              mol_type = other DNA
                              organism = synthetic construct
SEQUENCE: 272
cagtccgttt tgacgcaacc cccgtcactg agtgctgcgc ctggggcagac cataacgatc   60
gcctgctcag ggaccagcag taatataggc tctgattctg tatcatggtt ccagcaattc   120
cctggcacgg cacctcgcgt actgatctac gaaaataata agcgggccctc aggcatttca   180
gataggttct ctgggagcaa gagtggtaca agcgtaacgc tcggtatcac cggtctccag   240
acaggtgatg aagctgatta ctactgcgct acttttgaga gctctctttc agcttacgtg   300
tttggttccg ggaccaaagt gacagtcctc                                    330

SEQ ID NO: 273                moltype = AA   length = 120
FEATURE                       Location/Qualifiers
REGION                        1..120
                              note = Description of Artificial Sequence:
                               SyntheticKPS44-G8-HCvFW1 polypeptide
source                        1..120
                              mol_type = protein
                              organism = synthetic construct
SEQUENCE: 273
QVQLVESGGG LVKPGGSLRL SCAASGFTFK NAWMSWIRQA PGKGLEWVGR VKSEVDAGTI    60
DYGVPVRGRF TISRDDSQGT LYLQMNSLKT EDTGVYYCRA FYSGFPTGYW GQGTLVTVSS   120

SEQ ID NO: 274                moltype = AA   length = 120
FEATURE                       Location/Qualifiers
REGION                        1..120
```

```
                  note = Description of Artificial Sequence:
                  SyntheticKPS44-G8-HCvFW2 polypeptide
source            1..120
                  mol_type = protein
                  organism = synthetic construct
SEQUENCE: 274
QVHLVESGGG LVKPGGSLRL SCAASGFTFK NAWMSWIRQA PGKGLEWVGR VKSEVDAGTI    60
DYGVPVRGRF TISRDDSQGT LYLQMNSLKT EDTGVYYCRA FYSGFPTGYW GQGTLVTVSS   120
```